(12) United States Patent
Mitchell et al.

(10) Patent No.: US 11,839,155 B2
(45) Date of Patent: Dec. 5, 2023

(54) ORGANIC SEMICONDUCTING COMPOUNDS

(71) Applicant: RAYNERGY TEK INCORPORATION, Hsinchu (TW)

(72) Inventors: William Mitchell, Chandler's Ford (GB); Agnieszka Pron, Eastleigh (GB); Mansoor D'Lavari, Southampton (GB); Kane Heard, Southampton (GB); Jonathan Snow, Salisbury (GB); Ignasi Burgues, Southampton (GB); Quentin Huaulme, Southampton (GB)

(73) Assignee: RAYNERGY TEK INC., Hsinchu (TW)

( * ) Notice: Subject to any disclaimer, the term of this patent is extended or adjusted under 35 U.S.C. 154(b) by 155 days.

(21) Appl. No.: 17/042,662

(22) PCT Filed: Mar. 26, 2019

(86) PCT No.: PCT/EP2019/057499
§ 371 (c)(1),
(2) Date: Sep. 28, 2020

(87) PCT Pub. No.: WO2019/185578
PCT Pub. Date: Oct. 3, 2019

(65) Prior Publication Data
US 2022/0320445 A1    Oct. 6, 2022

(30) Foreign Application Priority Data
Mar. 28, 2018  (EP) .................................. 18164638

(51) Int. Cl.
*H10K 85/60* (2023.01)
*C07D 495/04* (2006.01)
*C07D 495/22* (2006.01)
*H10K 85/20* (2023.01)
*H10K 10/46* (2023.01)
*H10K 30/30* (2023.01)

(52) U.S. Cl.
CPC ....... *H10K 85/6576* (2023.02); *C07D 495/04* (2013.01); *C07D 495/22* (2013.01); *H10K 85/211* (2023.02); *H10K 85/655* (2023.02); *H10K 85/657* (2023.02); *H10K 10/488* (2023.02); *H10K 30/30* (2023.02)

(58) Field of Classification Search
CPC ................................................... H01L 51/0074
See application file for complete search history.

(56) References Cited

U.S. PATENT DOCUMENTS

| 2016/0155946 A1 | 6/2016 | Blouin et al. |
| 2017/0084839 A1 | 3/2017 | Nanson et al. |
| 2019/0237672 A1* | 8/2019 | Mitchell ............ C08G 61/123 |

FOREIGN PATENT DOCUMENTS

| CN | 106103436 A | 11/2016 |
| WO | 2018036914 A1 | 3/2018 |
| WO | 2019/052935 A1 | 3/2019 |

OTHER PUBLICATIONS

Danyang Ma, et al., The Design of highly efficient polymer solar cells with outstanding short-circuit current density based on small band gap electron acceptor, Dyes and Pigments (2018), doi: 10.1016/j.dyepig.2017.12.017.
R. Li, et al., Journal of Materials Chemistry A, J. Mater. Chem. A. 2017, DOI: 10.1039/C7TA06631G.
PCT International Search Report.
Notice of Allowance mailed to corresponding Chinese Patent Application No. 201980036987.3 dated Jun. 1, 2023.

* cited by examiner

*Primary Examiner* — William D Young
(74) *Attorney, Agent, or Firm* — Rosenberg, Klein & Lee

(57) ABSTRACT

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

25 Claims, No Drawings

ORGANIC SEMICONDUCTING COMPOUNDS

TECHNICAL FIELD

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photo-detectors (OPD), organic field effect transistors (OFET) and organic light emitting diodes (OLED), and to OE, OPV, PSC, OPD, OFET and OLED devices comprising these compounds, compositions or polymer blends.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, perovskite-based solar cell (PSC) devices, sensors, memory elements and logic circuits to name just a few. The organic semiconducting materials are typically present in the electronic device in the form of a thin layer, for example of between 50 and 300 nm thickness.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 10%.

Another particular area of importance is OFETs. The performance of OFET devices is principally based upon the charge carrier mobility of the semiconducting material and the current on/off ratio, so the ideal semiconductor should have a low conductivity in the off state, combined with high charge carrier mobility ($>1\times10^{-3}$ cm$^2$V$^{-1}$ s$^{-1}$). In addition, it is important that the semiconducting material is stable to oxidation i.e. it has a high ionisation potential, as oxidation leads to reduced device performance. Further requirements for the semiconducting material are good processability, especially for large-scale production of thin layers and desired patterns, and high stability, film uniformity and integrity of the organic semiconductor layer.

Organic photodetectors (OPDs) are a further particular area of importance, for which conjugated light-absorbing polymers offer the hope of allowing efficient devices to be produced by solution-processing technologies, such as spin casting, dip coating or ink jet printing, to name a few only.

The photosensitive layer in an OPV or OPD device is usually composed of at least two materials, a p-type semiconductor, which is typically a conjugated polymer, an oligomer or a defined molecular unit, and an n-type semiconductor, which is typically a fullerene or substituted fullerene, graphene, a metal oxide, or quantum dots.

However, the OSC materials disclosed in prior art for use in OE devices have several drawbacks. For example, the fullerenes or fullerene derivatives which have hitherto been used as electron acceptors in OPV or OPD devices are often difficult to synthesize or purify, and/or do not absorb light strongly in the visible and near IR spectrum >700 nm, do not allow easy modification of their HOMO and LUMO energy levels, or do often not form a favourable morphology and/or miscibility with the donor material.

Therefore, there is still a need for OSC materials for use in OE devices like OPVs, PSCs, OPDs and OFETs, which have advantageous properties, in particular good processability, a high solubility in organic solvents, good structural organization and film-forming properties. In addition, the OSC materials should be easy to synthesize, especially by methods suitable for mass production. For use in OPV cells, the OSC materials should especially have a low bandgap, which enables improved light harvesting by the photoactive layer and can lead to higher cell efficiencies, high stability and long lifetime. For use in OFETs the OSC materials should especially have high charge-carrier mobility, high on/off ratio in transistor devices, high oxidative stability and long lifetime.

It was an aim of the present invention to provide new OSC compounds, especially n-type OSCs, which can overcome the drawbacks of the OSCs from prior art, and which provide one or more of the above-mentioned advantageous properties, especially easy synthesis by methods suitable for mass production, good processability, high stability, long lifetime in OE devices, good solubility in organic solvents, high charge carrier mobility, and a low bandgap. Another aim of the invention was to extend the pool of OSC materials and n-type OSCs available to the expert. Other aims of the present invention are immediately evident to the expert from the following detailed description.

The inventors of the present invention have found that one or more of the above aims can be achieved by providing compounds as disclosed and claimed hereinafter.

These compounds represent a novel, alternative type of n-type organic semiconductors, which do not include a fullerene moiety, and which are hereinafter also referred to as "non-fullerene acceptor(s)" or "NFA(s)".

These NFA compounds comprise a polycyclic core as shown in formula I, and further comprise one or two terminal groups which are electron withdrawing relative to the central polycyclic core, and do optionally further comprise one or more aromatic or heteroaromatic spacer groups which are located between the polycyclic core and the terminal groups and which can be electron withdrawing or electron donating relative to the polycyclic core.

As a result, these compounds have an acceptor-donor-acceptor (A-D-A) or A-D structure, wherein the polycyclic core acts as donor and the terminal groups, optionally together with the spacer groups, act as acceptor.

It has been found that compounds comprising the aforementioned structural features can be used as n-type OSCs which show advantageous properties as described above.

In prior aret A-D-A type NFA compounds have been reported comprising an IDT core that is flanked by two terminal 2-(3-oxo-2,3-dihydroinden-1-ylidene)malononitrile withdrawing groups, as disclosed for example in Y. Lin et al., Adv. Mater., 2015, 27, 1170; H. Lin et al., Adv. Mater., 2015, 27, 7299; N. Qiu et al., Adv. Mater., 2017, 29, 1604964; CN104557968 A and CN105315298 A.

H. Feng et al., Chem. Mater. 2017, 29, 7908 disclose A-D-A type NFA compounds with a fluorenedicylco-pentadithiophene core and two terminal acceptor groups, and their use as acceptor for polymer solar cells

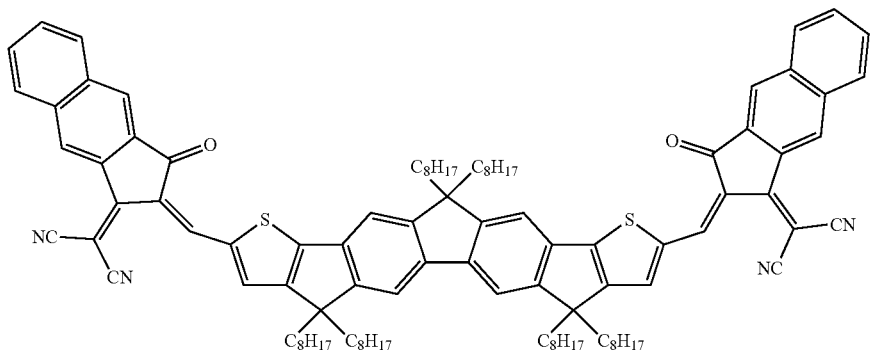

R. Li et al., J. Mater. Chem. 2017, 5, 23926 disclose A-D-A type NFA with an indacenodithiophene core and two terminal acceptor groups, and their use as acceptor for polymer solar cells.

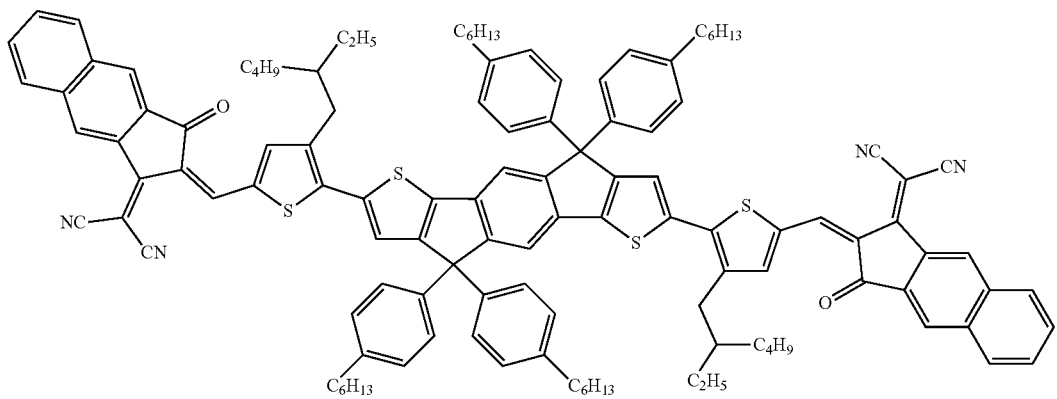

However, compounds as disclosed and claimed hereinafter have hitherto not been disclosed in prior art for use as n-type semiconductors.

SUMMARY

The invention relates to a compound of formula I

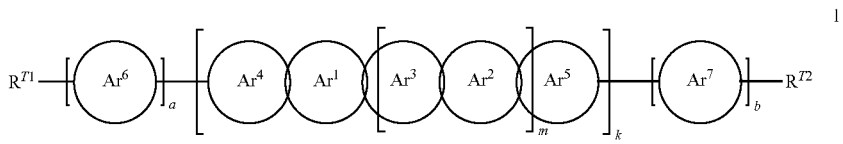

wherein the individual radicals, independently of each other and on each occurrence identically or differently, have the following meanings $Ar^1$, $Ar^2$ a group selected from the following formulae

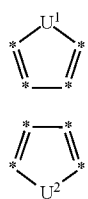

$Ar^3$ a group selected from the following formulae and their mirror images

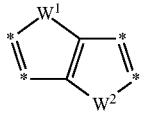

A3a

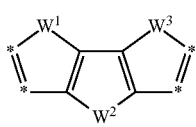

A3b

-continued
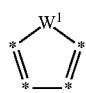
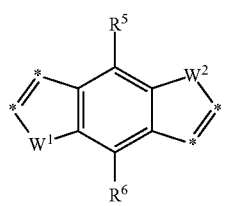
A3d
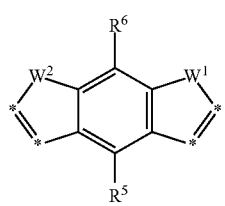
A3e
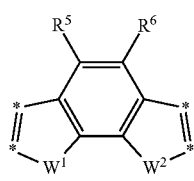
A3f
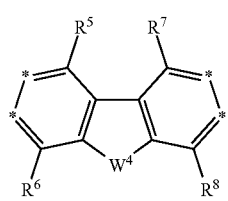
A3g
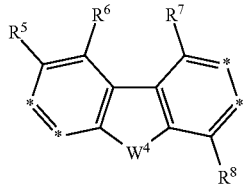
A3h
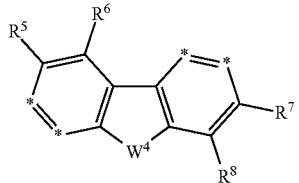
A3i
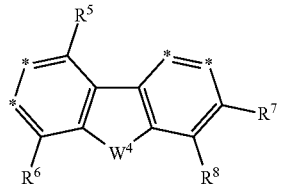
A3j
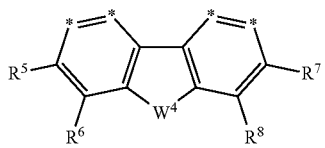
A3k
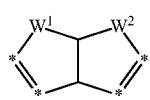
A3l
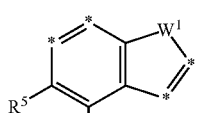
A3m
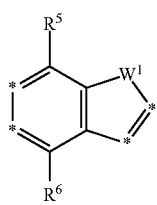
A3n
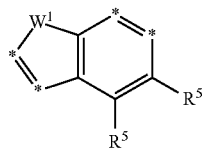
A3o
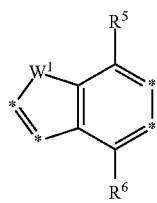
A3p
A3q
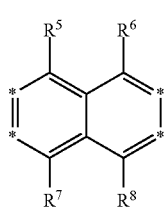
A3r
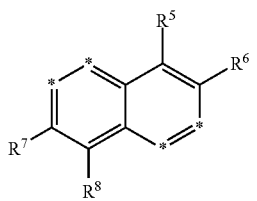
A3s -continued
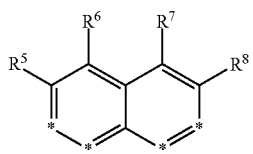
A3t
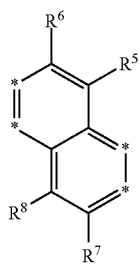
A3u
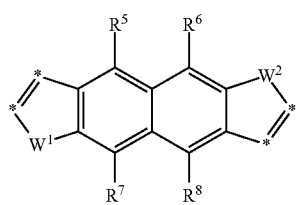
A3v
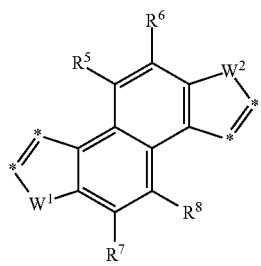
A3w
Ar⁴ a group selected from the following formulae and their mirror images
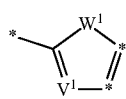
A4a
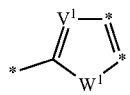
A4b
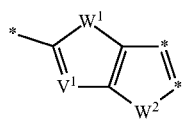
A4c
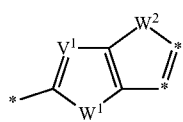
A4d
-continued
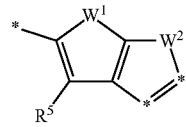
A4e
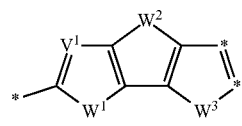
A4f
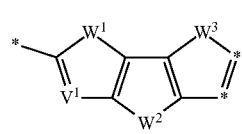
A4g
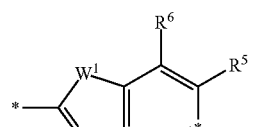
A4h
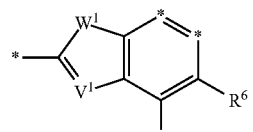
A4i
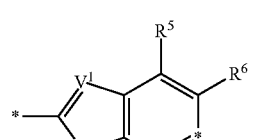
A4j
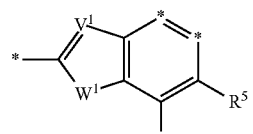
A4k
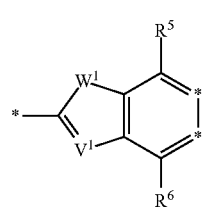
A4l
A4m A4n 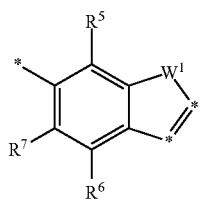
A4o 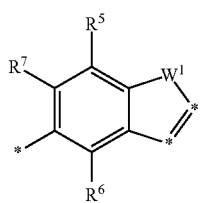
A4p 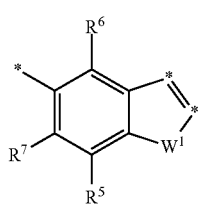
A4q 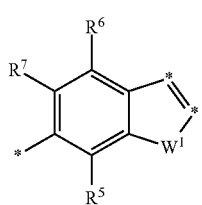
A4r 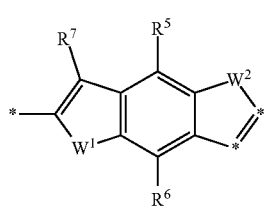
A4s 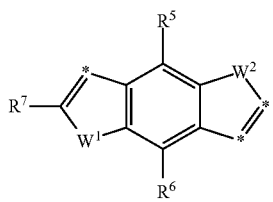
A4t 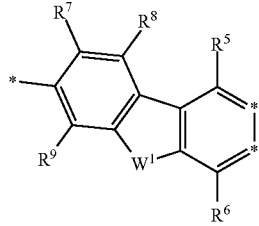
A4u 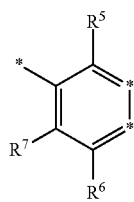
A4v 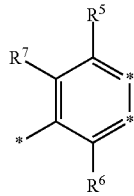
A4w 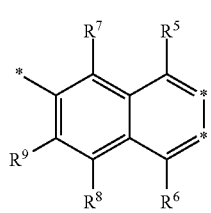
A4x 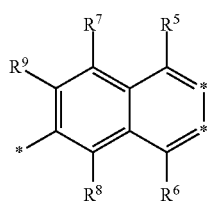
$Ar^5$ a group selected from the following formulae and their mirror images
A5a 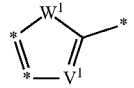
A5b 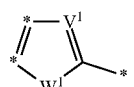
A5c 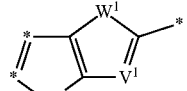
A5d 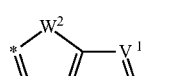
A5e 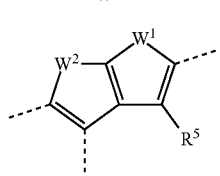

-continued
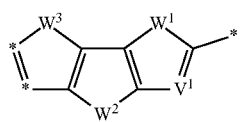
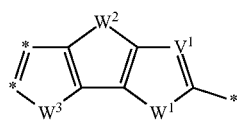
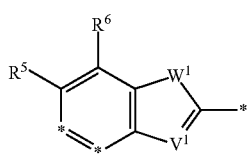
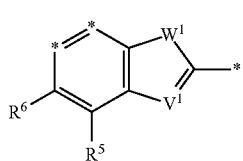
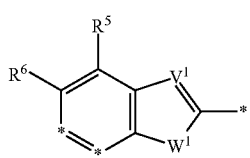
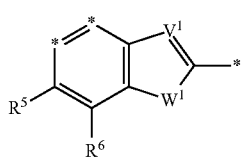
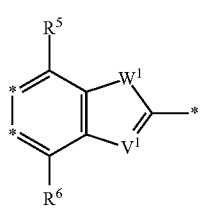
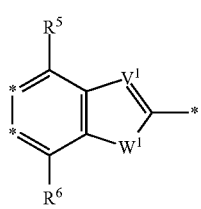
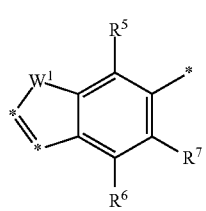
-continued
A5f
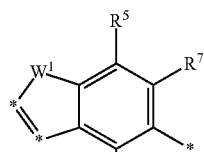
A5g
A5h
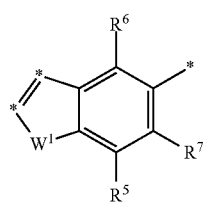
A5i
A5j
A5k
A5l
A5m
A5n
A5o
A5p
A5q
A5r
A5s
A5t
A5u

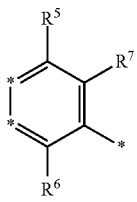

A5v

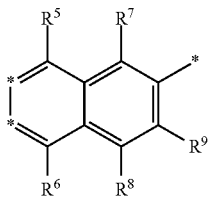

A5w

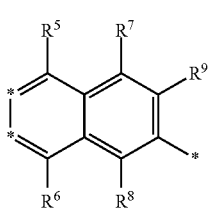

A5x

Ar$^{6,7}$ arylene or heteroarylene that has from 5 to 20 ring atoms, is mono- or polycyclic, optionally contains fused rings, and is unsubstituted or substituted by one or more identical or different groups R$^1$ or L$^S$, or CY$^1$=CY$^2$ or —C≡C—, U$^1$, U$^2$ CR$^1$R$^2$, SiR$^1$R$^2$, GeR$^1$R$^2$, C=CR$^1$R$^2$, NR$^1$ or C=O, preferably CR$^1$R$^2$, V$^1$ CR$^3$ or N, W$^1$, W$^2$, W$^3$ S, O, Se or C=O, preferably S, W$^4$ S, O, Se, C=O or NR$^1$, R$^{1-9}$ H, F, Cl, CN, or straight-chain, branched or cyclic alkyl with 1 to 30, preferably 1 to 20, C atoms, in which one or more CH$_2$ groups are optionally replaced by —O—, —S—, —C(=O)—, —C(=S)—, —C(=O)—O—, —O—C(=O)—, —NR$^o$—, —SiR$^o$R$^{oo}$—, —CF$_2$—, —CR$^o$=CR$^{oo}$—, —CY$^1$=CY$^2$— or —C≡C— in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L$^S$, and the pair of R$^1$ and R$^2$, together with the C, Si or Ge atom to which they are attached, may also form a spiro group with 5 to 20 ring atoms which is mono- or polycyclic, does optionally contain fused rings, and is unsubstituted or substituted by one or more identical or different groups L$^S$, R$^{T1}$, R$^{T2}$ an electron withdrawing group, Y$^1$, Y$^2$ H, F, Cl or CN, L$^S$ F, Cl, —NO$_2$, —CN, —NC, —NCO, —NCS, —OCN, —SCN, R$^o$, OR$^o$, SR$^o$, —C(=O)X$^o$, —C(=O)R$^o$, —C(=O)—OR$^o$, —O—C(=O)—R$^o$, —NH$_2$, —NHR$^o$, —NR$^o$R$^{oo}$, —C(=O)NHR$^o$, —C(=O)NR$^o$R$^{oo}$, —SO$_3$R$^o$, —SO$_2$R$^o$, —OH, —NO$_2$, —CF$_3$, —SF$_5$, or optionally substituted silyl, or carbyl or hydrocarbyl with 1 to 30, preferably 1 to 20 C atoms that is optionally substituted and optionally comprises one or more hetero atoms, preferably F, —CN, R$^o$, —OR$^o$, —SR$^o$, —C(=O)—R$^o$, —C(=O)—OR$^o$, —O—C(=O)—R$^o$, —O—C(=O)—OR$^o$, —C(=O)—NHR$^o$, or —C(=O)—NR$^o$R$^{oo}$, R$^o$, R$^{oo}$ H or straight-chain or branched alkyl with 1 to 20, preferably 1 to 12, C atoms that is optionally fluorinated, X$^o$ halogen, preferably F or Cl, a, b 0 or an integer from 1 to 10, preferably 0, 1, 2, 3, 4 or 5, very preferably 0, 1, 2 or 3, k an integer from 1 to 10, preferably 1, 2, 3, 4, 5, 6 or 7, very preferably 1, 2 or 3, most preferably 1, m 0 or an integer from 1 to 10, preferably 0, 1, 2, 3, 4, 5, 6 or 7, very preferably 0, 1, 2 or 3, wherein at least one of R$^{T1}$ and R$^{T2}$ is an electron withdrawing group of formula TG

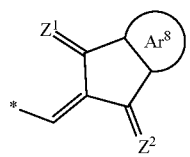

TG

Ar$^8$ bi- or polycyclic arylene or heteroarylene having from 8 to 20 ring atoms which is optionally substituted with one or more groups L, L F, Cl, —NO$_2$, —CN, —NC, —NCO, —NCS, —OCN, —SCN, R$^o$, OR$^o$, SR$^o$, —C(=O)X$^o$, —C(=O)R$^o$, —C(=O)—OR$^o$, —O—C(=O)—R$^o$, —NH$_2$, —NHR$^o$, —NR$^o$R$^{oo}$, —C(=O)NHR$^o$, —C(=O)NR$^o$R$^{oo}$, —SO$_3$R$^o$, —SO$_2$R$^o$, —OH, —NO$_2$, —CF$_3$, —SF$_5$, preferably F, —CN, R$^o$, —OR$^o$, —SR$^o$, —C(=O)—R$^o$, —C(=O)—OR$^o$, —O—C(=O)—R$^o$, —O—C(=O)—OR$^o$, —C(=O)—NHR$^o$, —C(=O)—NR$^o$R$^{oo}$, Z$^1$, Z$^2$ O or C(CN)$_2$ or C(CN)(C(=O)R, preferably one of Z$^1$ and Z$^2$ is O and the other is C(CN)$_2$, and wherein at least one group Ar$^3$ denotes thieno[3,2-b]thiophene and/or at least one of the groups Ar$^4$ and Ar$^5$ denotes thieno[3,2-b]thiophene that is optionally substituted with R$^3$.

The invention further relates to novel synthesis methods for preparing compounds of formula I, and novel intermediates used therein.

The invention further relates to the use of compounds of formula I as semiconductor, preferably as electron acceptor or n-type semiconductor, preferably in a semiconducting material, an electronic or optoelectronic device, or a component of an electronic or optoelectronic device.

The invention further relates to the use of compounds of formula I as dyes or pigments.

The invention further relates to a composition comprising one or more compounds of formula I, and further comprising one or more compounds having one or more of a semiconducting, hole or electron transport, hole or electron blocking, insulating, binding, electrically conducting, photoconducting, photoactive or light emitting property.

The invention further relates to a composition comprising one or more compounds of formula I, and further comprising a binder, preferably an electrically inert binder, very preferably an electrically inert polymeric binder.

The invention further relates to a composition comprising a compound of formula I, and further comprising one or more electron donors or p-type semiconductors, preferably selected from conjugated polymers.

The invention further relates to a composition comprising one or more n-type semiconductors, at least one of which is a compound of formula I, and further comprising one or more p-type semiconductors.

The invention further relates to a composition comprising one or more n-type semiconductors, at least one of which is a compound of formula I, and at least one other of which is a fullerene or fullerene derivative, and further comprising one or more p-type semiconductors, preferably selected from conjugated polymers.

The invention further relates to a bulk heterojunction (BHJ) formed from a composition comprising a compound of formula I as electron acceptor or n-type semiconductor, and one or more compounds which are electron donor or p-type semiconductors, and are preferably selected from conjugated polymers.

The invention further relates to the use of a compound of formula I or a composition as described above and below, as semiconducting, charge transporting, electrically conducting, photoconducting, photoactive or light emitting material.

The invention further relates to the use of a compound of formula I or a composition as described above and below, in an electronic or optoelectronic device, or in a component of such a device or in an assembly comprising such a device.

The invention further relates to a semiconducting, charge transporting, electrically conducting, photoconducting, photoactive or light emitting material, comprising a compound of formula I or a composition as described above and below.

The invention further relates to an electronic or optoelectronic device, or a component thereof, or an assembly comprising it, which comprises a compound of formula I or a composition as described above and below.

The invention further relates to an electronic or optoelectronic device, or a component thereof, or an assembly comprising it, which comprises a semiconducting, charge transporting, electrically conducting, photoconducting or light emitting material as described above and below.

The invention further relates to a formulation comprising one or more compounds of formula I, or comprising a composition or semiconducting material as described above and below, and further comprising one or more solvents, preferably selected from organic solvents.

The invention further relates to the use of a formulation as described above and below for the preparation of an electronic or optoelectronic device or a component thereof.

The invention further relates to an electronic or optoelectronic device or a component thereof, which is obtained through the use of a formulation as described above and below.

The electronic or optoelectronic device includes, without limitation, organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cells (PSC), laser diodes, Schottky diodes, photoconductors, photodetectors, thermoelectric devices.

Preferred devices are OFETs, OTFTs, OPVs, PSCs, OPDs and OLEDs, in particular OPDs and BHJ OPVs or inverted BHJ OPVs.

The component of the electronic or optoelectronic device includes, without limitation, charge injection layers, charge transport layers, interlayers, planarizing layers, antistatic films, polymer electrolyte membranes (PEM), conducting substrates and conducting patterns.

The assembly comprising an electronic or optoelectronic device includes, without limitation, integrated circuits (IC), radio frequency identification (RFID) tags, security markings, security devices, flat panel displays, LC windows, backlights of flat panel displays, electrophotographic devices, electrophotographic recording devices, organic memory devices, sensor devices, biosensors and biochips.

In addition the compounds of formula I and compositions as described above and below can be used as dichroitic dyes, especially in smart windows such as LC windows, as electrode materials in batteries, or in components or devices for detecting and discriminating DNA sequences.

Terms and Definitions

Unless stated otherwise, in the units, polymers and compounds according to the present invention the electron withdrawing groups $R^{T1}$ and $R^{T2}$ are understood to be electron withdrawing relative to the polycyclic core.

As used herein, the terms "indaceno group" and "indaceno-type group" will be understood to mean a group comprising two cyclopentadiene rings, or heterocyclic, vinylidene or ketone derivatives thereof, that are fused to a central aromatic or heteroaromatic aromatic ring Ar, and which can have cis- or trans-configuration, as exemplarily shown below

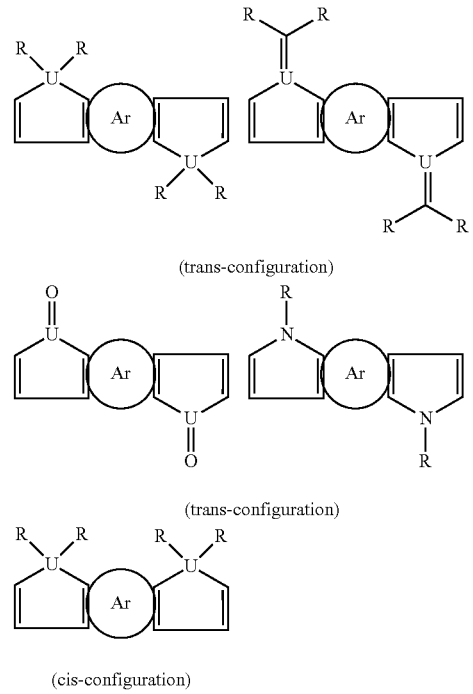

wherein U is e.g. C, Si or Ge and R is a carbyl or hydrocarbyl group.

Unless stated otherwise, in a polymer according to the present invention the units of formula I have electron acceptor property ("acceptor units").

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "donor unit" will be understood to mean a unit, preferably a conjugated arylene or heteroarylene unit, which has an electron donating or electron pushing property towards a neighboured conjugated unit. The term "acceptor unit" will be understood to mean a unit, preferably a conjugated arylene or heteroarylene unit, which has an electron accepting or electron withdrawing property towards a neighboured conjugated unit. The term "spacer unit" will be understood to mean a unit which can be conjugated or non-conjugated and is located between the polycyclic donor core and the terminal group $R^{T1}$ or $R^{T2}$.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "conjugated" will be understood to mean a compound (for example a polymer) that contains mainly C atoms with $sp^2$-hybridization (or optionally also sp-hybridization), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the term "polymer" will be understood to mean a molecule of high relative molecular mass, the structure of which essentially comprises multiple repetitions of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5, very preferably ≥10, repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit an asterisk (*) will be understood to mean a chemical linkage, usually a single bond, to an adjacent unit or to a terminal group in the polymer backbone. In a ring, like for example a benzene or thiophene ring, an asterisk (*) will be understood to mean a C atom that is fused to an adjacent ring.

As used herein, in a formula showing a ring, a polymer or a repeat unit a dashed line (------) will be understood to mean a single bond.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerization reaction, like for example a group having the meaning of $R^{31}$ or $R^{32}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerization reaction. Alternatively the endcapper can be added in situ to the reaction mixture before or during the polymerization reaction. In situ addition of an endcapper can also be used to terminate the polymerization reaction and thus control the molecular weight of the forming polymer. Typical endcap groups are for example H, phenyl and lower alkyl.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, chlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, Sn, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has up to 40, preferably up to 25, very preferably up to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 1 to 40, preferably 6 to 40 C atoms, wherein each of these groups optionally contains one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are each optionally replaced by a hetero atom, preferably selected from N, O, P, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups $L^S$.

$L^S$ is selected from F, Cl, —CN, —NO$_2$, —NC, —NCO, —NCS, —OCN, —SCN, —R°, —OR°, —SR°, —C(=O)X°, —C(=O)R°, —C(=O)—OR°, —O—C(=O)—R°, —NH$_2$, —NHR°, —NR°R°°, —C(=O)NHR°, —C(=O)NR°R°°, —SO$_3$R°, —SO$_2$R°, —OH, —CF$_3$, —SF$_5$, or optionally substituted silyl, or carbyl or hydrocarbyl with 1 to 30, preferably 1 to 20 C atoms that is optionally substituted and optionally comprises one or more hetero atoms, wherein X° is halogen, preferably F or Cl, and R°, R°° each independently denote H or straight-chain or branched alkyl with 1 to 20, preferably 1 to 12 C atoms that is optionally fluorinated.

Preferably $L^S$ is selected from F, —CN, R°, —OR°, —SR°, —C(=O)—R°, —C(=O)—OR°, —O—C(=O)—R°, —O—C(=O)—OR°, —C(=O)—NHR° and —C(=O)—NR°R°°.

Further preferably $L^S$ is selected from F or alkyl, alkoxy, oxaalkyl, thioalkyl, fluoroalkyl, fluoroalkoxy, alkylcarbonyl, alkoxycarbonyl, with 1 to 16 C atoms, or alkenyl or alkynyl with 2 to 16 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30, very preferably 5 to 20, ring C atoms, is mono- or polycyclic and may also contain fused rings, preferably contains 1, 2, 3 or 4 fused or unfused rings, and is optionally substituted with one or more groups $L^S$ as defined above.

A heteroaryl group as referred to above and below preferably has 4 to 30, very preferably 5 to 20, ring C atoms, wherein one or more of the ring C atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups $L^S$ as defined above.

An arylalkyl or heteroarylalkyl group as referred to above and below preferably denotes —(CH$_2$)$_a$-aryl or —(CH$_2$)$_a$-heteroaryl, wherein a is an integer from 1 to 6, preferably 1, and "aryl" and "heteroaryl" have the meanings given above and below. A preferred arylalkyl group is benzyl which is optionally substituted by $L^S$.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may each be replaced by N, naphthalene, thiophene, selenophene, thienothiophene, dithienothiophene, fluorene and oxazole, all of which can be unsubstituted, mono- or polysubstituted with $L^S$ as defined above. Very preferred aryl and heteroaryl groups are selected from phenyl, pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, 2,5-dithiophene-2',5'-diyl, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with $L^S$ as defined above. Further examples of aryl and heteroaryl groups are those selected from the groups shown hereinafter.

An alkyl group or an alkoxy group, i.e., where the terminal $CH_2$ group is replaced by —O—, can be straight-chain or branched. Particularly preferred straight-chains have 2, 3, 4, 5, 6, 7, 8, 12 or 16 carbon atoms and accordingly denote preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are each replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, can be straight-chain. Particularly preferred straight-chains are 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly, it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl or 5,5-bis-(ethoxycarbonyl)-hexyl.

A thioalkyl group, i.e., where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridized vinyl carbon atom is replaced.

A fluoroalkyl group can be perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 3,7-dimethyloctyl, 3,7,11-trimethyldodecyl, 2-propylpentyl, in particular 2-methylbutyl, 2-methylbutoxy, 2-methylpentoxy, 3-methyl-pentoxy, 2-ethyl-hexoxy, 2-butyloctoxyo, 2-hexyldecoxy, 2-octyldodecoxy, 3,7-dimethyloctoxy, 3,7,11-trimethyldodecoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methyl-heptyloxy-carbonyl, 2-methylbutyryloxy, 3-methylvaleroyloxy, 4-methylhexanoyloxy, 2-chloro-propionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl and 2-fluoromethyloctyloxy for example. Very preferred are 2-methylbutyl, 2-ethylhexyl, 2-butyloctyl, 2-hexyldecyl, 2-octyldodecyl, 3,7-dimethyloctyl, 3,7,11-trimethyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the substituents on an aryl or heteroaryl ring are independently of each other selected from primary, secondary or tertiary alkyl, alkoxy, oxaalkyl, thioalkyl, alkylcarbonyl or alkoxycarbonyl with 1 to 30 C atoms, wherein one or more H atoms are each optionally replaced by F, or aryl, aryloxy, heteroaryl or heteroaryloxy that is optionally alkylated, alkoxylated, alkylthiolated or esterified and has 4 to 30, preferably 5 to 20, ring atoms. Further preferred substituents are selected from the group consisting of the following formulae

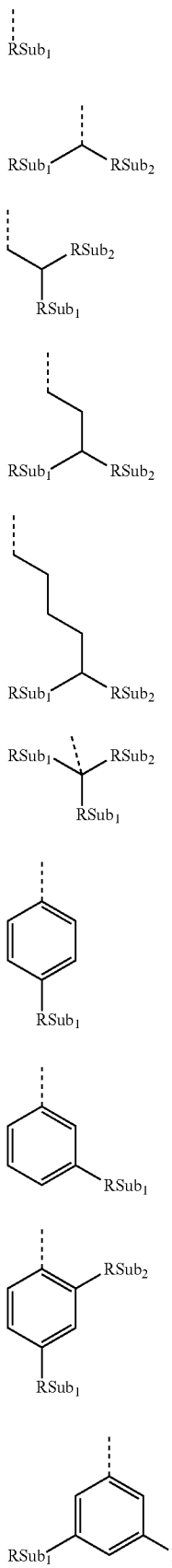
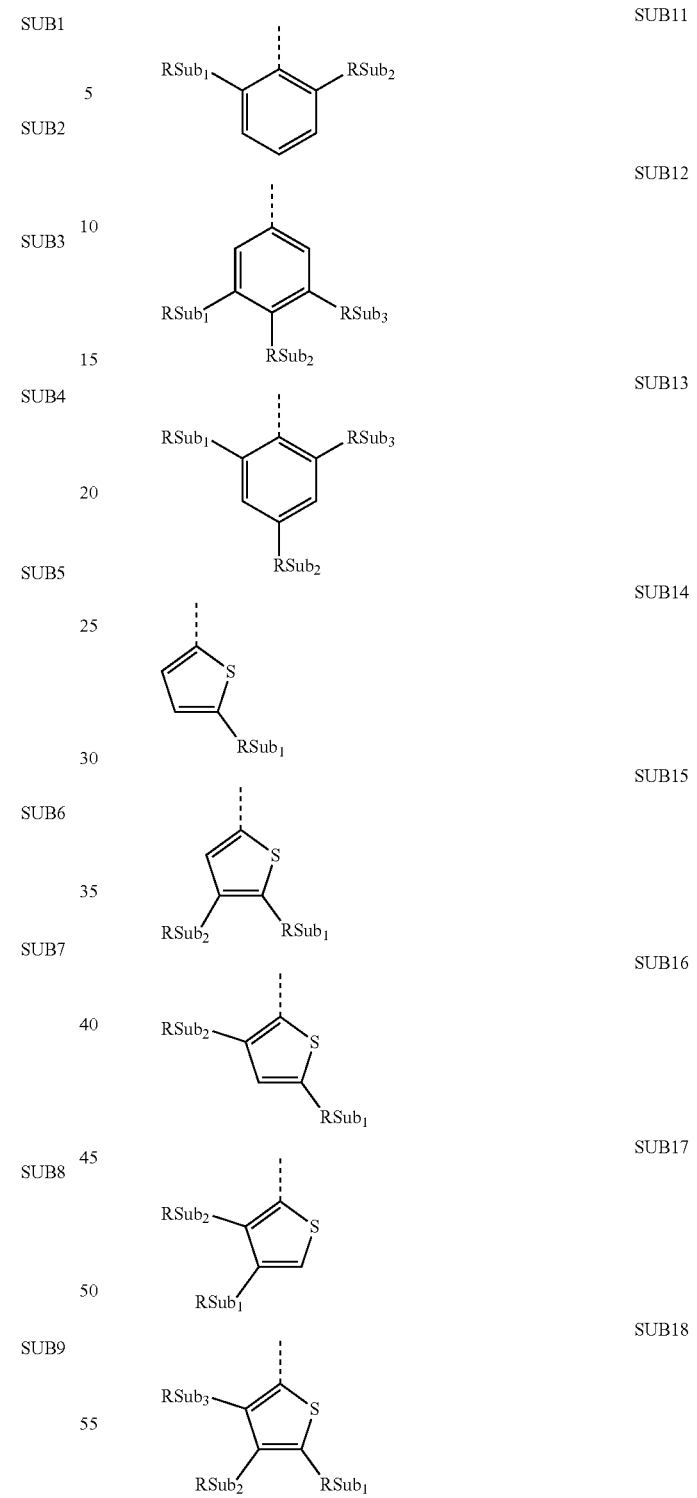

wherein RSub$_{1-3}$ each denote L$^S$ as defined above and below and where at least, preferably all, of RSub$_{1-3}$ is alkyl, alkoxy, oxaalkyl, thioalkyl, alkyl-carbonyl or alkoxycarbonyl with up to 24 C atoms, preferably up to 20 C atoms, that is optionally fluorinated, and wherein the dashed line denotes the link to the ring to which these groups are attached. Very preferred among these substituents are those wherein all RSub$_{1-3}$ subgroups are identical.

As used herein, if an aryl(oxy) or heteroaryl(oxy) group is "alkylated or alkoxylated", this means that it is substituted with one or more alkyl or alkoxy groups having from 1 to 24 C-atoms and being straight-chain or branched and wherein one or more H atoms are each optionally substituted by an F atom.

Above and below, $Y^1$ and $Y^2$ are independently of each other H, F, Cl or CN.

As used herein, —CO—, —C(═O)— and —C(O)— will be understood to mean a carbonyl group, i.e. a group having the structure

As used herein, C═$CR^1R^2$ will be understood to mean a group having the structure

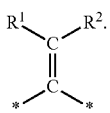

As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer or an intermediate is preferably Br or I.

Above and below, the term "mirror image" means a moiety that can be obtained from another moiety by flipping it vertically or horizontally across an external symmetry plane or a symmetry plane extending through the moiety. For example the moiety

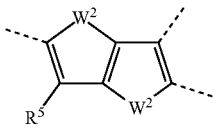

also includes the mirror images

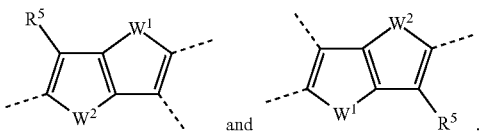

DETAILED DESCRIPTION

The compounds of the present invention are easy to synthesize and exhibit advantageous properties. They show good processability for the device manufacture process, high solubility in organic solvents, and are especially suitable for large scale production using solution processing methods.

The compounds of formula I are especially suitable as (electron) acceptor or n-type semiconductor, and for the preparation of blends of n-type and p-type semiconductors which are suitable for use in OPD or BHJ OPV devices.

The compounds of formula I are further suitable to replace the fullerene compounds that have hitherto been used as n-type semiconductor in OPV or OPD devices.

Besides, the compounds of formula I show the following advantageous properties:

1) Introduction of an extended pi-conjugated terminal group(s) influences electronic and optical properties of the compounds thus enable higher short circuit current (Jsc)

2) Introduction of an extended pi-conjugated terminal group(s) influences solubility, thus processability of the material which is especially important for large scale manufacturing 3) Introduction of an extended pi-conjugated terminal groups influences intra- and inter-molecular packing enabling improved morphology thus higher performance.

4) When using the compounds as n-type OSC in a composition with a p-type OSC in the photoactive layer of an OPV or OPD, additional fine-tuning of the HOMO and LUMO levels of the polycyclic unit in formula I, for example through substitution and/or careful selection of the groups $R^{T1}$ and $R^{T2}$, can reduce the energy loss in the electron transfer process between the n-type acceptor and the p-type donor material in the photoactive layer.

5) Further optimization of the HOMO and LUMO levels of the polycyclic unit in formula I through substitution and/or careful selection of the groups $R^{T1}$ and $R^{T2}$ units can increase the open circuit potential ($V_{oc}$).

The synthesis of the compounds of formula I can be achieved based on methods that are known to the skilled person and described in the literature, as will be further illustrated herein.

Preferred groups $Ar^1$ and $Ar^2$ in formula I are on each occurrence identically or differently selected from the following formulae and their mirror images

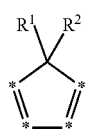
A1a

A2a

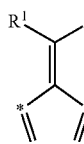
A1b

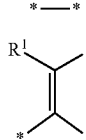
A2b

Especially preferred groups $Ar^1$ and $Ar^2$ are selected from formulae A1a and A2a.

In the compounds of formula I the groups $Ar^1$ and $Ar^2$ can be selected such that the indaceno-type groups have trans- or cis-configuration.

A first preferred embodiment of the present invention relates to compounds of formula I wherein m>0 and all indaceno-type groups have trans-configuration, i.e. one of the two groups $Ar^1$ and $Ar^2$ that are fused to the same group $Ar^3$ is of formula A1 and the other is of formula A2, as exemplarily illustrated below.

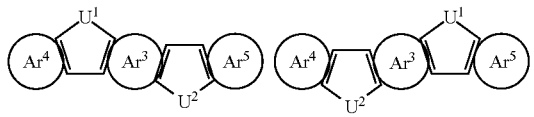

trans-configuration.

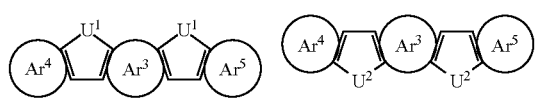

cis-configuration

Preferred compounds units of formula I according to this first preferred embodiment are selected from the following subformulae This second preferred embodiment includes compounds of formula I having an "all-cis" configuration as exemplarily shown in formula I3 and I4 below, and compounds of

I1

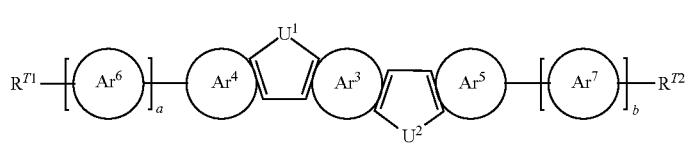

I2

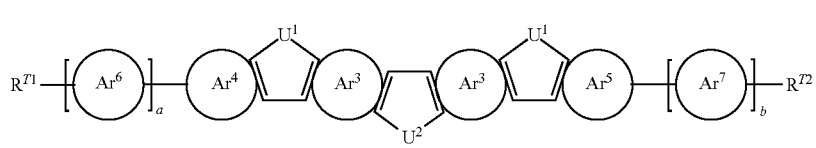

wherein $U^1$, $U^2$, $Ar^3$, $Ar^4$, $Ar^5$, $Ar^6$, $Ar^7$, $R^{T1}$, $R^{T2}$, a and b, independently of each other and on each occurrence identically or differently, have the meanings given in formula I or one of the preferred meanings given above and below.

formula I including both trans-configuration and cis-configuration, as exemplarily shown in formula I5 below.

Preferred compounds of formula I according to this second preferred embodiment are selected from the following subformulae

I3

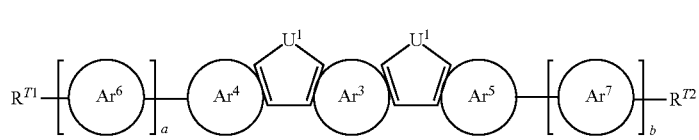

I4

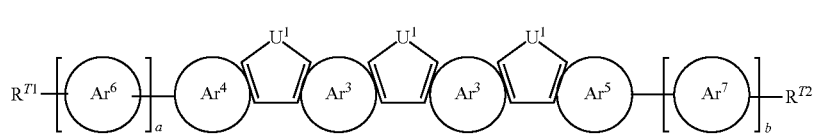

I5

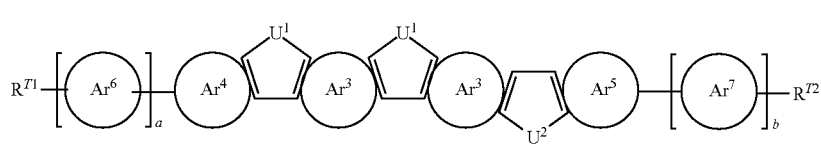

Preferred compounds of formula I1 and I2 are those wherein all of the groups $U^1$ and $U^2$ denote $CR^1CR^2$.

wherein $U^1$, $U^2$, $Ar^3$, $Ar^4$, $Ar^5$, $Ar^6$, $Ar^7$, $R^{T1}$, $R^{T2}$, a and b, independently of each other and on each occurrence identically or differently, have the meanings given in formula I or one of the preferred meanings given above and below.

A second preferred embodiment of the present invention relates to compounds of formula I wherein m>0 and at least one, preferably all, indaceno-type groups have cis-configuration, i.e. the groups $Ar^1$ and $Ar^2$ that are fused to the same group $Ar^3$ are both of formula A1 or both of formula A2, as exemplarily illustrated below.

Preferred repeating units of formula I3, I4 and I5 are those wherein all groups $U^1$ and $U^2$ denote $CR^1CR^2$.

A third preferred embodiment of the present invention relates to compounds of formula I wherein m=0. Preferred compounds of formula I according to this third preferred embodiment are selected from the following subformulae

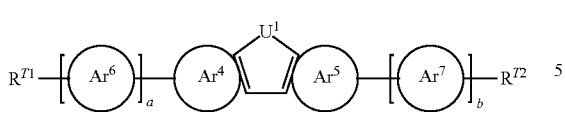      I6 wherein $U^1$, $U^2$, $Ar^3$, $Ar^4$, $Ar^5$, $Ar^6$, $Ar^7$, $R^{T1}$, $R^{T2}$, a and b, independently of each other and on each occurrence identically or differently, have the meanings given in formula I or one of the preferred meanings given above and below.

In the compounds of formula I at least one of $Ar^1$ denotes

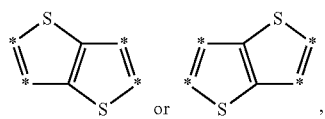

and/or
$Ar^2$ denotes

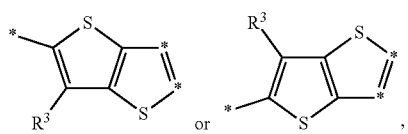

and/or
$Ar^3$ denotes

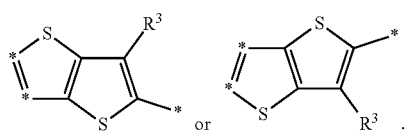

Very preferred compounds of formula I are those wherein at least one of
$Ar^1$ denotes

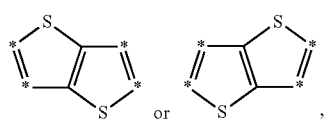

Preferred groups $Ar^3$ in formula I and I1-I5 and their subformulae are on each occurrence identically or differently selected from the following formulae and their mirror images

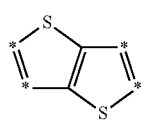      A3a1

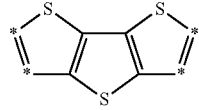      A3b1

      A3c1

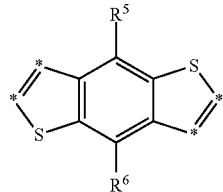      A3d1

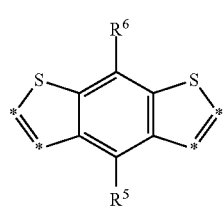      A3e1

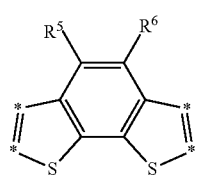      A3f1

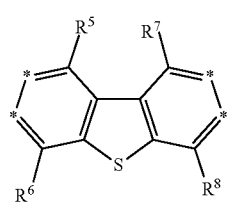      A3g1

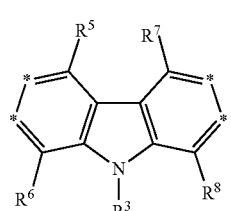      A3g2

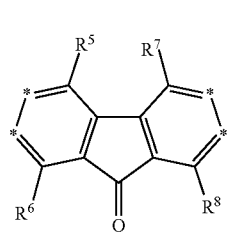      A3g3

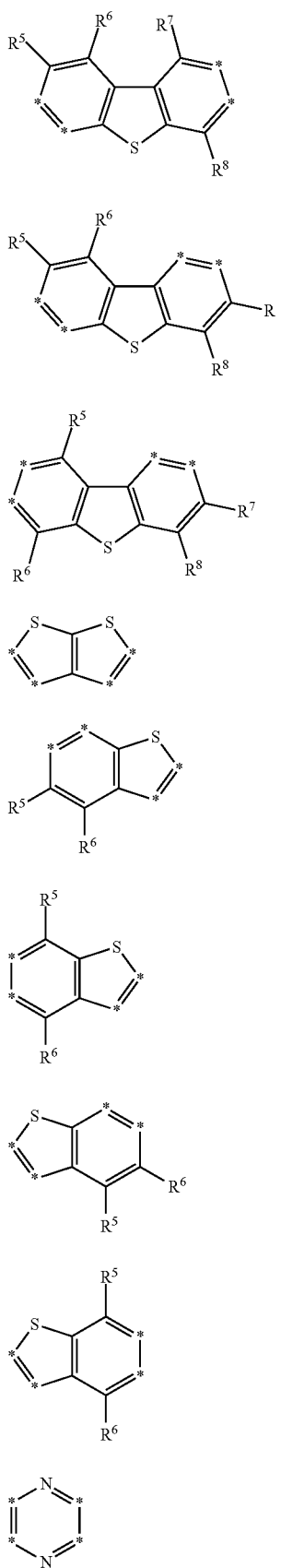
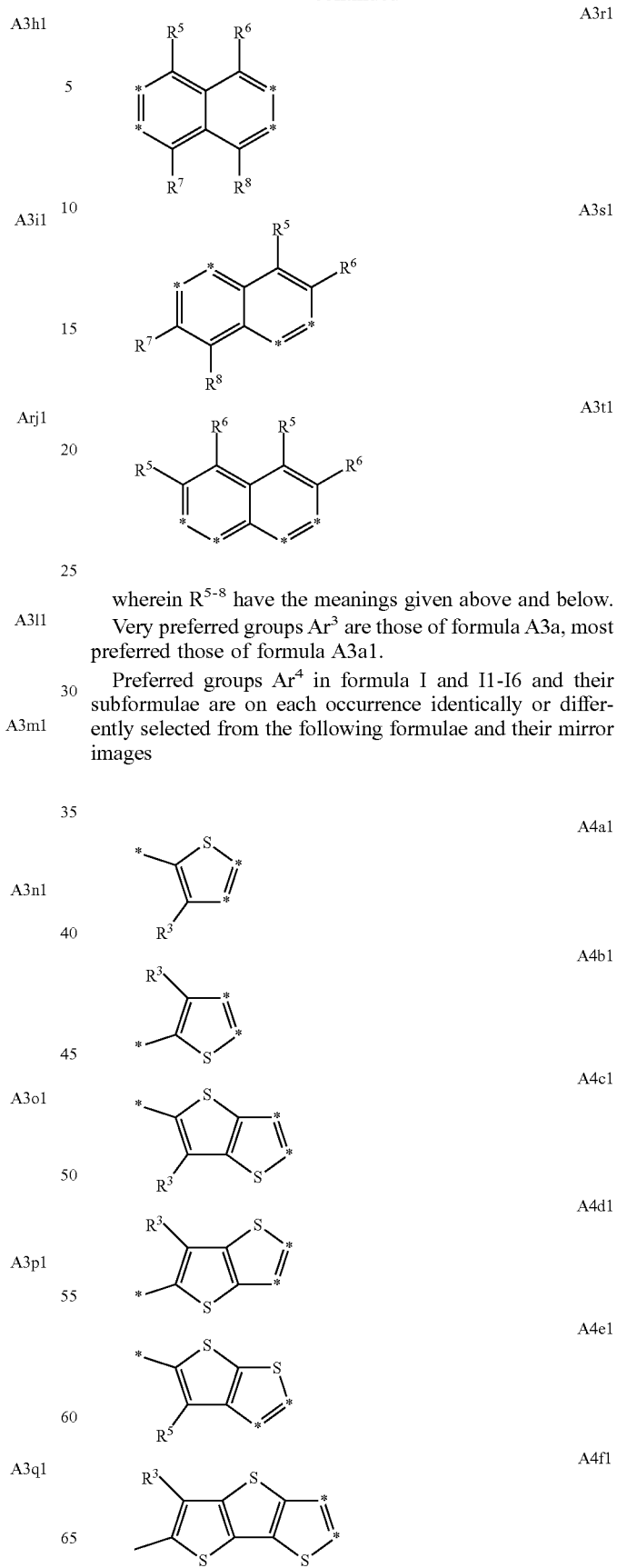
wherein R⁵⁻⁸ have the meanings given above and below.
Very preferred groups Ar³ are those of formula A3a, most preferred those of formula A3a1.
Preferred groups Ar⁴ in formula I and I1-I6 and their subformulae are on each occurrence identically or differently selected from the following formulae and their mirror images

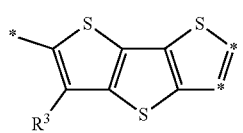
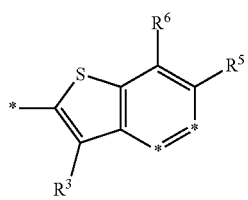
A4h1
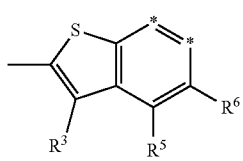
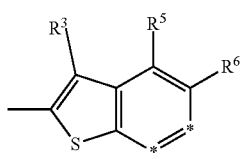
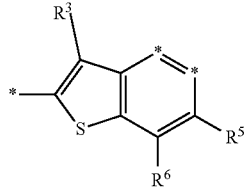
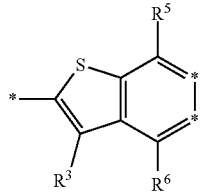
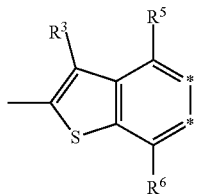
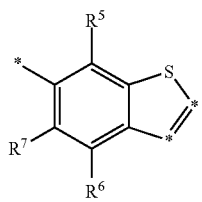
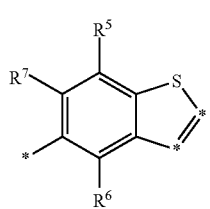
A4g1
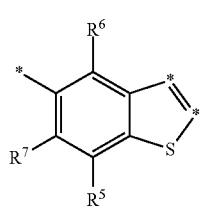
A4i1
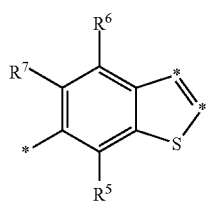
A4j1
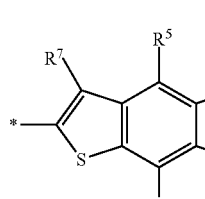
A4k1
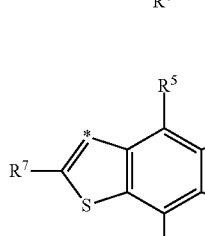
A4l1
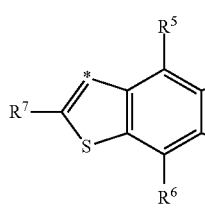
A4m1
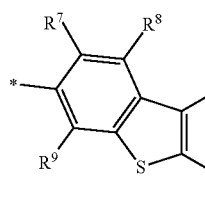
A4n1
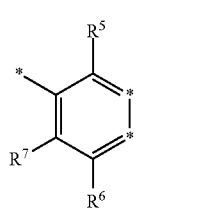
A4o1
A4p1
A4q1
A4r1
A4s1
A4t1
A4u1

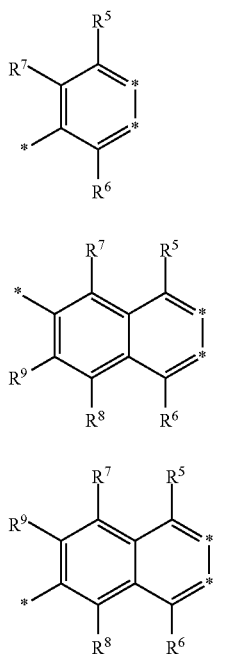
A4v1
A4w1
A4x1
wherein R³⁻⁹ have the meanings given above and below.
Very preferred groups Ar⁴ are those of formula A4a1, A4b1, A4c1, A4d1, A4u1, A4v1.
Preferred groups Ar⁵ in formula I and I1-I6 and their subformulae are on each occurrence identically or differently selected from the following formulae and their mirror images
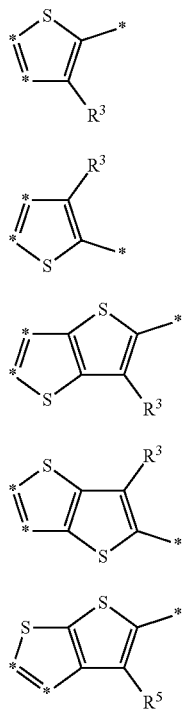
A5a1
A5b1
A5c1
A5d1
A5e1
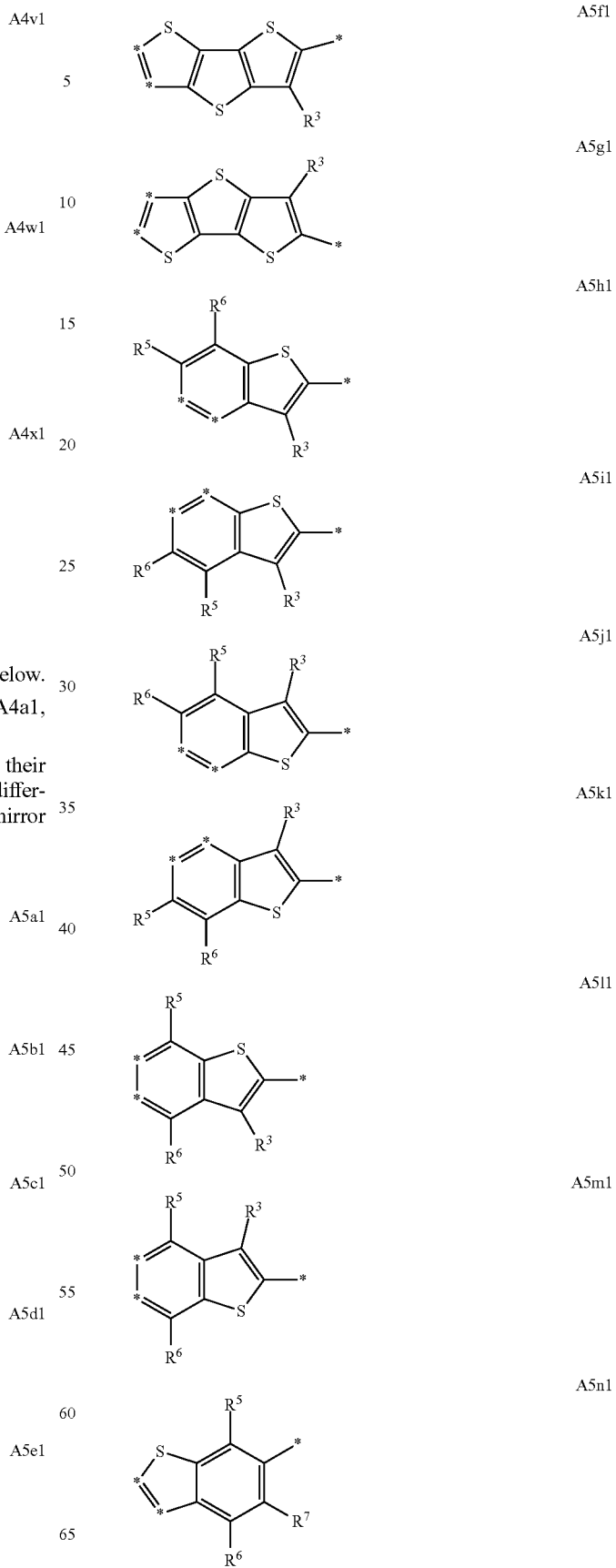
A5f1
A5g1
A5h1
A5i1
A5j1
A5k1
A5l1
A5m1
A5n1

A5o1

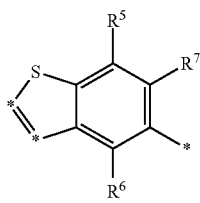

A5p1

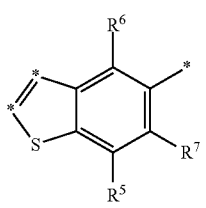

A5q1

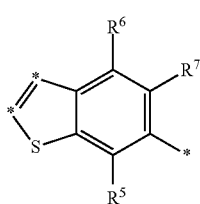

A5r1

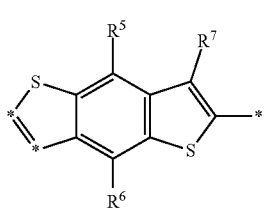

A5s1

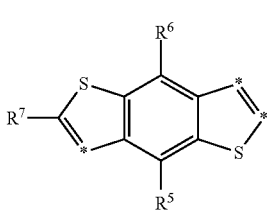

A5t1

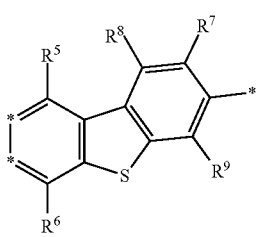

A5u1

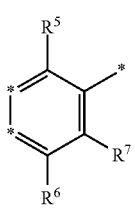

A5v1

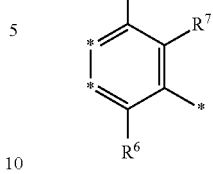

A5w1

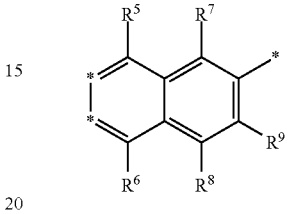

A5x1

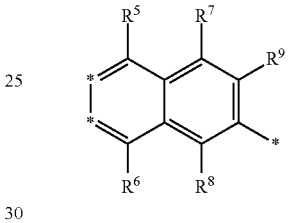

wherein $R^{3-9}$ have the meanings given above and below.

Very preferred groups $Ar^5$ are those of formula A5a1, A5b1, A5c1, A5d1, A5u1, A5v1.

Preferred groups $Ar^6$ and $Ar^7$ in formula I and I1-I6 and their subformulae are each independently and on each occurrence identically or differently selected from arylene or heteroarylene which has from 5 to 20 ring atoms, which is mono- or polycyclic, which optionally contains fused rings, and which is unsubstituted or substituted by one or more identical or different groups $L^S$, or from —$CY^1$=$CY^2$—.

Very preferred groups $Ar^6$ and $Ar^7$ in formula I and I1-I6 and their subformulae are each independently and on each occurrence identically or differently selected from the following formulae and their mirror images:

AR1

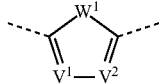

AR2

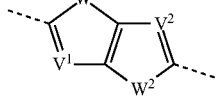

AR3

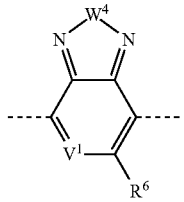

AR4

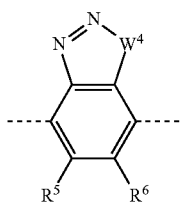

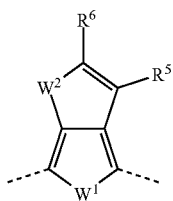

AR5

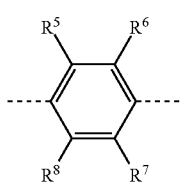

AR6

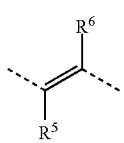

AR7 wherein, independently of each other and on each occurrence identically or differently, $V^2$ is $CR^4$ or N, $R^4$ has one of the meanings given for $R^3$, and $V^1$, $W^1$, $W^2$, $W^4$, $R^{5-9}$ are as defined above and below.

More preferred groups $Ar^6$ and $Ar^7$ in formula I and I1-I6 and their subformulae are each independently, and on each occurrence identically or differently, selected from the following formulae and their mirror images

AR1-1

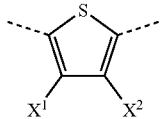

AR1-2

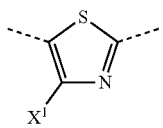

AR1-3

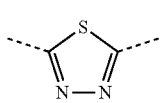

AR2-1

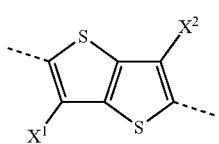

AR2-2

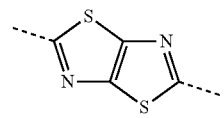

AR3-1

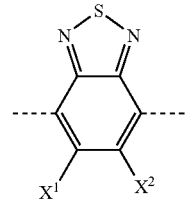

AR3-2

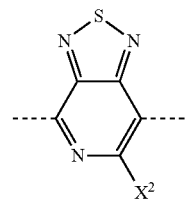

AR3-3

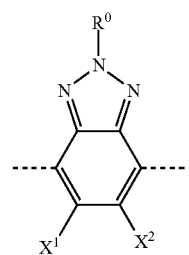

AR4-1

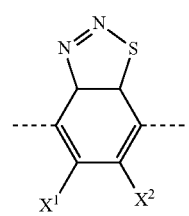

AR5-1

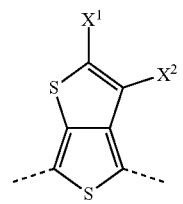

AR6-1

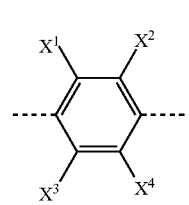

AR7-1

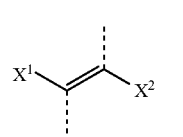

wherein $X^1$, $X^2$, $X^3$ and $X^4$ have one of the meanings given for $R^1$ above and below, and preferably denote H, F, Cl, —CN, $R^0$, $OR^0$ or $C(=O)OR^0$, and $R^0$ is as defined above and below.

Preferred formulae AR1-1 to AR6-1 are those containing at least one, preferably one, two or four substituents $X^{1-4}$ selected from F and Cl, very preferably F.

In formula AR6-1 preferably one or two, very preferably all of $X^{1-4}$ are F.

Preferred groups $Ar^6$ and $Ar^7$ are selected from formulae AR1, AR2, AR3, AR5 and AR7. Very preferred groups $Ar^6$ and $Ar^7$ are selected from formulae AR1-1, AR1-2, AR2-1, AR3-1, AR3-2, AR5-1 and AR7-1, most preferably from formulae AR1-1, AR1-2, AR2-1, AR2-2, AR3-1 and AR7-1.

In formula I and I1-I6 and their subformulae, preferably both $R^{T1}$ and $R^{T2}$ are electron withdrawing groups, at least one of which is selected of formula TG.

In a preferred embodiment of the present invention both $R^{T1}$ and $R^{T2}$ are selected from formula TG or its preferred subformulae as described above and below.

In another preferred embodiment of the present invention one of $R^{T1}$ and $R^{T2}$ is selected from formula TG and the other is an electron withdrawing group which is different from formula TG.

In formula TG $Ar^8$ is preferably bi- or polycyclic arylene or heteroarylene that consists of 2, 3 or 4 fused rings selected from benzene, thiohene and pyrazine, each of which is optionally substituted by one or more groups L as defined above.

Preferably group $Ar^8$ in formula TG is on each occurrence identically or differently selected from the following formulae and their mirror images

A8-1

A8-2

A8-3

A8-4

A8-5

A8-6

-continued

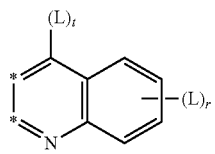
A8-7

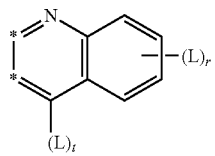
A8-8

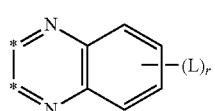
A8-9

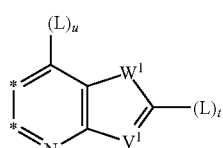
A8-10

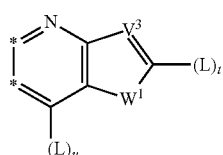
A8-11

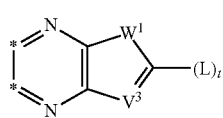
A8-12

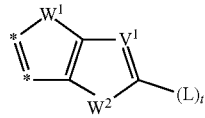
A8-13

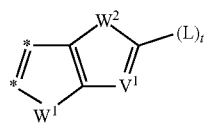
A8-14

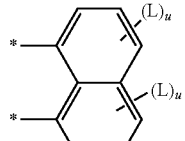
A8-15

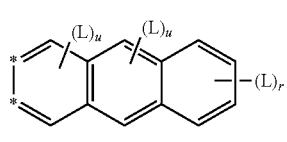
A8-16

A8-17

-continued

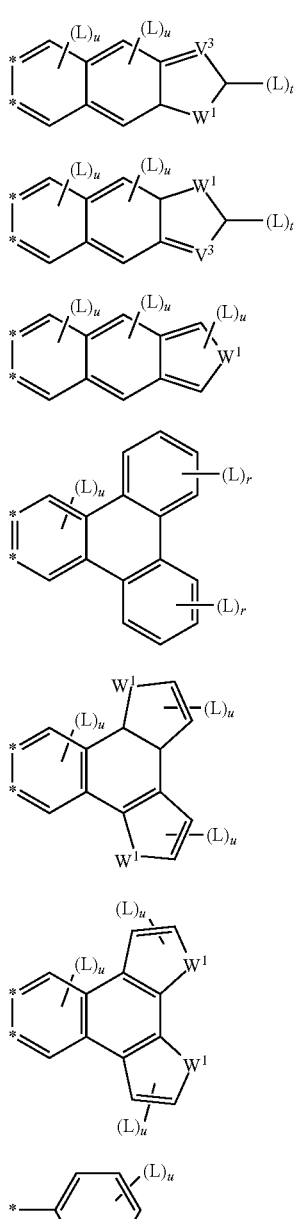

wherein, independently of each other and on each occurrence identically or differently, $W^1$ and L have the meanings given above and below, $V^3$ is N or $C(L)_r$, r is 0, 1, 2, 3 or 4, u is 0, 1 or 2, and t is 0 or 1.

Very preferably in formulae A8-1 to A8-23 $V^1$ is $C(L)_t$ and $W^1$ is S.

Very preferred groups $Ar^8$ are selected from formulae A8-1, A8-2, A8-3, A8-4, A8-5 and A8-6.

Very preferred groups $Ar^8$ are selected from formulae the following subformulae

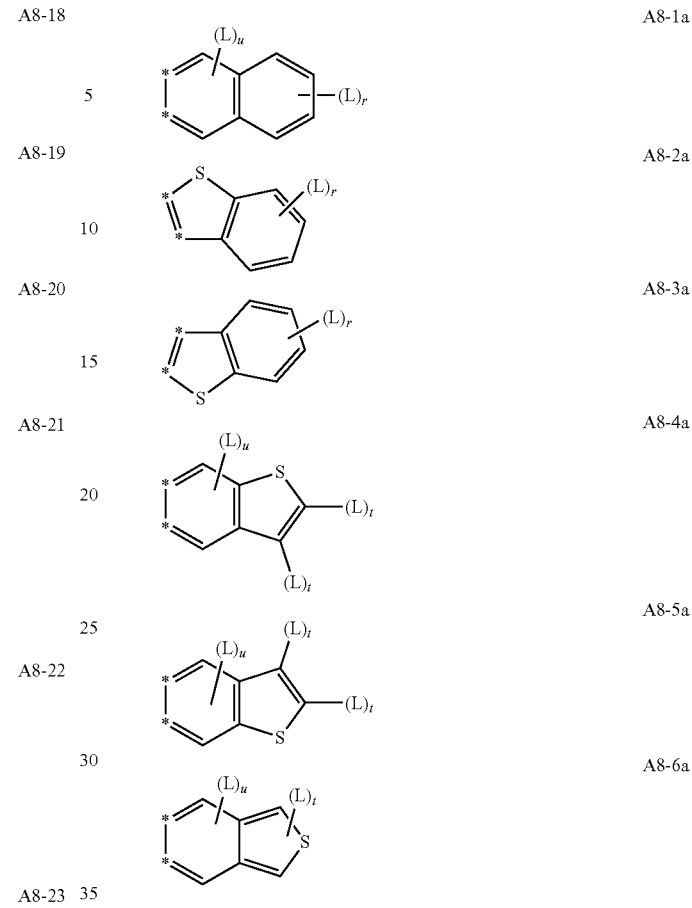

wherein L, r, t and u, independently of each other and on each occurrence identically or differently, have the meanings given above.

In formula TG preferably one of $Z^1$ and $Z^2$ is O and the other is $C(CN)_2$.

Preferred groups $R^{T1}$ and $R^{T2}$ in formula I are selected from the following subformulae

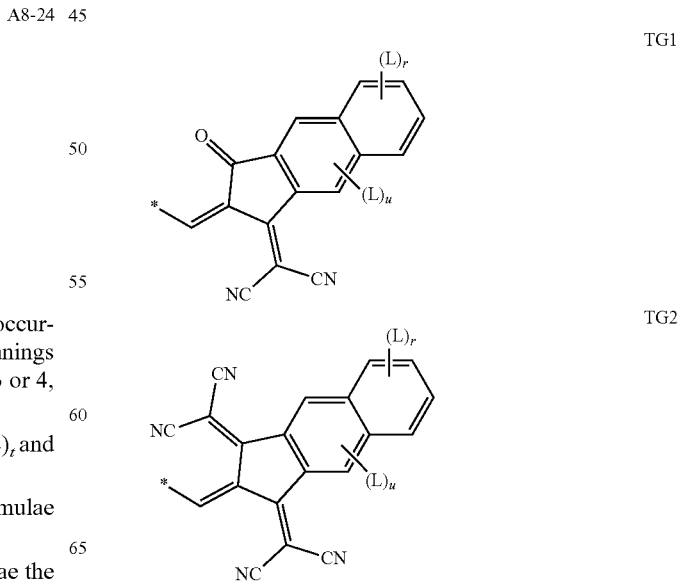

TG3 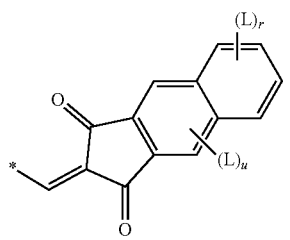
TG4 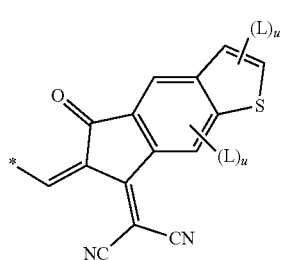
TG5 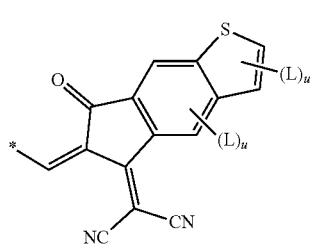
TG6 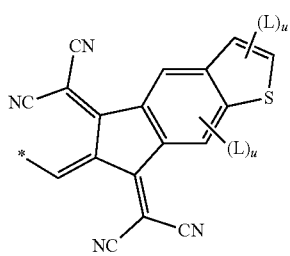
TG7 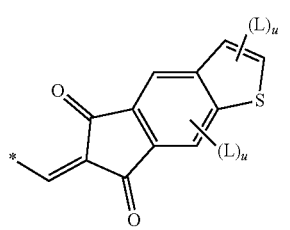
TG8 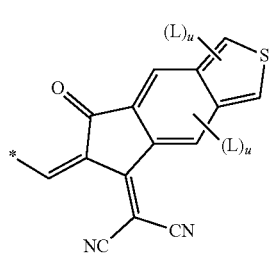
TG9 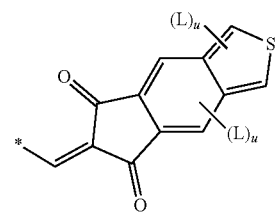
TG10 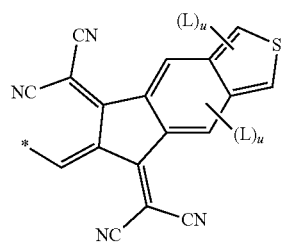
TG11 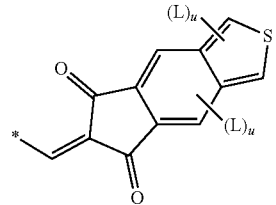
TG12 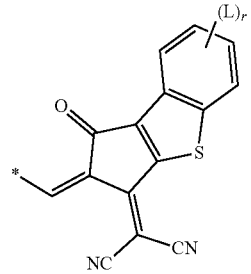
TG13 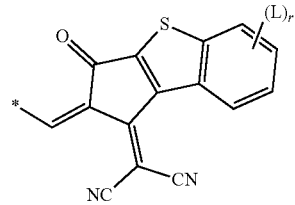
TG14 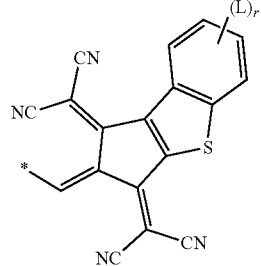

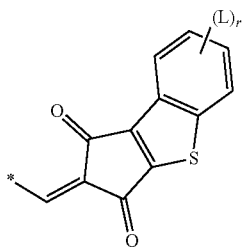

TG15 wherein L, u and r have the meanings given above.

Very preferably $R^{T1}$ and $R^{T2}$ are selected from formulae TG1, TG4, TG5, TG8, TG9, TG12 and TG13, most preferably from formula TG1.

In another preferred embodiment of the present invention one of $R^{T1}$ and $R^{T2}$ is selected from formula TG, preferably wherein $Ar^8$, $Z^1$ and $Z^2$ have one of the preferred meanings described above, preferably selected from formulae TG1-TG15, more preferably selected from formulae TG1, TG4, TG5, TG8, TG9, TG12 and TG13, most preferably from formula TG1, and the other of $R^{T1}$ and $R^{T2}$ is an electron withdrawing group which is different from formula TG.

In this preferred embodiment, the group $R^{T1}$ or $R^{T2}$ which is different from formula TG is preferably selected from the group consisting of F, Cl, Br, —NO$_2$, —CN, —CF$_3$, —CF$_2$—R*, —SO$_2$—R*, —SO$_3$—R*, —C(=O)—H, —C(=O)—R*, —C(=S)—R*, —C(=O)—CF$_2$—R*, —C(=O)—OR*, —C(=S)—OR*, —O—C(=O)—R*, —O—C(=S)—R*, —C(=O)—SR*, —S—C(=O)—R*, —C(=O)NR*R**, —NR*—C(=O)—R*, —NHR*, —NR*R**, —CR*=CR*R**, —C≡C—R*, —C≡C—SiR*RR*, —SiR*RR*, —CH=CH(CN), —CH=C(CN)$_2$, —C(CN)=C(CN)$_2$, —CH=C(CN)(R$^a$), CH=C(CN)—C(=O)—OR*, —CH=C(CO—OR*)$_2$, —CH=C(CO—NR*R**)$_2$, and the group consisting of the following formulae

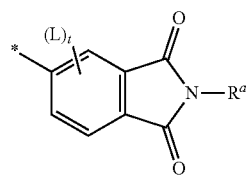

T1

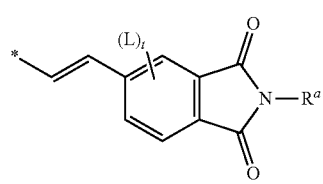

T2

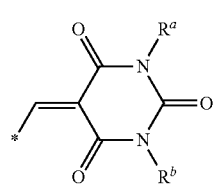

T3

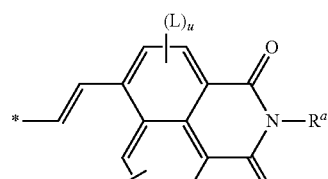

T4

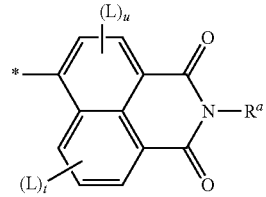

T5

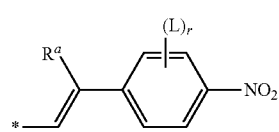

T6

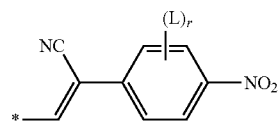

T7

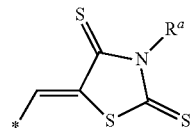

T8

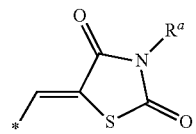

T9

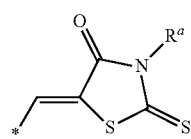

T10

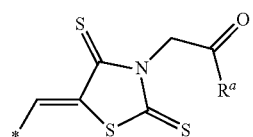

T11

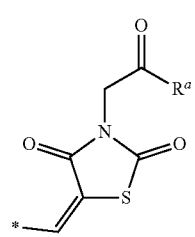

T12

-continued
T13 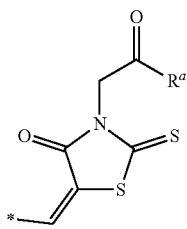
T14 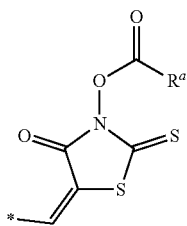
T15 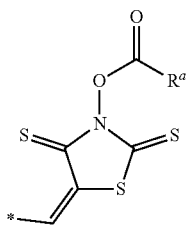
T16 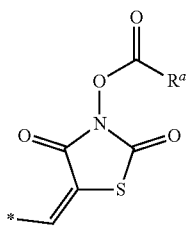
T17 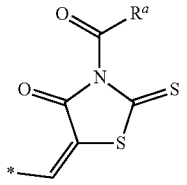
T18 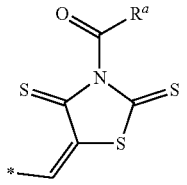
T19 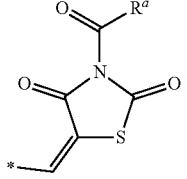
-continued
T20 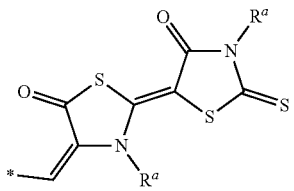
T21 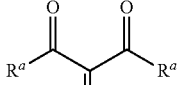
T22 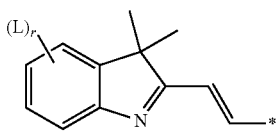
T23 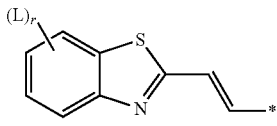
T24 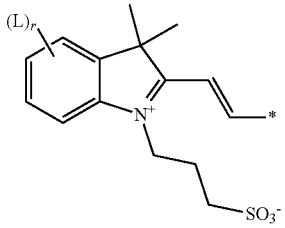
T25 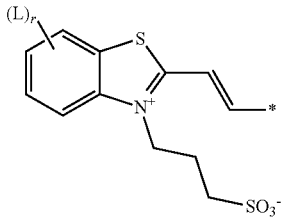
T26 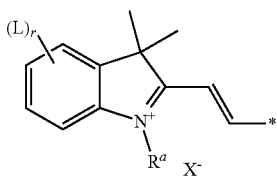
T27 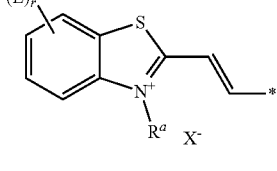
T28 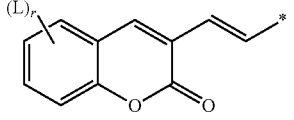

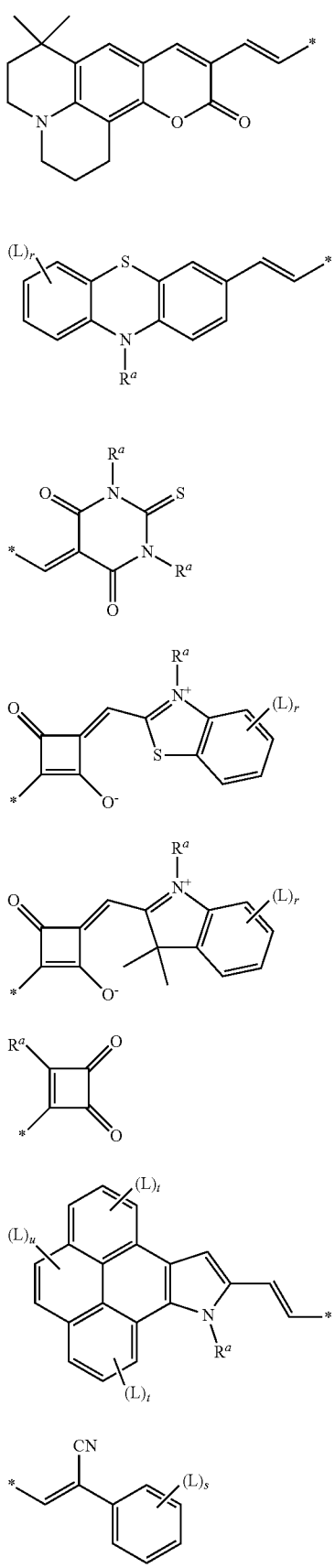

-continued
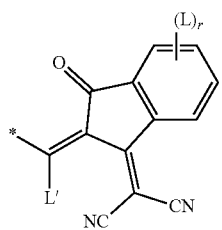
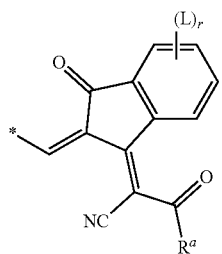
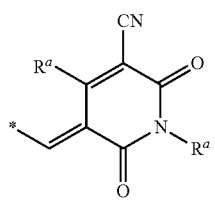
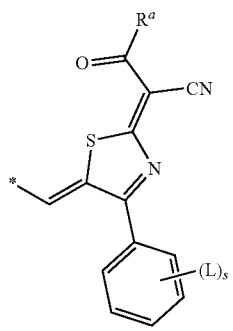
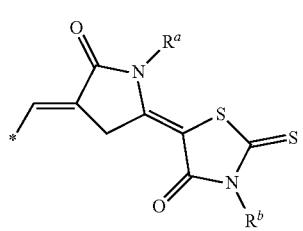
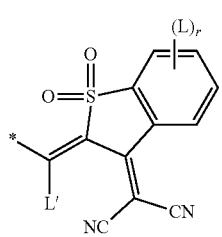
-continued
T47
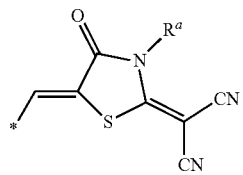
T48
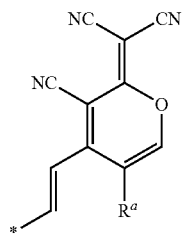
T49
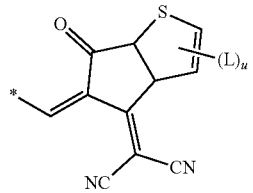
T50
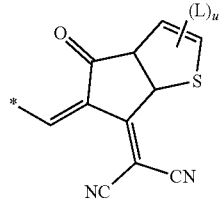
T51
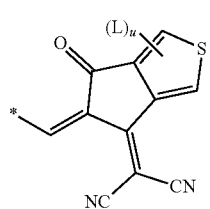
T52
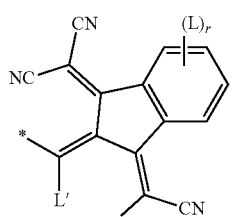
T53
T54
T55
T56
T57
T58
T59
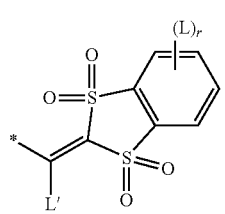

-continued

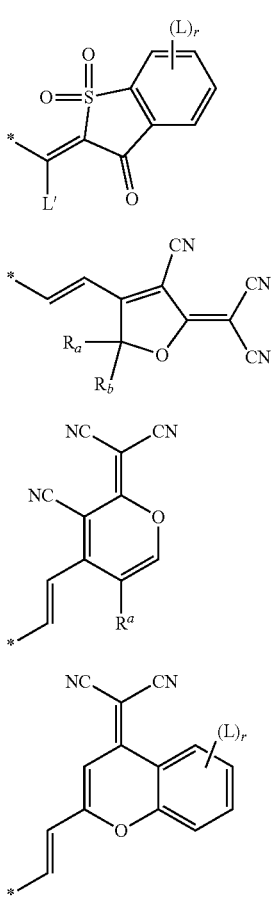

T60

T61

T62

T63 wherein the individual radicals, independently of each other and on each occurrence identically or differently, have the following meanings $R^a$, $R^b$ aryl or heteroaryl, each having from 4 to 30, preferably from 5 to 20, ring atoms, optionally containing fused rings and being unsubstituted or substituted with one or more groups L, or one of the meanings given for L, R*, R, R* alkyl with 1 to 20 C atoms which is straight-chain, branched or cyclic, and is unsubstituted, or substituted with one or more F or Cl atoms or CN groups, or perfluorinated, and in which one or more C atoms are optionally replaced by —O—, —S—, —C(=O)—, —C(=S)—, —SiR°R°°—, —NR°R°°—, —CHR°=CR°°— or —C≡C— such that O- and/or S-atoms are not directly linked to each other, L F, Cl, —NO$_2$, —CN, —NC, —NCO, —NCS, —OCN, —SCN, R°, OR°, SR°, —C(=O)X°, —C(=O)R°, —C(=O)—OR°, —O—C(=O)—R°, —NH$_2$, —NHR°, —NR°R°°, —C(=O)NHR°, —C(=O)NR°R°°, —SO$_3$R°, —SO$_2$R°, —OH, —NO$_2$, —CF$_3$, —SF$_5$, preferably F, —CN, R°, —OR°, —SR°, —C(=O)—R°, —C(=O)—OR°, —O—C(=O)—R°, —O—C(=O)—OR°, —C(=O)—NHR°, —C(=O)—NR°R°°, L' H or one of the meanings of L, R°, R°°H or straight-chain or branched alkyl with 1 to 20, preferably 1 to 12 C atoms that is optionally fluorinated, $Y^1$, $Y^2$ F, Cl or CN, $X^0$ halogen, preferably F or Cl, r 0, 1, 2, 3 or 4, s 0, 1, 2, 3, 4 or 5, t 0, 1, 2 or 3, u 0, 1 or 2, and wherein at least one of $R^{T1}$ and $R^{T2}$ denotes an electron withdrawing group.

Preferred groups $R^{T1}$ and $R^{T2}$ which are different from formula TG are each independently selected from —CN, —C(=O)—OR*, —C(=S)—OR*, —CH=CH(CN), —CH=C(CN)$_2$, —C(CN)=C(CN)$_2$, —CH=C(CN)(R$^a$), CH=C(CN)—C(=O)—OR*, —CH=C(CO—OR*)$_2$, and formulae T1-T63.

Very preferred groups $R^{T1}$ and $R^{T2}$ which are different from formula TG are each independently selected from formulae T3, T10, T31, T36, T37, T38, T39, T47, T52, T59 and T60, wherein preferably L' is H, $R^a$ and $R^b$ denote H or $C_1$-$C_{12}$-alkyl, r is 0 and s is 0.

The above formulae TG1-TG15 and T1-T63 are meant to also include their respective E- or Z-stereoisomer with respect to the C=C bond in α-position to the adjacent group $Ar^6$ or $Ar^7$, thus for example the group

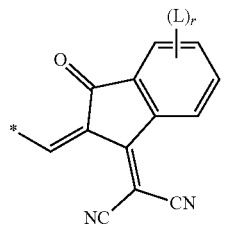

may also denote

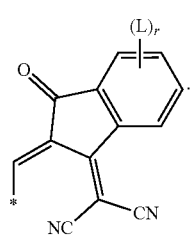

In the compounds of formula I, I1-I6 and their subformulae $R^1$ and $R^2$ are preferably different from H.

In a preferred embodiment of the present invention, in the compounds of formula I, I1-I6 and their subformulae $R^1$ and $R^2$ are selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention, in the compounds of formula I, I1-I6 and their subformulae $R^1$ and $R^2$ are selected from mono- or polycyclic aryl or heteroaryl, each of which is optionally substituted with one or more groups $L^S$ as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5- positions, or thiophene that is optionally substituted, preferably in 5-position, 4,5-positions or 3,5-positions, with alkyl, alkoxy or thioalkyl having 1 to 16 C atoms, most preferably from formulae SUB7-SUB18 above.

In the compounds of formula I, I1-I6 and their subformulae $R^3$ and $R^4$ are preferably H.

In another preferred embodiment of the present invention, in the compounds of formula I, I1-I6 and their subformulae $R^3$ and $R^4$ are different from H.

In another preferred embodiment of the present invention, in the compounds of formula I, I1-I6 and their subformulae $R^3$ and $R^4$ are selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention, in the compounds of formula I, I1-I6 and their subformulae $R^3$ and $R^4$ are selected from mono- or polycyclic aryl or heteroaryl, each of which is optionally substituted with one or more groups $L^S$ as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, more preferably from formulae SUB7-SUB18 above, most preferably from formulae SUB14-SUB18 above.

In a preferred embodiment of the present invention, in the compounds of formula I, I1-I6 and their subformulae $R^{5-9}$ are H.

In another preferred embodiment of the present invention, in the compounds of formula I, I1-I6 and their subformulae at least one of $R^{5-9}$ is different from H.

In a preferred embodiment of the present invention, in the compounds of formula I, I1-I6 and their subformulae $R^{5-9}$, when being different from H, are each independently selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention, in the compounds of formula I, I1-I6 and their subformulae $R^{5-9}$, when being different from H, are each independently selected are selected from mono- or polycyclic aryl or heteroaryl, each of which is optionally substituted with one or more groups $L^S$ as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, more preferably from formulae SUB7-SUB18 above, most preferably from formulae SUB14-SUB18 above.

Preferred aryl and heteroaryl groups $R^{1-9}$, when being different from H, are each independently selected from the following formulae

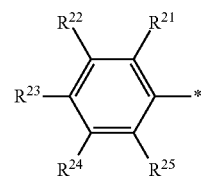 S1

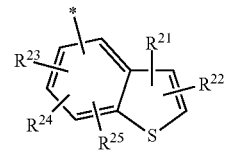 S2

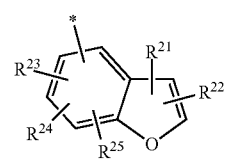 S3

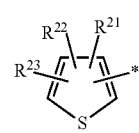 S4

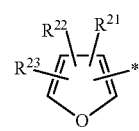 S5

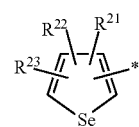 S6

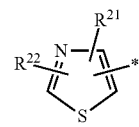 S7

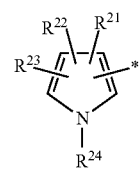 S8

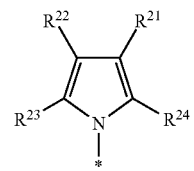 S9

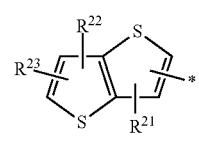 S10

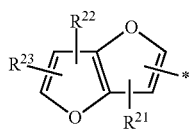

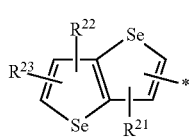

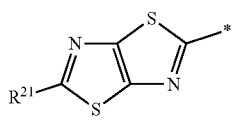

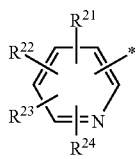

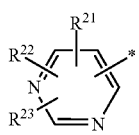

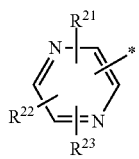

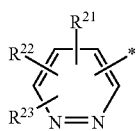

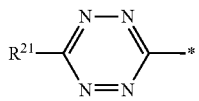

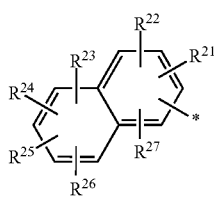

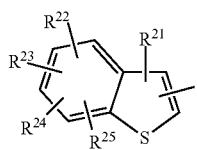

S11

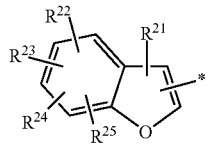

S12

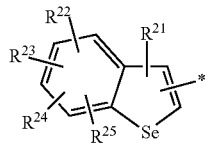

S13

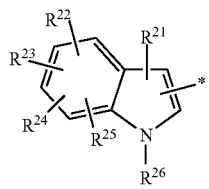

S14

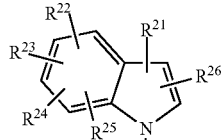

S15

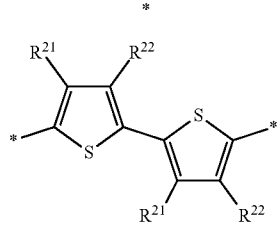

S16

S17

S18

S19

S20

S21

S22

S23

S24

S25

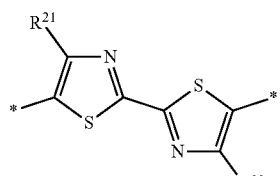

S26

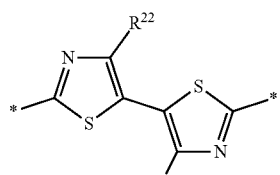

S27 wherein $R^{21-127}$, independently of each other, and on each occurrence identically or differently, denote H, F, Cl, CN, or straight-chain, branched or cyclic alkyl with 1 to 30, preferably 1 to 20, C atoms, in which one or more $CH_2$ groups are each optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are each optionally replaced by F, Cl, Br, I or CN, and in which one or more $CH_2$ or $CH_3$ groups are each optionally replaced by a cationic or anionic group.

Very preferred aryl and heteroaryl groups $R^{1-8}$, when being different from H, are each independently selected from formulae S1, S4, S5, S7 and S10.

Most preferred aryl and heteroaryl groups $R^{1-9}$ are each independently selected from formulae SUB7-SUB16 as defined above.

In another preferred embodiment one or more of $R^{1-9}$ denote a straight-chain, branched or cyclic alkyl group with 1 to 50, preferably 2 to 50, very preferably 2 to 30, more preferably 2 to 24, most preferably 2 to 16 C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms and very preferably is selected from formulae SUB1-6.

Further preferred cationic groups are selected from the group consisting of the following formulae

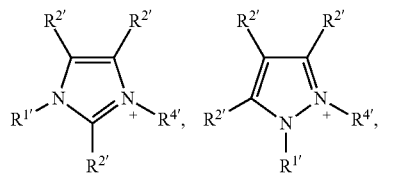

imidazolium    1H-pyrazolium

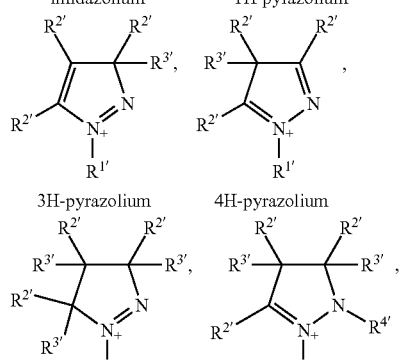

3H-pyrazolium    4H-pyrazolium 1-pyrazolium    2-pyrazolium

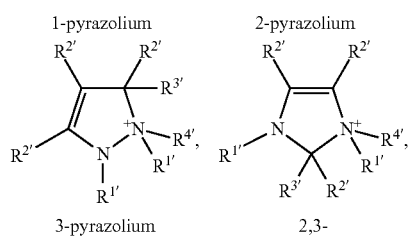

3-pyrazolium    2,3-dihydroimidazolinium

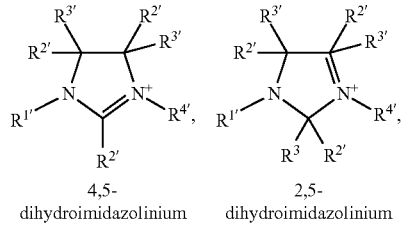

4,5-dihydroimidazolinium    2,5-dihydroimidazolinium

-continued

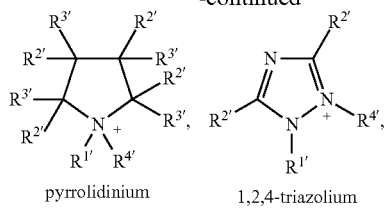

pyrrolidinium    1,2,4-triazolium

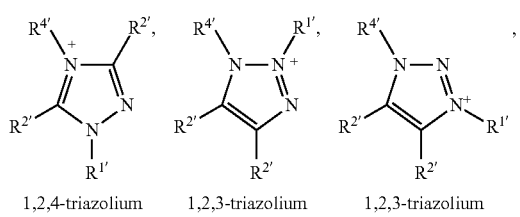

1,2,4-triazolium    1,2,3-triazolium    1,2,3-triazolium

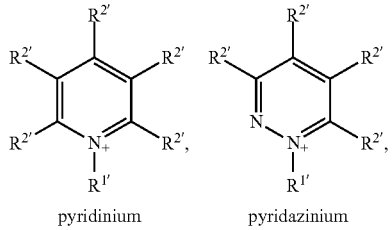

pyridinium    pyridazinium

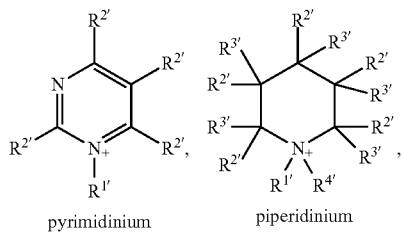

pyrimidinium    piperidinium

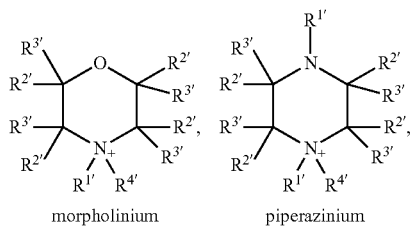

morpholinium    piperazinium

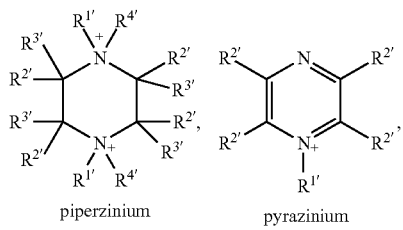

piperzinium    pyrazinium

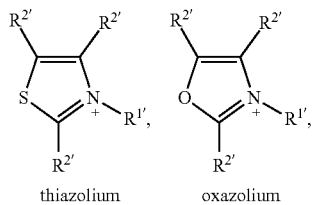

thiazolium    oxazolium

-continued

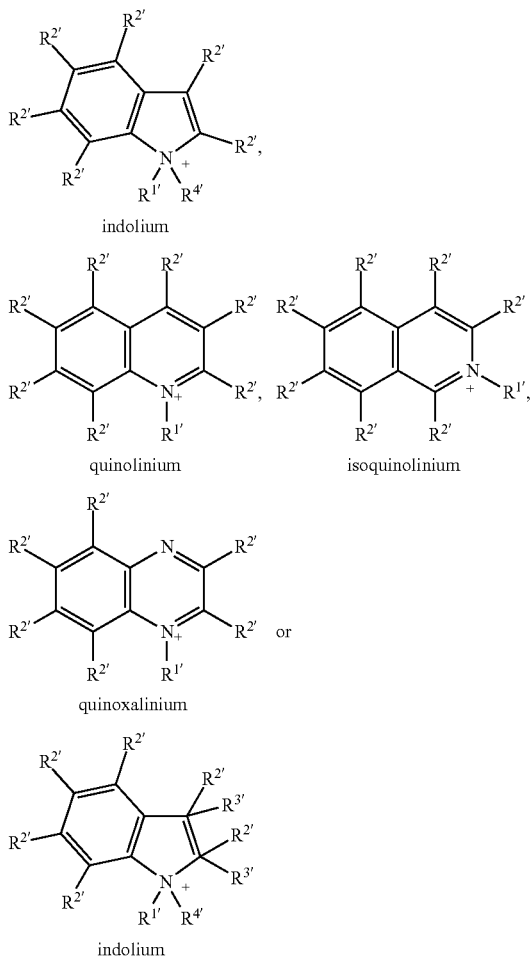

indolium quinolinium isoquinolinium quinoxalinium indolium wherein $R^{1'}$, $R^{2'}$, $R^{3'}$ and $R^{4'}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents $L^S$ as defined above, or denote a link to the respective group $R^{1-9}$.

In the above cationic groups of the above-mentioned formulae any one of the groups $R^{1'}$, $R^{2'}$, $R^{3'}$ and $R^{4'}$ (if they replace a $CH_3$ group) can denote a link to the respective group $R^{1-10}$, or two neighbored groups $R^{1'}$, $R^{2'}$, $R^{3'}$ or $R^{4'}$ (if they replace a $CH_2$ group) can denote a link to the respective group $R^1$.

The anionic group is preferably selected from the group consisting of borate, imide, phosphate, sulfonate, sulfate, succinate, naphthenate or carboxylate, very preferably from phosphate, sulfonate or carboxylate.

In a preferred embodiment of the present invention $Ar^1$ is different from formulae A1c and A1c1 and $Ar^2$ is different from formulae A2c and A2c1.

In another preferred embodiment of the present invention $Ar^1$ is different from $Ar^2$ and is not a mirror image of $Ar^2$.

Preferred compounds of formula I and I1-I6 are selected from formula IA

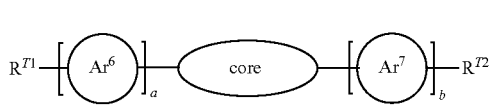

IA wherein $Ar^6$, $Ar^7$, $R^{T1}$, $R^{T2}$, a and b, independently of each other and on each occurrence identically or differently, have the meanings given in formula I or one of the preferred meanings given above and below, and "Core" is, on each occurrence identically or differently, a polycyclic divalent group selected from the following formulae

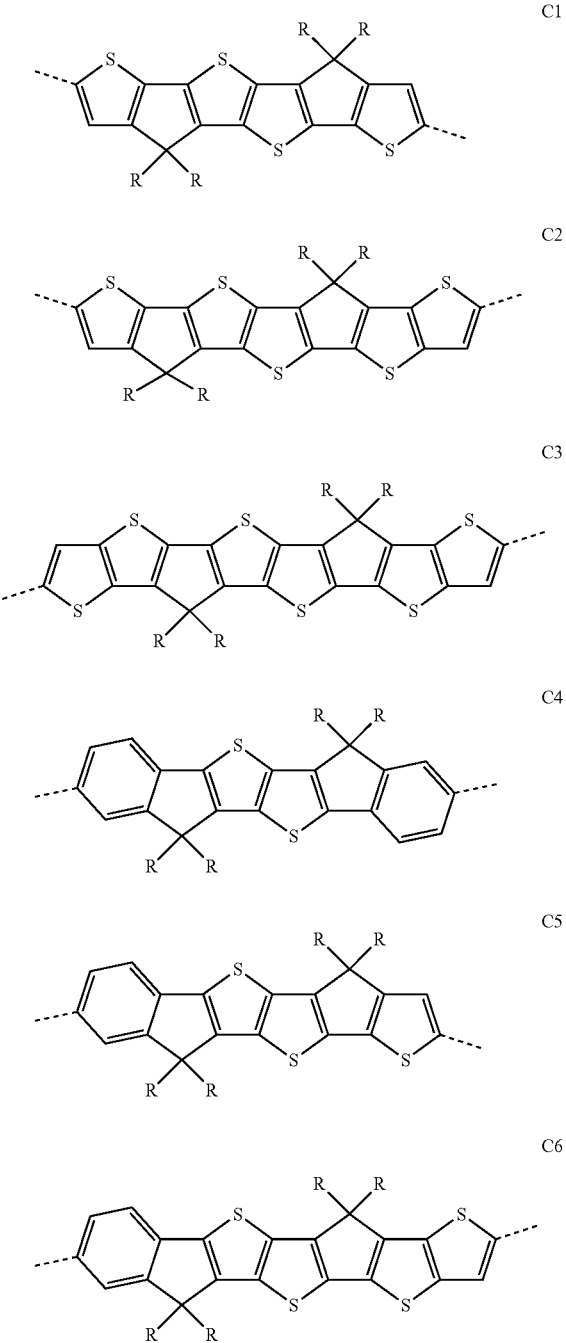

-continued
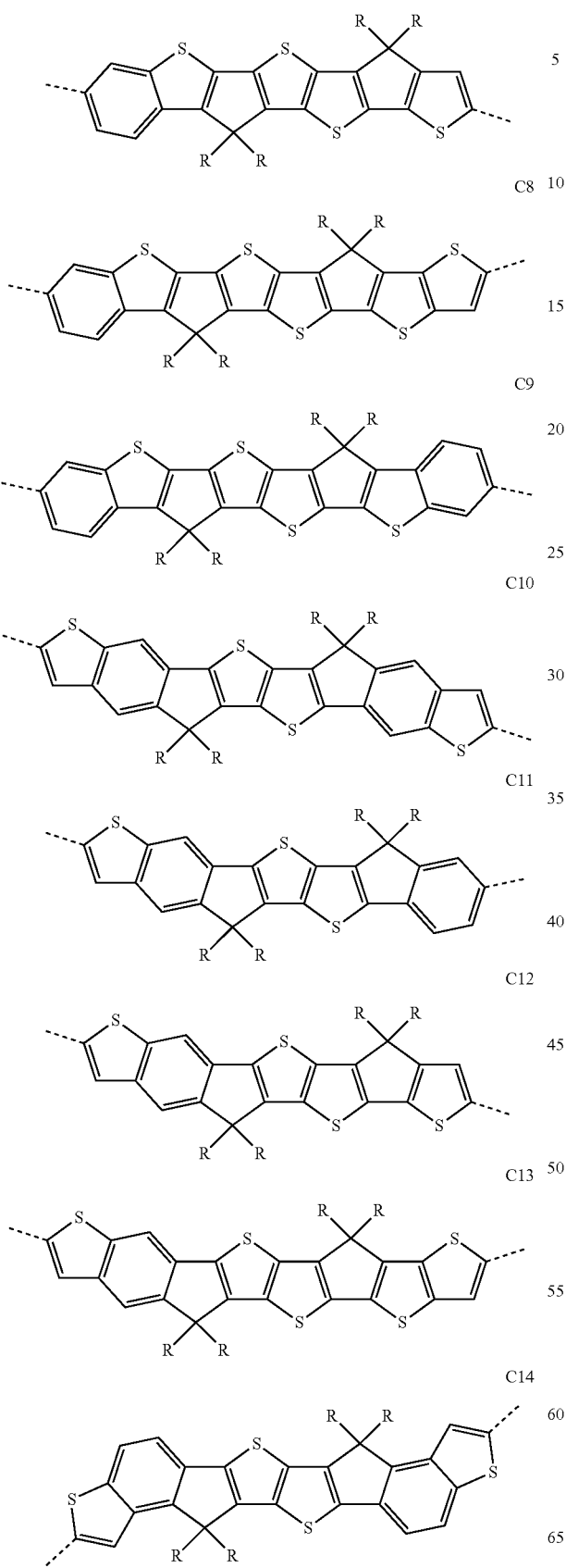
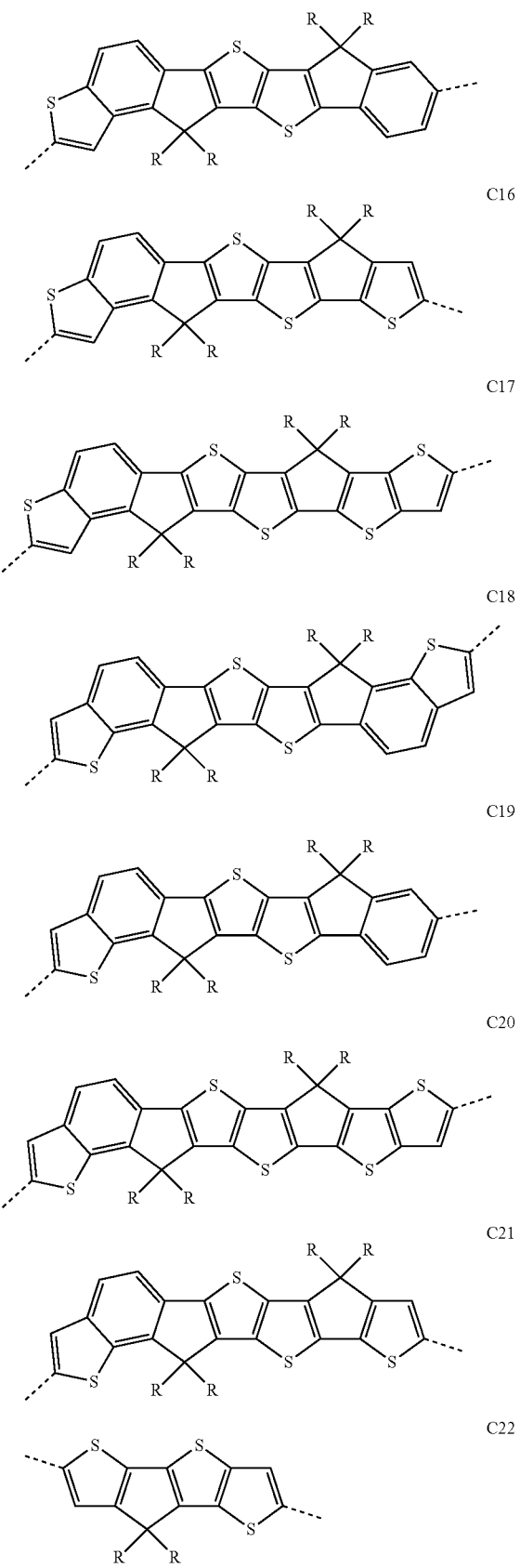

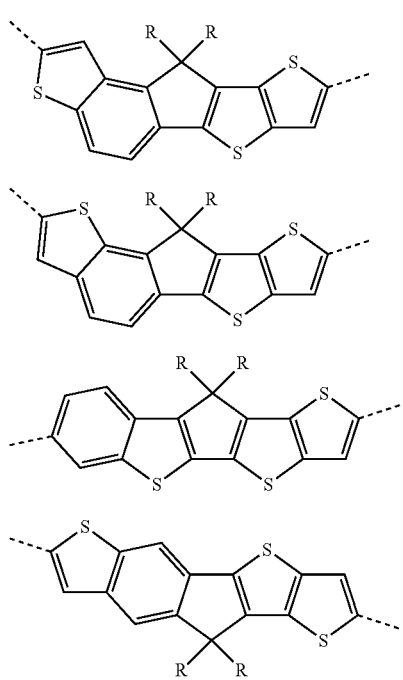
C23
C24
C25
C26
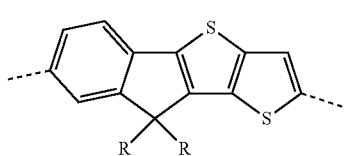
C27
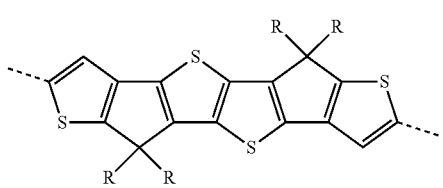
C28
wherein R has on each occurrence identically or differently one of the meanings of $R^1$ as given above and below.
Very preferred are the core groups of formula C1, C2, C3, C4, C22, C28.
Very preferred compounds of formula I, I1-I6 and I1A are selected from the following subformulae
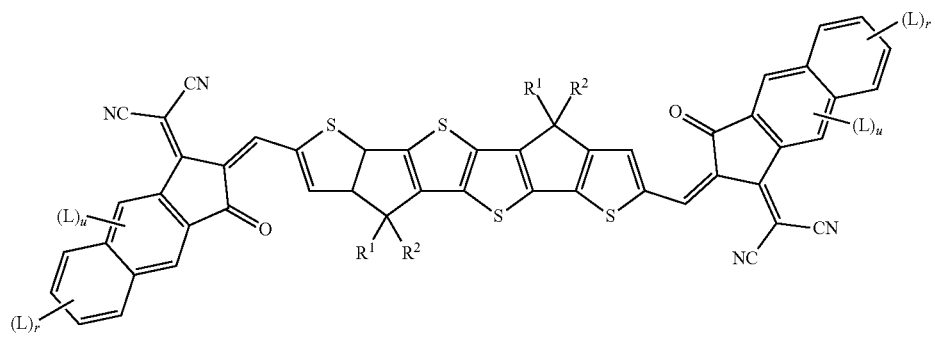
I1A1
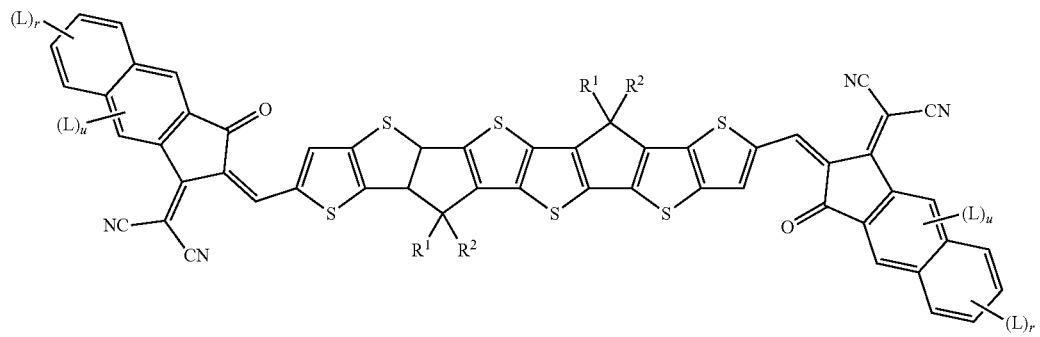
I1A2

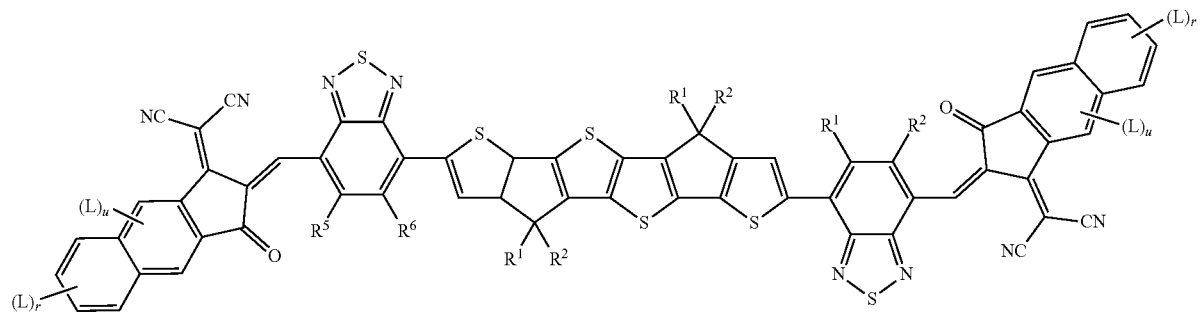
I1A3
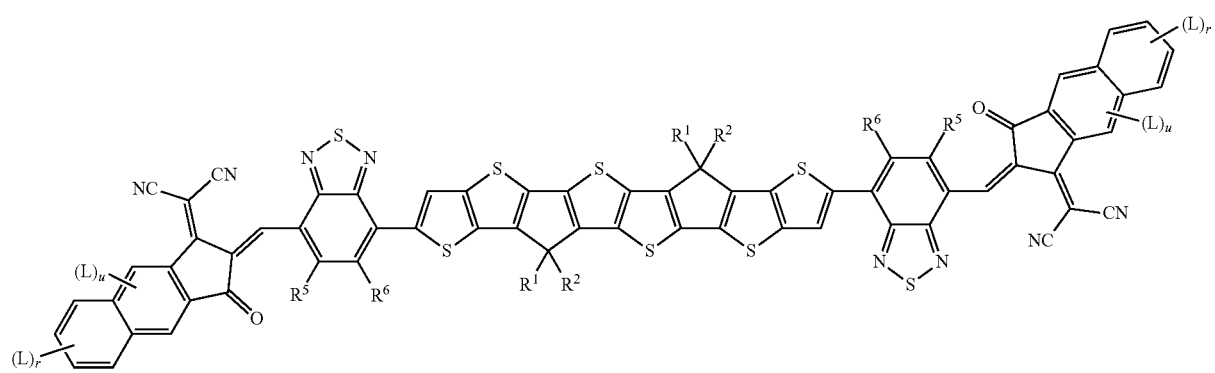
I1A4
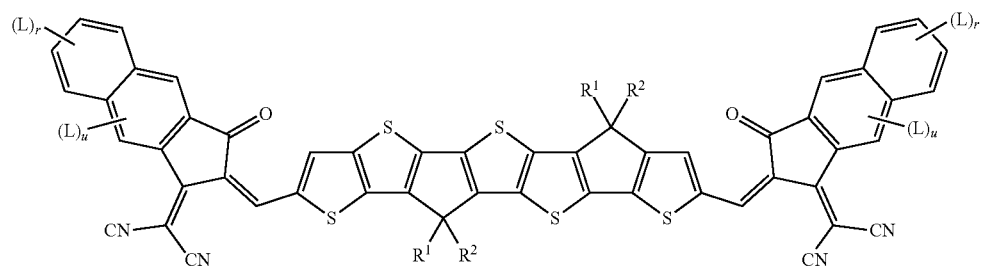
I1A5
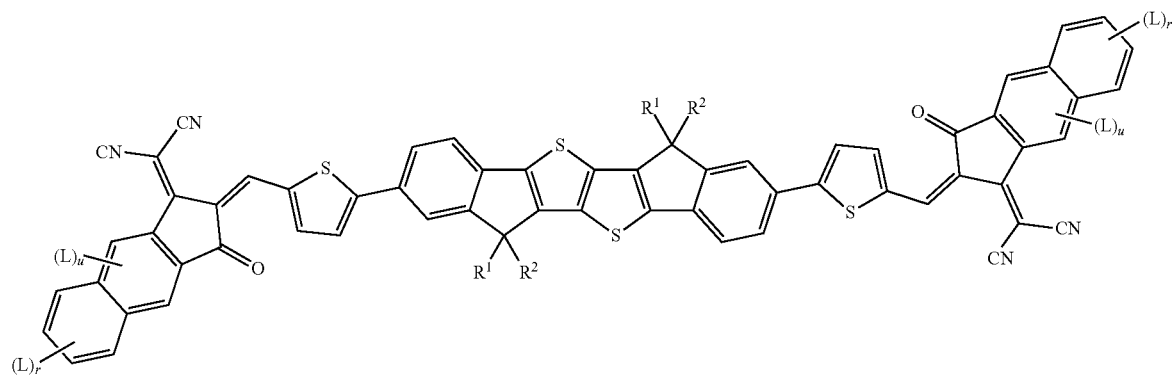
I1A6

-continued

I1A7

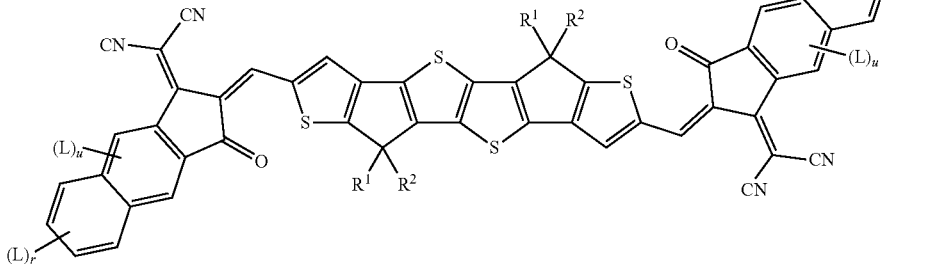

wherein R¹, R², R⁵, R⁶, L, r and u have the meanings given above and below.

Further preferred compounds of formula I, I1-I6, I1A, I1A1-I1A7 and their subformulae are selected from the following preferred embodiments or any combination thereof:
- a is 1 or 2, preferably 1,
- b is 1 or 2, preferably 1,
- a=b=0,
- a=b=1 or 2,
- m is 0,
- m is >0, preferably 1, 2 or 3,
- k is 1,
- $U^1$ and $U^2$ denote $CR^1R^2$,
- $W^1$, $W^2$ and $W^3$ are S or Se, preferably S,
- $W^4$ is S or $NR^0$, preferably S,
- $V^1$ is $CR^3$,
- $V^2$ is $CR^4$,
- $V^1$ is N,
- $V^2$ is N,
- $V^1$ is $CR^3$ and $V^2$ is $CR^4$,
- $V^1$ is $CR^3$ and $V^2$ is N,
- $V^1$ and $V^2$ are N,
- u is 0 and r is 1 or 2,
- L is methyl or methoxy,
- $Ar^1$ and $Ar^2$ are selected of formula A1a, A1b, A2a and A2b, preferably of formula A1a and A2a,
- $Ar^3$ is selected from formulae A3a-A3w, preferably from formulae A3a1-A3t1, very preferably from formulae A3a1,
- $Ar^4$ is selected from formulae A4a-A4x, preferably from formulae A4a1-A4x1, very preferably from formulae A4a1, A4b1, A4c1, A4d1, A4u1 and A4v1,
- $Ar^5$ is selected from formulae A5a-A5x, preferably from formulae A5a1-A5x1, very preferably from formulae A5a1, A5b1, A5c1, A5d1, A5u1 and A5v1,
- in $Ar^3$ all substituents $R^{5-9}$ are H,
- in at least one group $Ar^3$ at least one, preferably one or two of $R^{5-9}$ are different from H,
- in one or both of $Ar^4$ and $Ar^5$ all substituents $R^{5-9}$ are H,
- in one or both of $Ar^5$ and $Ar^5$ at least one, preferably one or two of $R^{5-9}$ are different from H,
- in one or both of $Ar^6$ and $Ar^7$ all substituents $R^{5-9}$ are H,
- in one or both of $Ar^6$ and $Ar^7$ at least one, preferably one or two of $R^{5-9}$ are different from H,
- $Ar^6$ and $Ar^7$ are selected from formulae AR1, AR2, AR3, AR5 and AR7,
- $Ar^6$ and $Ar^7$ are selected from formulae AR1-1, AR1-2, AR2-1, AR3-1, AR3-2, AR5-1 and AR7-1, most preferably from formulae AR1-1, AR2-1, AR3-1 and AR7-1,
- $Ar^6$ and $Ar^7$ are selected from thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene, benzotriazole, thiadiazole[3,4-c]pyridine and vinyl, which are substituted by $X^1$, $X^2$, $X^3$ and $X^4$ as defined above,
- $Ar^6$ and $Ar^7$ are selected from thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene, benzotriazole, thiadiazole[3,4-c]pyridine and vinyl, wherein $X^1$, $X^2$, $X^3$ and $X^4$ are H,
- $Ar^6$ and $Ar^7$ are selected from thiophene, thiazole, thieno[3,2-b]thiophene, thiazolothiazole, benzene, 2,1,3-benzothiadiazole, 1,2,3-benzothiadiazole, thieno[3,4-b]thiophene, benzotriazole, thiadiazole[3,4-c]pyridine and vinyl, wherein one or more of $X^1$, $X^2$, $X^3$ and $X^4$ are different from H,
- $Ar^8$ is bi- or polycyclic arylene or heteroarylene consisting of 2, 3 or 4 fused rings selected from benzene, thiophene and pyrazine, each of which is optionally subsituted by one or more groups L as defined above,
- $Ar^8$ is selected from formulae A8-1 to A8-23, preferably formulae A8-1 to A8-6, very preferably from formulae A8-1a to A8-6a,
- $Z^1$ and $Z^2$ are selected from O and $C(CN)_2$,
- one of $Z^1$ and $Z^2$ is O and the other is $C(CN)_2$,
- $R^{T1}$ and $R^{T2}$ are both of formula TG,
- $R^{T1}$ and $R^{T2}$ are selected from the formulae TG1-TG15, preferably from formulae TG1, TG4, TG5, TG8, TG9, TG12 and TG13, most preferably from formula TG1,
- one of $R^{T1}$ and $R^{T2}$ is not of formula TG,
- one of $R^{T1}$ and $R^{T2}$ is selected from formulae T1 to T63,
- L' is H,
- L denotes F, Cl, CN, $NO_2$, or alkyl or alkoxy with 1 to 16 C atoms that is optionally fluorinated,
- t is 1 and L is F, Cl, CN, $NO_2$, or alkyl or alkoxy with 1 to 16 C atoms that is optionally fluorinated,
- u is 1 or 2 and L is F, Cl, CN, $NO_2$, or alkyl or alkoxy with 1 to 16 C atoms that is optionally fluorinated,
- $R^1$ and $R^2$ are different from H,
- $R^1$ and $R^2$, when being different from H, are each independently selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, or alkyl or alkoxy having 1 to 12 C atoms that is optionally fluorinated, more preferably from formulae SUB1-SUB6 above,
- $R^1$ and $R^2$, when being different from H, and are each independently selected from phenyl that is substituted, preferably in 4-position, or in 2,4-positions, or in 2,4,6-positions or in 3,5-positions, with alkyl or alkoxy having 1 to 20 C atoms, preferably 1 to 16 C atoms, very preferably 4-alkylphenyl wherein alkyl is C1-16 alkyl, most preferably 4-methylphenyl, 4-hex 4-octylphenyl or 4-dodecylphenyl, or 4-alkoxyphenyl wherein alkoxy is C1-16 alkoxy, most preferably 4-hexyloxyphenyl, 4-octyloxyphenyl or 4-dodecyloxyphenyl or 2,4-dialkylphenyl wherein alkyl is C1-16 alkyl, most preferably 2,4-dihexylphenyl or 2,4-dioctylphenyl or 2,4-dialkoxyphenyl wherein alkoxy is C1-16 alkoxy, most preferably 2,4-dihexyloxyphenyl or 2,4-dioctyloxyphenyl or 3,5-dialkylphenyl wherein alkyl is C1-16 alkyl, most preferably 3,5-dihexylphenyl or 3,5-dioctylphenyl or 3,5-dialkoxyphenyl wherein alkoxy is C1-16 alkoxy, most preferably 3,5-dihexyloxyphenyl or 3,5-dioctyloxyphenyl, or 2,4,6-trialkylphenyl wherein alkyl is C1-16 alkyl, most preferably 2,4,6-trihexylphenyl or 2,4,6-trioctylphenyl or 2,4,6-trialkoxyphenyl wherein alkoxy is C1-16 alkoxy, most preferably 2,4,6-trihexyloxyphenyl or 2,4,6-trioctyloxyphenyl or 4-thioalkylphenyl wherein thioalkyl is C1-16 thioalkyl, most preferably 4-thiohexylphenyl, 4-thiooctylphenyl or 4-thiododecylphenyl, or 2,4-dithioalkylphenyl wherein thioalkyl is C1-16 thioalkyl, most preferably 2,4-dithiohexylphenyl or 2,4-dithiooctylphenyl, or 3,5-dithioalkylphenyl wherein thioalkyl is C1-16 thioalkyl, most preferably 3,5-dithiohexylphenyl or 3,5-dithiooctylphenyl, or 2,4,6-trithioalkylphenyl wherein thioalkyl is C1-16 thioalkyl, most preferably 2,4,6-trithiohexylphenyl or 2,4,6-trithiooctylphenyl, or from thiophene that is optionally substituted, preferably in 5-position, 4,5-positions or 3,5-positions, with alkyl, alkoxy or thioalkyl having 1 to 16 C atoms, most preferably from formulae SUB7-SUB18 above, $R^3$ and $R^4$ are H, $R^3$ and $R^4$ are different from H, $R^3$ and $R^4$, when being different from H, are each independently selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated, or alkyl or alkoxy having 1 to 12 C atoms that is optionally fluorinated, more preferably from formulae SUB1-SUB6 above, $R^3$ and $R^4$ are different from H, and are each independently selected from phenyl that is substituted, preferably in 4-position, or in 2,4-positions, or in 2,4,6-positions or in 3,5-positions, with alkyl or alkoxy having 1 to 20 C atoms, preferably 1 to 16 C atoms, very preferably 4-alkylphenyl wherein alkyl is C1-16 alkyl, most preferably 4-methylphenyl, 4-hexylphenyl, 4-octylphenyl or 4-dodecylphenyl, or 4-alkoxyphenyl wherein alkoxy is C1-16 alkoxy, most preferably 4-hexyloxyphenyl, 4-octyloxyphenyl or 4-dodecyloxyphenyl or 2,4-dialkylphenyl wherein alkyl is C1-16 alkyl, most preferably 2,4-dihexylphenyl or 2,4-dioctylphenyl or 2,4-dialkoxyphenyl wherein alkoxy is C1-16 alkoxy, most preferably 2,4-dihexyloxyphenyl or 2,4-dioctyloxyphenyl or 3,5-dialkylphenyl wherein alkyl is C1-16 alkyl, most preferably 3,5-dihexylphenyl or 3,5-dioctylphenyl or 3,5-dialkoxyphenyl wherein alkoxy is C1-16 alkoxy, most preferably 3,5-dihexyloxyphenyl or 3,5-dioctyloxyphenyl, or 2,4,6-trialkylphenyl wherein alkyl is C1-16 alkyl, most preferably 2,4,6-trihexylphenyl or 2,4,6-trioctylphenyl or 2,4,6-trialkoxyphenyl wherein alkoxy is C1-16 alkoxy, most preferably 2,4,6-trihexyloxyphenyl or 2,4,6-trioctyloxyphenyl or 4-thioalkylphenyl wherein thioalkyl is C1-16 thioalkyl, most preferably 4-thiohexylphenyl, 4-thiooctylphenyl or 4-thiododecylphenyl, or 2,4-dithioalkylphenyl wherein thioalkyl is C1-16 thioalkyl, most preferably 2,4-dithiohexylphenyl or 2,4-dithiooctylphenyl, or 3,5-dithioalkylphenyl wherein thioalkyl is C1-16 thioalkyl, most preferably 3,5-dithiohexylphenyl or 3,5-dithiooctylphenyl, or 2,4,6-trithioalkylphenyl wherein thioalkyl is C1-16 thioalkyl, most preferably 2,4,6-trithiohexylphenyl or 2,4,6-trithiooctylphenyl, or from thiophene that is optionally substituted, preferably in 5-position, 4,5-positions or 3,5-positions, with alkyl, alkoxy or thioalkyl having 1 to 16 C atoms, more preferably from formulae SUB7-SUB18 above, most preferably from subformulae SUB14-SUB18, $R^{5-9}$ are H, at least one of $R^{5-9}$ is different from H, $R^{5-9}$, when being different from H, are each independently selected from F, Cl, CN or straight-chain or branched alkyl, alkoxy, sulfanylalkyl, sulfonylalkyl, alkylcarbonyl, alkoxycarbonyl and alkylcarbonyloxy, each having up to 20 C atoms and being unsubstituted or substituted by one or more F atoms, preferably from F, or alkyl or alkoxy having up to 16 C atoms that is optionally fluorinated, more preferably from formulae SUB1-SUB6 above, $R^{5-9}$, when being different from H, are each independently selected from aryl or heteroaryl, preferably phenyl or thiophene, each of which is optionally substituted with one or more groups $L^S$ as defined in formula IA and has 4 to 30 ring atoms, preferably from phenyl that is optionally substituted, preferably in 4-position, 2,4-positions, 2,4,6-positions or 3,5-positions, with alkyl or alkoxy having 1 to 20 C atoms, preferably 1 to 16 C atoms, more preferably from formulae SUB7-SUB18 above.

Another embodiment of the invention relates to a composition comprising a compound of formula I, and further comprising one or more electron donors or p-type semiconductors, preferably selected from conjugated polymers. Preferably, the conjugated polymer used in the said composition comprises at least one electron donating unit ("donor unit") and at least one electron accepting unit ("acceptor unit"), and optionally at least one spacer unit separating a donor unit from an acceptor unit, wherein each donor and acceptor units is directly connected to another donor or acceptor unit or to a spacer unit, and wherein all of the donor, acceptor and spacer units are each independently selected from arylene or heteroarylene that has from 5 to 20 ring atoms, is mono- or polycyclic, optionally contains fused rings, are is unsubstituted or substituted by one or more identical or different groups $L^S$ as defined above.

Preferably the spacer units, if present, are located between the donor and acceptor units such that a donor unit and an acceptor unit are not directly connected to each other.

Preferred conjugated polymers comprise, very preferably consist of, one or more units selected from formula U1, U2 and U3, and/or one or more units selected from formula U4, U5, U6 and U7

-(D-Sp)- U1

-(A-Sp)- U2

-(D)- U4

-(Sp-D-Sp)- U5

-(A)- U6

-(Sp-A-Sp)- U7 wherein D denotes a donor unit, A denotes an acceptor unit and Sp denotes a spacer unit, all of which are selected, independently of each other and on each occurrence identically or differently, from arylene or heteroarylene that has from 5 to 20 ring atoms, is mono- or polycyclic, optionally contains fused rings, are is unsubstituted or substituted by one or more identical or different groups L as defined above.

Very preferred are polymers of formula Pi-Pviii

-[(D-Sp)$_x$-(A-Sp)$_y$]$_n$- Pi

-[(A-D)$_x$-(A-Sp)$_y$]$_n$- Pii

-[(D)$_x$-(Sp-A-Sp)$_y$]$_n$- Piii

-[D-Sp-A-Sp]$_n$- Piv

-[D-A]$_n$- Pv

-[D-Sp-A-Sp]$_n$ Pvi

-[D$^1$-A-D$^2$-A]$_n$ Pvii

-[D-A$^1$-D-A$^2$]$_n$ Pviii wherein A, D and Sp are as defined in formula U1-U7, A and D can each, in case of multiple occurrence, also have different meanings, D$^1$ and D$^2$ have one of the meanings given for D and are different from each other, A$^1$ and A$^2$ have one of the meanings given for A and are different from each other, x and y denote the molar fractions of the corresponding units, x and y are each, independently of one another, a non-integer >0 and <1, with x+y=1, and n is an integer >1.

Especially preferred are repeating units and polymers of formulae U1-U7 and Pi-viii wherein D, D$^1$ and D$^2$ are selected from the group consisting of the following formulae

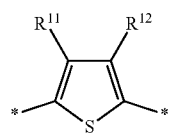
(D1)

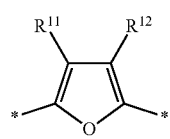
(D7)

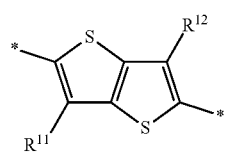
(D10)

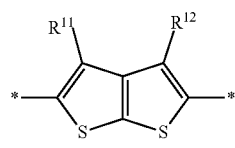
(D11)

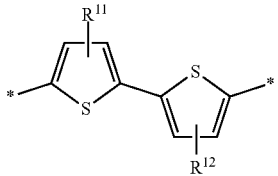
(D19)

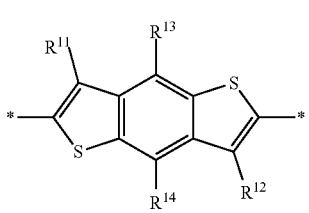
(D22)

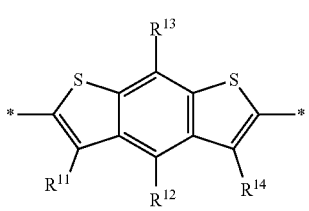
(D29)

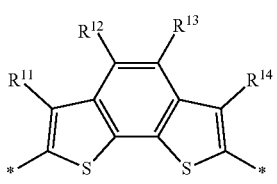
(D30)

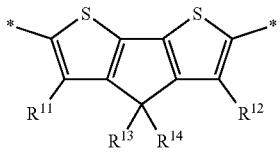
(D35)

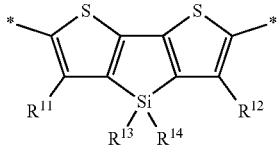
(D36)

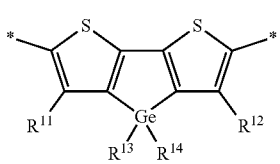
(D37)

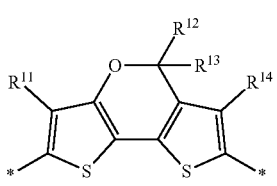
(D44)

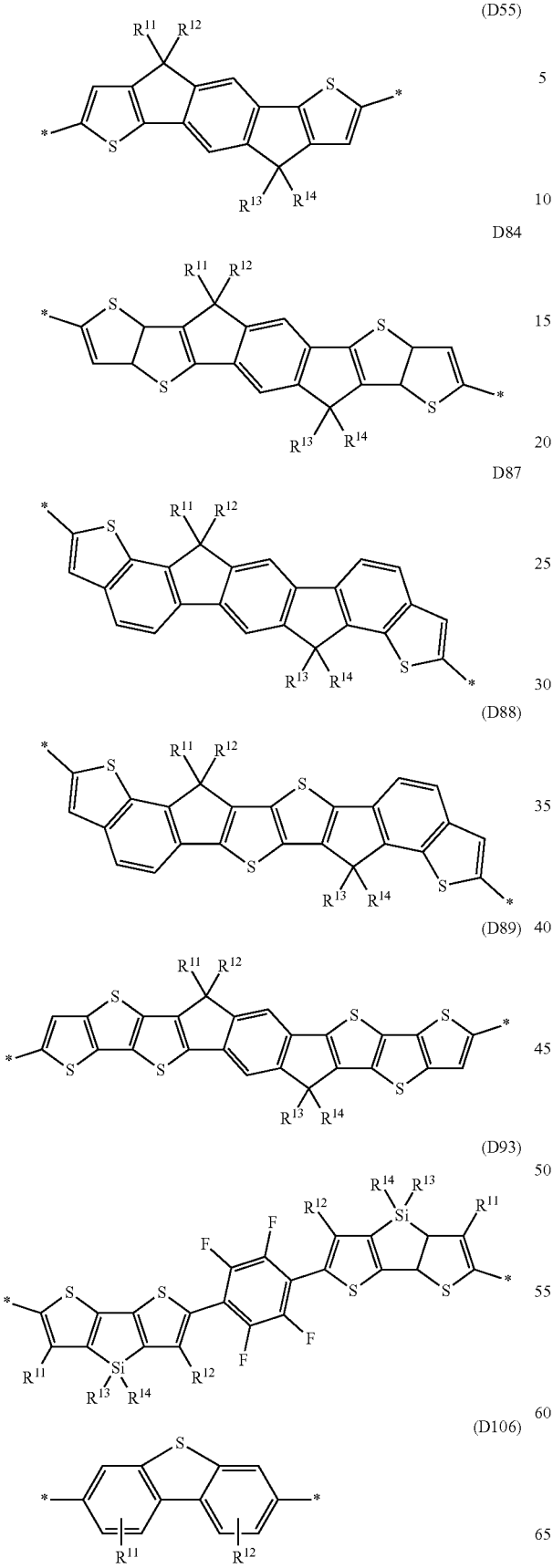
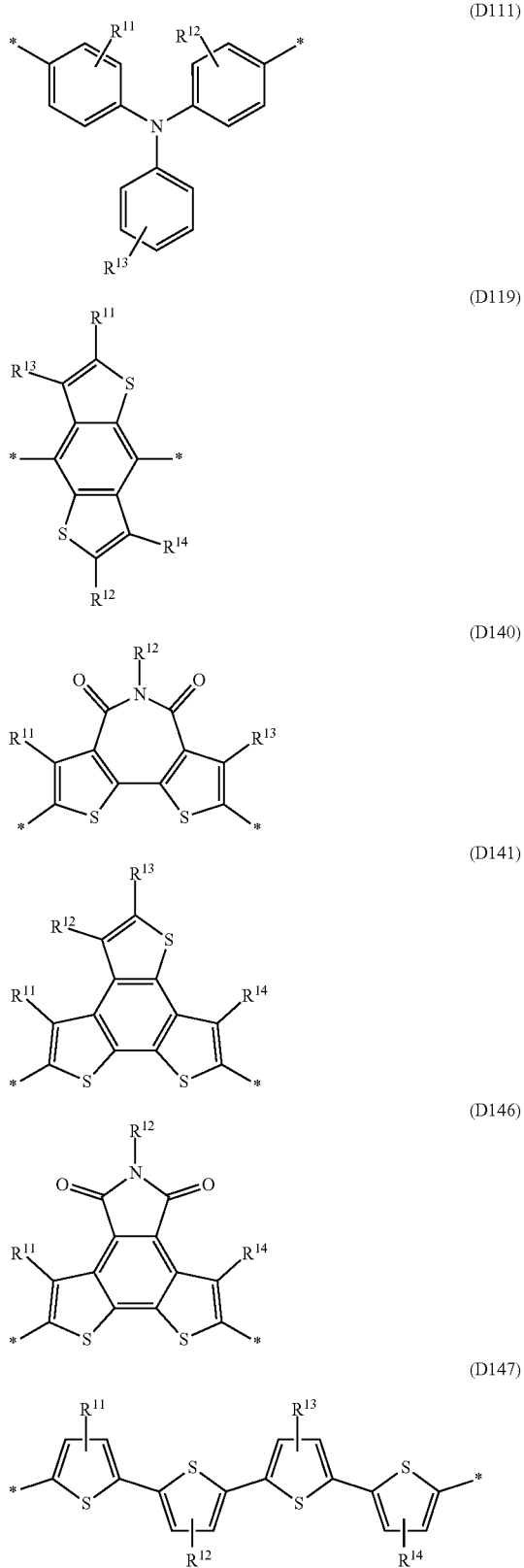
wherein $R^{11}$, $R^{12}$, $R^{13}$, $R^{14}$ independently of each other denote H or have one of the meanings of $L^S$, preferably of $R^7$, as defined above, and wherein preferably at least one of $R^{11}$, $R^{12}$, $R^{13}$ and $R^{14}$ is different from H and in formula D147 preferably $R^{12}$ and $R^{13}$ are F and $R^{11}$ and $R^{14}$ are H or C1-C30 alkyl.

Further preferred are repeating units and polymers of formulae U1-U7 and Pi-viii wherein A, $A^1$ and $A^2$ are selected from the group consisting of the following formulae

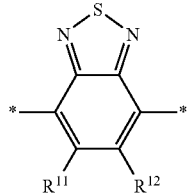
(A1)

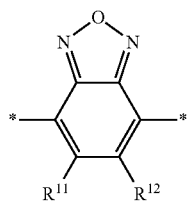
(A2)

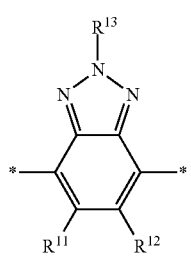
(A5)

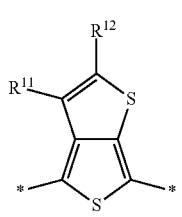
(A15)

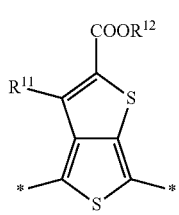
(A16)

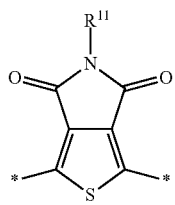
(A20)

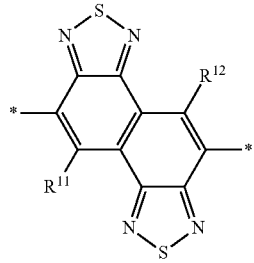
(A74)

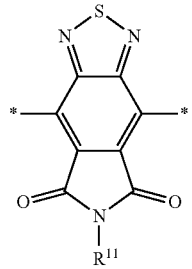
(A88)

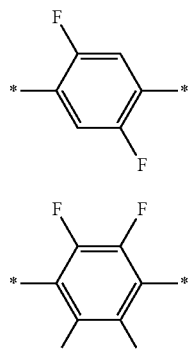
(A92)

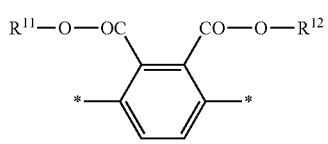
(A94)

(A98)

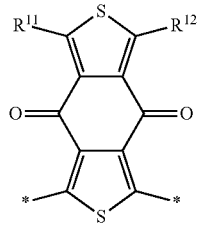
(A99)

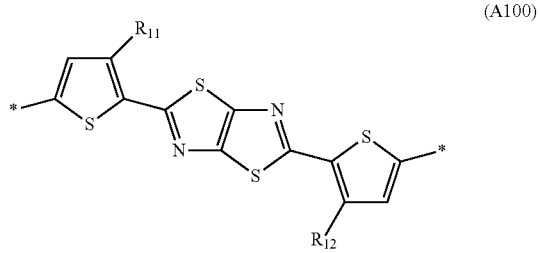
(A100)

wherein $R^{11}$, $R^{12}$, $R^{13}$, $R^{14}$ independently of each other denote H or have one of the meanings of $L^S$, preferably of $R^7$, as defined above.

Further preferred are repeating units and polymers of formulae U1-U7 and Pi-Pviii wherein Sp is selected from the group consisting of the following formulae

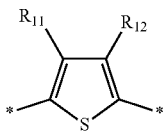
Sp1

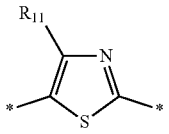
Sp2

Sp3

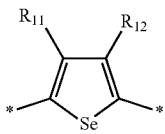
Sp4

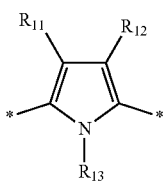
Sp5

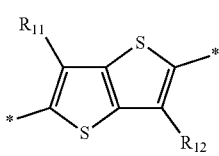
Sp6

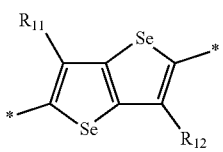
Sp7

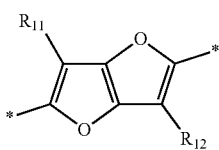
Sp8

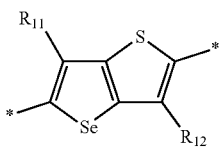
Sp9

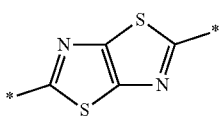
Sp10

-continued

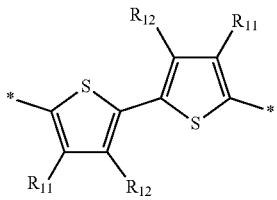
Sp11

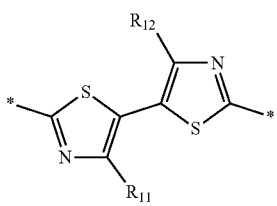
Sp12

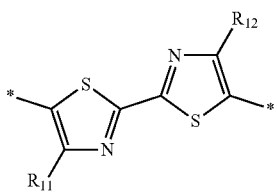
Sp13

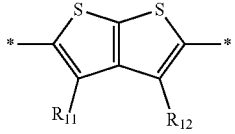
Sp14

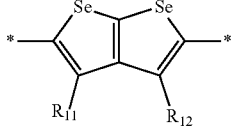
Sp15

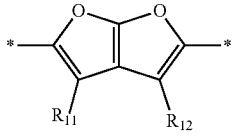
Sp16

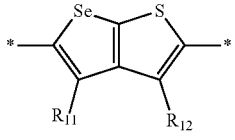
Sp17

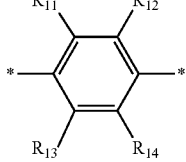
Sp18 wherein $R^{11}$, $R^{12}$, $R^{13}$, $R^{14}$ independently of each other denote H or have one of the meanings of L as defined above.

In the formulae Sp1 to Sp17 preferably $R^{11}$ and $R^{12}$ are H. In formula Sp18 preferably $R^{11-14}$ are H or F.

Preferably the conjugated polymer contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or
b) one or more acceptor units selected from the group consisting of the formulae A1, A2, A5, A15, A16, A20, A74, A88, A92, A94 and A98, A99, A100 and
c) optionally one or more spacer units selected from the group consisting of the formulae Sp1-Sp18, very preferably of the formulae Sp1, Sp6, Sp11 and Sp14, wherein the spacer units, if present, are preferably located between the donor and acceptor units such that a donor unit and an acceptor unit are not directly connected to each other.

In a second preferred embodiment the conjugated polymer comprises, preferably consists of one or more, preferably one, two, three or four, distinct repeating units D, and one or more, preferably one, two or three, distinct repeating units A.

Preferably the conjugated polymer according to this second preferred embodiment contains from one to six, very preferably one, two, three or four distinct units D and from one to six, very preferably one, two, three or four distinct units A, wherein d1, d2, d3, d4, d5 and d6 denote the molar ratio of each distinct unit D, and a1, a2, a3, a4, a5 and a6 denote the molar ratio of each distinct unit A, and each of d1, d2, d3, d4, d5 and d6 is from 0 to 0.6, and d1+d2+d3+d4+d5+d6 is from 0.2 to 0.8, preferably from 0.3 to 0.7, and each of a1, a2, a3, a4, a5 and a6 is from 0 to 0.6, and a1+a2+a3+a4+a5+d6 is from 0.2 to 0.8, preferably from 0.3 to 0.7, and d1+d2+d3+d4+d5+d6+a1+a2+a3+a4+a5+a6 is from 0.8 to 1, preferably 1.

Preferably the conjugated polymer according to this second preferred embodiment contains, preferably consists of
a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or
b) one or more acceptor units selected from the group consisting of the formulae A1, A2, A5, A15, A16, A20, A74, A88, A92, A94, A98, A99 and A100.

In the above conjugated polymers, like those of formula P and its subformulae, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The conjugated polymers are preferably statistical or random copolymers.

Very preferred conjugated polymers are selected from the following formulae

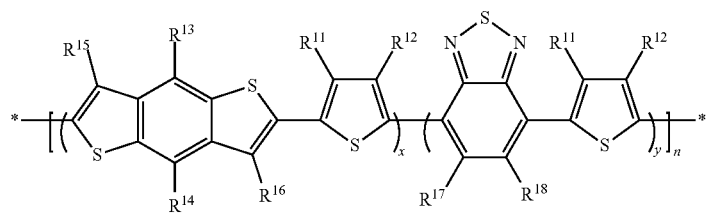

P1

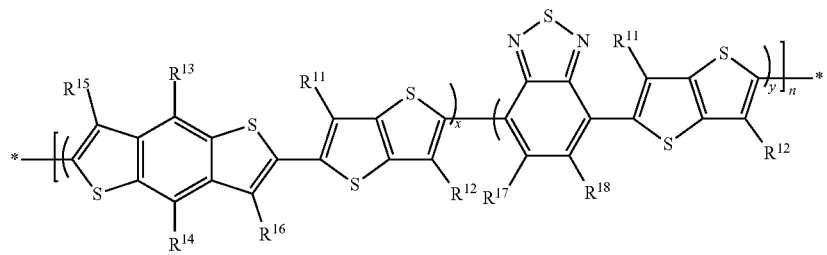

P2

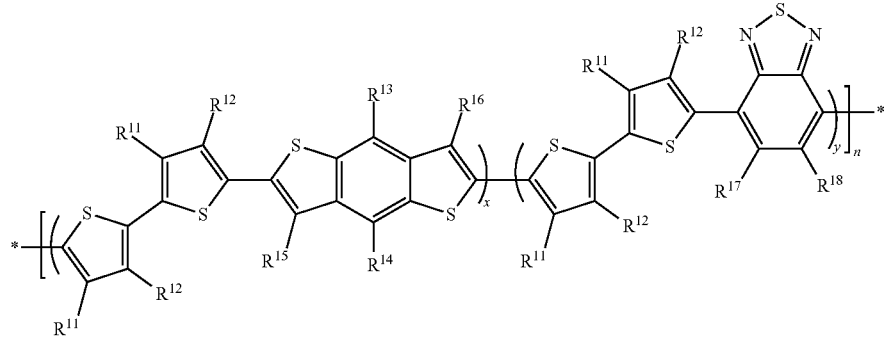

P3

-continued
P4
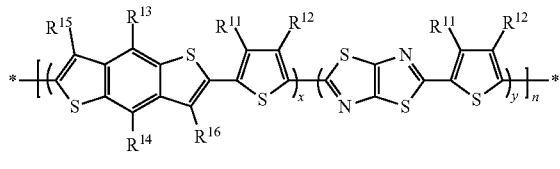
P5
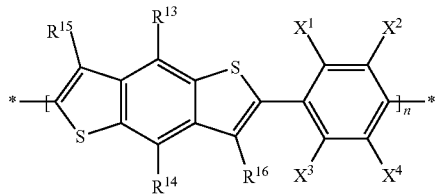
P6
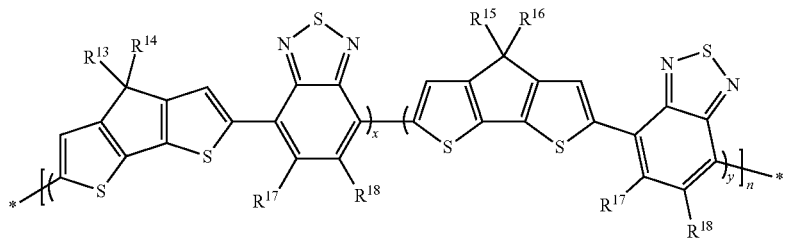
P7
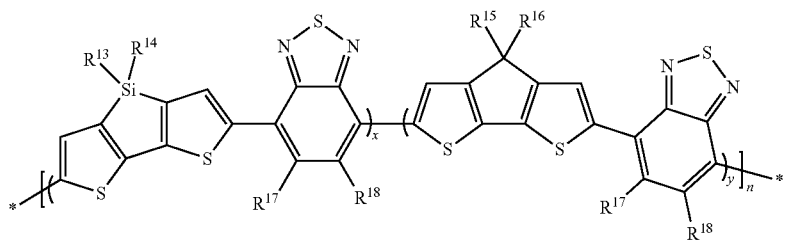
P8
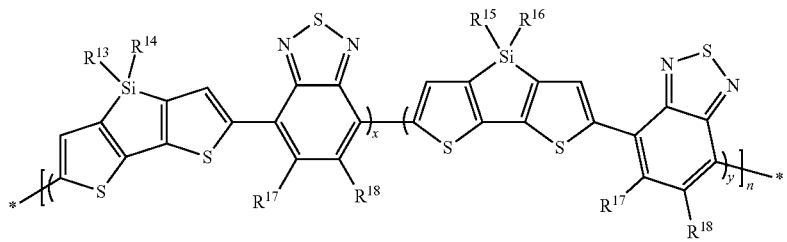
P9
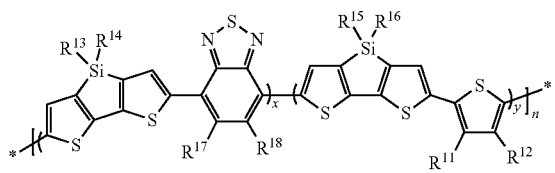
P10
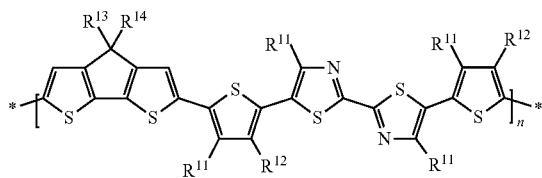
P11
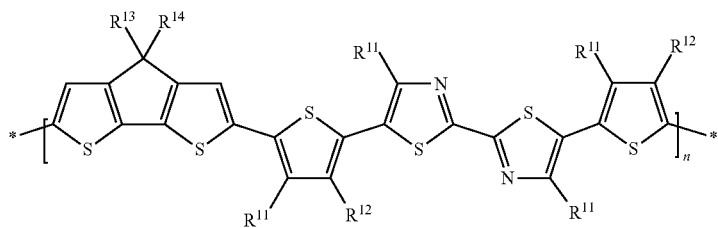

-continued
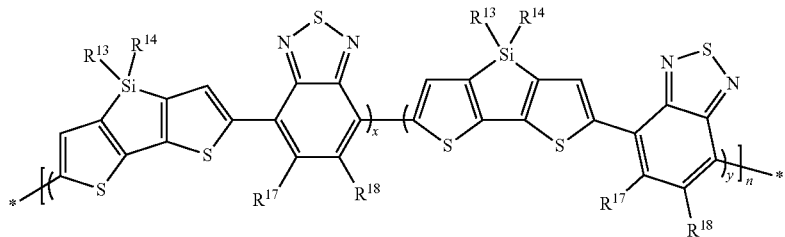
P12
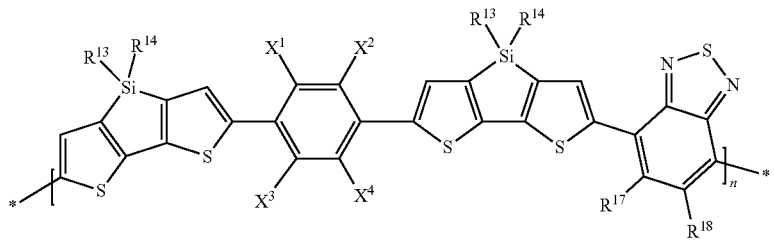
P13
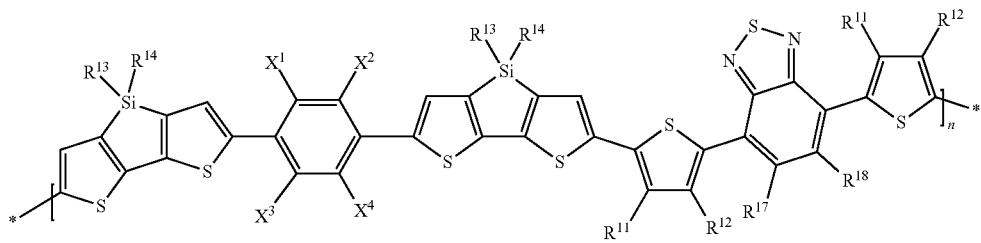
P14
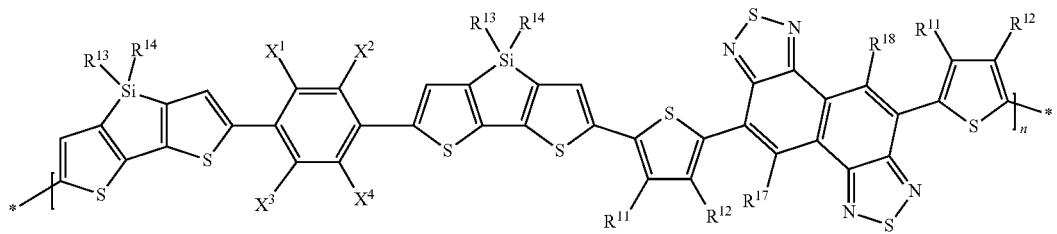
P15
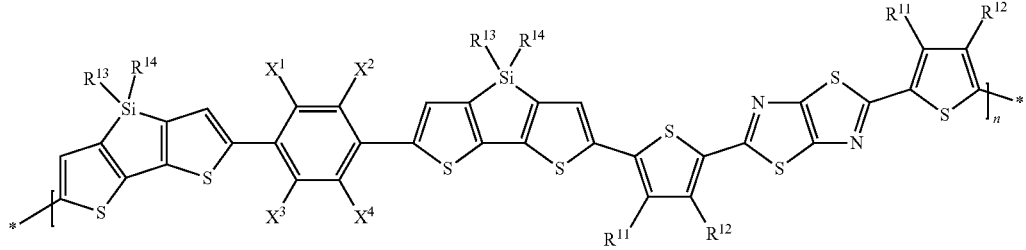
P16
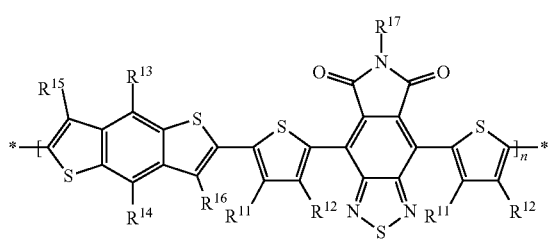
P17
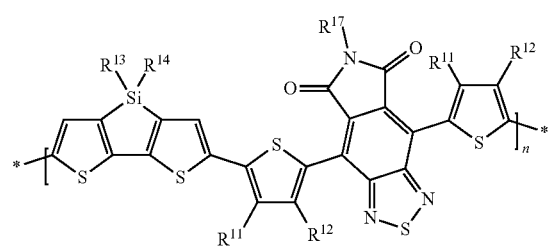
P18

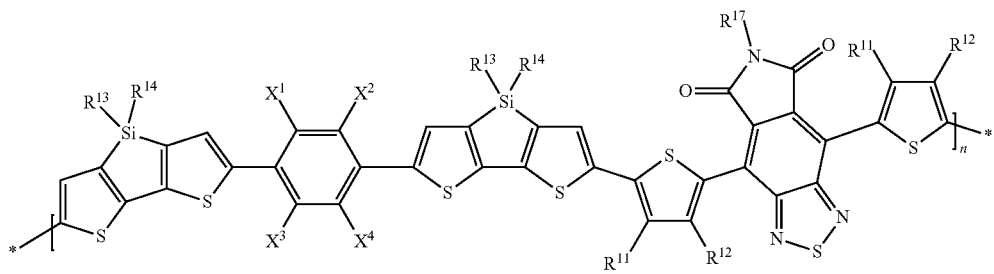
P19
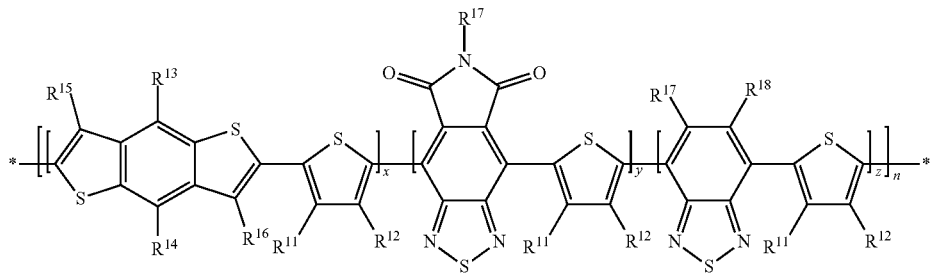
P20
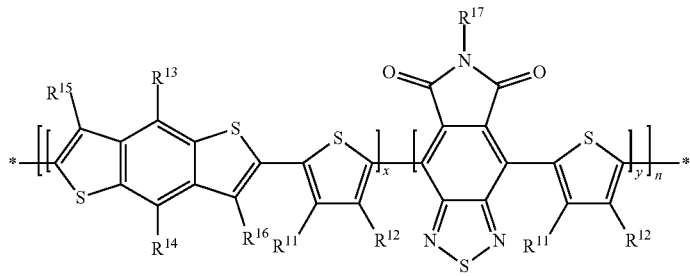
P21
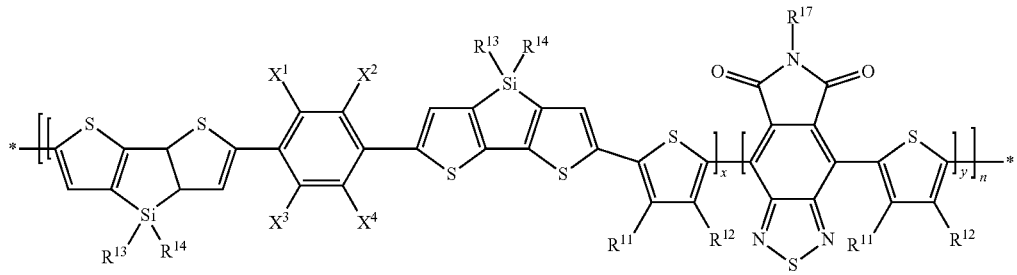
P22
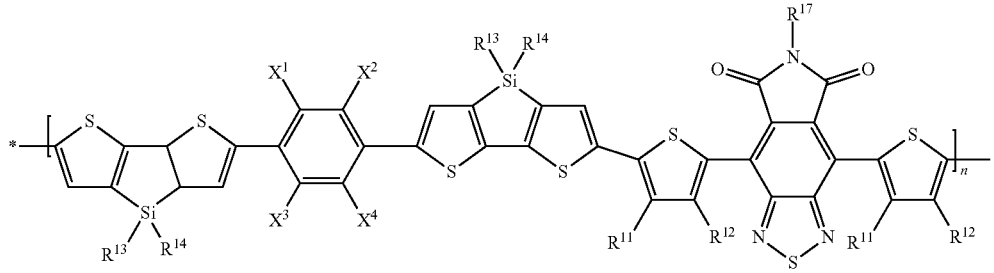
P23
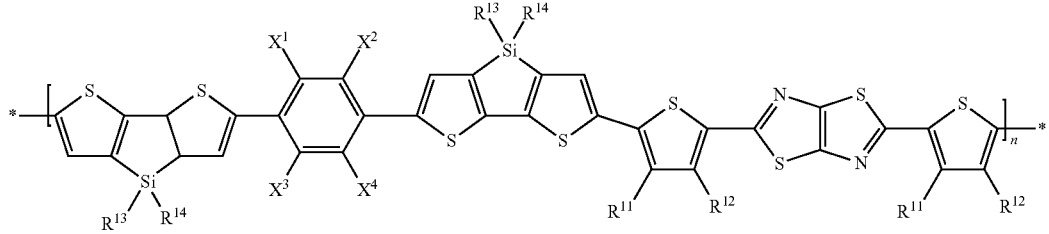
P24

-continued
P25
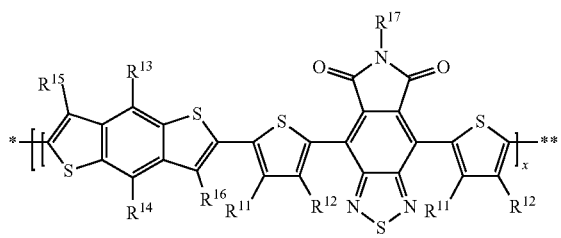
P26
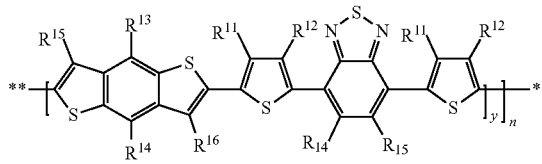
P27
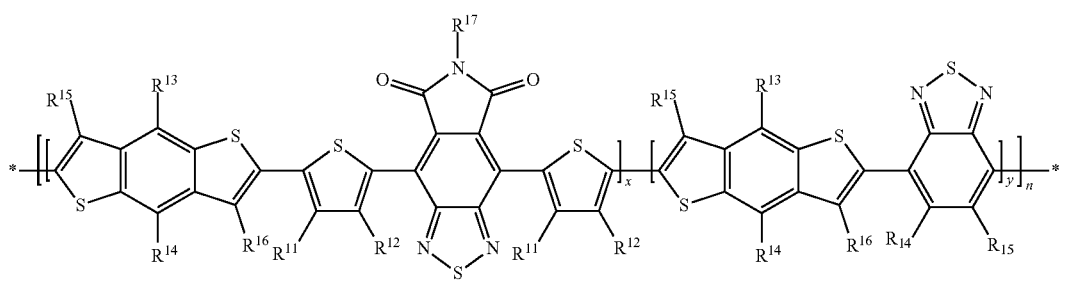
P28
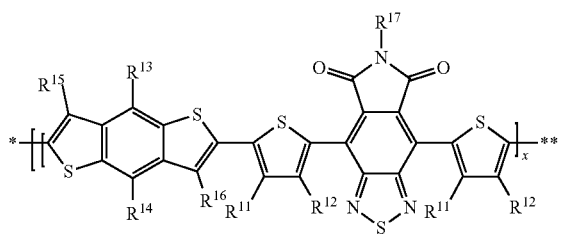
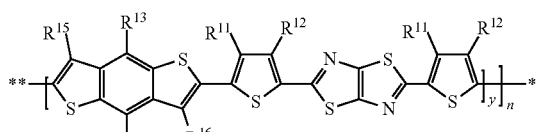
P29
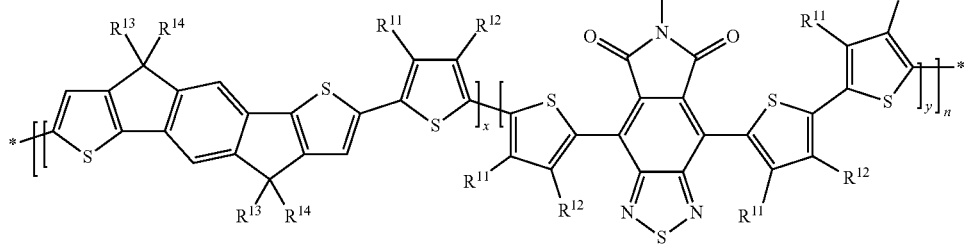
P30
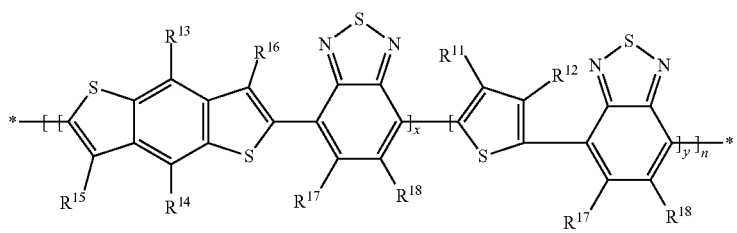
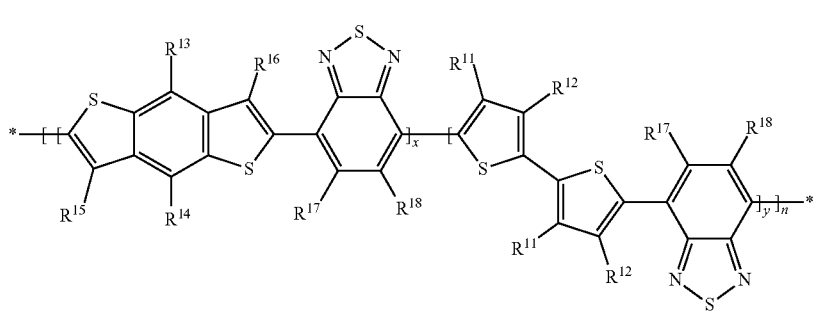

-continued
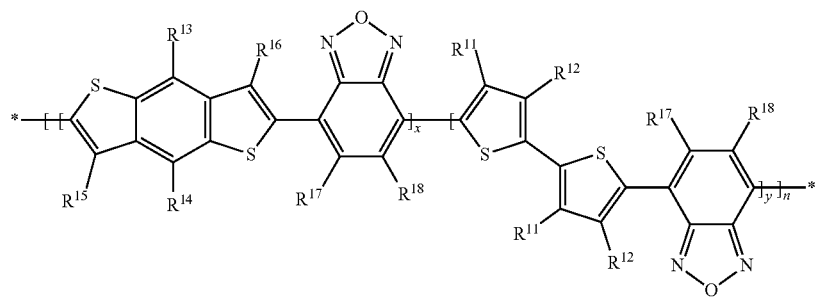
P31
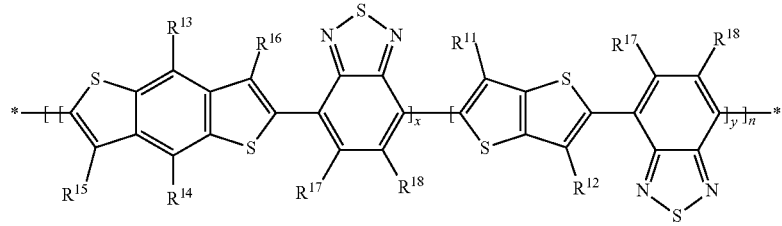
P32
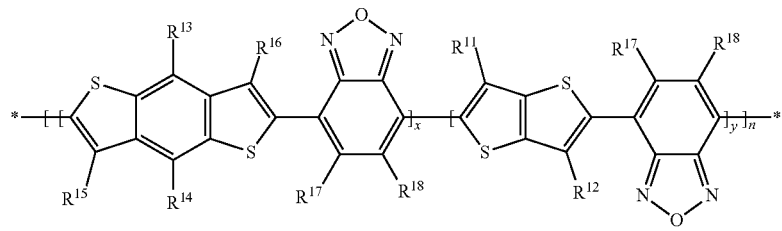
P33
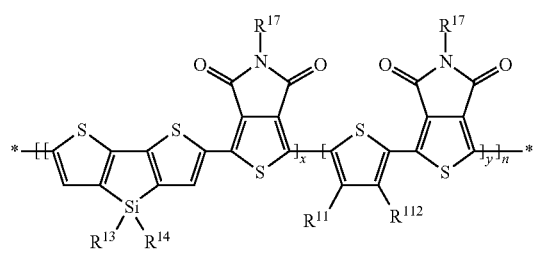
P34
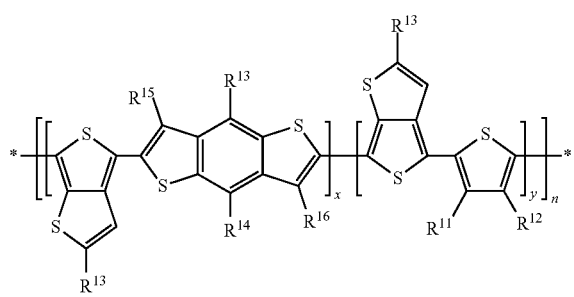
P35
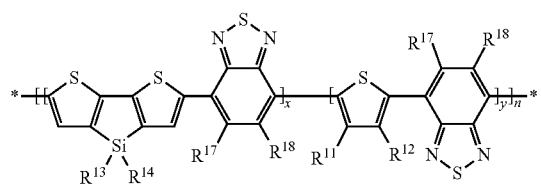
P36
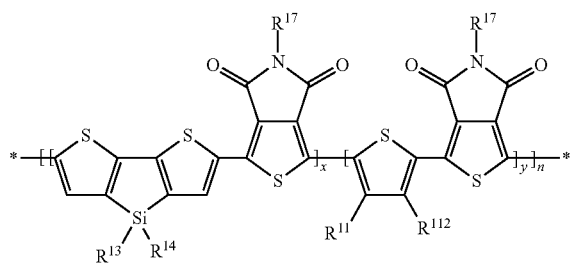
P37

-continued
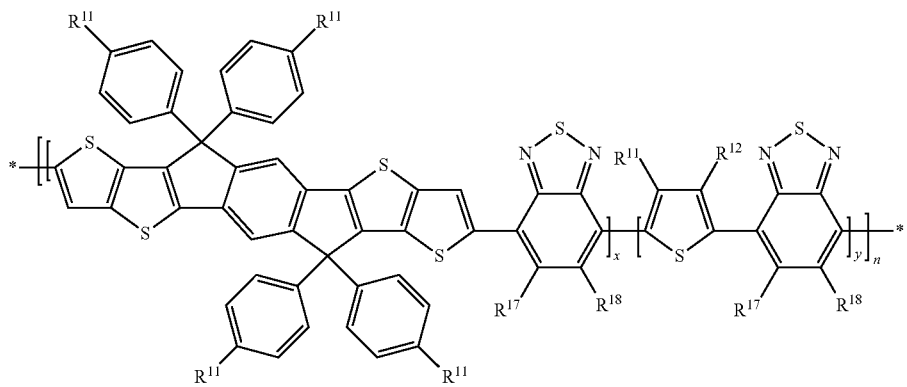
P38
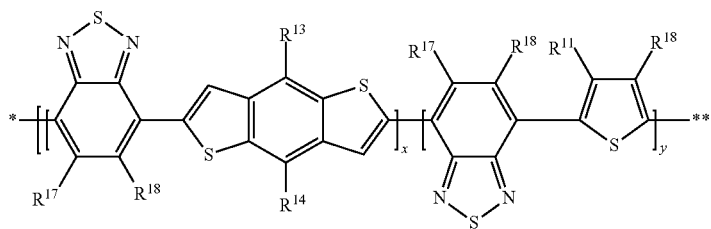
P39
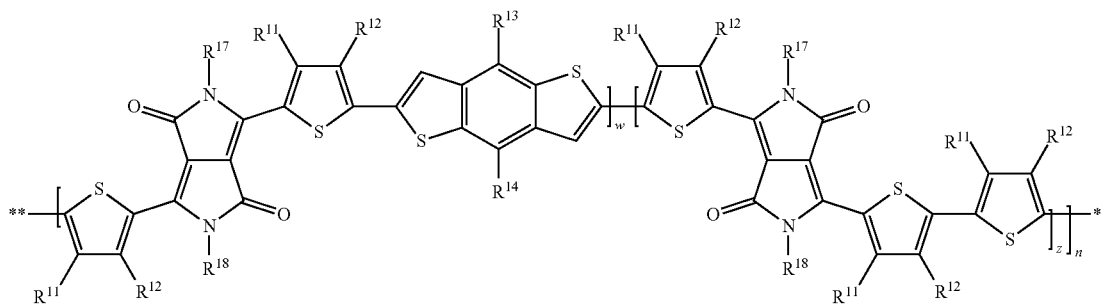
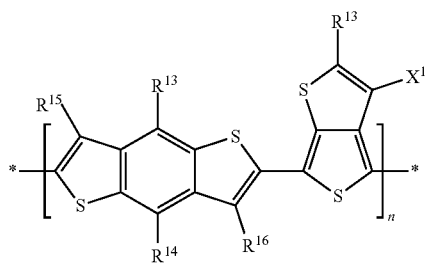
P40
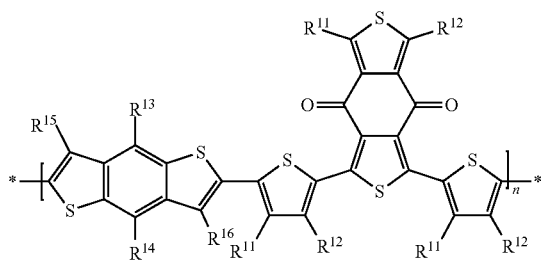
P41
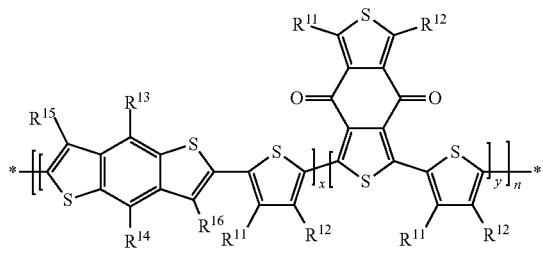
P42
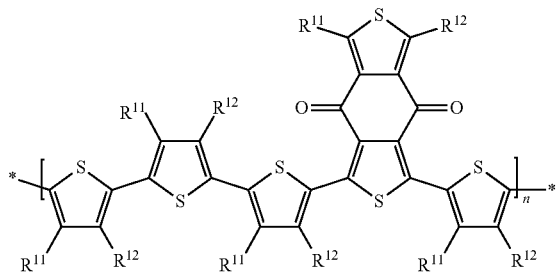
P43

-continued
P44
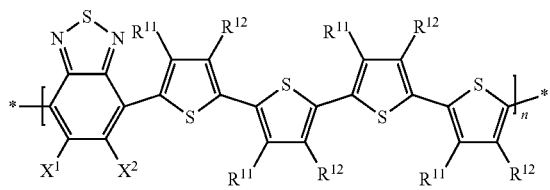
P45
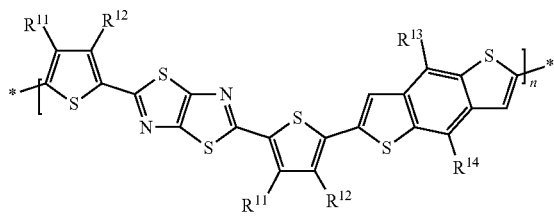
P46
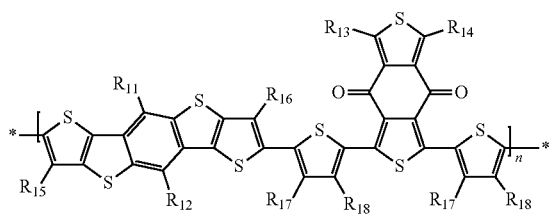
P47
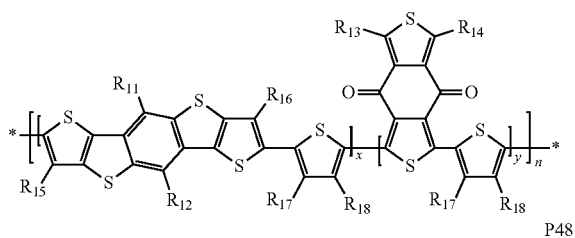
P48
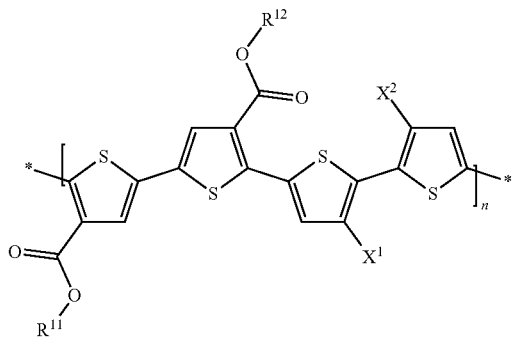
P49
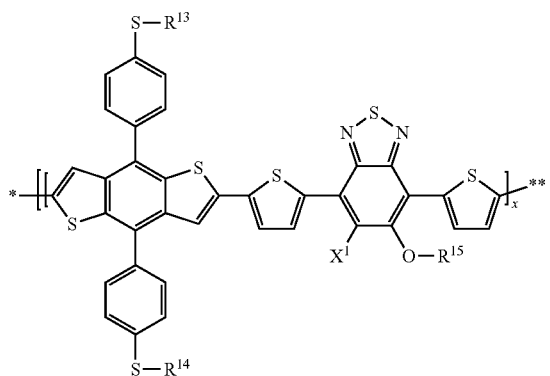
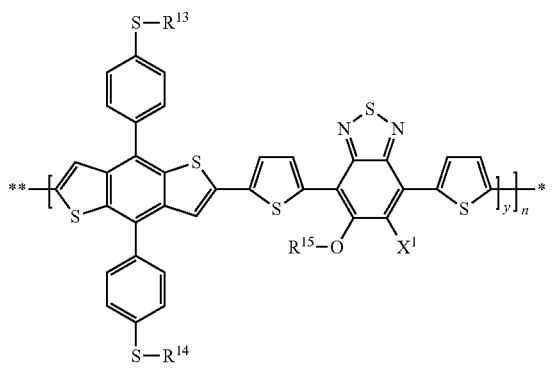
P50
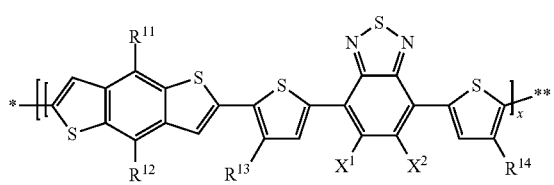
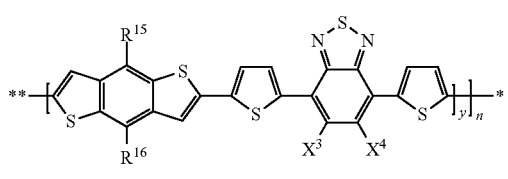
P51
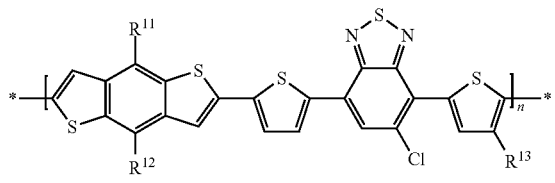
P52
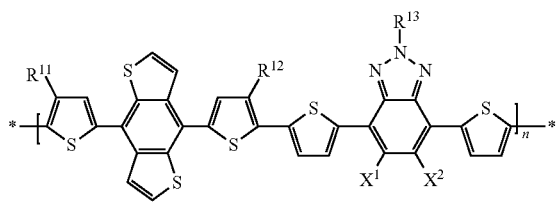

P53

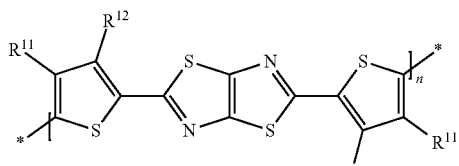

P54

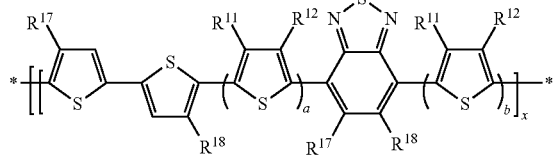

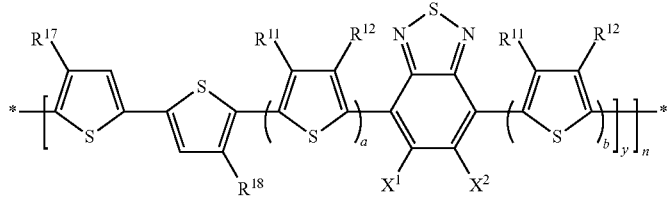

wherein $R^{11-14}$, x, y and n are as defined above, w and z have one of the meanings given for y, x+y+w+z=1, $R^{15}$, $R^{16}$, $R^{17}$ and $R^{18}$ have one of the meanings given for $R^{11}$, and $X^1$, $X^2$, $X^3$ and $X^4$ denote H, F or Cl.

Further preferred are polymers comprising one of the formulae P1-P54 as one or more repeating unit.

In the polymers of formula Pi-viii and P1-P54 which are composed of two building blocks [ ]$_x$, and [ ]$_y$, x and y are preferably from 0.1 to 0.9, very preferably from 0.25 to 0.75, most preferably from 0.4 to 0.6.

In the polymers of formula Pi-viii which are composed of three building blocks [ ]$_x$, [ ]$_y$, and [ ]$_z$, x, y and z are preferably from 0.1 to 0.8, very preferably from 0.2 to 0.6, most preferably from 0.25 to 0.4.

In the formulae P1-P54 preferably one or more of $X^1$, $X^2$, $X^3$ and $X^4$ denote F, very preferably all of $X^1$, $X^2$, $X^3$ and $X^4$ denote F or $X^1$ and $X^2$ denote H and $X^3$ and $X^4$ denote F.

In the formulae P1-P54 preferably $R^{11}$ and $R^{12}$ are H. Further preferably $R^{11}$ and $R^{12}$, when being different from H, denote straight-chain or branched alkyl with 1 to 30, preferably 1 to 20, C atoms that is optionally fluorinated.

In the formulae P1-P54, preferably $R^{15}$ and $R^{16}$ are H, and $R^{13}$ and $R^{14}$ are different from H.

In formula P54 preferably $R^{17}$ and $R^{18}$ are F. Further preferably in formula P54 one or both of $R^{11}$ and $R^{12}$ are C1-C30 alkyl.

In the formulae P1-P54, preferably $R^{13}$, $R^{14}$, $R^{15}$ and $R^{16}$, when being different from H, are each independently selected from the following groups:
the group consisting of straight-chain or branched alkyl, alkoxy or sulfanylalkyl with 1 to 30, preferably 1 to 20, C atoms that is optionally fluorinated,
the group consisting of straight-chain or branched alkylcarbonyl or alkylcarbonyloxy with 2 to 30, preferably 2 to 20, C atoms, that is optionally fluorinated.

In the formulae P1-P54, preferably $R^{17}$ and $R^{18}$, when being different from H, are each independently selected from the following groups:
the group consisting of straight-chain or branched alkyl, alkoxy or sulfanylalkyl with 1 to 30, preferably 1 to 20, C atoms that is optionally fluorinated,
the group consisting of straight-chain or branched alkylcarbonyl or alkylcarbonyloxy with 2 to 30, preferably 2 to 20, C atoms, that is optionally fluorinated.
the group consisting of F and Cl.

Further preferred are conjugated polymers selected of formula PT $R^{31}$-chain-$R^{32}$   PT wherein "chain" denotes a polymer chain selected of formula Pi-Pviii or P1-P54, and $R^{31}$ and $R^{32}$ have independently of each other one of the meanings of $R^{11}$ as defined above, or denote, independently of each other, F, Br, Cl, I, —CH$_2$Cl, —CHO, —CR'=CR''$_2$, —SiR'R''R''', —SiR'X'X'', —SiR'R''X', —SnR'R''R''', —BR'R'', —B(OR')(OR''), —B(OH)$_2$, —O—SO$_2$—R', —C≡CH, —C≡C—SiR'$_3$, —ZnX' or an endcap group, X' and X'' denote halogen, R', R'' and R''' have independently of each other one of the meanings of $R^0$ given in formula 1, and preferably denote alkyl with 1 to 12 C atoms, and two of R', R'' and R''' may also form a cyclosilyl, cyclostannyl, cycloborane or cycloboronate group with 2 to 20 C atoms together with the respective hetero atom to which they are attached.

Preferred endcap groups $R^{31}$ and $R^{32}$ are H, C$_{1-20}$ alkyl, or optionally substituted C$_{6-12}$ aryl or C$_{2-10}$ heteroaryl, very preferably H, phenyl or thiophene.

The compounds of formula IA, IB and their subformulae and the conjugated polymers of formula Pi-viii, P1-P54 and PT can be synthesized according to or in analogy to methods that are known to the skilled person and are described in the literature. Other methods of preparation can be taken from the examples.

For example, the compounds of the present invention can be suitably prepared by aryl-aryl coupling reactions, such as Yamamoto coupling, Suzuki coupling, Stille coupling, Sonogashira coupling, Heck coupling or Buchwald coupling. The educts can be prepared according to methods which are known to the person skilled in the art.

Preferred aryl-aryl coupling methods used in the synthesis methods as described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1. Stille coupling is described for example in Z. Bao et al., *J. Am. Chem. Soc.*, 1995, 117, 12426-12435 and C—H activation is described for example in M. Leclerc et al, *Angew. Chem. Int. Ed.*, 2012, 51, 2068-2071. For example, when using Yamamoto coupling, educts having two reactive halide groups are preferably used. When using Suzuki coupling, educts having two reactive boronic acid or boronic acid ester groups or two reactive halide groups are preferably used. When using Stille coupling, edcuts having two reactive stannane groups or two reactive halide groups are preferably used. When using Negishi coupling, educts having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-ideneacetone)dipalladium(0), bis(dibenzylideneacetone)palladium(0), or Pd(II) salts e.g. palladium acetate, with a phosphine ligand, for example triphenylphosphine, tris(ortho-tolyl)phosphine or tri(tert-butyl) phosphine. Suzuki coupling is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto coupling employs a Ni(0) complex, for example bis(1,5-cyclooctadienyl) nickel(0).

As alternatives to halogens as described above, leaving groups of formula —O—SO$_2$Z$^0$ can be used wherein Z$^0$ is an alkyl or aryl group, preferably C$_{1-10}$ alkyl or C$_{6-12}$ aryl. Particular examples of such leaving groups are tosylate, mesylate and triflate.

Especially suitable and preferred synthesis methods of the compounds of formula I and its subformulae are illustrated in the synthesis schemes shown hereinafter, wherein the individual radicals are as defined above and below.

Scheme 1a

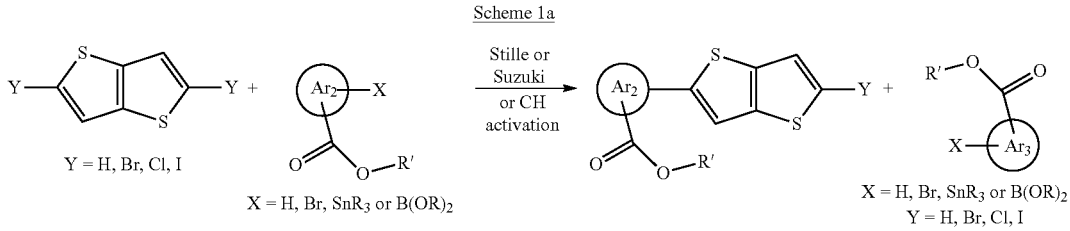

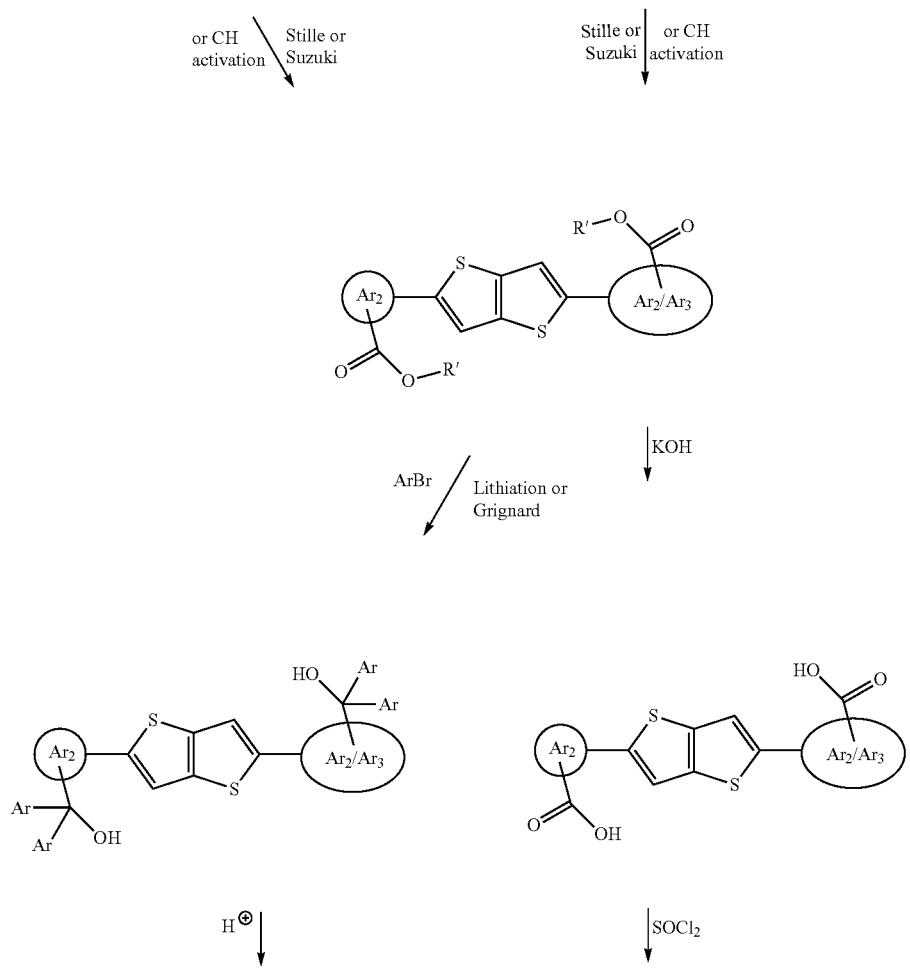

103
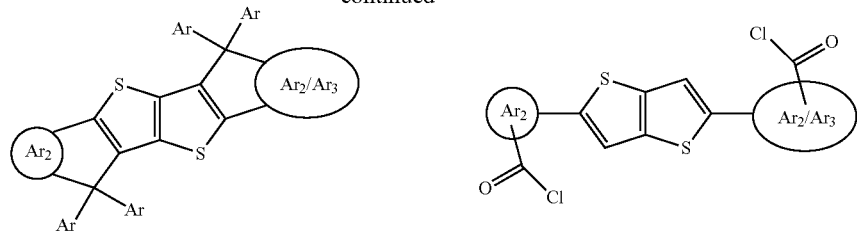
-continued
104
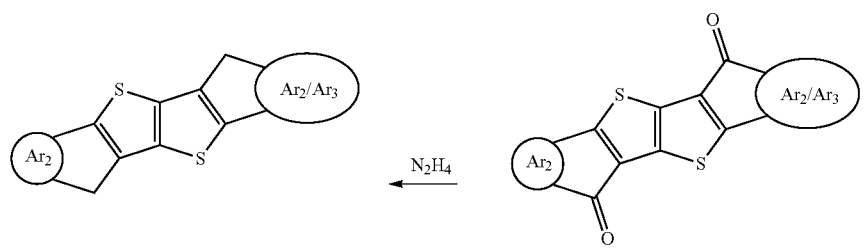
↓ AlCl₃
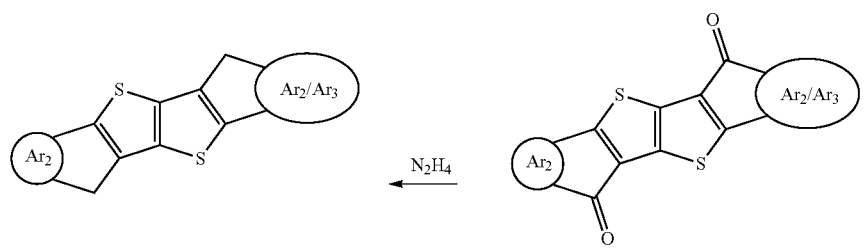
← N₂H₄
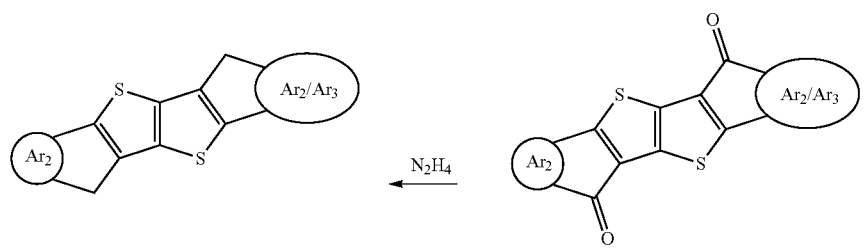
↓ RBr | base
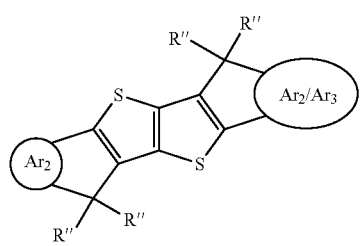
Scheme 1b
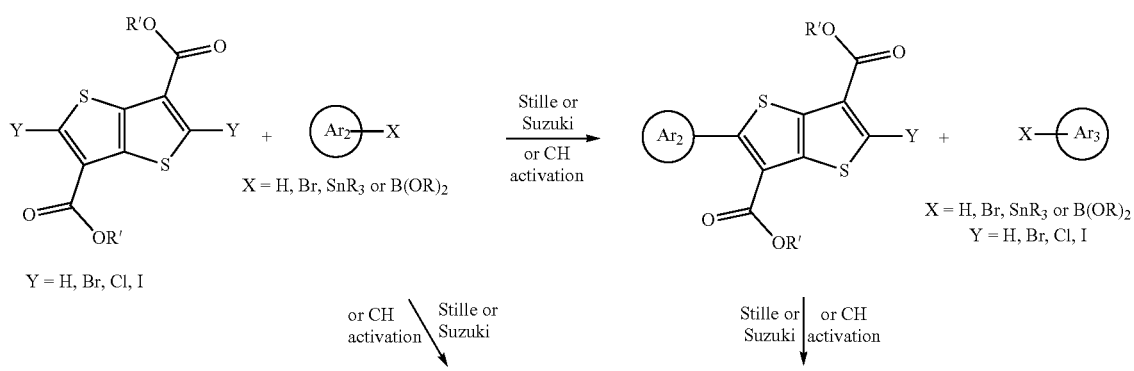

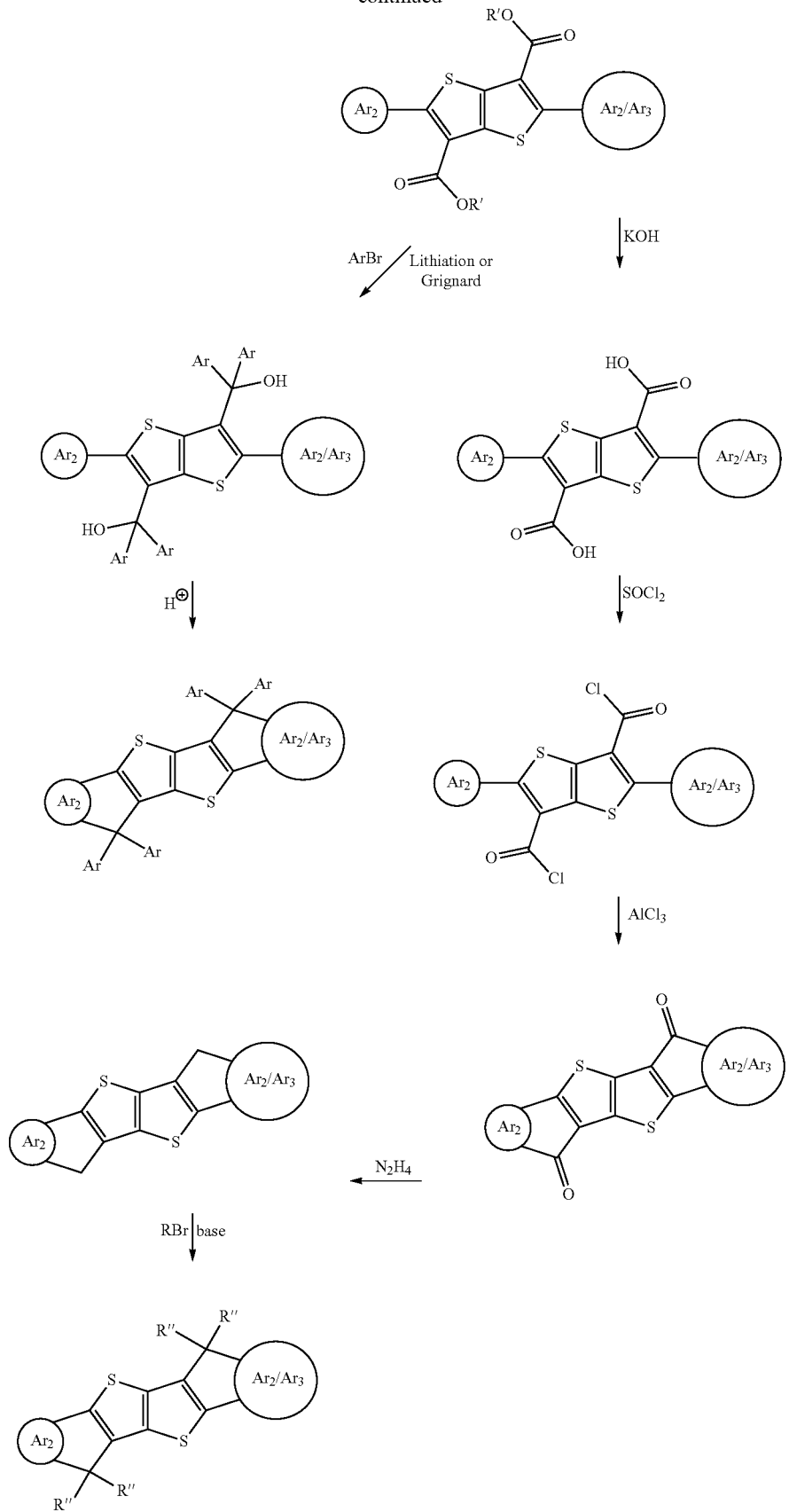

Scheme 2
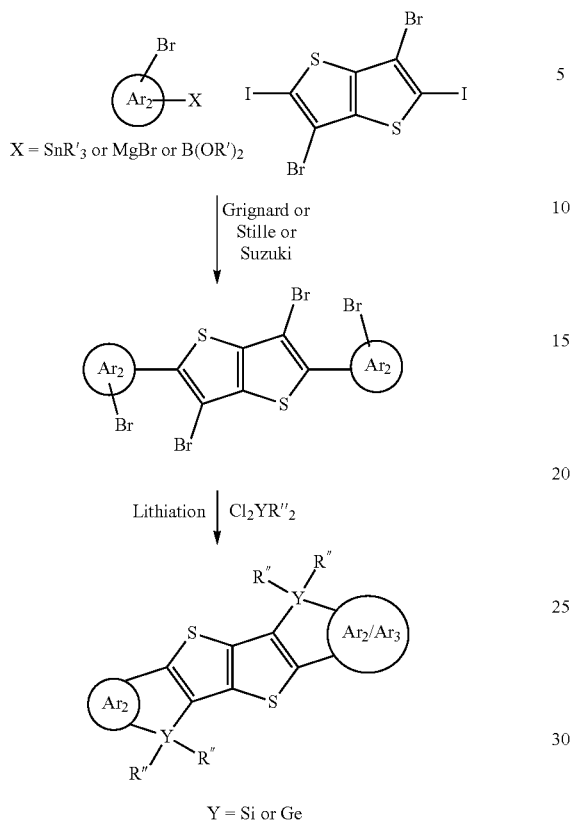
Scheme 3
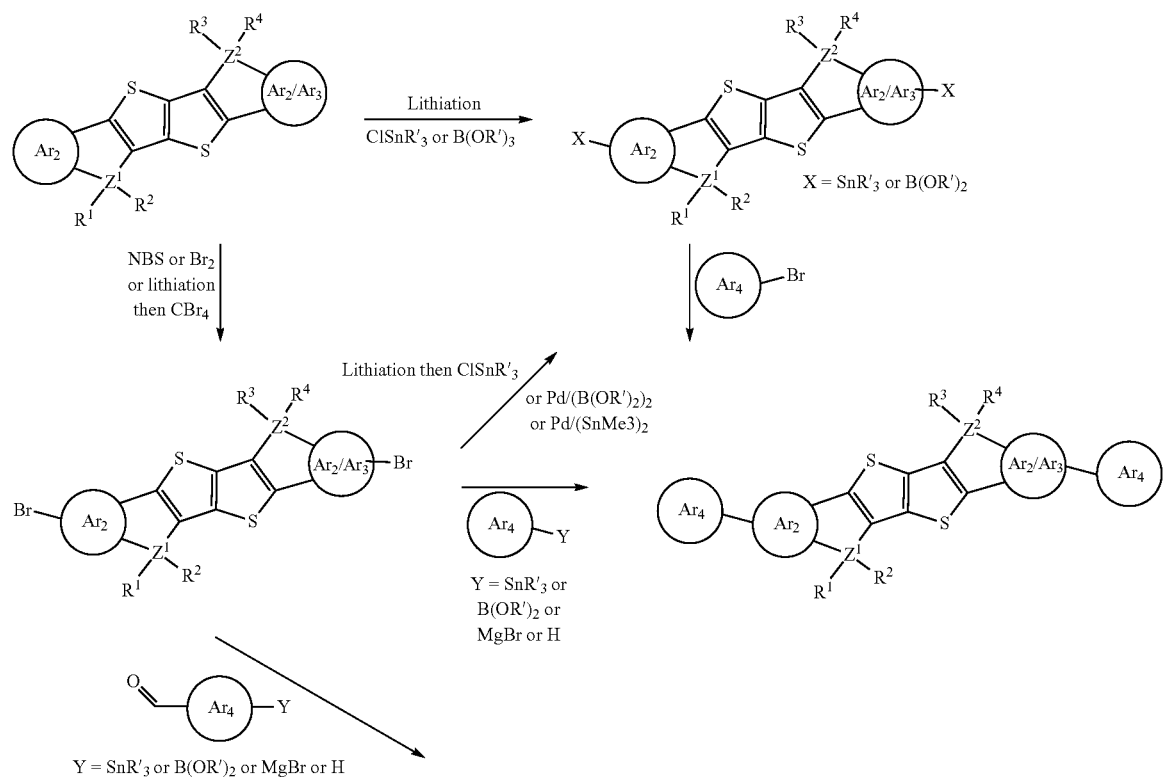

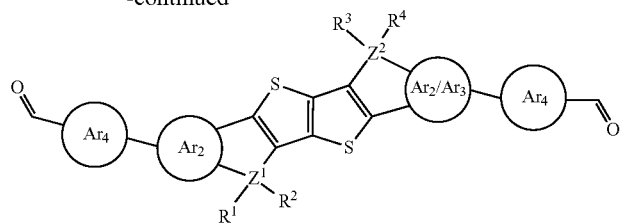
Scheme 4
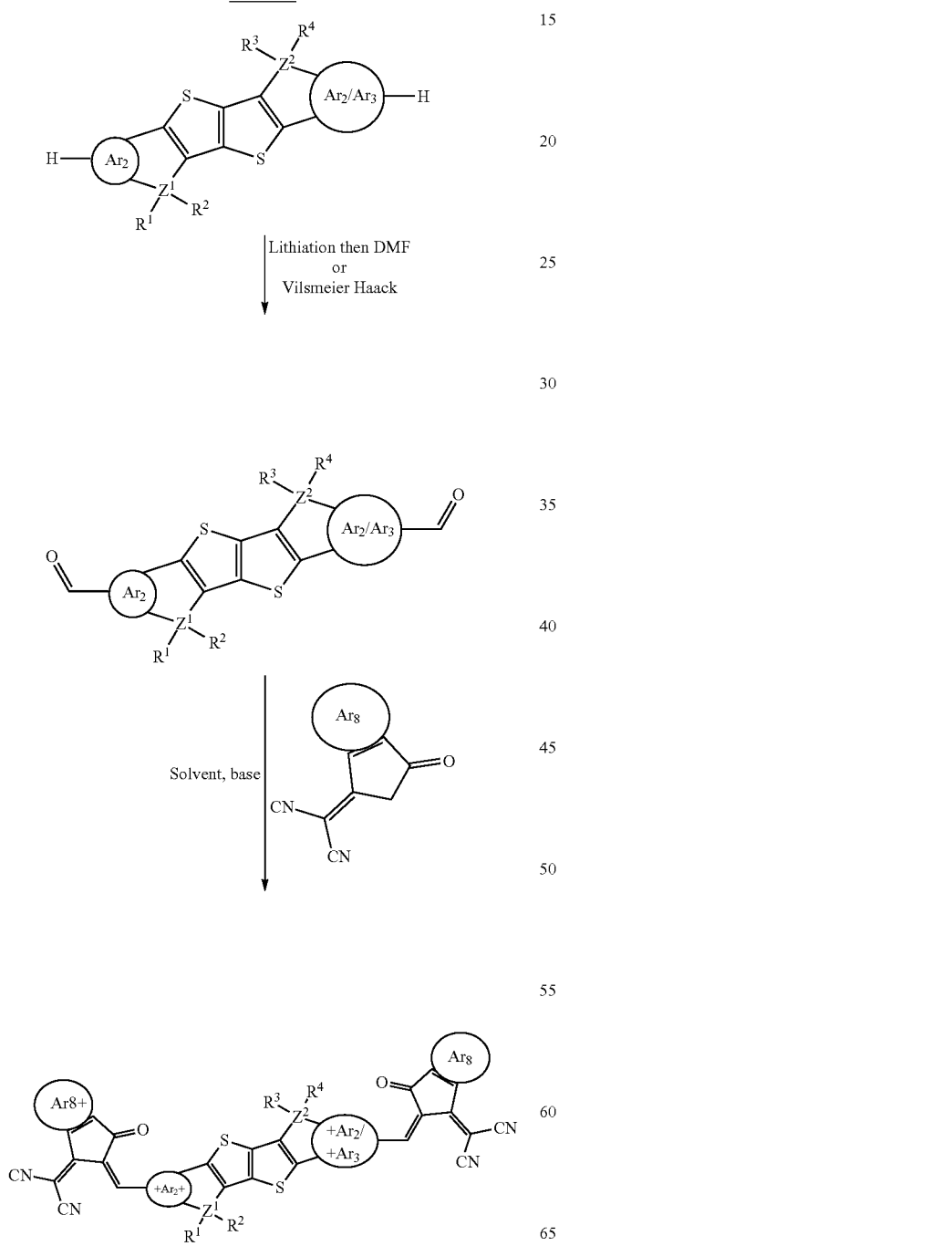

Scheme 5

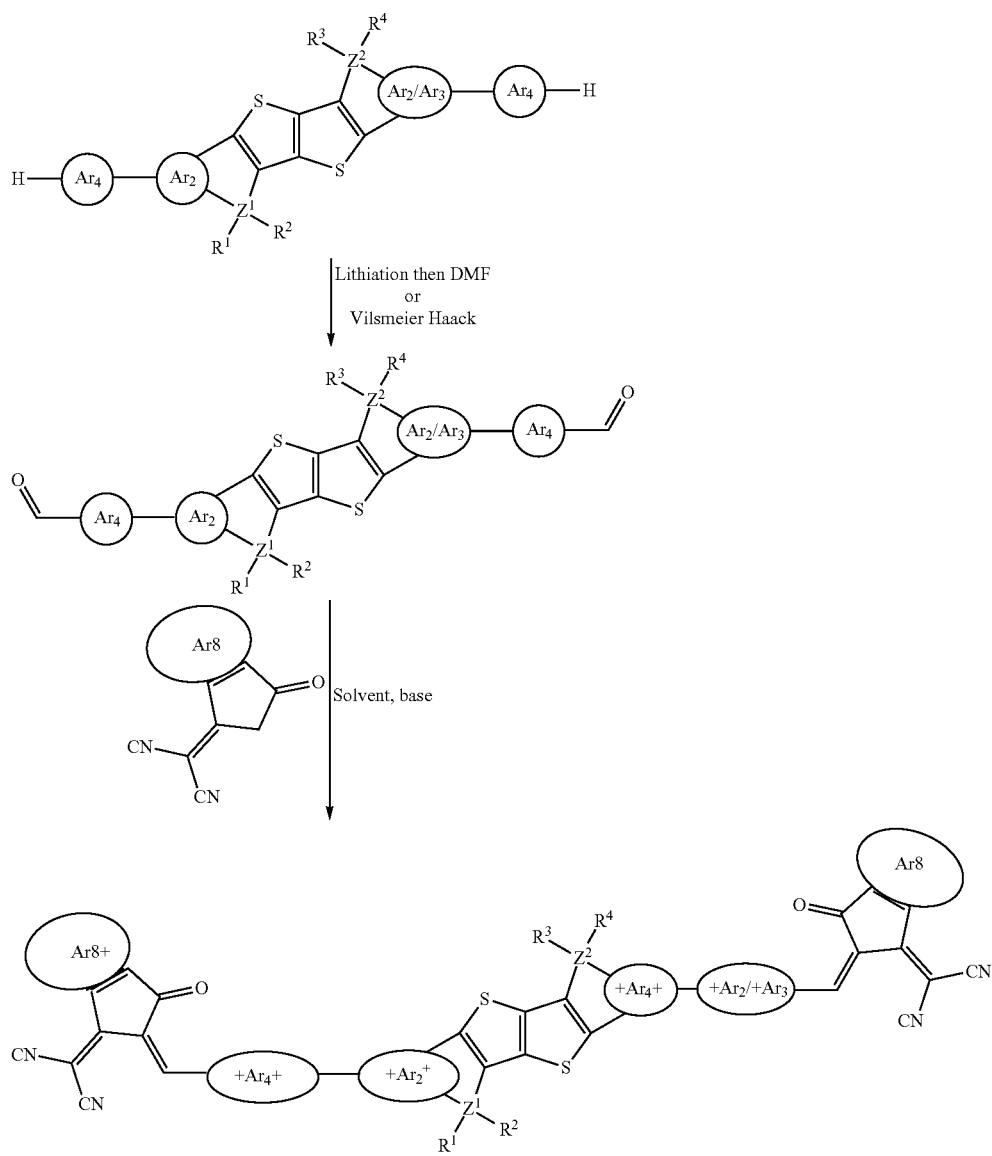

Novel methods of preparing compounds of formula I are another aspect of the invention.

The compound according to the present invention can also be used in compositions, for example together with monomeric or polymeric compounds having charge-transport, semiconducting, electrically conducting, photoconducting and/or light emitting semiconducting properties, or for example with compounds having hole blocking or electron blocking properties for use as interlayers or charge blocking layers in PSCs or OLEDs.

Thus, another aspect of the invention relates to a composition comprising one or more compounds according to the present invention and one or more small molecule compounds and/or polymers having one or more of a charge-transport, semiconducting, electrically conducting, photoconducting, hole blocking and electron blocking property.

The invention further relates to a composition comprising one or more compounds according to the present invention, and further comprising one or more p-type organic semiconductors, preferably selected from conjugated polymers.

The invention further relates to a composition comprising a first n-type semiconductor which is a compound according to the present invention, a second n-type semiconductor, which is preferably a fullerene or fullerene derivative, a non-fullerene acceptor small molecule, or an n-type conjugated polymer, and a p-type semiconductor, which is preferably a conjugated polymer.

In a preferred embodiment the second n-type OSC compound is a non-fullerene acceptor (NFA) small molecule having an A-D-A structure as described above with an electron donating polycyclic core and two terminal electron withdrawing groups attached thereto.

Suitable and preferred NFA small molecules for use as second n-type OSC in this preferred embodiment are for example those disclosed in Y. Lin et al., *Adv. Mater.*, 2015, 27, 1170; H. Lin et al., *Adv. Mater.*, 2015, 27, 7299; N. Qiu et al., *Adv. Mater.*, 2017, 29, 1604964; CN104557968 A and CN105315298 A, furthermore those disclosed in WO 2018/007479 A1.

In another preferred embodiment the second n-type OSC compound is a fullerene or substituted fullerene.

The fullerene is for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. *Chem. Mater.* 2004, 16, 4533).

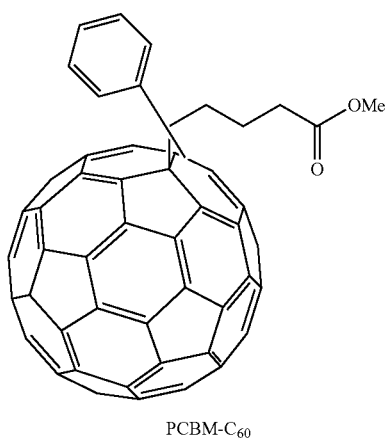

PCBM-$C_{60}$

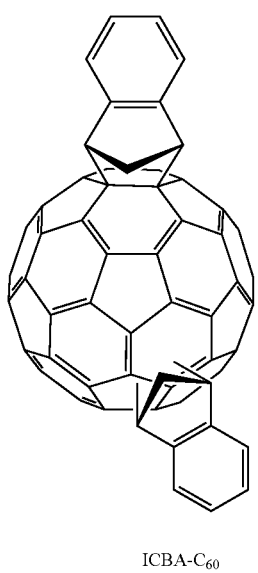

ICBA-$C_{60}$

Preferably the compound according to the present invention is blended with an n-type semiconductor such as a fullerene or substituted fullerene of formula Full-I to form the active layer in an OPV or OPD device,

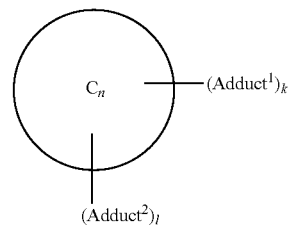

Full-I wherein $C_n$ denotes a fullerene composed of n carbon atoms, optionally with one or more atoms trapped inside, Adduct$^1$ is a primary adduct appended to the fullerene $C_n$ with any connectivity, Adduct$^2$ is a secondary adduct, or a combination of secondary adducts, appended to the fullerene $C_n$ with any connectivity, k is an integer $\geq 1$, and l is 0, an integer 1, or a non-integer >0.

In the formula Full-I and its subformulae, k preferably denotes 1, 2, 3 or, 4, very preferably 1 or 2.

The fullerene $C_n$ in formula Full-I and its subformulae may be composed of any number n of carbon atoms Preferably, in the compounds of formula XII and its subformulae the number of carbon atoms n of which the fullerene $C_n$ is composed is 60, 70, 76, 78, 82, 84, 90, 94 or 96, very preferably 60 or 70.

The fullerene $C_n$ in formula Full-I and its subformulae is preferably selected from carbon based fullerenes, endohedral fullerenes, or mixtures thereof, very preferably from carbon based fullerenes.

Suitable and preferred carbon based fullerenes include, without limitation, ($C_{60-Ih}$) [5,6]fullerene, ($C_{70-D5h}$) [5,6]fullerene, ($C_{76-D2}$*) [5,6]fullerene, ($C_{84-D2}$*) [5,6]fullerene, ($C_{84-D2d}$) [5,6]fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, Sc$_3$N@$C_{80}$, Y$_3$N@$C_{80}$, Sc$_3$C$_2$@$C_{80}$ or a mixture of two or more of the aforementioned metallofullerenes.

Preferably the fullerene $C_n$ is substituted at a [6,6] and/or [5,6] bond, preferably substituted on at least one [6,6] bond.

Primary and secondary adducts, named "Adduct1" and "Adduct 2" in formula Full-I and its subformulae, are each preferably selected from the following formulae

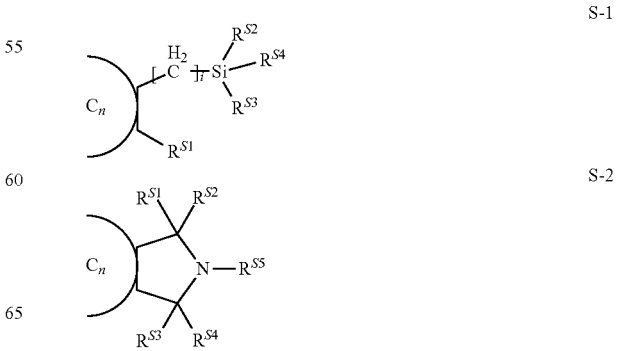

-continued

S-3 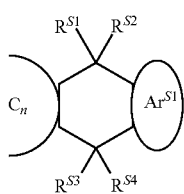

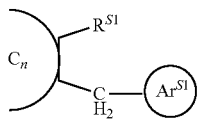 S-11

S-4 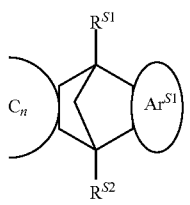

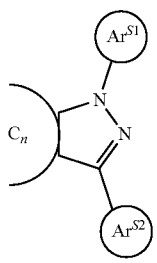 S-12

S-4 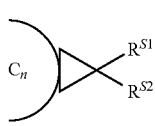

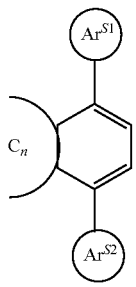 S-13

S-5 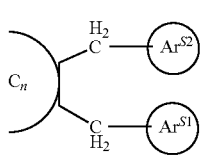

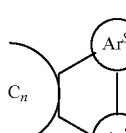

S-6 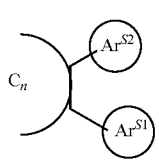

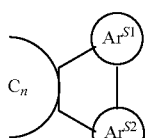 S-14

S-7 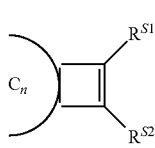

wherein $Ar^{S1}$, $Ar^{S2}$ denote, independently of each other, an aryl or heteroaryl group with 5 to 20, preferably 5 to 15, ring atoms, which is mono- or polycyclic, and which is optionally substituted by one or more identical or different substituents having one of the meanings of L as defined above and below, $R^{S1}$, $R^{S2}$, $R^{S3}$, $R^{S4}$ and $R^{S5}$ independently of each other denote H, CN or have one of the meanings of L as defined above and below, and i is an integer from 1 to 20, preferably from 1 to 12.

Preferred compounds of formula Full-I are selected from the following subformulae:

S-8 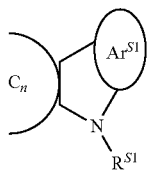

S-9 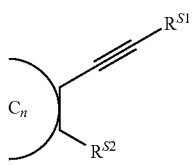

S-10 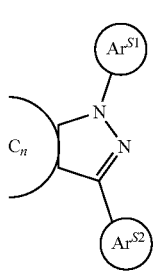

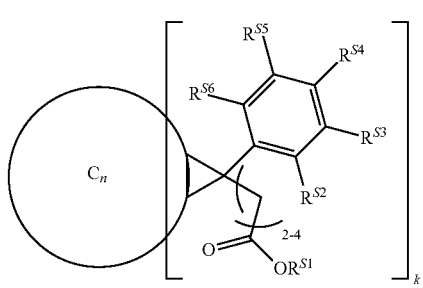 Full-Ia

-continued

Full-Ib

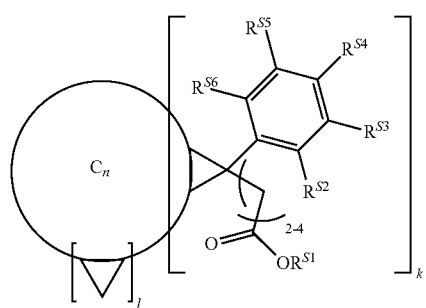

Full-Ic

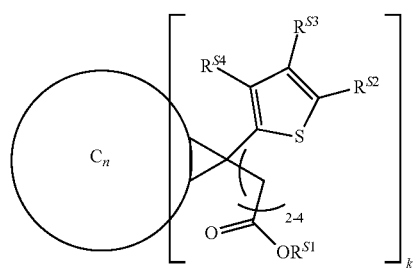

Full-Id

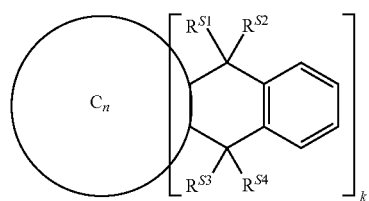

Full-Ie

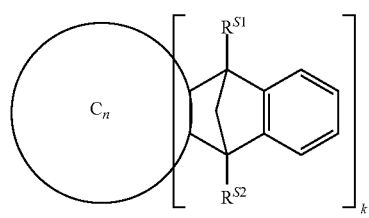

Full-If

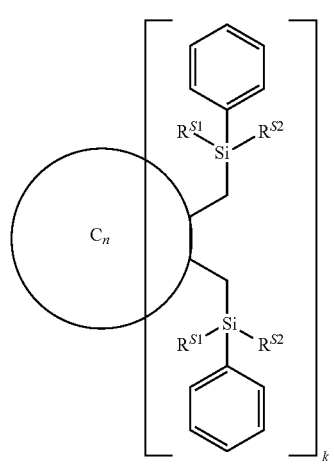

-continued

Full-Ig

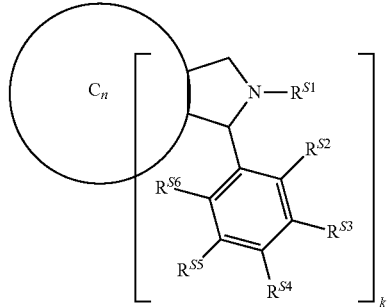

Full-Ih

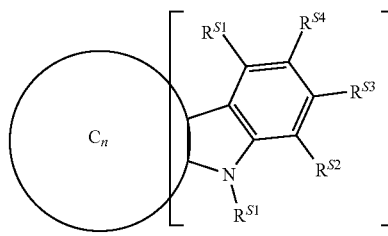

wherein $R^{S1}$, $R^{S2}$, $R^{S3}$, $R^{S4}$, $R^{S5}$ and $R^{S6}$ independently of each other denote H or have one of the meanings of $R^S$ as defined above and below.

Most preferably the fullerene is PCBM-C60, PCBM-C70, bis-PCBM-C60, bis-PCBM-C70, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-Ih), or bis-oQDM-C60.

In another preferred embodiment the second n-type OSC compound is a small molecule which does not contain a fullerene moiety, and which is selected from naphthalene or perylene carboximide derivatives.

Preferred naphthalene or perylene carboximide derivatives for use as n-type OSC compounds are described for example in *Adv. Sci.* 2016, 3, 1600117, *Adv. Mater.* 2016, 28, 8546-8551, *J. Am. Chem. Soc.*, 2016, 138, 7248-7251 and *J. Mater. Chem. A,* 2016, 4, 17604.

Preferred n-type OSC compounds of this preferred embodiment are selected from the following formulae
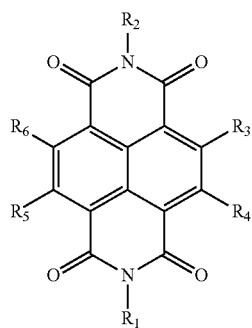
NDI1
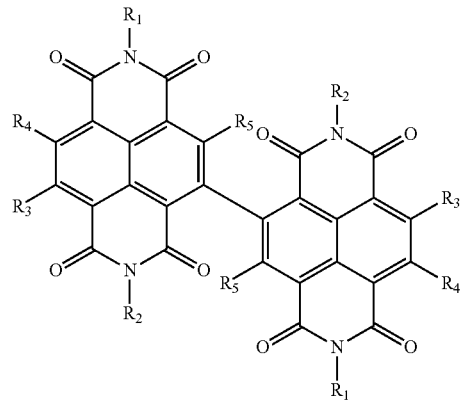
NDI2
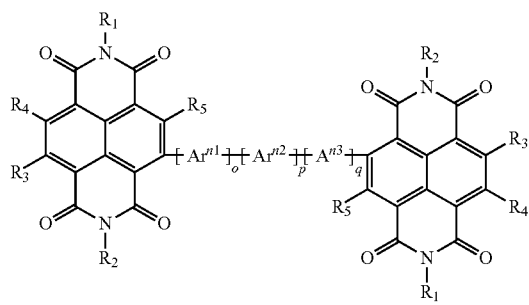
NDI3
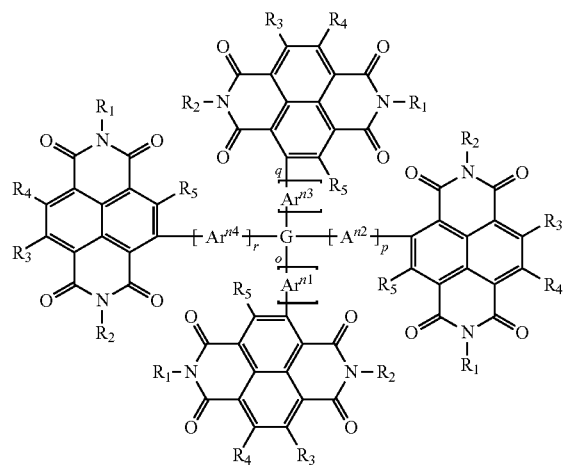
NDI4
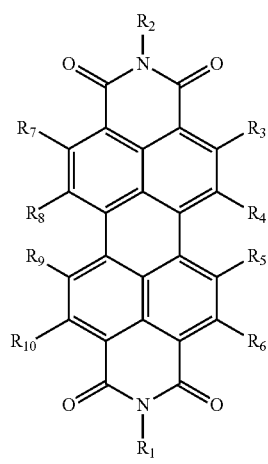
PDI1
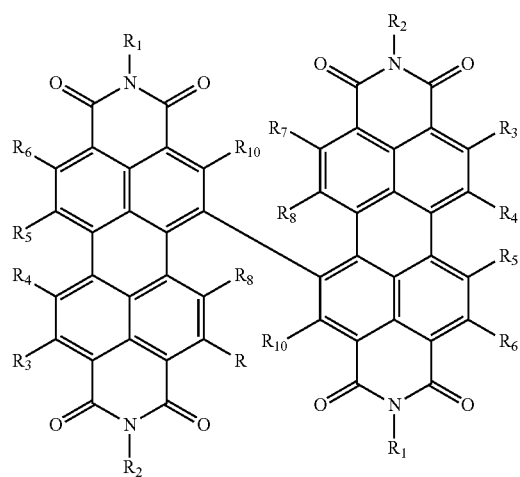
PDI2

-continued
PDI3
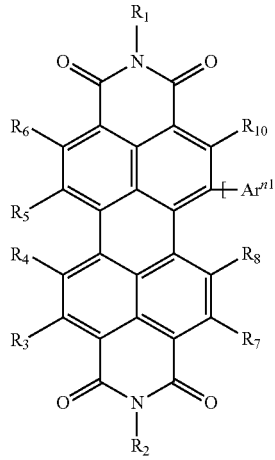
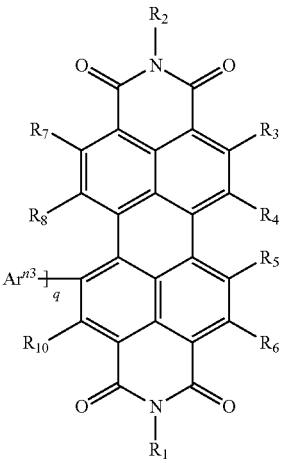
PDI4
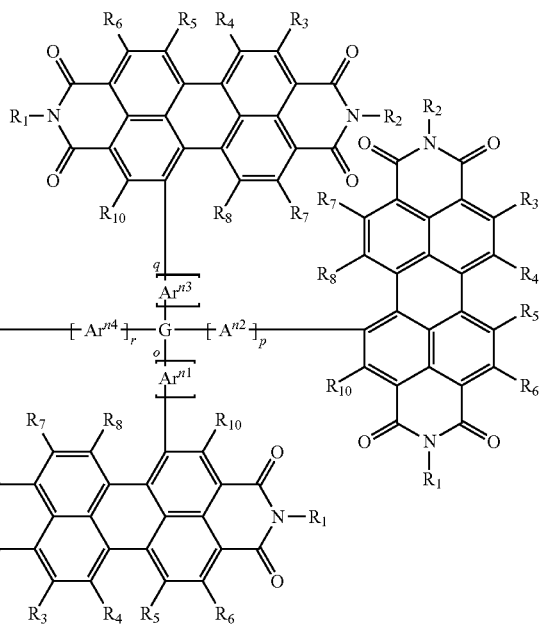
PDI5
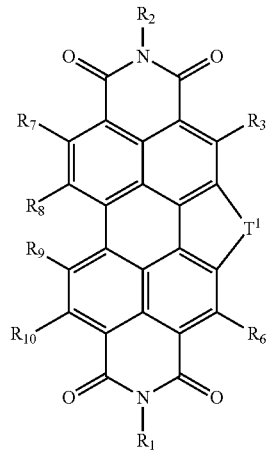
PDI6
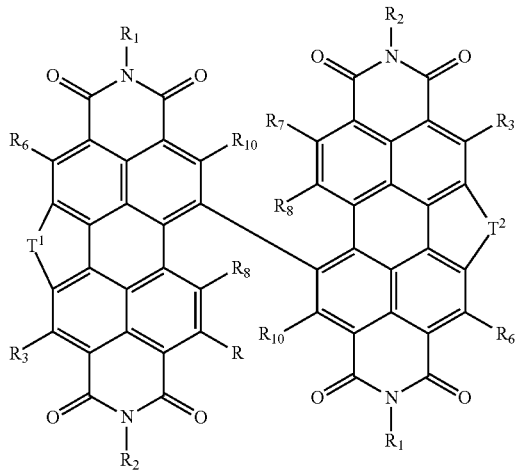

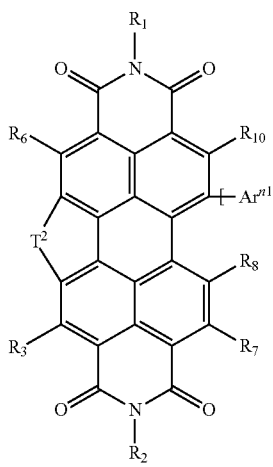
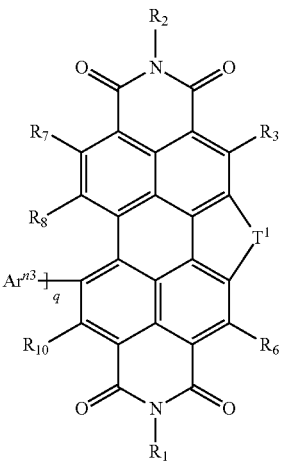
PDI7
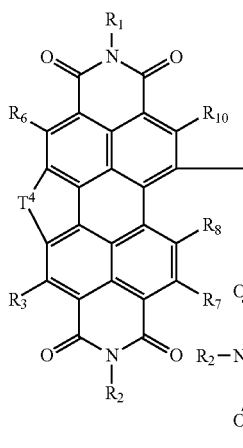
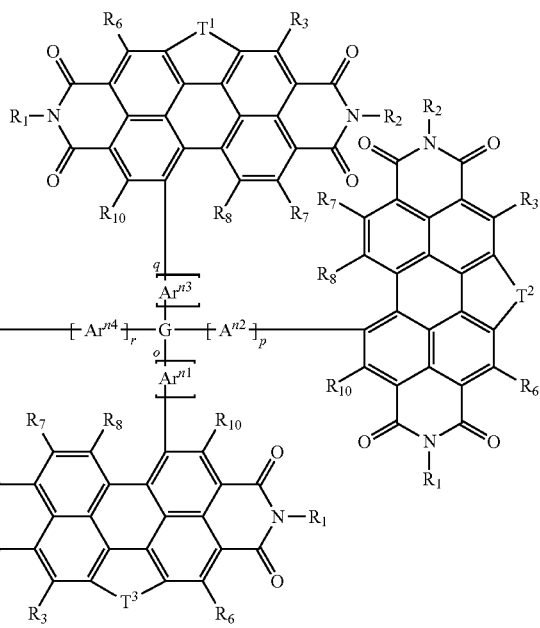
PDI8
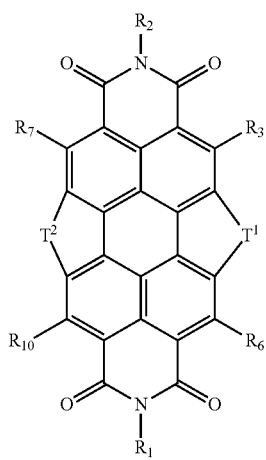
PDI9 wherein the individual radicals, independently of each other and on each occurrence identically or differently, have the following meanings $R^{1-10}$ $R^W$, H, F, Cl, or straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^o$—, —$SiR^oR^{oo}$—, —$CF_2$—, —$CR^o$=$CR^{oo}$—, —$CY^1$=$CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups $L^S$, $R^W$ an electron withdrawing group, preferably having one of the preferred meanings as given above for $R^{T1}$, very preferably CN, $Y^1$, $Y^2$ H, F, Cl or CN, $L^S$ F, Cl, —$NO_2$, —CN, —NC, —NCO, —NCS, —OCN, —SCN, $R^o$, $OR^o$, $SR^o$, —C(=O)$X^o$, —C(=O)$R^o$, —C(=O)—$OR^o$, —O—C(=O)—$R^o$, —$NH_2$, —$NHR^o$, —$NR^oR^{oo}$, —C(=O)$NHR^o$, —C(=O)$NR^oR^{oo}$, —$SO_3R^o$, —$SO_2R^o$, —OH, —$NO_2$, —$CF_3$, —$SF_5$, or optionally substituted silyl, or carbyl or hydrocarbyl with 1 to 30, preferably 1 to 20 C atoms that is optionally substituted and optionally comprises one or more hetero atoms, preferably F, —CN, $R^o$, —$OR^o$, —$SR^o$, —C(=O)—$R^o$, —C(=O)—$OR^o$, —O—C(=O)—$R^o$, —O—C(=O)—$OR^o$, —C(=O)—$NHR^o$, or —C(=O)—$NR^oR^{oo}$, $T^{1-4}$ —O—, —S—, —C(=O)—, —C(=S)—, —$CR^oR^{oo}$—, —$SiR^oR^{oo}$—, —$NR^o$—, —$CR^o$=$CR^{oo}$— or —C≡C—, G C, Si, Ge, C=C or a four-valent aryl or heteroaryl group that has from 5 to 20 ring atoms, is mono- or polycyclic, optionally contains fused rings, and is unsubstituted or substituted by one or more identical or different groups $R^1$ or $L^S$, $Ar^{n1-n4}$ independently of each other, and on each occurrence identically or differently arylene or heteroarylene that has from 5 to 20 ring atoms, is mono- or polycyclic, optionally contains fused rings, and is unsubstituted or substituted by one or more identical or different groups $R^1$ or $L^S$, or $CY^1$=$CY^2$ or —C≡C—, o, p, q, r 0 or an integer from 1 to 10.

In another preferred embodiment the second n-type OSC compound is a conjugated OSC polymer. Preferred n-type OSC polymers are described, for example, in Acc. Chem. Res., 2016, 49 (11), pp 2424-2434 and WO 2013/142841 A1.

Preferred n-type conjugated OSC polymers for use as second n-type OSC compound in this preferred embodiment comprise one or more units derived from perylene or naphthalene are poly[[N,N'-bis(2-octyldodecyl)naphthalene-1,4,5,8-bis(dicarboximide)-2,6-diyl]-alt-5,5'-(2,2'-bithiophene)], poly[[N,N'-bis(2-hexyldecyl)naphthalene-1,4,5,8-bis(dicarboximide)-2,6-diyl]-alt-5,5'-thiophene].

The composition according to the present invention can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more compounds according to the present invention or compositions as described above and below and one or more organic solvents.

Preferred solvents are aliphatic hydrocarbons, chlorinated hydrocarbons, aromatic hydrocarbons, ketones, ethers and mixtures thereof. Further suitable and preferred solvents used include 1,2,4-trimethylbenzene, 1,2,3,4-tetra-methyl benzene, pentylbenzene, mesitylene, cumene, cymene, cyclohexylbenzene, diethylbenzene, tetralin, indane, 1,5-dimethyltetraline, decalin, 1-methylnaphthalene, 2,6-lutidine, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoromethylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene, a mixture of o-, m-, and p-xylene, 2-fluoro-m-xylene, 3-fluoro-o-xylene, tetrahydrofuran, morpholine, 1,4-dioxane, 2-methylthiophene, 3-methylthiophene, chloroform, 1,2-dichloroethane, dichloromethane, carbon tetrachloride, 1,2-dichloroethane, 1,1,1-trichloroethane, 1,1,2,2-tetrachloroethane, acetone, methylethylketone, propiophenone, acetophenone, cyclohexanone, ethyl acetate, n-butyl acetate, ethyl benzoate, ethyl benzoate, dimethylacetamide, dimethylsulfoxide, or mixtures of the aforementioned. Solvents with relatively low polarity are generally preferred.

Examples of especially preferred solvents include, without limitation, dichloromethane, trichloromethane, chlorobenzene, o-dichlorobenzene, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetralin, 2-methylthiophene, 3-methylthiophene, decaline, indane, methyl benzoate, ethyl benzoate, mesitylene, or mixtures thereof.

The concentration of the compounds or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers and compounds of the present invention, although it is desirable to have at least one true solvent in a blend.

The compositions and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

In a composition according to the present invention comprising a compound according to the present invention, and a polymer, the ratio compound:polymer is preferably from 5:1 to 1:5 by weight, more preferably from 3:1 to 1:3 by weight, most preferably 2:1 to 1:2 by weight.

The composition according to the present invention may also comprise a polymeric binder, preferably from 0.001 to 95% by weight. Examples of binder include polystyrene (PS), polydimethylsilane (PDMS), polypropylene (PP) and polymethylmethacrylate (PMMA).

A binder to be used in the formulation as described before, which is preferably a polymer, may comprise either an insulating binder or a semiconducting binder, or mixtures thereof, may be referred to herein as the organic binder, the polymeric binder or simply the binder.

Preferably, the polymeric binder comprises a weight average molecular weight in the range of 1,000 to 5,000,000 g/mol, especially 1,500 to 1,000,000 g/mol and more preferable 2,000 to 500,000 g/mol. Surprising effects can be achieved with polymers having a weight average molecular weight of at least 10,000 g/mol, more preferably at least 100,000 g/mol.

In particular, the polymer can have a polydispersity index $M_w/M_n$ in the range of 1.0 to 10.0, more preferably in the range of 1.1 to 5.0 and most preferably in the range of 1.2 to 3.

Preferably, the inert binder is a polymer having a glass transition temperature in the range of −70 to 160° C., preferably 0 to 150° C., more preferably 50 to 140° C. and most preferably 70 to 130° C. The glass transition temperature can be determined by measuring the DSC of the polymer (DIN EN ISO 11357, heating rate 10° C. per minute).

The weight ratio of the polymeric binder to the compound according to the present invention is preferably in the range of 30:1 to 1:30, particularly in the range of 5:1 to 1:20 and more preferably in the range of 1:2 to 1:10.

According to a preferred embodiment the binder preferably comprises repeating units derived from styrene monomers and/or olefin monomers. Preferred polymeric binders can comprise at least 80%, preferably 90% and more preferably 99% by weight of repeating units derived from styrene monomers and/or olefins.

Styrene monomers are well known in the art. These monomers include styrene, substituted styrenes with an alkyl substituent in the side chain, such as α-methylstyrene and a-ethylstyrene, substituted styrenes with an alkyl substituent on the ring such as vinyltoluene and p-methylstyrene, halogenated styrenes such as monochlorostyrenes, dichlorostyrenes, tribromostyrenes and tetrabromostyrenes.

Olefin monomers consist of hydrogen and carbon atoms. These monomers include ethylene, propylene, butylenes, isoprene and 1,3-butadiene.

According to a preferred embodiment of the present invention, the polymeric binder is polystyrene having a weight average molecular weight in the range of 50,000 to 2,000,000 g/mol, preferably 100,000 to 750,000 g/mol, more preferably in the range of 150,000 to 600,000 g/mol and most preferably in the range of 200,000 to 500,000 g/mol.

Further examples of suitable binders are disclosed for example in US 2007/0102696 A1. Especially suitable and preferred binders are described in the following.

The binder should preferably be capable of forming a film, more preferably a flexible film.

Suitable polymers as binders include poly(1,3-butadiene), polyphenylene, polystyrene, poly(α-methylstyrene), poly(α-vinylnaphtalene), poly(vinyltoluene), polyethylene, cis-polybutadiene, polypropylene, polyisoprene, poly(4-methyl-1-pentene), poly (4-methylstyrene), poly(chorotrifluoroethylene), poly(2-methyl-1,3-butadiene), poly(p-xylylene), poly(α-α-α'-α' tetrafluoro-p-xylylene), poly[1,1-(2-methyl propane)bis(4-phenyl)carbonate], poly(cyclohexyl methacrylate), poly(chlorostyrene), poly(2,6-dimethyl-1,4-phenylene ether), polyisobutylene, poly(vinyl cyclohexane), poly(vinylcinnamate), poly(4-vinylbiphenyl), 1,4-polyisoprene, polynorbornene, poly(styrene-block-butadiene); 31% wt styrene, poly(styrene-block-butadiene-block-styrene); 30% wt styrene, poly(styrene-co-maleic anhydride) (and ethylene/butylene) 1-1.7% maleic anhydride, poly(styrene-block-ethylene/butylene-block-styrene) triblock polymer 13% styrene, poly(styrene-block-ethylene-propylene-block-styrene) triblock polymer 37% wt styrene, poly(styrene-block-ethylene/butylene-block-styrene) triblock polymer 29% wt styrene, poly(1-vinylnaphthalene), poly(1-vinylpyrrolidone-co-styrene) 64% styrene, poly(1-vinylpyrrolidone-co-vinyl acetate) 1.3:1, poly(2-chlorostyrene), poly(2-vinylnaphthalene), poly(2-vinylpyridine-co-styrene) 1:1, poly(4,5-Difluoro-2,2-bis(CF3)-1,3-dioxole-co-tetrafluoroethylene) Teflon, poly(4-chlorostyrene), poly(4-methyl-1-pentene), poly(4-methylstyrene), poly(4-vinylpyridine-co-styrene) 1:1, poly(alpha-methylstyrene), poly(butadiene-graft-poly(methyl acrylate-co-acrylonitrile)) 1:1:1, poly(butyl methacrylate-co-isobutyl methacrylate) 1:1, poly(butyl methacrylate-co-methyl methacrylate) 1:1, poly(cyclohexylmethacrylate), poly(ethylene-co-1-butene-co-1-hexene) 1:1:1, poly(ethylene-co-ethylacrylate-co-maleic anhydride); 2% anhydride, 32% ethyl acrylate, poly(ethylene-co-glycidyl methacrylate) 8% glycidyl methacrylate, poly(ethylene-co-methyl acrylate-co-glycidyl meth-acrylate) 8% glycidyl metha-crylate 25% methyl acrylate, poly(ethylene-co-octene) 1:1, poly(ethylene-co-propylene-co-5-methylene-2-norbornene) 50% ethylene, poly(ethylene-co-tetrafluoroethylene) 1:1, poly(isobutyl methacrylate), poly(isobutylene), poly(methyl methacrylate)-co-(fluorescein O-methacrylate) 80% methyl methacrylate, poly(methyl methacrylate-co-butyl methacrylate) 85% methyl methacrylate, poly(methyl methacrylate-co-ethyl acrylate) 5% ethyl acrylate, poly(propylene-co-butene) 12% 1-butene, poly(styrene-co-allyl alcohol) 40% allyl alcohol, poly(styrene-co-maleic anhydride) 7% maleic anhydride, poly(styrene-co-maleic anhydride) cumene terminated (1.3:1), poly(styrene-co-methyl methacrylate) 40% styrene, poly(vinyltoluene-co-alpha-methylstyrene) 1:1, poly-2-vinylpyridine, poly-4-vinylpyridine, poly-alpha-pinene, polymethylmethacrylate, polybenzylmethacrylate, polyethylmethacrylate, polyethylene, polyethylene terephthalate, polyethylene-co-ethylacrylate 18% ethyl acrylate, polyethylene-co-vinylacetate 12% vinyl acetate, polyethylene-graft-maleic anhydride 0.5% maleic anhydride, polypropylene, polypropylene-graft-maleic anhydride 8-10% maleic anhydride, polystyrene poly(styrene-block-ethylene/butylene-block-styrene) graft maleic anhydride 2% maleic anhydride 1:1:1 others, poly(styrene-block-butadiene) branched 1:1, poly(styrene-block-butadiene-block-styrene), 30% styrene, poly(styrene-block-isoprene) 10% wt styrene, poly(styrene-block-isoprene-block-styrene) 17% wt styrene, poly(styrene-co-4-chloromethylstyrene-co-4-methoxymethylstyrene 2:1:1, polystyrene-co-acrylonitrile 25% acrylonitrile, polystyrene-co-alpha-methylstyrene 1:1, polystyrene-co-butadiene 4% butadiene, polystyrene-co-butadiene 45% styrene, polystyrene-co-chloromethylstyrene 1:1, polyvinylchloride, polyvinylcinnamate, polyvinylcyclohexane, polyvinylidenefluoride, polyvinylidenefluoride-co-hexafluoropropylene assume 1:1, poly(styrene-block-ethylene/propylene-block-styrene) 30% styrene, poly(styrene-block-ethylene/propylene-block-styrene) 18% styrene, poly(styrene-block-ethylene/propylene-block-styrene) 13% styrene, poly(styrene-block ethylene block-ethylene/propylene-block styrene) 32% styrene, poly(styrene-block ethylene block-ethylene/propylene-block styrene) 30% styrene, poly(styrene-block-ethylene/butylene-block-styrene) 31 styrene, poly(styrene-block-ethylene/butylene-block-styrene) 34% styrene, poly(styrene-block-ethylene/butylene-block-styrene) 30% styrene, poly(styrene-block-ethylene/butylene-block-styrene) 60%, styrene, branched or non-branched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders to be used in the formulations as described before are polystryrene, poly(α-methylstyrene), polyvinylcinnamate, poly(4-vinylbiphenyl), poly(4-methylstyrene), and polymethyl methacrylate. Most preferred insulating binders are polystyrene and polymethyl methacrylate.

The binder can also be selected from crosslinkable binders, like e.g. acrylates, epoxies, vinylethers, thiolenes etc. The binder can also be mesogenic or liquid crystalline.

The organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility of at least $10^{-5}$ cm$^2$V$^{-1}$s$^{-1}$, more preferably at least $10^{-4}$ cm$^2$V$^{-1}$s$^{-1}$.

A preferred semiconducting binder comprises a homopolymer or copolymer (including block-copolymer) containing arylamine (preferably triarylamine).

The compounds and compositions according to the present invention are useful as charge transport, semiconducting, electrically conducting, photoconducting or light emitting materials in optical, electronic, optoelectronic, electroluminescent or photoluminescent components or devices. In these devices, the compounds and compositions of the present invention are typically applied as thin layers or films.

Thus, the present invention also provides the use of the compound or composition or layer in an electronic device.

The compound or composition may be used as a high mobility semiconducting material in various devices and apparatus. The compound or composition may be used, for example, in the form of a semiconducting layer or film. Accordingly, in another aspect, the present invention provides a semiconducting layer for use in an electronic device, the layer comprising a compound or composition according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The compounds according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a compound according to the present invention can be carried out for example by photolithography, electron beam lithography or laser patterning.

For use as thin layers in electronic or optoelectronic devices the compounds, compositions or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

For the fabrication of OPV devices and modules area printing method compatible with flexible substrates are preferred, for example slot dye coating, spray coating and the like.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent.

Suitable solvents should be selected to ensure full dissolution of all components, like p-type and n-type OSCs, and take into account the boundary conditions (for example rheological properties) introduced by the chosen printing method. For inkjet printing solvents and solvent mixtures with high boiling temperatures are preferred. For spin coating alkylated benzenes like xylene and toluene are preferred.

Apart from the requirements stated above the solvents should not have any detrimental effect on the chosen print head. Additionally, the solvents should preferably have boiling points >100° C., preferably >140° C. and more preferably >150° C. in order to prevent operability problems caused by the solution drying out inside the print head.

Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, and diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The invention additionally provides an OE device comprising a compound or composition or organic semiconducting layer according to the present invention.

Preferred OE devices are OFETs, TFTs, ICs, logic circuits, capacitors, RFID tags, OLEDs, OLETs, OPEDs, OPVs, PSCs, OPDs, solar cells, laser diodes, photoconductors, photodetectors, electrophotographic devices, electrophotographic recording devices, organic memory devices, sensor devices, charge injection layers, Schottky diodes, planarizing layers, antistatic films, conducting substrates and conducting patterns.

Very preferred OE devices are OPV, PSC and OPD devices, OFETs, and OLEDs, in particular OPD, PSC and bulk heterojunction (BHJ) OPV devices. In an OFET, for example, the active semiconductor channel between the drain and source may comprise the compound or composition of the invention. As another example, in an OLED device, the charge (hole or electron) injection or transport layer may comprise the compound or composition of the invention.

An OPV or OPD device according to the present invention preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an insulating polymer, like for example nafion, polyethyleneimine or polystyrene-sulphonate, an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammoniumhexyl)thiophene], or poly [(9,9-bis(3'-(N,N-dimethylamino)propyl)-2,7-fluorene)-alt-2,7-(9,9-dioctylfluorene)] or an organic compound, like for example tris(8-quinolinolato)-aluminum(III) ($Alq_3$), 4,7-diphenyl-1,10-phenanthroline.

The OPV device can for example be of any type known from the literature (see e.g. Waldauf et al., *Appl. Phys. Lett.,* 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode,
  an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1, 1'biphenyl-4,4'-diamine) or NBD (N,N'-dyphenyl-N—N'-bis(1-napthylphenyl)-1,1'biphenyl-4,4'-diamine),
  a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF or PFN,
  a low work function electrode, preferably comprising a metal like for example aluminum, serving as cathode,
  wherein at least one of the electrodes, preferably the anode, is transparent to visible light, and
  wherein the n-type semiconductor is a compound according to the present invention.

A second preferred OPV device according to the invention is an inverted OPV device and comprises the following layers (in the sequence from bottom to top):
  optionally a substrate,
  a high work function metal or metal oxide electrode, comprising for example ITO, serving as cathode,
  a layer having hole blocking properties, preferably comprising an organic polymer, polymer blend, metal or metal oxide like $TiO_x$, $ZnO_x$, Ca, Mg, poly(ethyleneimine), poly(ethyleneimine) ethoxylated or poly [(9,9-bis(3'-(N,N-dimethylamino)propyl)-2,7-fluorene)-alt-2,7-(9,9-dioctylfluorene)],
  a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic polymer or polymer blend, metal or metal oxide, for example PEDOT:PSS, nafion, a substituted triaryl amine derivative like for example TBD or NBD, or $WO_x$, $MoO_x$, $NiO_x$, Pd or Au, an electrode comprising a high work function metal like for example silver, serving as anode,
    wherein at least one of the electrodes, preferably the cathode, is transparent to visible light, and
    wherein the n-type semiconductor is a compound according to the present invention.

In the OPV devices of the present invention the p-type and n-type semiconductor materials are preferably selected from the materials, like the compound/polymer/fullerene systems, as described above.

When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater*, 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

Another preferred embodiment of the present invention relates to the use of a compound or composition according to the present invention as dye, hole transport layer, hole blocking layer, electron transport layer and/or electron blocking layer in a DSSC or a perovskite-based solar cell (PSC), and to a DSSC or PSC comprising a compound or composition according to the present invention.

DSSCs and PSCs can be manufactured as described in the literature, for example in Chem. Rev. 2010, 110, 6595-6663, Angew. Chem. Int. Ed. 2014, 53, 2-15 or in WO2013171520A1

A preferred OE device according to the invention is a solar cell, preferably a PSC, comprising a light absorber which is at least in part inorganic as described below.

In a solar cell comprising the light absorber according to the invention there are no restrictions per se with respect to the choice of the light absorber material which is at least in part inorganic.

The term "at least in part inorganic" means that the light absorber material may be selected from metalorganic complexes or materials which are substantially inorganic and possess preferably a crystalline structure where single positions in the crystalline structure may be allocated by organic ions.

Preferably, the light absorber comprised in the solar cell according to the invention has an optical band-gap $\leq 2.8$ eV and $\geq 0.8$ eV.

Very preferably, the light absorber in the solar cell according to the invention has an optical band-gap $\leq 2.2$ eV and $\geq 1.0$ eV.

The light absorber used in the solar cell according to the invention does preferably not contain a fullerene. The chemistry of fullerenes belongs to the field of organic chemistry. Therefore fullerenes do not fulfil the definition of being "at least in part inorganic" according to the invention.

Preferably, the light absorber which is at least in part inorganic is a material having perovskite structure or a material having 2D crystalline perovskite structure.

The term "perovskite" as used above and below denotes generally a material having a perovskite crystalline structure or a 2D crystalline perovskite structure.

The term perovskite solar cell (PSC) means a solar cell comprising a light absorber which is a material having perovskite structure or a material having 2D crystalline perovskite structure.

The light absorber which is at least in part inorganic is without limitation composed of a material having perovskite crystalline structure, a material having 2D crystalline perovskite structure (e.g. CrystEngComm, 2010,12, 2646-2662), $Sb_2S_3$ (stibnite), $Sb_2(S_xSe_{(x-1)})_3$, $PbS_xSe_{(x-1)}$, $CdS_xSe_{(x-1)}$, ZnTe, CdTe, $ZnS_xSe_{(x-1)}$, InP, FeS, $FeS_2$, $Fe_2S_3$, $Fe_2SiS_4$, $Fe_2GeS_4$, $Cu_2S$, CuInGa, $CuIn(Se_xS_{(1-x)})_2$, $Cu_3Sb_xBi_{(x-1)}$, $(S_ySe_{(y-1)})_3$, $Cu_2SnS_3$, $SnS_xSe_{(x-1)}$, $Ag_2S$, $AgBiS_2$, BiSI, BiSeI, $Bi_2(S_xSe_{(x-1)})_3$, $BiS_{(1-x)}Se_xI$, $WSe_2$, AlSb, metal halides (e.g. $BiI_3$, $Cs_2SnI_6$), chalcopyrite (e.g. $CuIn_xGa_{(1-x)}(S_ySe_{(1-y)})_2$), kesterite (e.g. $Cu_2ZnSnS_4$, $Cu_2ZnSn(Se_xS_{(1-x)})_4$, $Cu_2Zn(Sn_{1-x}Ge_x)S_4$) and metal oxide (e.g. CuO, $Cu_2O$) or a mixture thereof.

Preferably, the light absorber which is at least in part inorganic is a perovskite.

In the above definition for light absorber, x and y are each independently defined as follows: ($0 \leq x \leq 1$) and ($0 \leq y \leq 1$).

Very preferably, the light absorber is a special perovskite namely a metal halide perovskite as described in detail above and below. Most preferably, the light absorber is an organic-inorganic hybrid metal halide perovskite contained in the perovskite solar cell (PSC).

In one particularly preferred embodiment of the invention, the perovskite denotes a metal halide perovskite with the formula $ABX_3$, where A is a monovalent organic cation, a metal cation or a mixture of two or more of these cations B is a divalent cation and X is F, Cl, Br, I, $BF_4$ or a combination thereof.

Preferably, the monovalent organic cation of the perovskite is selected from alkylammonium, wherein the alkyl group is straight chain or branched having 1 to 6 C atoms, formamidinium or guanidinium or wherein the metal cation is selected from $K^+$, $Cs^+$ or $Rb^+$.

Suitable and preferred divalent cations B are $Ge^{2+}$, $Sn^{2+}$ or $Pb^{2+}$.

Suitable and preferred perovskite materials are $CsSnI_3$, $CH_3NH_3Pb(I_{1-x}Cl_x)_3$, $CH_3NH_3PbI_3$, $CH_3NH_3Pb(I_{1-x}Br_x)_3$, $CH_3NH_3Pb(I_{1-x}(BF_4)_x)_3$, $CH_3NH_3Sn(I_{1-x}Cl_x)_3$, $CH_3NH_3SnI_3$ or $CH_3NH_3Sn(I_{1-x}Br_x)_3$ wherein x is each independently defined as follows: ($0<x \leq 1$).

Further suitable and preferred perovskites may comprise two halides corresponding to formula $Xa_{(3-x)}Xb_{(x)}$, wherein Xa and Xb are each independently selected from Cl, Br, or I, and x is greater than 0 and less than 3.

Suitable and preferred perovskites are also disclosed in WO 2013/171517, claims 52 to 71 and claims 72 to 79, which is entirely incorporated herein by reference. The materials are defined as mixed-anion perovskites comprising two or more different anions selected from halide anions and chalcogenide anions. Preferred perovskites are disclosed on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The invention further relates to a solar cell comprising the light absorber, preferably a PSC, as described above and below, wherein the compound according to the present invention is employed as a layer between one electrode and the light absorber layer.

The invention further relates to a solar cell comprising the light absorber, preferably a PSC, as described above and below, wherein the compound according to the present invention is comprised in an electron-selective layer.

The electron selective layer is defined as a layer providing a high electron conductivity and a low hole conductivity favoring electron-charge transport.

The invention further relates to a solar cell comprising the light absorber, preferably a PSC, as described above and below, wherein the compound according to the present invention is employed as electron transport material (ETM) or as hole blocking material as part of the electron selective layer.

Preferably, the compound according to the present invention is employed as electron transport material (ETM).

In an alternative preferred embodiment, the compound according to the present invention is employed as hole blocking material.

The device architecture of a PSC device according to the invention can be of any type known from the literature.

A first preferred device architecture of a PSC device according to the invention comprises the following layers (in the sequence from bottom to top):
  optionally a substrate which, in any combination, can be flexible or rigid and transparent, semi-transparent or non-transparent and electrically conductive or non-conductive;
  a high work function electrode, preferably comprising a doped metal oxide, for example fluorine-doped tin oxide (FTO), tin-doped indium oxide (ITO), or aluminum-doped zinc oxide;
  an electron-selective layer which comprises one or more electron-transporting materials, at least one of which is a compound according to the present invention, and which, in some cases, can also be a dense layer and/or be composed of nanoparticles, and which preferably comprises a metal oxide such as $TiO_2$, $ZnO_2$, $SnO_2$, $Y_2O_5$, $Ga_2O_3$, $SrTiO_3$, $BaTiO_3$ or combinations thereof;
  optionally a porous scaffold which can be conducting, semi-conducting or insulating, and which preferably comprises a metal oxide such as $TiO_2$, $ZnO_2$, $SnO_2$, $Y_2O_5$, $Ga_2O_3$, $SrTiO_3$, $BaTiO_3$, $Al_2O_3$, $ZrO_2$, $SiO_2$ or combinations thereof, and which is preferably composed of nanoparticles, nanorods, nanoflakes, nanotubes or nanocolumns;
  a layer comprising a light absorber which is at least in part inorganic, particularly preferably a metal halide perovskite as described above which, in some cases, can also be a dense or porous layer and which optionally partly or fully infiltrates into the underlying layer;
  optionally a hole selective layer, which comprises one or more hole-transporting materials, and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;
  and a back electrode which can be metallic, for example made of Au, Ag, Al, Cu, Ca, Ni or combinations thereof, or non-metallic and transparent, semi-transparent or non-transparent.

A second preferred device architecture of a PSC device according to the invention comprises the following layers (in the sequence from bottom to top):
  optionally a substrate which, in any combination, can be flexible or rigid and transparent, semi-transparent or non-transparent and electrically conductive or non-conductive;
  a high work function electrode, preferably comprising a doped metal oxide, for example fluorine-doped tin oxide (FTO), tin-doped indium oxide (ITO), or aluminum-doped zinc oxide;
  optionally a hole injection layer which, for example, changes the work function of the underlying electrode, and/or modifies the surface of the underlying layer and/or helps to planarize the rough surface of the underlying layer and which, in some cases, can also be a monolayer;
  optionally a hole selective layer, which comprises one or more hole-transporting materials and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;
  a layer comprising a light absorber which is at least in part inorganic, particularly preferably a metal halide perovskite as described or preferably described above;
  an electron-selective layer, which comprises one or more electron-transporting materials, at least one of which is a compound according to the present invention and which, in some cases, can also be a dense layer and/or be composed of nanoparticles, and which, for example, can comprise a metal oxide such as $TiO_2$, $ZnO_2$, $SnO_2$, $Y_2O_5$, $Ga_2O_3$, $SrTiO_3$, $BaTiO_3$ or combinations thereof, and/or which can comprise a substituted fullerene, for example [6,6]-phenyl C61-butyric acid methyl ester, and/or which can comprise a molecular, oligomeric or polymeric electron-transport material, for example 2,9-Dimethyl-4,7-diphenyl-1,10-phenanthroline, or a mixture thereof;
  and a back electrode which can be metallic, for example made of Au, Ag, Al, Cu, Ca, Ni or combinations thereof, or non-metallic and transparent, semi-transparent or non-transparent.

To produce electron selective layers in PSC devices according to the invention, the compounds according to the present invention, optionally together with other compounds or additives in the form of blends or mixtures, may be deposited by any suitable method. Liquid coating of devices is more desirable than vacuum deposition techniques. Solution deposition methods are especially preferred. Formulations comprising the compounds according to the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot die coating or pad printing. For the fabrication of PSC devices and modules, deposition techniques for large area coating are preferred, for example slot die coating or spray coating.

Formulations that can be used to produce electron selective layers in optoelectronic devices according to the invention, preferably in PSC devices comprise one or more compounds according to the present invention or preferred embodiments as described above in the form of blends or mixtures optionally together with one or more further electron transport materials and/or hole blocking materials and/or binders and/or other additives as described above and below, and one or more solvents.

The formulation may include or comprise, essentially consist of or consist of the said necessary or optional constituents as described above or below. All compounds or components which can be used in the formulations are either known or commercially available, or can be synthesized by known processes.

The formulation as described before may be prepared by a process which comprises:
(i) first mixing a compound according to the present invention, optionally a binder or a precursor of a binder as described before, optionally a further electron transport material, optionally one or more further additives as described above and below and a solvent or solvent mixture as described above and below and
(ii) applying such mixture to a substrate; and optionally evaporating the solvent(s) to form an electron selective layer according to the present invention.

In step (i) the solvent may be a single solvent for the compound according to the present invention and the organic binder and/or further electron transport material may each be dissolved in a separate solvent followed by mixing the resultant solutions to mix the compounds.

Alternatively, the binder may be formed in situ by mixing or dissolving a compound according to the present invention in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound in a suitable solvent as described before, and the solution deposited for example by dipping, spraying, painting or printing it on a substrate to form a liquid layer and then removing the solvent to leave a solid layer. It will be appreciated that solvents are chosen which are able to dissolve all ingredients of the formulation, and which upon evaporation from the solution blend give a coherent defect free layer.

Besides the said components, the formulation as described before may comprise further additives and processing assistants. These include, inter alia, surface-active substances (surfactants), lubricants and greases, additives which modify the viscosity, additives which increase the conductivity, dispersants, hydrophobicizing agents, adhesion promoters, flow improvers, antifoams, deaerating agents, diluents, which may be reactive or unreactive, fillers, assistants, processing assistants, dyes, pigments, stabilizers, sensitizers, nanoparticles and inhibitors.

Additives can be used to enhance the properties of the electron selective layer and/or the properties of any of the neighbouring layers and/or the performance of the optoelectronic device according to the invention. Additives can also be used to facilitate the deposition, the processing or the formation of the electron selective layer and/or the deposition, the processing or the formation of any of the neighbouring layers. Preferably, one or more additives are used which enhance the electrical conductivity of the electron selective layer and/or passivate the surface of any of the neighbouring layers.

Suitable methods to incorporate one or more additives include, for example exposure to a vapor of the additive at atmospheric pressure or at reduced pressure, mixing a solution or solid containing one or more additives and a material or a formulation as described or preferably described before, bringing one or more additives into contact with a material or a formulation as described before, by thermal diffusion of one or more additives into a material or a formulation as described before, or by ion-implantation of one or more additives into a material or a formulation as described before.

Additives used for this purpose can be organic, inorganic, metallic or hybrid materials. Additives can be molecular compounds, for example organic molecules, salts, ionic liquids, coordination complexes or organometallic compounds, polymers or mixtures thereof. Additives can also be particles, for example hybrid or inorganic particles, preferably nanoparticles, or carbon based materials such as fullerenes, carbon nanotubes or graphene flakes.

Examples for additives that can enhance the electrical conductivity are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$), cations (e.g. $H^+$, $Li^+$, $Na^+$, $K^+$, $Rb^+$, $Cs^+$, $Co^{3+}$ and $Fe^{3+}$), $O_2$, redox active salts (e.g. $XeOF_4$, $(NO_2^+)(SbF_6^-)$, $(NO_2^+)(SbCl_6^-)$, $(NO_2^+)(BF_4^-)$, $NOBF_4$, $NOPF_6$, $AgClO_4$, $H_2IrCl_6$ and La$(NO_3)_3 \cdot 6H_2O$), strongly electron-accepting organic molecules (e.g. 2,3,5,6-tetrafluoro-7,7,8,8-tetracyanoquinodimethane (F4-TCNQ)), transition metal oxides (e.g. $WO_3$, $Re_2O_7$ and $MoO_3$), metal-organic complexes of cobalt, iron, bismuth and molybdenum, (p-$BrC_6H_4)_3NSbCl_6$, bismuth (III) tris(trifluoroacetate), $FSO_2OOSO_2F$, acetylcholine, $R_4N^+$, (R is an alkyl group), $R_4P^+$ (R is a straight-chain or branched alkyl group 1 to 20), $R_6As^+$ (R is an alkyl group), $R_3S^+$ (R is an alkyl group) and ionic liquids (e.g. 1-Ethyl-3-methylimidazolium bis(trifluoromethylsulfonyl)imide). Suitable cobalt complexes beside of tris(2-(1H-pyrazol-1-yl)-4-tert-butylpyridine)-cobalt(III) tris(bis(trifluoromethylsulfonyl)imide)) are cobalt complex salts as described in WO 2012/114315, WO 2012/114316, WO 2014/082706, WO 2014/082704, EP 2883881 or JP 2013-131477.

Suitable lithium salts are beside of lithium bis(trifluoromethylsulfonyl)imide, lithium tris(pentafluoroethyl)trifluorophosphate, lithium dicyanamide, lithium methylsulfate, lithium trifluormethanesulfonate, lithium tetracyanoborate, lithium dicyanamide, lithium tricyanomethide, lithium thiocyanate, lithium chloride, lithium bromide, lithium iodide, lithium hexafluorophosphate, lithium tetrafluoroborate, lithium perchlorate, lithium hexafluoroantimonate, lithium hexafluoroarsenate or a combination of two or more. A preferred lithium salt is lithium bis(trifluoromethylsulfonyl) imide.

Preferably, the formulation comprises from 0.1 mM to 50 mM, preferably from 5 to 20 mM of the lithium salt.

Suitable device structures for PSCs comprising a compound according to the present invention and a mixed halide perovskite are described in WO 2013/171517, claims 52 to 71 and claims 72 to 79, which is entirely incorporated herein by reference.

Suitable device structures for PSCs comprising a compound according to the present invention and a dielectric scaffold together with a perovskite are described in WO 2013/171518, claims 1 to 90 or WO 2013/171520, claims 1 to 94 which are entirely incorporated herein by reference.

Suitable device structures for PSCs comprising a compound according to the present invention, a semiconductor and a perovskite are described in WO 2014/020499, claims 1 and 3 to 14, which is entirely incorporated herein by reference The surface-increasing scaffold structure described therein comprises nanoparticles which are applied and/or fixed on a support layer, e.g. porous $TiO_2$.

Suitable device structures for PSCs comprising a compound according to the present invention and comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film.

The invention further relates to a method of preparing a PSC as described above or below, the method comprising the steps of:
providing a first and a second electrode;
providing an electron selective layer comprising a compound according to the present invention.

The invention relates furthermore to a tandem device comprising at least one device according to the invention as described above and below. Preferably, the tandem device is a tandem solar cell.

The tandem device or tandem solar cell according to the invention may have two semi-cells wherein one of the semi cells comprises the compounds, oligomers or polymers in the active layer as described or preferably described above. There exists no restriction for the choice of the other type of semi cell which may be any other type of device or solar cell known in the art.

There are two different types of tandem solar cells known in the art. The so called 2-terminal or monolithic tandem solar cells have only two connections. The two subcells (or synonymously semi cells) are connected in series. Therefore, the current generated in both subcells is identical (current matching). The gain in power conversion efficiency is due to an increase in voltage as the voltages of the two subcells add up. The other type of tandem solar cells is the so called 4-terminal or stacked tandem solar cell. In this case, both subcells are operated independently. Therefore, both subcells can be operated at different voltages and can also generate different currents. The power conversion efficiency of the tandem solar cell is the sum of the power conversion efficiencies of the two subcells.

The invention furthermore relates to a module comprising a device according to the invention as described before or preferably described before.

The compounds and compositions according to the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds and compositions of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound or a composition according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers,
optionally a substrate.
wherein the semiconductor layer preferably comprises a compound according to the present invention.

The OFET device can be a top gate device or a bottom gate device.

Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds and compositions (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidized and reduced form of the materials according to the present invention. Either loss or gain of electrons results in formation of a highly delocalized ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalized ionic centers in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$ $AgClO_4$, $H_2IrCl_6$, La$(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the materials according to the present invention can be used as an organic "metal" in applications including, but not limited to, charge injection layers and ITO planarizing layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarization charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

According to another use, the materials according to the present invention are suitable for use in liquid crystal (LC) windows, also known as smart windows, as described for example in US 2016/0108317 A1.

The materials according to the present invention may also be combined with photoisomerizable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.,* 1999, 96, 12287; D. Wang, X. Gong, P. S. Heeger, F. Rininsland, G. C. Bazan and A. J. Heeger, *Proc. Natl. Acad. Sci. U.S.A.,* 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius.

The invention will now be described in more detail by reference to the following examples, which are illustrative only and do not limit the scope of the invention.

Example 1

Intermediate 1

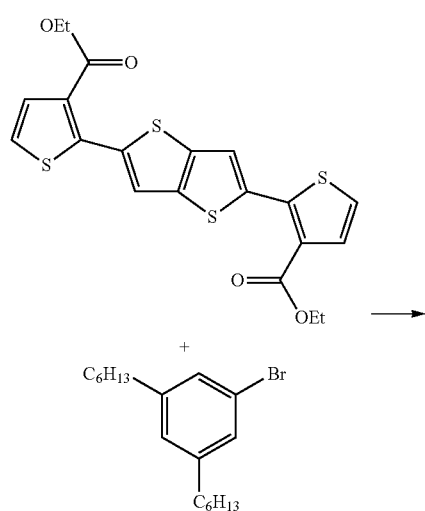

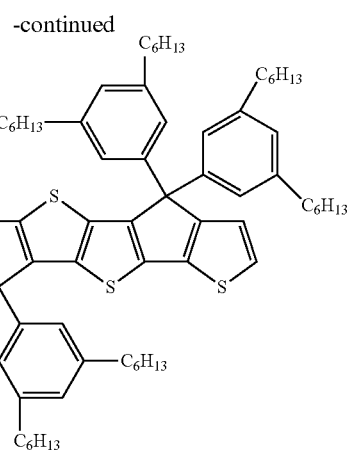

To a solution of 1-bromo-3,5-dihexyl-benzene (14.5 g, 44.6 mmol) in anhydrous tetrahydrofuran (60 cm$^3$) at −78° C. is added dropwise n-butyllithium (17.8 cm$^3$, 44.6 mmol, 2.5 M in hexane) over 10 minutes. The reaction is stirred for 2 hours and ethyl 2-[5-(3-ethoxycarbonyl-2-thienyl)thieno[3,2-b]thiophen-2-yl]thiophene-3-carboxylate (4.00 g, 8.92 mmol) added. The reaction is warmed to 23° C. and stirred for 17 hours. Water (100 cm$^3$) is added and the product extracted with ether (100 cm$^3$). The organic phase is washed with water (2×50 cm$^3$), dried over anhydrous magnesium sulfate, filtered and the solvent removed in vacuo. The crude is purified by flash chromatography (40-60 petrol then dichloromethane). The solid is suspended in toluene (40 cm$^3$), p-toluene sulphonic acid (2.0 g) added and the reaction mixture heated at 60° C. for 4 hours. The solid is collected by filtration, washed with toluene (50 cm$^3$) and purified by flash chromatography using a graded solvent system (40-60 petrol:dichloromethane; 1:0 to 19:1) to give intermediate 1 (2.50 g, 21%) as a pale brown oil. $^1$H NMR (400 MHz, CDCl$_3$) 7.07 (2H, d, J 4.9), 6.96 (2H, d, J 4.9), 6.78 (4H, d, J 1.6), 6.74 (8H, d, J 1.5), 2.40 (16H, t, J 8.0), 1.40-1.48 (16H, m), 1.10-1.26 (48H, m), 0.69-0.82 (24H, m).

Intermediate 2

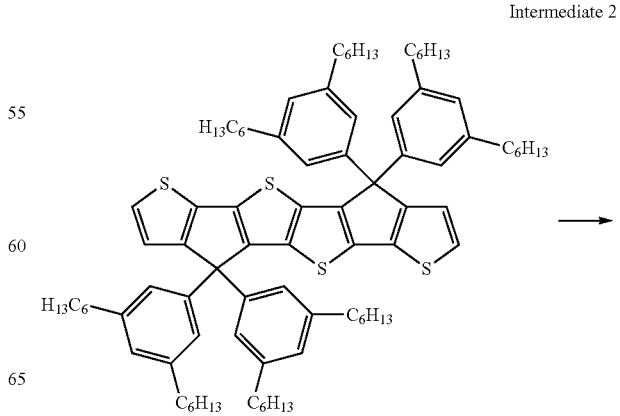

-continued

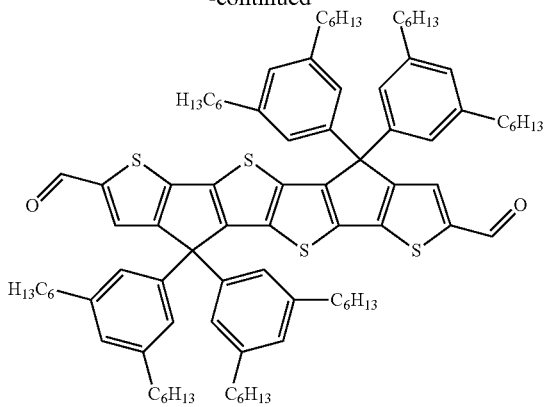

To intermediate 1 (0.50 g, 0.38 mmol), anhydrous N,N-dimethylformamide (0.40 cm$^3$, 5.2 mmol) and chloroform (20 cm$^3$) at 0° C. is added dropwise phosphorus oxychloride (0.47 cm$^3$, 5.0 mmol). The reaction is heated at 70° C. for 18 hours before cooling to 60° C. Saturated aqueous sodium acetate solution (7 cm$^3$) is added and the mixture stirred for 1 hour. The organic phase is separated and washed with water (20 cm$^3$), dried with anhydrous sodium sulphate, filtered and the solvent removed in vacuo. The solid is triturated in acetone (3×5 cm$^3$) and then collected by filtration to give intermediate 2 (400 mg, 76%) as a bright orange solid. $^1$H NMR (400 MHz, CD$_2$Cl$_2$) 9.78 (2H, s), 7.64 (2H, s), 6.90 (4H, d, J 1.6), 6.78 (8H, d, J 1.6), 2.46 (16H, d, J 7.9), 1.42-1.51 (16H, m), 1.17-1.28 (48H, m), 0.76-0.85 (24H, m).

Compound 1

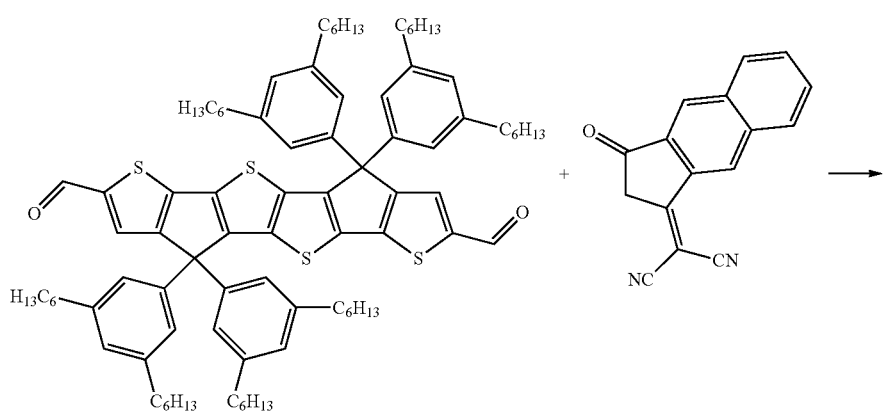

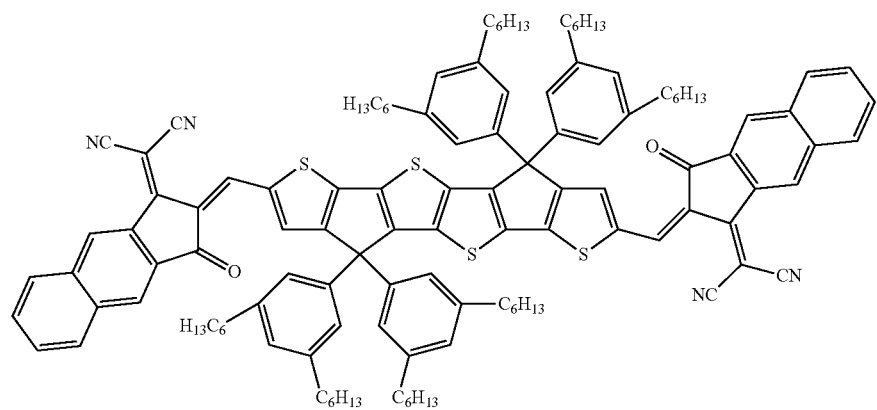

To a solution of intermediate 2 (150 mg, 0.11 mmol) in chloroform (15 cm³) is added 2-(3-oxo-2,3-dihydro-cyclopenta[b]naphthalen-1-ylidene)-malononitrile (188 mg, 0.77 mmol). The suspension is purged with nitrogen and pyridine (0.62 cm³) is added. The resulting mixture is stirred for 3 hours. The reaction is diluted with methanol (25 cm³), filtered and the solid washed with methanol (3×5 cm³). The crude is purified using column chromatography (40-60 petrol:dichloromethane; 1:3). The solid is dissolved in chloroform (4 cm³) at 70° C. before acetone (4 cm³) is added, the suspension cooled to 23° C., filtered and the solid washed with a solution of acetone/chloroform (1:1; 2×3 cm³) to afford compound 1 (60 mg, 30%) as a dark green solid. $^1$H NMR (400 MHz, CDCl$_3$) 9.19 (2H, s), 8.97 (2H, s), 8.36 (2H, s), 8.03-8.13 (4H, m), 7.66-7.77 (6H, m), 6.98 (4H, t, J 1.5), 6.83 (8H, d, J 1.5), 2.54 (16H, t, J 7.9), 1.50-1.61 (16H, m), 1.22-1.38 (48H, m), 0.86 (24H, d, J 12.9).

Example 2 chloride (1.5 cm³, 5.5 mmol) is added. The mixture is then allowed to warm to 23° C. over 72 hours and the solvent removed in vacuo. The crude is purified by passing through a zeolite plug (40-60 petrol) followed by trituration in ethanol (2×100 cm³) to give a mixture of intermediate 3 and tributyltin chloride (2.7 g) as a dark brown oil. $^1$H NMR (400 MHz, CD$_2$Cl$_2$) 6.99 (2H, s), 6.64-6.85 (12H, m), 2.38 (16H, t, J 7.7), 0.57-1.69 (98H, m).

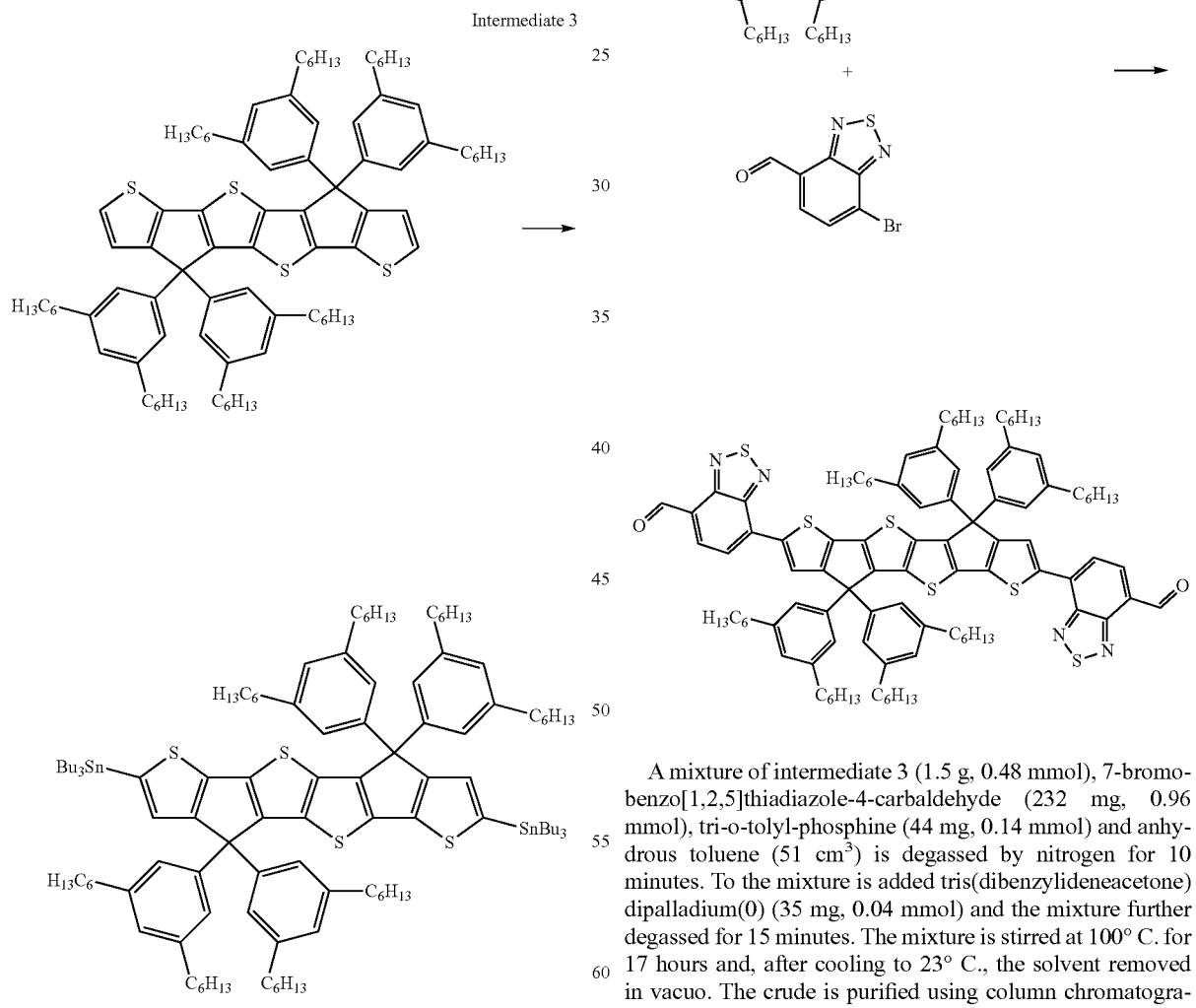

Intermediate 3

Intermediate 4

A mixture of intermediate 3 (1.5 g, 0.48 mmol), 7-bromo-benzo[1,2,5]thiadiazole-4-carbaldehyde (232 mg, 0.96 mmol), tri-o-tolyl-phosphine (44 mg, 0.14 mmol) and anhydrous toluene (51 cm³) is degassed by nitrogen for 10 minutes. To the mixture is added tris(dibenzylideneacetone)dipalladium(0) (35 mg, 0.04 mmol) and the mixture further degassed for 15 minutes. The mixture is stirred at 100° C. for 17 hours and, after cooling to 23° C., the solvent removed in vacuo. The crude is purified using column chromatography (40-60 petrol:dichloromethane; 7:3) to give intermediate 4 (650 mg, 84%) as a dark blue solid. $^1$H NMR (400 MHz, CDCl$_3$) 10.67-10.73 (2H, m), 8.34 (2H, s), 8.20 (2H, d, J 7.6), 7.93 (2H, d, J 7.6), 6.94 (12H, s), 2.54 (16H, t, J 7.7), 1.51-1.64 (16H, m), 1.20-1.36 (48H, m), 0.77-0.88 (24H, m).

To a solution of intermediate 1 (1.60 g, 1.2 mmol) in anhydrous tetrahydrofuran (47 cm³) at −78° C. is added dropwise n-butyllithium (1.96 cm³, 4.9 mmol, 2.5 M in hexane) over 20 minutes. After addition, the reaction mixture is stirred at −78° C. for 60 minutes and then tributyltin

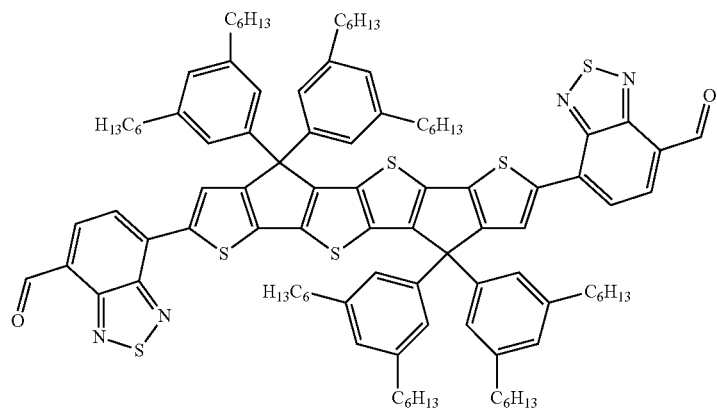

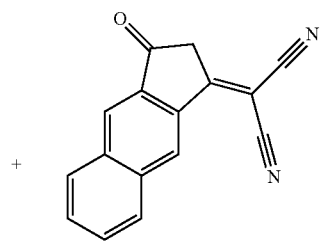

Compound 2

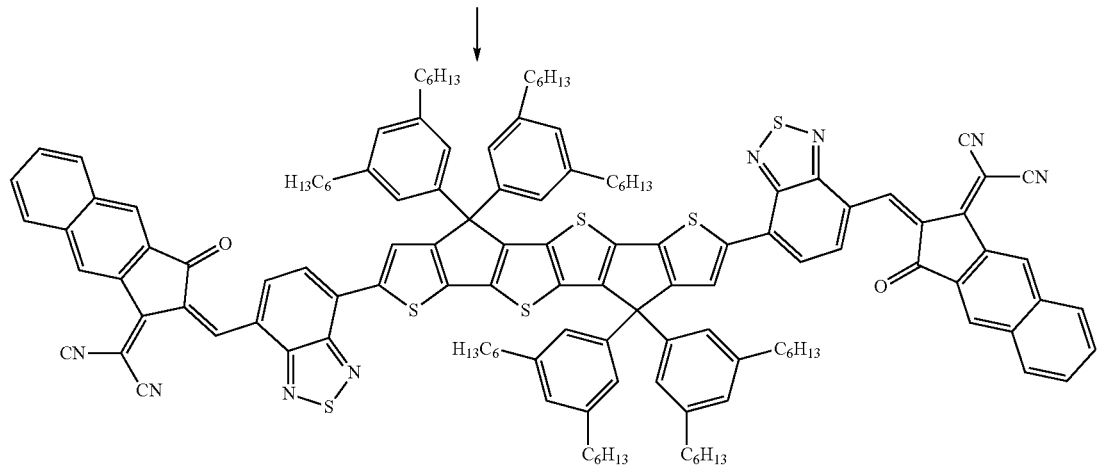

To a degassed solution of intermediate 4 (200 mg, 0.123 mmol), pyridine (0.69 cm$^3$) and anhydrous chloroform (9.7 cm$^3$) is added 2-(3-oxo-2,3-dihydro-cyclopenta[b]naphthalen-1-ylidene)-malononitrile (89 mg, 0.37 mmol) and the mixture stirred for 30 minutes. The ice bath is then removed, and the mixture stirred for a further 60 minutes. The reaction mixture is poured into acetonitrile (250 cm$^3$) and stirred for 1 hour. The resulting suspension is collected by filtration and washed well with ethanol (50 cm$^3$) and acetone (50 cm$^3$). The crude product is purified by silica plug (40-60 petrol: dichloromethane; 1:1) followed by trituration with acetonitrile. The solid is collected by filtration to give compound 2 (180 mg, 71%) as a black solid. $^1$H NMR (400 MHz, CDCl$_3$) 9.57 (2H, br s), 9.34 (2H, d, J 8.1), 9.11-9.20 (2H, m), 8.23-8.41 (4H, m), 7.86-8.08 (6H, m), 7.59-7.70 (4H, m), 6.86 (12H, br s), 2.47 (16H, t, J 7.6), 1.40-1.59 (16H, m), 1.09-1.29 (48H, m), 0.67-0.84 (24H, m).

To a solution of 2,5-dichloro-thieno[3,2-b]thiophene (17.3 g, 82.7 mmol) in anhydrous tetrahydrofuran (173 cm$^3$) at 5° C. is added ethyl chloroformate (23.7 cm$^3$, 248 mmol). A solution of 2,2,6,6-tetramethylpiperidinylmagnesium chloride lithium chloride complex (207 cm$^3$, 207 mmol, 1.0 M in tetrahydrofuran) is then added dropwise over 1 hour. The reaction is slowly warmed to 23° C. and stirred for 42 hours. Water (200 cm$^3$) is added, the mixture stirred for 10 minutes, the solid collected by filtration and washed with water (2×100 cm$^3$). The solid is triturated in acetone (200 cm$^3$), the solid collected by filtration and washed with acetone (2×100 cm$^3$) to give intermediate 5 (26.6 g, 91%) as a white solid. $^1$H NMR (400 MHz, CDCl$_3$) 4.46 (4H, q, J 7.1), 1.47 (6H, t, J 7.1).

Example 3

Intermediate 6

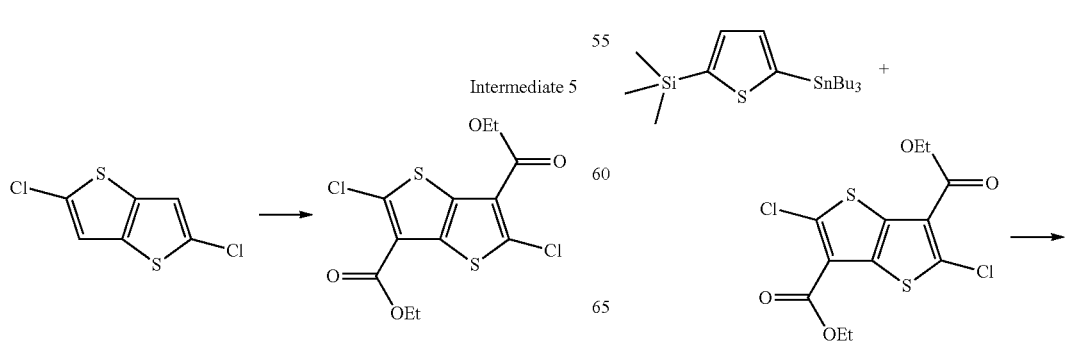

-continued

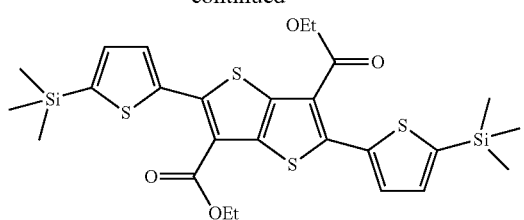

Trimethyl-(5-tributylstannanyl-thiophen-2-yl)-silane (30.5 g, 61.7 mmol), intermediate 5 (10.0 g, 28.3 mmol) and tetrakis(triphenylphosphine)palladium(0) (657 mg, 0.57 mmol) are suspended in anhydrous toluene (100 cm$^3$) and heated at 100° C. for 18 hours. The reaction is cooled to 23° C. and methanol (250 cm$^3$) added. The suspension is cooled in an ice-bath, the solid collected by filtration and washed with methanol (200 cm$^3$). The crude is purified by silica pad (dichloromethane) followed by column chromatography (40-60 petrol:dichloromethane; 60:40) to give intermediate 6 (7.68 g, 46%) as a yellow solid. $^1$H NMR (400 MHz, CDCl$_3$) 7.42 (2H, d, J 3.5), 7.02 (2H, d, J 3.5), 4.19 (4H, q, J 7.1), 1.19 (6H, t, J 7.1), 0.15 (18H, s).

To a solution of 1-bromo-4-octyloxy-benzene (14.1 g, 49.5 mmol) in anhydrous tetrahydrofuran (73 cm$^3$) at −78° C. is added dropwise t-butyllithium (58.2 cm$^3$, 99.0 mmol, 1.7 M in pentane) over 20 minutes. The reaction is warmed to between −28° C. and −35° C. for 30 minutes. A second portion of 1-bromo-4-octyloxy-benzene (3.0 g, 11 mmol) is added and the reaction mixture stirred for 30 minutes. The reaction is cooled to −78° C. and a solution of intermediate 6 (4.89 g, 8.25 mmol) in anhydrous tetrahydrofuran (30 cm$^3$) is rapidly added. The reaction is warmed to 23° C. and stirred for 60 hours. Water (50 cm$^3$) is added and the organics extracted with ether (300 cm$^3$). The organic phase is washed with water (3×100 cm$^3$), dried over anhydrous magnesium sulfate, filtered and the solvent removed in vacuo. The crude is purified by column chromatography using a graded solvent system (40-60 petrol:dichloromethane; 9:1 to 4:1) to give intermediate 7 (3.17 g, 29%) as a pale brown solid. $^1$H NMR (400 MHz, CDCl$_3$) 7.16-7.23 (8H, m), 6.88 (2H, d, J 3.4), 6.78-6.85 (8H, m), 6.51 (2H, d, J 3.4), 3.97 (8H, t, J 6.6), 3.37 (2H, s), 1.75-1.84 (8H, m), 1.27-1.52 (40H, m), 0.82-0.95 (12H, m), 0.25 (18H, s).

Intermediate 8 - Route A

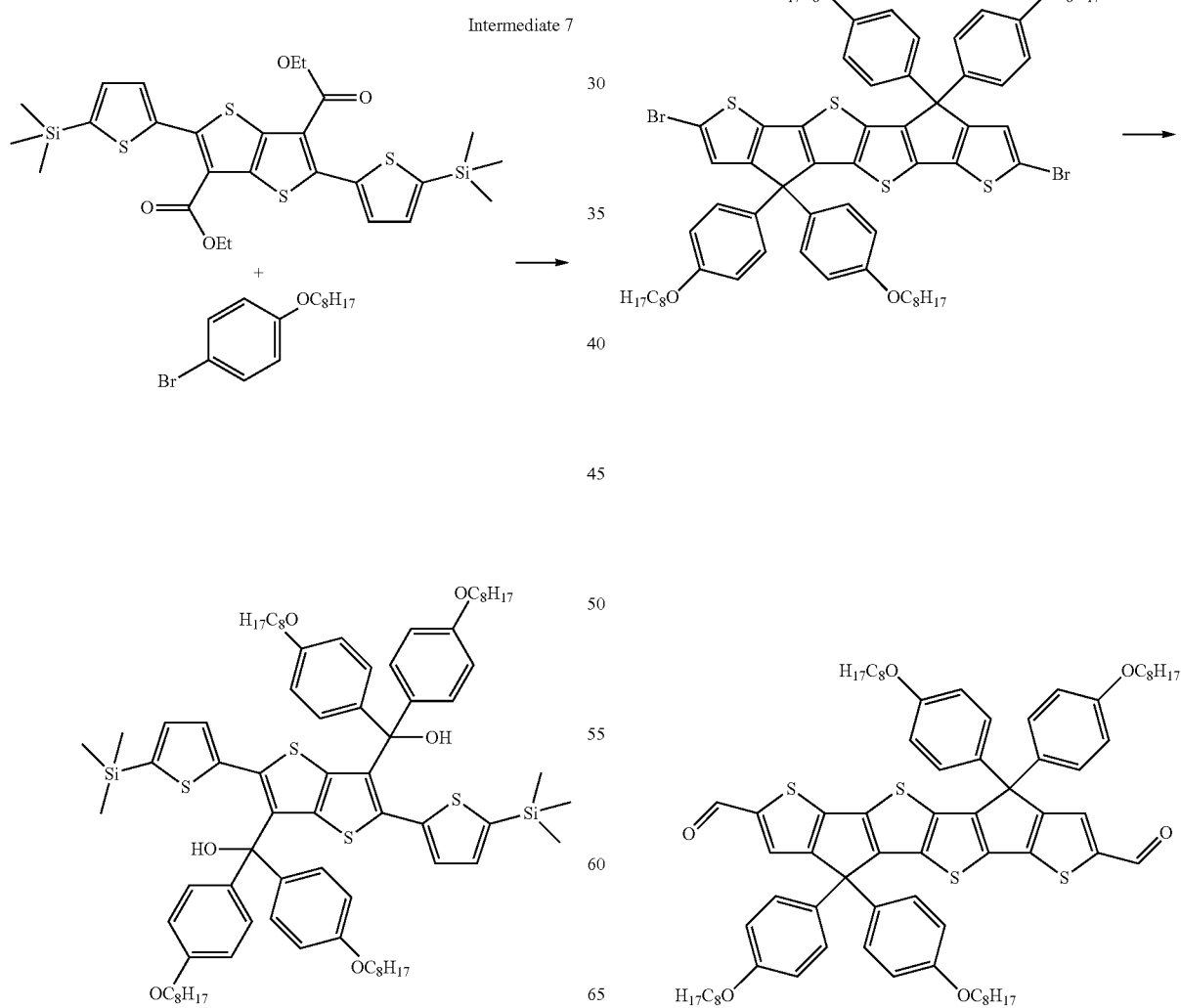

To a solution of 2,7-dibromo-4,4,9,9-tetrakis(4-(octyloxy)phenyl)-4,9-dihydro-thieno[3',2':4,5]cyclopenta[1,2-b]thieno[2",3":3',4']cyclopenta[1', 2':4,5]thieno[2,3-d]thiophene (1.00 g, 0.77 mmol) in tetrahydrofuran (25 cm³) at −78° C. is added dropwise n-butyllithium (0.92 cm³, 2.30 mmol, 2.5 M in hexanes). The reaction is stirred for a further 1 hour and quenched with N,N-dimethylformamide (1.13 cm³, 23.0 mmol). The reaction is warmed to 23° C. and stirred for 18 hours. Water (50 cm³) is added and the organics extracted with dichloromethane (3×30 cm³). The combined organic phase is washed with water (2×20 cm³), dried over anhydrous magnesium sulfate, filtered and concentrated in vacuo. The crude is purified by column chromatography using a graded solvent system (40-60 petrol:dichloromethane; 6:4 to 4:6) to give intermediate 8 (330 mg, 36%) as an orange oil. ¹H NMR (400 MHz, CDCl₃) 9.72 (2H, s), 7.58 (2H, s), 7.00-7.08 (8H, m), 6.69-6.82 (8H, m), 3.83 (8H, t, J 6.5), 1.61-1.71 (8H, m), 1.34 (8H, m), 1.11-1.33 (32H, m), 0.72-0.90 (12H, m).

Intermediate 8-Route B

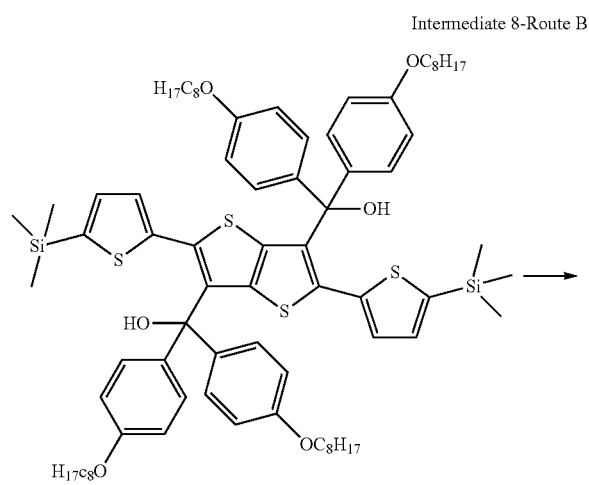

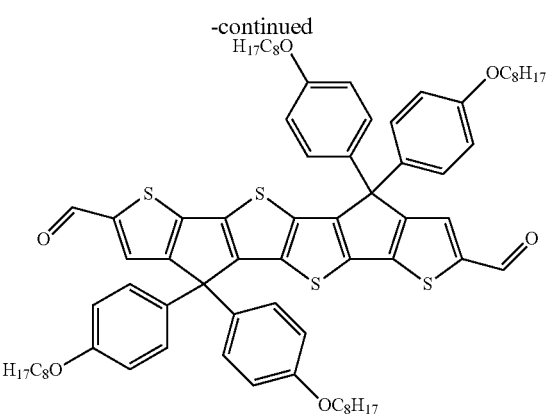

To a degassed solution of intermediate 7 (6.00 g, 4.52 mmol) in toluene (240 cm³) is added Amberlyst 15 strong acid (24 g), the mixture further degassed and then heated at 75° C. for 18 hours. The solution is cooled to about 50° C., filtered and the solid washed with toluene (200 cm³). The filtrate is concentrated and triturated with 80-100 petrol (3×30 cm³) and the solid collected by filtration. The solid is dissolved in chloroform (120 cm³), N,N-dimethylformamide (5.3 g, 72 mmol) added and the solution cooled to 0° C. Phosphorus(V) oxychloride (10.4 g, 67.9 mmol) is added over 10 minutes. The reaction mixture is then heated at 65° C. for 18 hours. Aqueous sodium acetate solution (150 cm³, 2 M) is added at 65° C. and the reaction mixture stirred for 1 hour. Saturated aqueous sodium acetate solution is added until the mixture is pH 6 and the reaction stirred for a further 30 minutes. The aqueous phase is extracted with chloroform (2×25 cm³) and the combined organic layer washed with water (50 cm³), dried over anhydrous magnesium sulfate, filtered and the solvent removed in vacuo. The solid is triturated in 80-100 petrol and the solid collected by filtration to give intermediate 8 (3.06 g, 56%) as an orange oil. ¹H NMR (400 MHz, CDCl₃) 9.72 (2H, s), 7.58 (2H, s), 7.00-7.08 (8H, m), 6.69-6.82 (8H, m), 3.83 (8H, t, J 6.5), 1.61-1.71 (8H, m), 1.34 (8H, m), 1.11-1.33 (32H, m), 0.72-0.90 (12H, m).

Compound 3

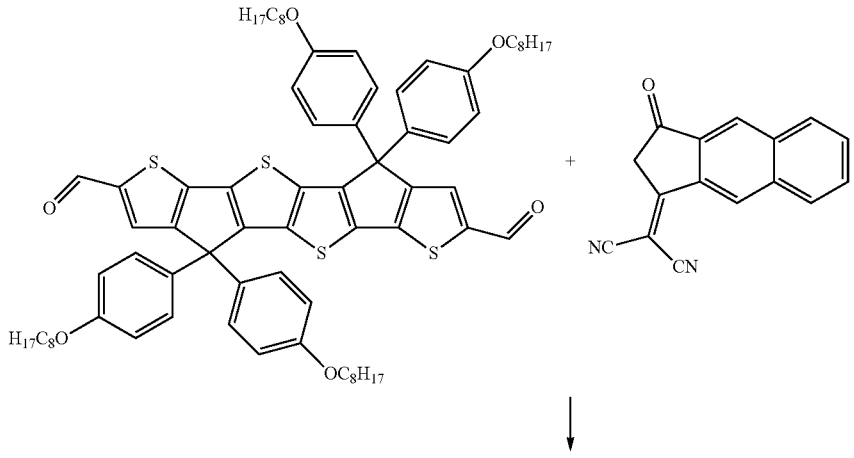

-continued

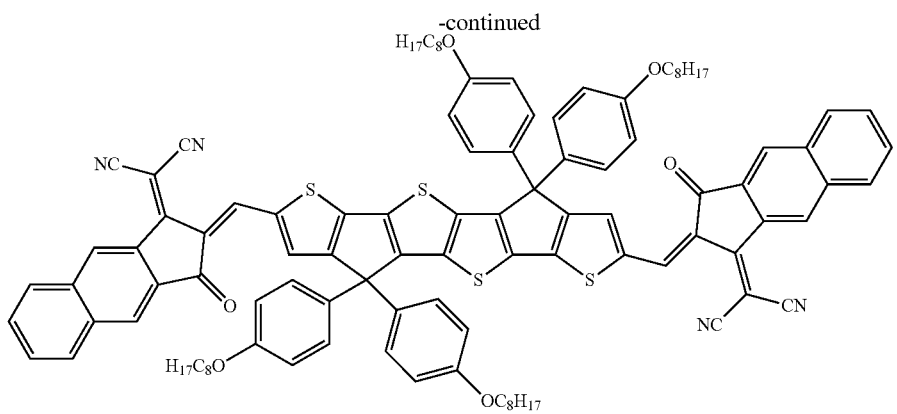

Intermediate 8 (120 mg, 0.10 mmol) and 2-(3-oxo-2,3-dihydro-cyclopenta[b]naphthalen-1-ylidene)-malononitrile (190 mg, 0.78 mmol) are dissolved in chloroform (2.9 cm$^3$) at 50° C. and degassed with nitrogen for 20 minutes. Pyridine (1.1 cm$^3$) is added and the reaction stirred for 5 hours at 50° C. Methanol (25 cm$^3$) is added, the suspension cooled to 23° C. and filtered. The solid is dissolved in chloroform (6 cm$^3$), acetone (18 cm$^3$) is added followed by methanol (24 cm$^3$) at 40° C. The suspension is cooled to 23° C. and filtered. The solid is washed with chloroform:methanol (1:1; 5 cm$^3$). The recrystallization cycle is then repeated to afford compound 3 (32 mg, 20%) as a green solid. $^1$H NMR (400 MHz, CDCl$_3$) 9.18 (2H, s), 8.94 (2H, s), 8.37 (2H, s), 8.02-8.11 (4H, m), 7.64-7.75 (6H, m), 7.15-7.22 (8H, m), 6.84-6.92 (8H, m), 5.32 (8H, s), 3.95 (8H, t, J 6.5), 1.74-1.82 (8H, m), 1.45 (8H, t, J 7.5), 1.25-1.40 (40H, m), 0.89 (12H, d, J 7.0).

Example 4

Interemediate 9

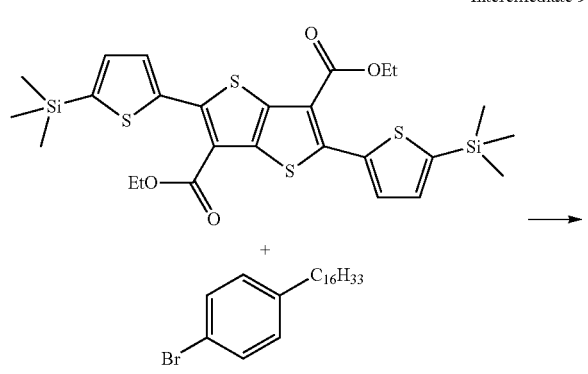

-continued

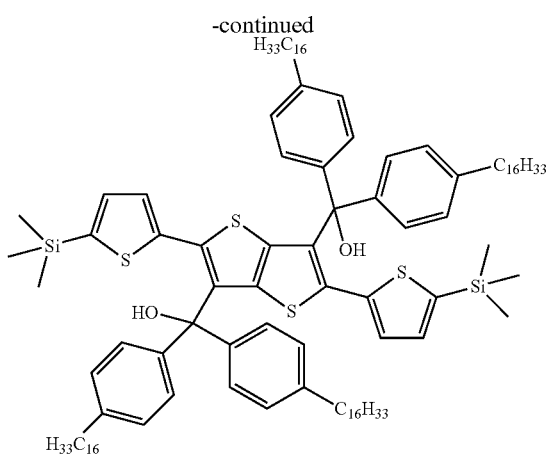

To a solution of 1-bromo-4-hexadecyl-benzene (19.3 g, 50.6 mmol) suspended in anhydrous tetrahydrofuran (400 cm$^3$) at −35° C. is added a solution of t-butyllithium (59.5 cm$^3$, 101 mmol, 1.7 M in pentane) over 30 minutes. The suspension is warmed to −25° C. to provide a solution which is then re-cooled to −40° C. and stirred for 1 hour before intermediate 6 (5.00 g, 8.43 mmol), dissolved in tetrahydrofuran (50 cm$^3$) is added dropwise. The resulting suspension is warmed to 23° C. and stirred for 16 hours. Water (20 cm$^3$) is added slowly to the mixture followed by another portion of water (300 cm$^3$). The biphasic solution is extracted with ether (300 cm$^3$) and the organic phase is washed with water (2×250 cm$^3$), brine (100 cm$^3$), dried over magnesium sulphate, filtered and concentrated in vacuo. The crude product is dissolved in acetone (200 cm$^3$) and cooled in an ice bath. Methanol (200 cm$^3$) is added portion wise, the solid is collected by filtration and washed with methanol to give intermediate 9 (14 g, 97%) as an off white solid. $^1$H NMR (400 MHz, CDCl$_3$) 6.94-7.01 (8H, m), 6.84-6.94 (8H, m), 6.61 (2H, d, J 3.4), 6.22 (2H, d, J 3.4), 3.19 (2H, s), 2.38 (8H, t, J 7.7), 1.36-1.43 (8H, m), 0.97-1.15 (104H, m), 0.67 (12H, t, J 6.8), 0.00 (18H, s).

Intermediate 10

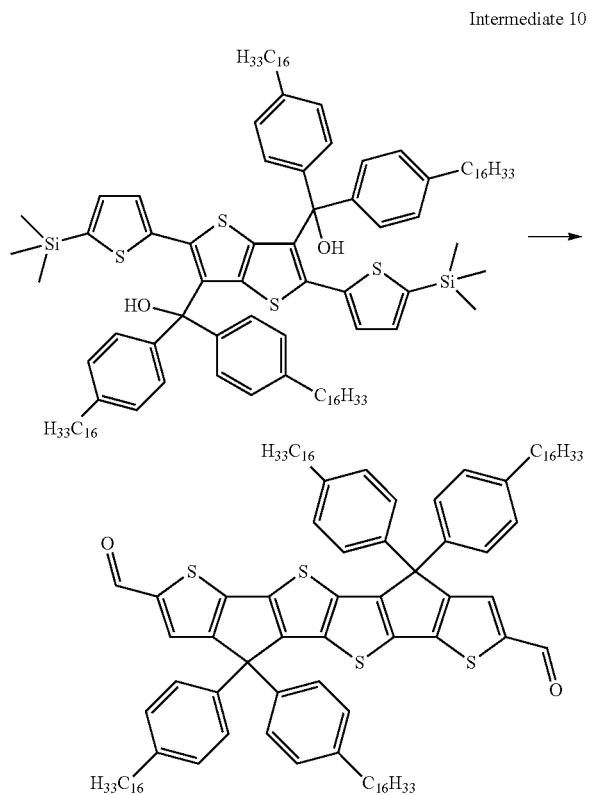

To a nitrogen flushed solution of intermediate 9 (5.0 g, 2.9 mmol) in toluene (200 cm$^3$) at 55° C. is added p-toluene sulphonic acid (1.67 g, 8.8 mmol), the reaction is further flushed with nitrogen for 10 minutes. The reaction is stirred at 55° C. for 16 hours. Upon cooling to 23° C. the reaction is filtered, concentrated in vacuo and purified by column chromatography (40-60 petrol:dichloromethane; 9:1). The purified material is taken up in chloroform (100 cm$^3$), cooled to 0° C. and N,N-dimethylformamide (12 g) and phosphorus oxychloride (6.72 g, 43.8 mmol) added. The reaction is heated at 65° C. for 16 hours. Water (25 cm$^3$) is slowly added to the mixture followed by an aqueous sodium acetate solution (250 cm$^3$, 5 M). The biphasic solution is stirred for 1 hour and the aqueous phase is extracted with dichloromethane (2×30 cm$^3$). The combined organic phase is washed with water (2×50 cm$^3$), dried over magnesium sulphate, filtered and concentrated in vacuo. The product is triturated in acetone and filtered off. The solid is purified by column chromatography (40-60 petrol:dichloromethane; 4:1). The resulting solid is triturated in boiling 40-60 petrol, and the solid collected by filtration to give intermediate 10 (1.59 g, 34%) as an orange solid. $^1$H NMR (400 MHz, CDCl$_3$) 9.82 (2H, s), 7.70 (2H, s), 7.08-7.18 (16H, m), 2.53-2.60 (8H, m), 1.53-1.65 (8H, m), 1.26 (104H, d, J 3.4), 0.89 (12H, t, J 6.8).

Compound 4

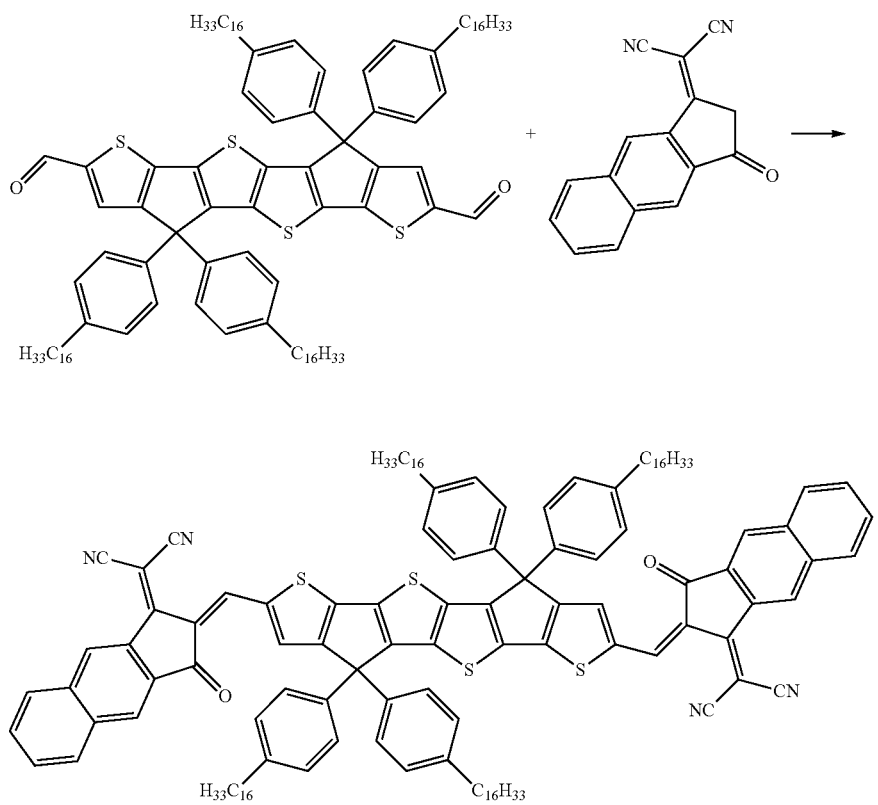

To a nitrogen purged suspension of intermediate 10 (100 mg, 0.06 mmol) and 2-(3-oxo-2,3-dihydro-cyclopenta[b]naphthalen-1-ylidene)-malononitrile (77 mg, 0.32 mmol) in chloroform (2.5 cm³) is added pyridine (0.36 cm³) and the solution flushed with nitrogen for a further 10 minutes. The reaction is stirred at 23° C. for 18 hours, diluted with methanol (20 cm³) and filtered. The solid is washed with methanol (2×5 cm³). The crude material is dissolved in chloroform (20 cm³) at 40° C. Acetone (40 cm³) is added slowly to the mixture followed by methanol (5 cm³). The suspension is cooled to 23° C. and filtered to give compound 4 (22 mg, 18%) as a green solid. ¹H NMR (400 MHz, CDCl₃) 9.18 (2H, s), 8.94 (2H, s), 8.37 (2H, s), 8.00-8.14 (4H, m), 7.75 (2H, s), 7.64-7.72 (4H, m), 7.17 (16H, s), 2.61 (8H, t, J 7.9), 1.51-1.71 (8H, m), 1.25 (84H, s), 0.87 (12H, t, J 6.6).

Example 5

Intermediate 11

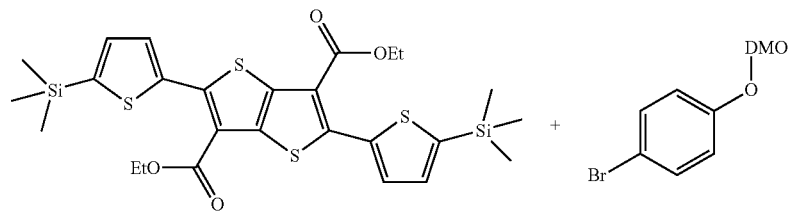

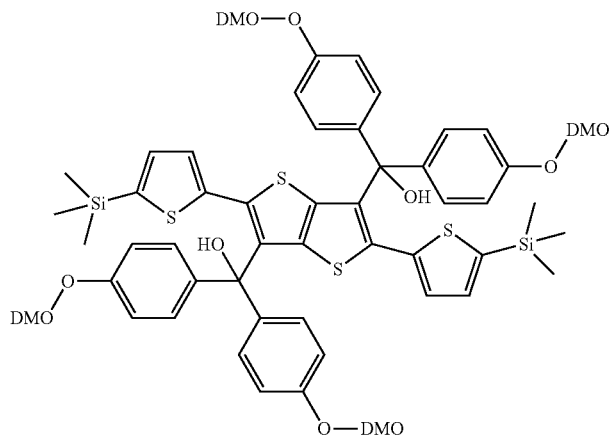

Anhydrous tetrahydrofuran (2 cm³) is added to a flask containing oven dried magnesium turnings (246 mg, 10.1 mmol) and an iodine crystal. The mixture is maintained at reflux while a solution of 1-bromo-4-(3,7-dimethyl-octyloxy)-benzene (3.07 g, 10.1 mmol) in anhydrous tetrahydrofuran (5 cm³) is added portionwise over 10 minutes. The reaction is then heated to reflux for 2 hours. The resulting Grignard reagent is transferred over 5 minutes to a flask containing intermediate 6 (1.00 g, 1.69 mmol) dissolved in anhydrous tetrahydrofuran (10 cm³) and maintained at 65° C. The mixture is heated at 65° C. for 6 hours. Upon cooling to 23° C., the solution is partioned between water (30 cm³) and ether (30 cm³). Hydrochloric acid (2 N) is added slowly until the phases become clear. The organic phase is washed with water (2×30 cm³), dried over anhydrous magnesium sulphate, filtered and concentrated in vacuo. The crude product is purified by column chromatography (40-60 petrol:dichloromethane; 1:1) to give intermediate 11 (1.26 g, 53%) as a yellow/green oil. ¹H NMR (400 MHz, CDCl₃) 7.16-7.23 (8H, m), 6.88 (2H, d, J 3.4), 6.79-6.86 (8H, m), 6.52 (2H, d, J 3.4), 3.95-4.06 (8H, m), 3.38 (2H, s), 1.07-1.91 (40H, m), 0.95 (12H, d, J 6.5), 0.87-0.92 (24H, m), 0.25 (18H, s).

Intermediate 12

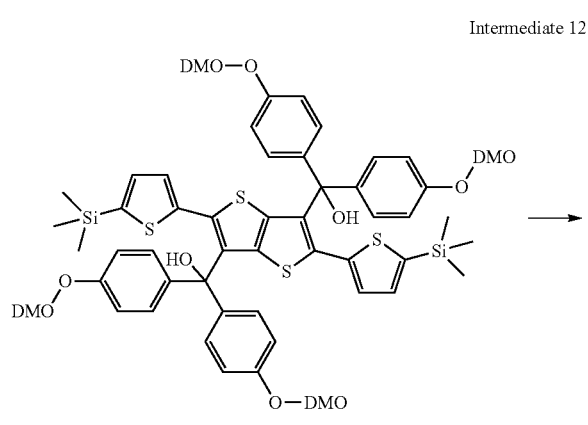

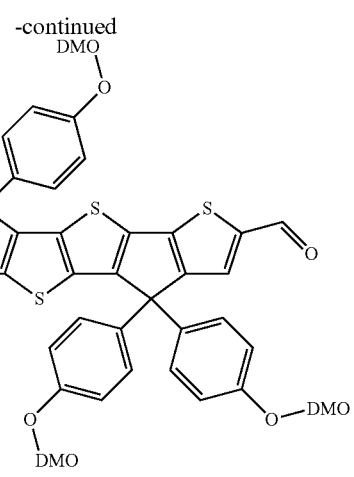

DMO = 3,7-dimethyloctyl

Intermediate 11 (1.26 g, 0.89 mmol) is dissolved in toluene (50 cm³) and heated at 75° C. The resulting solution is flushed with nitrogen for 20 minutes. Amberlyst 15 strong acid (5.0 g) is added. The nitrogen flush is maintained for a further 10 minutes and the reaction mixture is stirred for 17 hours. The reaction mixture is filtered and the solid washed with hot toluene (3×10 cm³). The filtrate is concentrated in vacuo and passed through a silica plug (40-60 petrol: dichloromethane; 5:1). The resulting solid is dissolved in N,N-dimethylformamide (1.04 g, 14.3 mmol) and chloroform (25 cm³) and cooled in an ice-bath. Phosphorus oxychloride (2.05 g, 13.4 mmol) is added portionwise over 5 minutes. The reaction is stirred for 30 minutes at 0° C. and then heated at 65° C. for 16 hours. Upon cooling to 23° C., water (5 cm³) is slowly added followed by slow addition of aqueous sodium acetate (50 cm³, 10 M). The biphasic suspension is stirred for 1 hour and then cooled to 23° C. The aqueous phase is extracted with dichloromethane (20 cm³). The combined organic phase is washed with water (2×20 cm³), dried over anhydrous magnesium sulphate, filtered and concentrated in vacuo. The resulting solid is triturated in acetone (10 cm³), filtered and washed with acetone (2×2 cm³) to give intermediate 12 (200 mg, 17%) as an orange solid. ¹H NMR (400 MHz, CDCl₃) 9.73 (2H, s), 7.59 (2H, s), 7.02-7.09 (8H, m), 6.71-6.78 (8H, m), 3.86 (8H, ddt, J 9.4, 7.1, 3.3), 0.98-1.78 (40H, m), 0.83 (12H, d, J 6.5), 0.78 (24H, d, J 6.6).

Compound 5

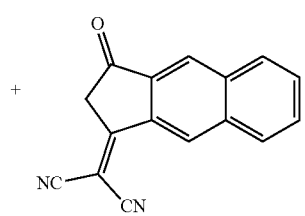

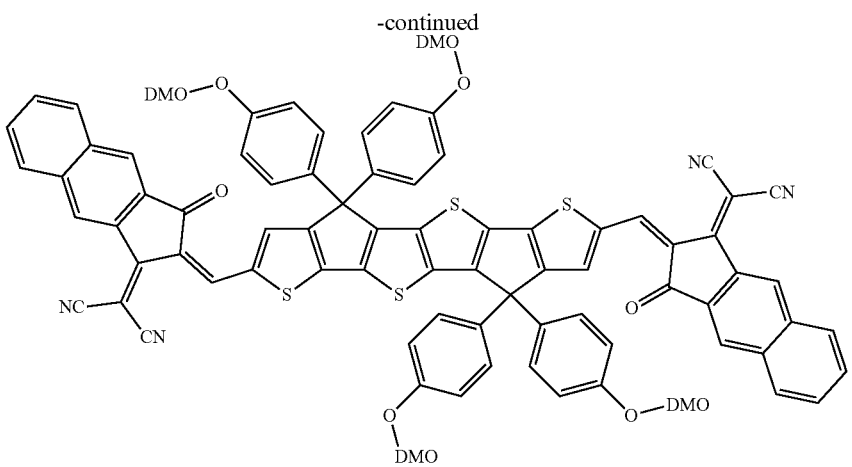

DMO = 3,7-dimethyloctyl

A solution of intermediate 12 (100 mg, 0.08 mmol) and 2-(3-oxo-2,3-dihydro-cyclopenta[b]naphthalen-1-ylidene)-malononitrile (92.9 mg, 0.38 mmol) in chloroform (2.5 cm³) is purged with nitrogen for 10 minutes before addition of pyridine (0.43 cm³). The solution is purged with nitrogen for a further 10 minutes and then stirred for 16 hours at 23° C. The mixture is diluted with methanol (20 cm³) and filtered. The solid is washed with methanol (2×5 cm³) and purified by column chromatography (40-60 petrol:dichloromethane; 3:2). The solid is dissolved in chloroform (6 cm³) and acetone (12 cm³) added at 40° C. followed by methanol (2 cm³). The solid is collected by filtration to give compound 5 (26 mg, 19%) as a green solid. $^1$H NMR (400 MHz, CDCl$_3$) 9.19 (2H, s), 8.96 (2H, s), 8.38 (2H, s), 8.08 (4H, dt, J 9.6, 5.8), 7.66-7.77 (6H, m), 7.14-7.23 (8H, m), 6.84-6.93 (8H, m), 3.99 (8H, q, J 6.0), 1.07-1.94 (40H, m), 1.20 (40H, s), 0.94 (12H, d, J 6.5), 0.87 (24H, d, J 6.6).

Example 6

Intermediate 13

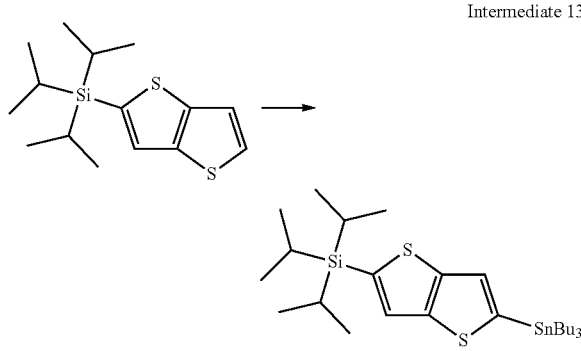

To a solution of triisopropyl-thieno[3,2-b]thiophen-2-yl-silane (11.9 g, 40.0 mmol) in anhydrous tetrahydrofuran (100 cm³) at −78° C. is added drop-wise n-butyllithium (20.8 cm³, 52.0 mmol, 2.5 M in hexane) over 20 minutes. After addition, the reaction mixture is stirred at −78° C. for 120 minutes and then tributyltin chloride (15.8 cm³, 56.0 mmol) is added. The mixture is then allowed to warm to 23° C. over 17 hours and the solvent removed in vacuo. The crude is diluted in 40-60 petrol (250 cm³) and filtered through a zeolite plug (50 g). The plug is washed with additional 40-60 petrol (250 cm³). The solvent is removed in vacuo to give intermediate 13 (23.1 g, 99%) as a clear oil.

$^1$H NMR (400 MHz, CD$_2$Cl$_2$) 7.27 (1H, d, J 0.7), 7.1 (1H, s), 1.35-1.63 (9H, m), 1.17-1.34 (12H, m), 0.98-1.13 (18H, m), 0.65-0.91 (9H, m).

Intermediate 14

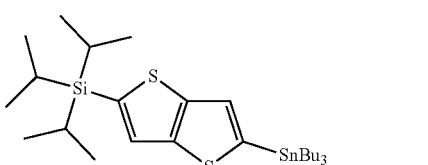

+

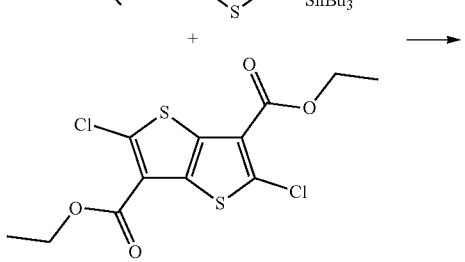

→

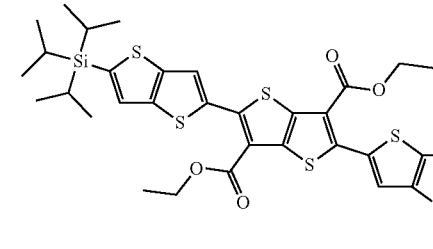

A mixture of intermediate 5 (7.5 g, 21 mmol), intermediate 13 (17.8 g, 30.4 mmol) and anhydrous toluene (300 cm³) is degassed by nitrogen for 25 minutes. To the mixture is added tetrakis(triphenylphosphine)palladium(0) (500 mg, 0.43 mmol) and the mixture further degassed for 15 minutes. The mixture is stirred at 85° C. for 17 hours. The reaction mixture is filtered hot through a celite plug (50 g) and washed through with hot toluene (100 cm³). The solvent reduced in vacuo to ~100 cm³ and cooled in an ice bath to form a suspension. The product is filtered, washed with water (100 cm³) and methanol (100 cm³), collected to give intermediate 14 (9.5 g, 71%) as a yellow crystalline solid. $^1$H NMR (400 MHz, CDCl$_3$) 7.75 (2H, d, J 0.7), 7.30 (2H, d, J 0.7), 4.36 (4H, q, J 7.2), 1.23-1.43 (12H, m), 1.07 (36H, d, J 7.3).

Intermediate 15

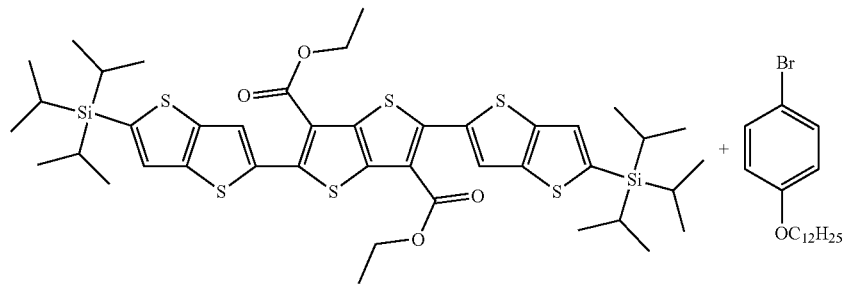

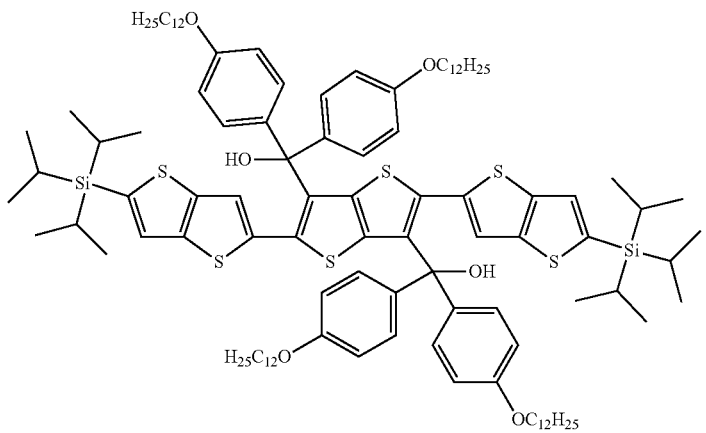

To a suspension of 1-bromo-4-dodecyloxy-benzene (10.6 g, 30.9 mmol) in anhydrous tetrahydrofuran (167 cm$^3$) at −78° C. is added dropwise t-butyllithium (36.4 cm$^3$, 61.8 mmol, 1.7 M in pentane) over 60 minutes.

After addition, the reaction mixture is stirred at −78° C. for 120 minutes and then intermediate 14 (6.0 g, 6.9 mmol) added. The mixture is then allowed to warm to 23° C. over 17 hours. Diethyl ether (200 cm$^3$) and water (200 cm$^3$) are added and the mixture stirred at 23° C. for 30 minutes. The product is extracted with diethyl ether (3×200 cm$^3$). The combined organics is dried over anhydrous magnesium sulfate, filtered and the solvent removed in vacuo. The crude is purified by column chromatography (40-60 petrol:diethyl ether; 7:3). The solid triturated with methanol (200 cm$^3$) and collected by filtration to give intermediate 15 (10.3 g, 82%) as a cream solid. $^1$H NMR (400 MHz, CDCl$_3$) 7.15-7.23 (10H, m), 6.77-6.85 (8H, m), 6.65 (2H, d, J 0.7), 3.45 (2H, s), 3.95 (8H, s), 1.71-1.85 (8H, m), 1.20-1.52 (72H, m), 1.11 (36H, d, J 7.3), 0.82-0.95 (12H, m).

Intermediate 16

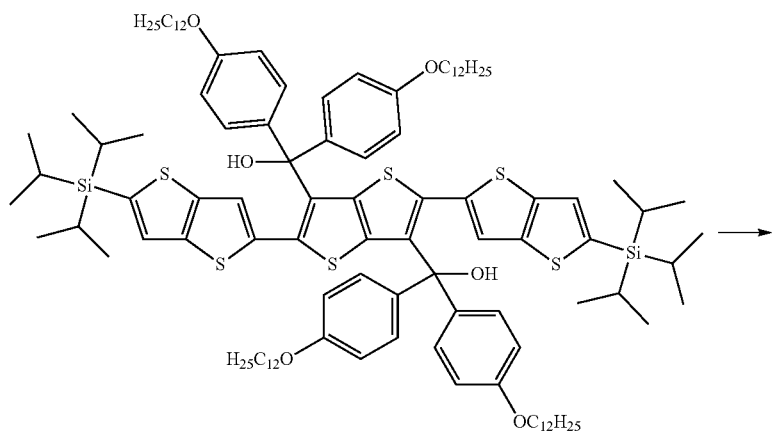

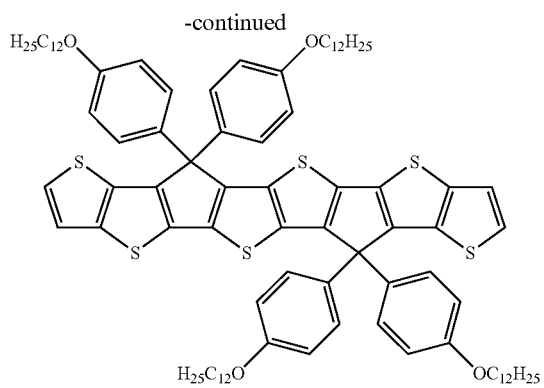

Nitrogen gas is bubbled through a solution of intermediate 15 in anhydrous toluene (250 cm³) at 0° C. for 60 minutes. Amberlyst 15 strong acid (50 g) is added and the mixture degassed for a further 30 minutes. The resulting suspension is stirred at 70° C. for 2 hours. The reaction mixture allowed to cool to 23° C., filtered and the solvent removed in vacuo. The crude is triturated with acetone (200 cm³). The solid is collected by filtration to give intermediate 16 (4.2 g, 89%) as a dark orange solid. ¹H NMR (400 MHz, CDCl₃) 7.26-7.32 (4H, m), 7.16-7.24 (8H, m), 6.75-6.93 (8H, m), 3.91 (8H, t, J 6.5), 1.67-1.82 (8H, m), 1.37-1.48 (8H, m), 1.19-1.37 (64H, m), 0.80-1.00 (12H, m).

Intermediate 17

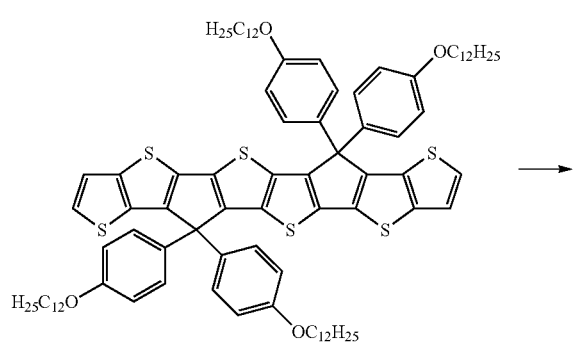

→

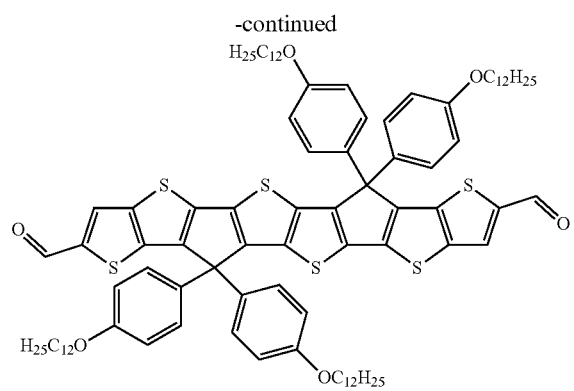

To a solution of intermediate 16 (600 mg, 0.41 mmol) in anhydrous tetrahydrofuran (24 cm³) at −78° C. is added dropwise n-butyllithium (0.7 cm³, 1.6 mmol, 2.5 M in hexane) over 10 minutes. After addition, the reaction mixture is stirred at −78° C. for 60 minutes. N,N-dimethylformamide (0.16 cm³, 2.4 mmol) is added and the mixture allowed to warm to 23° C. over 2 hours. Diethyl ether (50 cm³) and water (50 cm³) are added and the mixture stirred at 23° C. for 30 minutes. The product is extracted with diethyl ether (3×100 cm³). The combined organics are dried over anhydrous magnesium sulfate, filtered and the solvent removed in vacuo. The crude is purified by column chromatography (40-60 petrol:dichloromethane; 8:2) to give intermediate 17 (380 mg, 61%) as a dark red oil. ¹H NMR (400 MHz, CDCl₃) 9.90 (2H, s), 7.94 (2H, s), 7.08-7.23 (8H, m), 6.78-6.93 (8H, m), 3.91 (8H, t, J 6.5), 1.65-1.85 (8H, m), 1.17-1.51 (72H, m), 0.82-0.96 (12H, m).

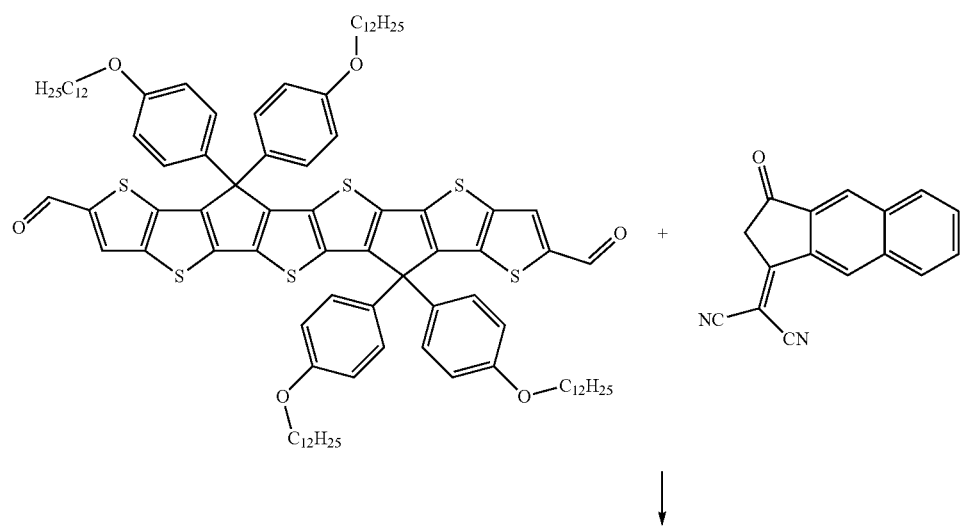
Compound 6
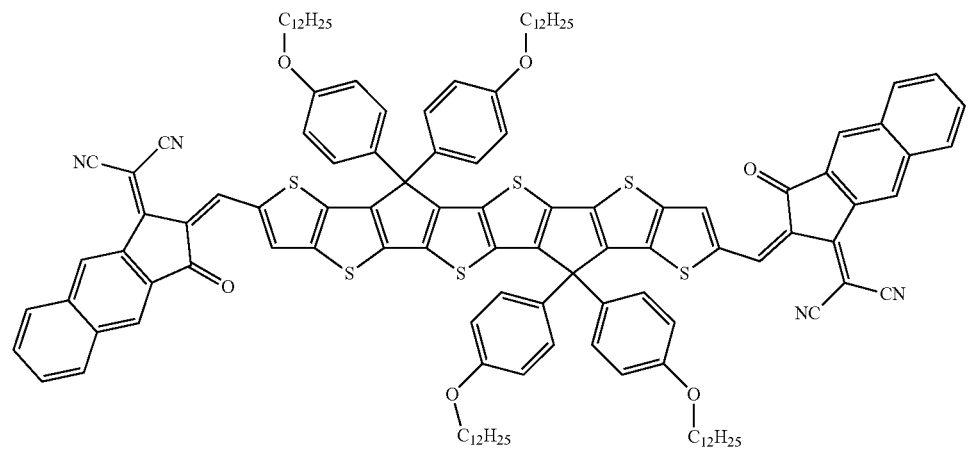

2-(3-Oxo-2,3-dihydro-cyclopenta[b]naphthalen-1-ylidene)-malononitrile (114 mg, 0.47 mmol) is added to a degassed solution of intermediate 16 (240 mg, 0.16 mmol) in a mixture of pyridine (1 cm³) and anhydrous chloroform (9 cm³). The mixture is stirred for 4 hours followed by addition of methanol (30 cm³). The precipitate is collected by filtration and rinsed with methanol (5 cm³). The solid is purified by column chromatography (chloroform) followed by trituration (dichloromethane) to give compound 6 (235 mg, 76%) as a green solid. ¹H NMR (400 MHz, CDCl₃) 9.11 (2H, s), 8.91 (2H, s), 8.37 (2H, s), 8.10 (2H, s), 7.99-8.07 (4H, m), 7.64-7.74 (4H, m), 7.22-7.27 (8H, m), 6.88-6.95 (8H, m), 3.93 (8H, t, J 6.5), 1.74 (8H, q, J 6.9), 1.38-1.47 (8H, m), 1.16-1.36 (64H, m), 0.86 (12H, t, J 6.6).

Example 7

Intermediate 17

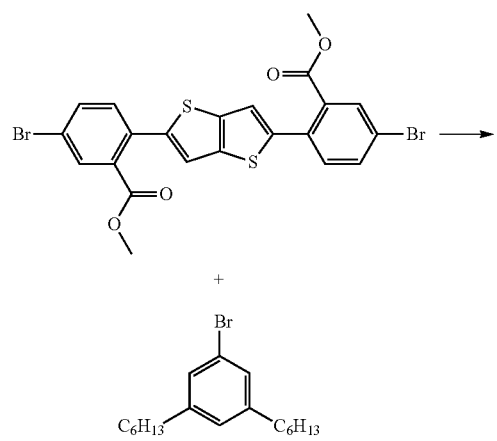

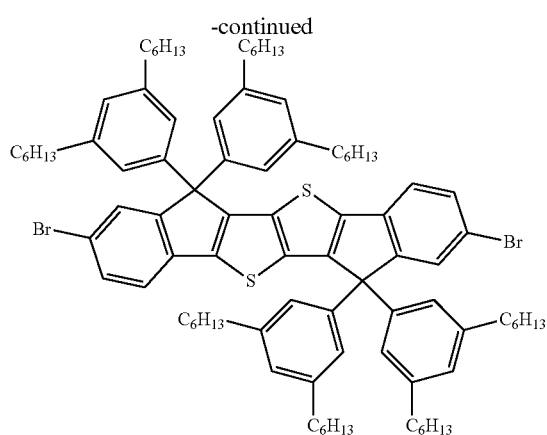

To a solution of 1-bromo-3,5-dihexyl-benzene (9.00 g, 27.7 mmol) in anhydrous tetrahydrofuran (135 cm³) at −78° C. is added dropwise n-butyllithium (11.1 cm³, 27.7 mmol, 2.5 M in hexanes) over 10 minutes. The reaction is stirred for one hour and methyl 5-bromo-2-[5-(4-bromo-2-methoxy-carbonyl-phenyl)thieno[3,2-b]thiophen-2-yl]benzoate (3.13 g, 5.53 mmol) added. The reaction is warmed to 23° C. and stirred for 18 hours. The reaction is partitioned between diethyl ether (50 cm³) and water (100 cm³). The organic phase is washed with water (30 cm³), brine (30 cm³), dried over anhydrous magnesium sulfate, filtered and concentrated in vacuo. The crude is triturated with 40-60 petrol, and the solid suspended in toluene (50 cm³). p-Toluene sulphonic acid (2.5 g) is added and the reaction mixture stirred for 17 hours. The suspension is filtered, concentrated in vacuo and purified by column chromatography using a graded solvent system (40-60 petrol:dichloromethane; 1:0 to 1:1). The resulting material is triturated in acetone and the solid collected by filtration to give intermediate 17 (2.71 g, 34%) as a yellow solid. ¹H NMR (400 MHz, CDCl₃) 7.42 (2H, d, J 1.7), 7.32 (2H, dd, J 8.1, 1.8), 7.11 (2H, d, J 8.1), 6.80 (4H, t, J 1.5), 6.71 (8H, d, J 1.5), 2.40 (16H, t, J 7.7), 1.38-1.48 (16H, m), 1.11-1.24 (48H, m), 0.70-0.79 (24H, m).

Intermediate 18

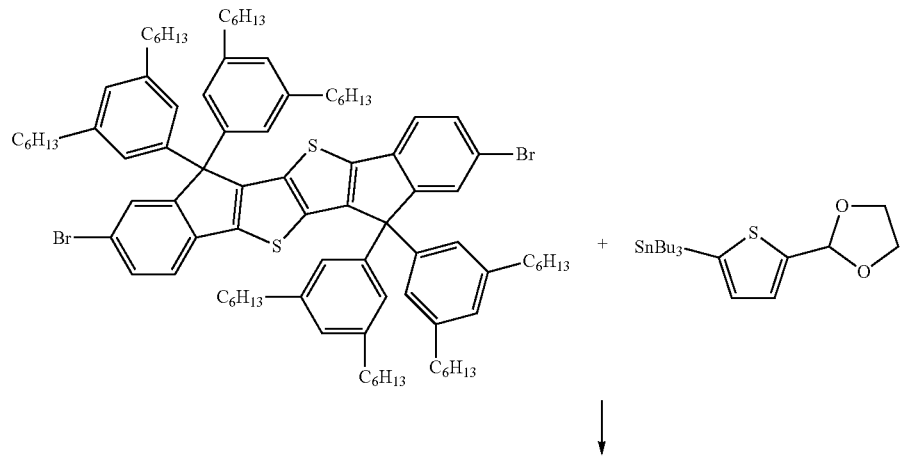

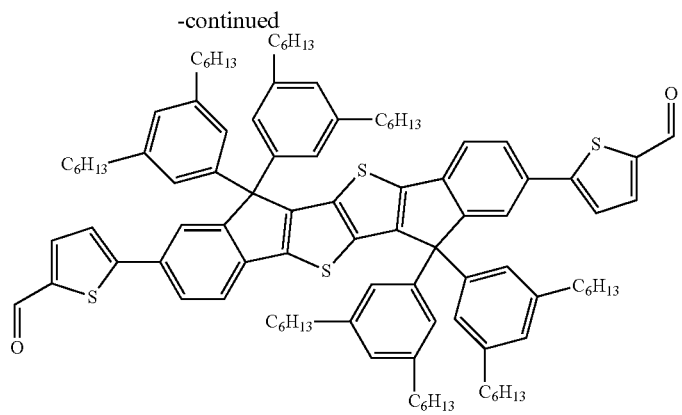

To a degassed solution of intermediate 17 (250 mg, 0.17 mmol), tributyl-(5-[1,3]dioxolan-2-yl-thiophen-2-yl)-stannane (0.18 cm³, 0.40 mmol) and tris(o-tolyl)phospine (16 mg, 0.05 mmol) in toluene (12.5 cm³) is added bis(dibenzylideneacetone)palladium(0) (16 mg, 0.02 mmol) and the mixture further degassed. The reaction is then heated to an external temperature of 140° C. for 6 hours. The reaction mixture is allowed to cool to 23° C. and concentrated in vacuo. The crude is purified by column chromatography using a graded solvent system (40-60 petrol:dichloromethane; 3:10 to 1:9). The resulting oil is dissolved in chloroform (30 cm³) and stirred with hydrochloric acid (10 cm³, 2.5 N) for 18 hours. The organic phase is concentrated in vacuo and the residue purified by column chromatography using a graded solvent system (40-60 petrol:dichloromethane; 4:1 to 1:4). The resulting solid is triturated in acetone and the solid collected by filtration to give intermediate 18 (170 mg, 65%) as a yellow solid. ¹H NMR (400 MHz, CDCl₃) 9.78 (2H, s), 7.59-7.65 (4H, m), 7.55 (2H, dd, J 8.0, 1.6), 7.31 (2H, d, J 8.0), 7.24 (2H, d, J 3.9), 6.82 (4H, s), 6.78 (8H, s), 2.41 (16H, t, J 7.6), 1.39-1.49 (16H, m), 1.17 (48H, m), 0.69-0.85 (24H, m).

Compound 7

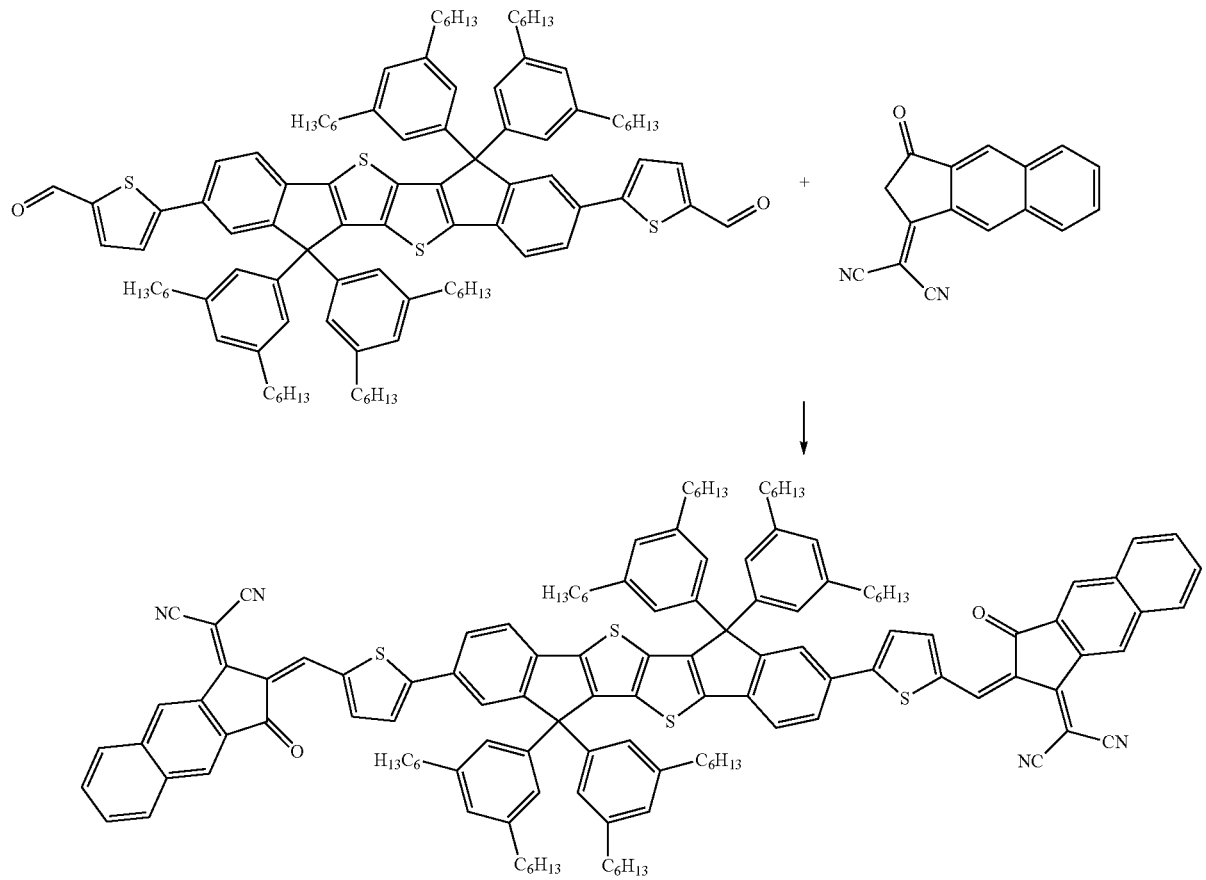

2-(3-Oxo-2,3-dihydro-cyclopenta[b]naphthalen-1-ylidene)-malononitrile (105 mg, 0.43 mmol) is added to a nitrogen purged solution of intermediate 18 (130 mg, 0.09 mmol) in anhydrous chloroform (9 cm³) and anhydrous pyridine (1 cm³). The resulting mixture is stirred for 3 hours before methanol (30 cm³) is added. The resulting precipitate is collected by filtration and rinsed with methanol (50 cm³). The solid is purified by column chromatography using a graded solvent system (cyclohexane:chloroform; 1:1 to 2:8), followed by trituration (acetone:chloroform) to give compound 7 (105 mg, 62%) as a black solid. ¹H NMR (400 MHz, CDCl₃) 9.22 (2H, s), 8.95 (2H, s), 8.41 (2H, s), 8.03-8.14 (4H, m), 7.82-7.91 (6H, m), 7.67-7.77 (4H, m), 7.43-7.50 (4H, m), 6.95 (4H, t, J 1.5), 6.92 (8H, d, J 1.5), 2.54 (16H, t, J 7.6), 1.51-1.64 (16H, m), 1.20-1.37 (48H, m), 0.78-0.86 (24H, m).

Example 8

Intermediate 19

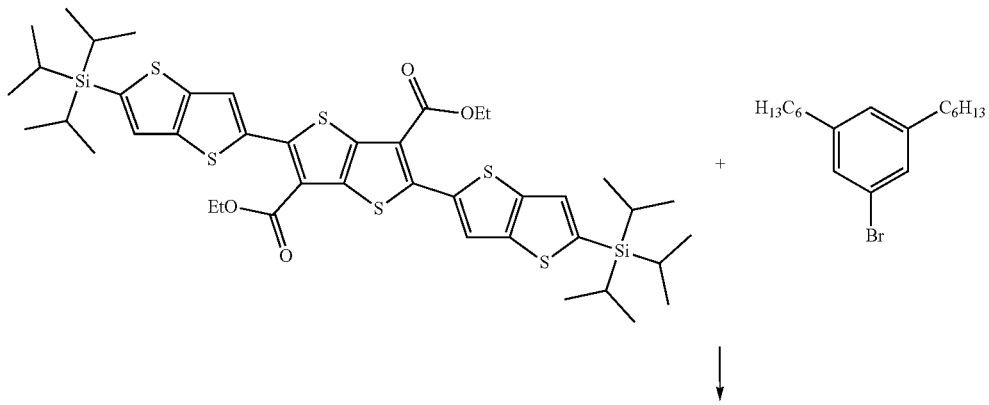

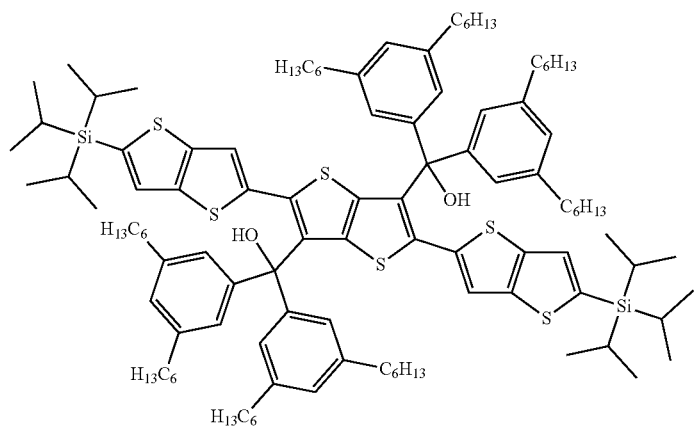

To a solution of 1-bromo-3,5-dihexyl-benzene (5.24 g, 16.0 mmol) in anhydrous tetrahydrofuran (100 cm³) at −78° C. is added dropwise n-butyllithium (6.41 cm³, 16.0 mmol, 2.5 M in tetrahydrofuran) over 30 minutes. After addition, the reaction mixture is stirred at −78° C. for 120 minutes and then intermediate 14 (2.8 g, 3.2 mmol) added. The mixture is then allowed to warm to 23° C. over 17 hours. Water (100 cm³) is added and mixture stirred for 1 hour. The product is extracted with diethyl ether (3×200 cm³). The combined organic phase is washed with water (2×50 cm³), dried over anhydrous magnesium sulfate, filtered and the solvent removed in vacuo. The crude is purified by column chromatography using a graded solvent system (40-60 petrol: diethyl ether; 20:1 to 4:1) to give intermediate 19 (3.54 g, 63%) as a pale cream oil. $^1$H NMR (400 MHz, $CD_2Cl_2$) 7.23 (2H, s), 6.86-7.01 (12H, m), 6.51 (2H, s), 3.41 (2H, s), 2.42-2.61 (16H, m), 1.49-1.61 (16H, m), 1.22-1.45 (54H, m), 1.15 (36H, d, J 7.3), 0.78-0.95 (24H, m).

Intermediate 20

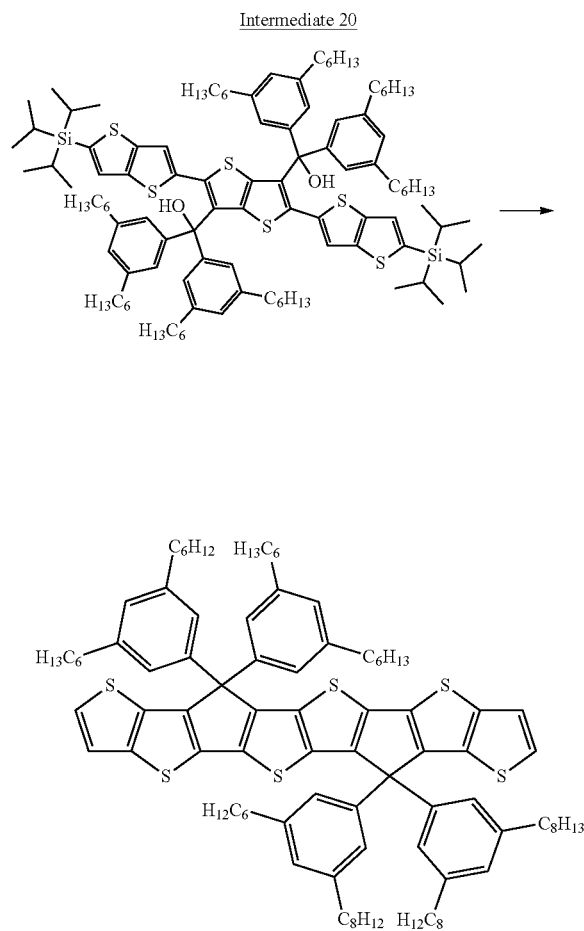

Intermediate 19 (2.95 g, 1.67 mmol) is added to a degassed suspension of Amberlyst 15 strong acid (12 g) in anhydrous diethyl ether (100 cm³) at 0° C. The mixture is further degassed with nitrogen for 30 minutes. The resulting suspension is stirred at 23° C. for 2 hours before it is filtered through a thin celite plug and washed with diethyl ether (200 cm³). After removing solvent in vacuo, the crude material is purified by column chromatography (40-60 petrol). This material is dissolved in anhydrous tetrahydrofuran (50 cm³) and cooled to 0° C. Tetrabutylammonium fluoride (3.34 cm³, 3.34 mmol, 1 M in tetrahydrofuran) is added and the resulting solution is stirred for 30 minutes at 23° C. The solvent is then removed in vacuo and the resulting residue is suspended in methanol (200 cm³) which is stirred for 30 minutes. The solid is collected by filtration to give intermediate 20 (2.02 g, 85%). $^1$H NMR (400 MHz, $CDCl_3$) 7.13-7.21 (4H, m), 6.71-6.84 (12H, m), 2.33-2.49 (16H, m), 1.38-1.48 (16H, m), 1.08-1.22 (48H, m), 0.70-0.80 (24H, m).

Intermediate 21

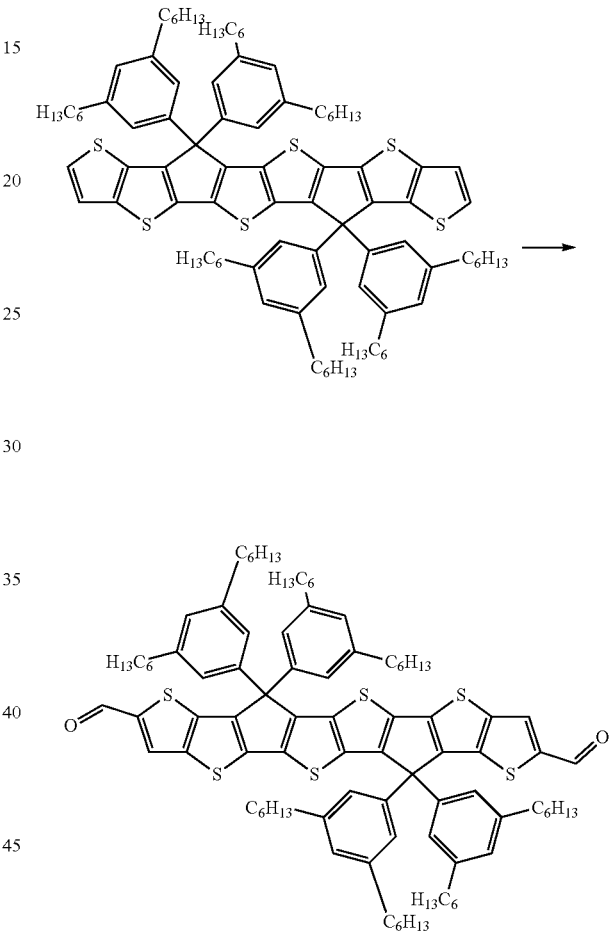

To a solution of intermediate 21 (600 mg, 0.42 mmol) in anhydrous tetrahydrofuran (25 cm³) at −78° C. is added dropwise n-butyllithium (0.68 cm³, 1.7 mmol, 2.5 M in hexane) over 10 minutes. After addition, the reaction mixture is stirred at −78° C. for 60 minutes. N,N-Dimethylformamide (0.17 cm³, 2.5 mmol) is added and the mixture allowed to warm to 23° C. over 2 hours. The reaction is quenched with water (50 cm³) and the mixture stirred for 30 minutes. The product is extracted with diethyl ether (3×50 cm³) and the combined organics dried over anhydrous magnesium sulfate, filtered and the solvent removed in vacuo. The crude is purified by column chromatography (40-60 petrol:dichloromethane; 8:2) to give intermediate 21 (450 mg, 72%) as a dark red solid. $^1$H NMR (400 MHz, $CDCl_3$) 9.79 (2H, s), 7.85 (2H, s), 6.83 (4H, s), 6.71 (8H, d, J 1.0), 2.41 (16H, t, J 7.6), 1.39-1.50 (16H, m), 1.15 (48H, br. s.), 0.70-0.80 (24H, m).

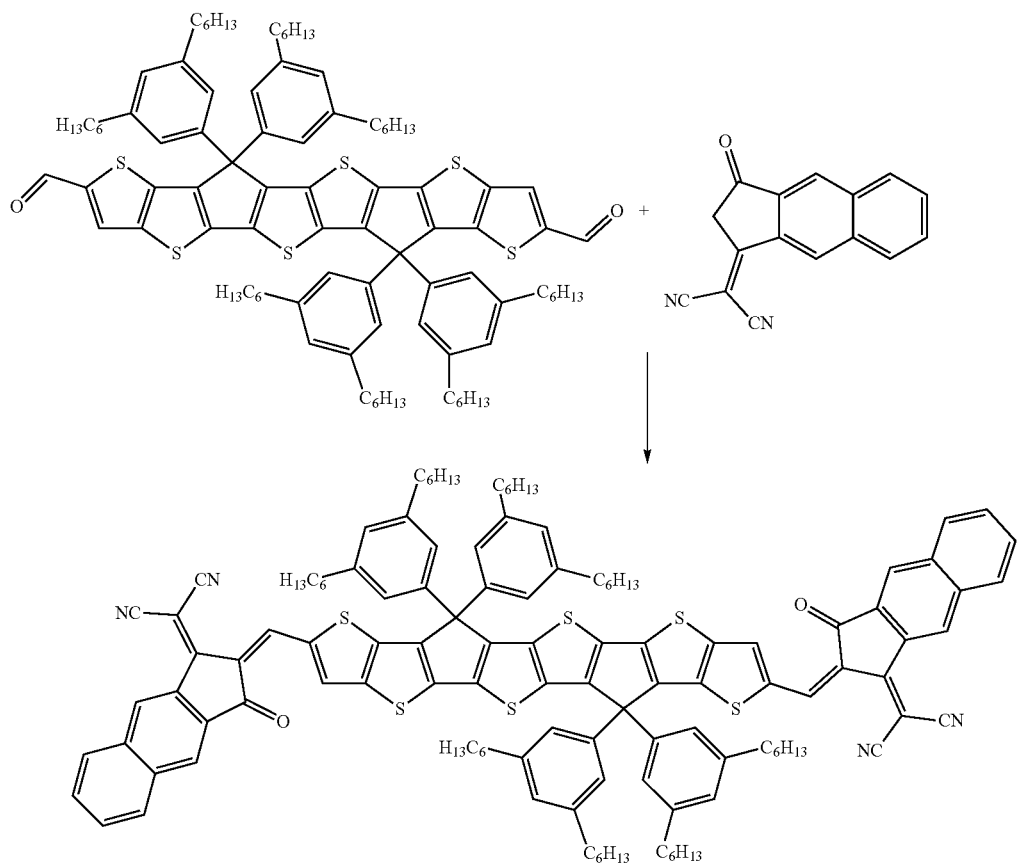

Compound 8

2-(3-Oxo-2,3-dihydro-cyclopenta[b]naphthalen-1-ylidene)-malononitrile (46 mg, 0.19 mmol) is added to a nitrogen saturated solution of intermediate 21 (92 mg, 0.06 mmol) in a mixture of chloroform (1 cm³) and pyridine (9 cm³). The solution is stirred for 3 hours. Methanol (30 cm³) is added, the solid collected by filtration and washed with methanol (50 cm³). The crude is purified by silica pad (cyclohexane:chloroform; 1:1) followed by trituration (dichloromethane:acetone; 1:1) to give compound 8 (75 mg, 67%) as a black solid. $^1$H NMR (400 MHz, CDCl$_3$) 9.19 (2H, s), 8.98 (2H, s), 8.33 (2H, s), 8.16 (2H, s), 8.10 (2H, dd, J 6.3, 3.4), 8.04 (2H, dd, J 6.2, 3.4), 7.72 (4H, dt, J 6.3, 3.4), 6.97 (4H, t, J 1.5), 6.90 (8H, d, J 1.5), 2.56 (16H, t, J 7.7), 1.50-1.64 (16H, m), 1.14-1.32 (48H, m), 0.73-0.84 (24H, m).

Example 9

Intermediate 22

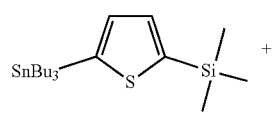

To a degassed mixture of intermediate 5 (7.1 g, 20 mmol), trimethyl-(5-tributylstannanyl-thiophen-2-yl)-silane (10 g, 23 mmol) and anhydrous toluene (300 cm³) is added tetrakis(triphenylphosphine)palladium(0) (500 mg, 0.4 mmol) and the mixture further degassed for 15 minutes. The mixture is stirred at 85° C. for 17 hours. The reaction mixture is filtered hot through a celite plug and washed through with hot toluene. The crude product is purified by column chromatography (40-60 petrol:dichloromethane: 4:1) to give intermediate 22 (2.3 g, 21%) as a pale yellow solid. $^1$H NMR (400 MHz, CDCl$_3$) 7.40 (1H, d, J 3.7), 6.99-7.03 (1H, m), 4.13-4.29 (4H, m), 1.15-1.28 (6H, m), 0.10-0.37 (9H, s).

Intermediate 23

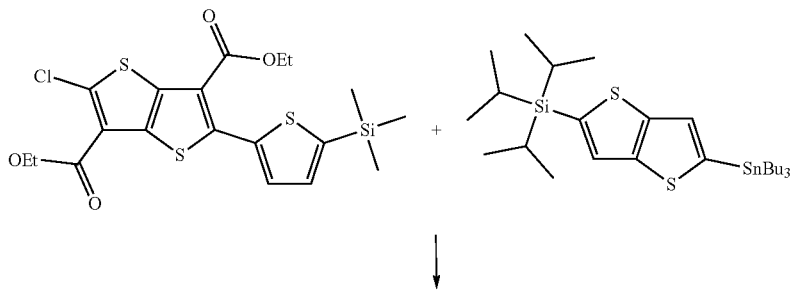

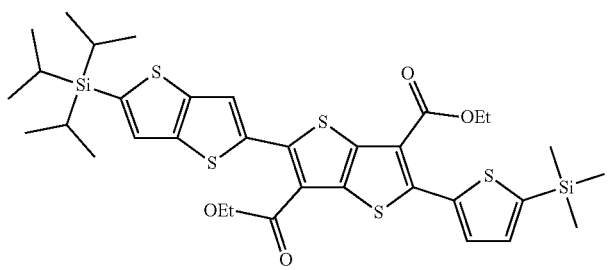

To a degassed mixture of intermediate 22 (2.2 g, 4.6 mmol), intermediate 13 (3.4 g, 5.8 mmol) and anhydrous toluene (300 cm³) is added tetrakis(triphenylphosphine) palladium(0) (0.5 g, 0.4 mmol) and the mixture further degassed for 15 minutes. The mixture is stirred at 85° C. for 17 hours. The reaction mixture is filtered hot through a celite plug and washed through with hot toluene. The crude product is stirred in acetone (100 cm³) for 1 hour to form a heavy suspension. The solid is collected by filtration to give intermediate 23 (3.2 g, 75%) as a pale brown solid. $^1$H NMR (400 MHz, CDCl$_3$) 7.80-7.86 (1H, s), 7.65 (1H, d, J 3.4), 7.38 (1H, s), 7.24 (1H, d, J 3.4), 4.43 (4H, m), 1.31-1.51 (10H, m), 1.15 (18H, d, J 7.3), 0.38 (9H, s).

Intermediate 24

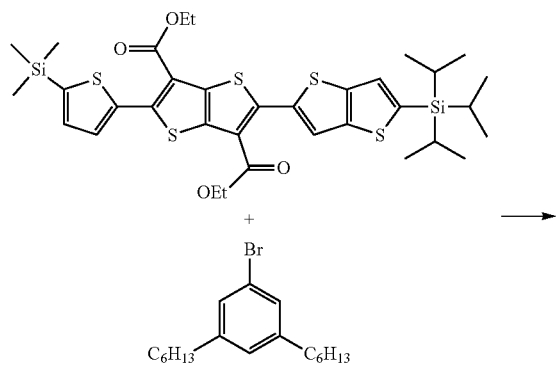

-continued

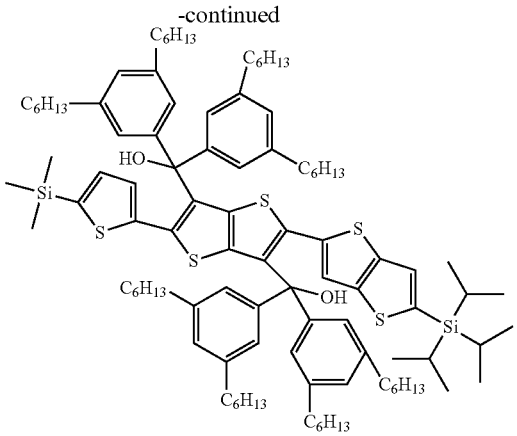

To a solution of 1-bromo-3,5-dihexyl-benzene (4.9 g, 15 mmol) in anhydrous tetrahydrofuran (100 cm³) at −78° C. is added dropwise n-butyllithium (6.0 cm³, 15 mmol, 2.5 M in hexane) over 30 minutes. After addition, the reaction mixture is stirred at −78° C. for 120 minutes. Intermediate 23 (2.2 g, 3.0 mmol) is added and the mixture allowed to warm to 23° C. over 17 hours. Diethyl ether (100 cm³) and water (100 cm³) are added and the mixture stirred for 30 minutes. The product is extracted with diethyl ether (3×100 cm³). The organics are combined and dried over anhydrous magnesium sulfate, filtered and the solvent removed in vacuo to give intermediate 24 (2.30 g, 47%) as a brown oil. $^1$H NMR (400 MHz, CD$_2$Cl$_2$) 7.21 (1H, s), 7.06 (1H, s), 6.80-7.03 (12H, m), 6.42-6.55 (2H, m), 3.36 (2H, d, J 4.4), 2.44-2.62 (16H, m), 1.48-1.65 (16H, m), 1.24-1.35 (49H, m), 1.11-1.17 (18H, m), 0.83-0.94 (24H, m), 0.26 (9H, s).

Intermediate 25

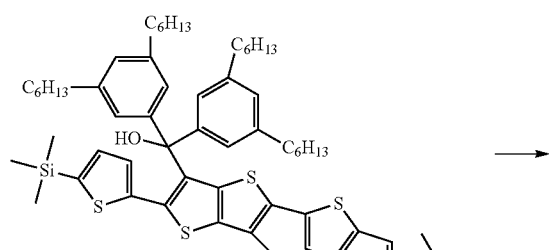

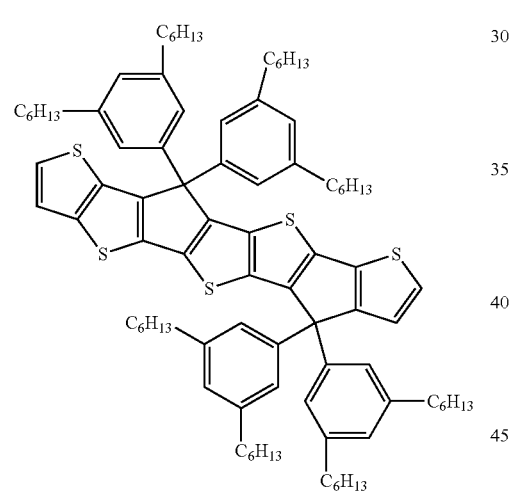

Nitrogen gas is bubbled through a suspension of Amberlyst 15 strong acid (8.8 g) in anhydrous diethyl ether (100 cm³) at 0° C. for 60 minutes. Intermediate 24 (2.2 g, 1.4 mmol) is added whilst the mixture is degassed for a further 30 minutes. The resulting suspension is stirred at 23° C. for 2 hours. The reaction mixture is filtered and the solvent removed in vacuo. The crude is taken up in anhydrous tetrahydrofuran (50 cm³) and tetrabutylammonium fluoride (2.7 cm³, 2.7 mmol, 1 M in tetrahydrofuran) added. The mixture is stirred for 1 hour, diethyl ether (100 cm³) and water (200 cm³) added and the mixture stirred for 30 minutes. The product is extracted with diethyl ether (3×100 cm³). The organics are combined and dried over anhydrous magnesium sulfate, filtered and the solvent removed in vacuo. The crude is purified by column chromatography (40-60 petrol:dichloromethane; 9:1) to give intermediate 25 (1.0 g, 54%) as a dark orange solid. ¹H NMR (400 MHz, CDCl₃) 7.25-7.31 (1H, m), 7.21-7.25 (1H, m), 7.17 (1H, d, J 4.9), 7.05 (1H, d, J 4.9), 6.81-6.91 (12H, m), 2.40-2.57 (16H, m), 1.54 (16H, d, J 6.8), 1.25 (48H, d, J 7.3), 0.85 (24H, q, J 6.2).

Intermediate 26

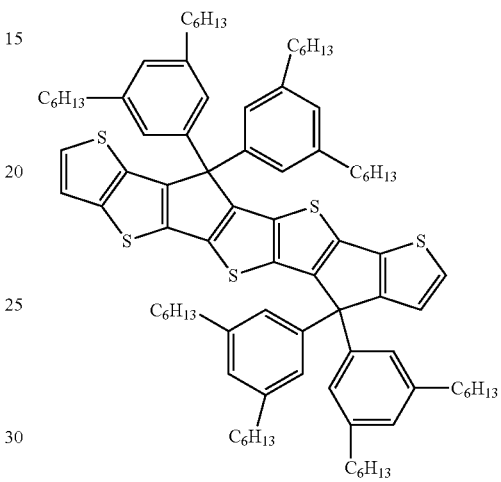

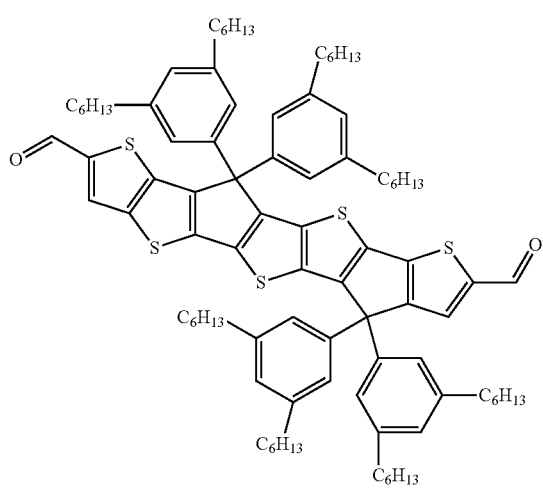

To a solution of intermediate 25 (500 mg, 0.37 mmol) in anhydrous tetrahydrofuran (22 cm³) at −78° C. is added dropwise n-butyllithium (0.6 cm³, 1.5 mmol, 2.5 M in hexane) over 10 minutes. After addition, the reaction mixture is stirred at −78° C. for 60 minutes. N,N-Dimethylformamide (0.15 cm³, 2.2 mmol) is added and the mixture allowed to warm to 23° C. over 17 hours. Diethyl ether (50 cm³) and water (50 cm³) are added and the mixture stirred for 30 minutes. The product is extracted with diethyl ether (3×100 cm³) and the combined organics dried over anhydrous magnesium sulfate, filtered and the solvent removed in vacuo. The crude is purified by column chromatography (40-60 petrol:dichloromethane; 8:2) to give intermediate 26 (95 mg, 18%) as a dark red oil. ¹H NMR (400 MHz, CDCl₃) 9.70-9.85 (1H, s), 9.69-9.75 (1H, s), 7.83-7.87 (1H, s), 7.56 (1H, s), 6.83 (4H, s), 6.71 (8H, dd, J 12.8, 1.3), 2.29-2.53 (16H, m), 1.36-1.55 (16H, m), 1.05-1.27 (48H, m), 0.76 (24H, q, J 6.8).

Intermediate 27

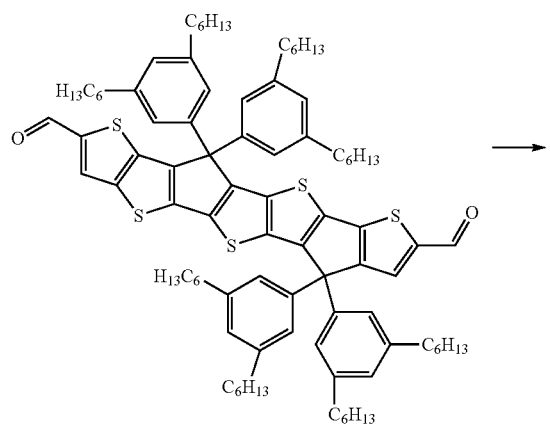

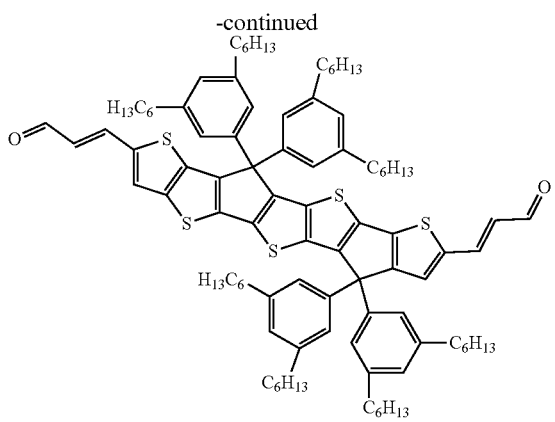

To a solution of intermediate 26 (1.00 g, 0.71 mmol) and tributyl(1,3-dioxolan-2-ylmethyl)-phosphonium bromide (573 mg, 1.55 mmol) in tetrahydrofuran (50 cm³) is added sodium hydride (169 mg, 4.23 mmol, 60% dispersion in mineral oil). The reaction is then stirred for 18 hours. The reaction is cooled to 0° C. and hydrochloric acid (5 cm³, 10% in water) is added and the mixture stirred at 0° C. for 40 minutes and at 23° C. for 2 hours. Water (25 cm³) is added and the mixture extracted with ether (3×50 cm³). The combined organic layer is washed with brine (50 cm³) before drying over anhydrous magnesium sulfate, filtered and the solvent removed in vacuo. The crude is triturated in acetonitrile (100 cm³) at 50° C. for 1 hour. The solvent is decanted and the material dried to give intermediate 27 (920 mg, 89%) as a dark purple oil. ¹H NMR (400 MHz, CDCl₃) 9.48-9.55 (2H, m), 7.41-7.52 (3H, m), 7.18 (1H, s), 6.64-6.89 (12H, m), 6.27-6.42 (2H, m), 2.34-2.50 (16H, m), 1.39-1.54 (16H, m), 1.10-1.29 (48H, m), 0.70-0.80 (24H, m).

Compound 9

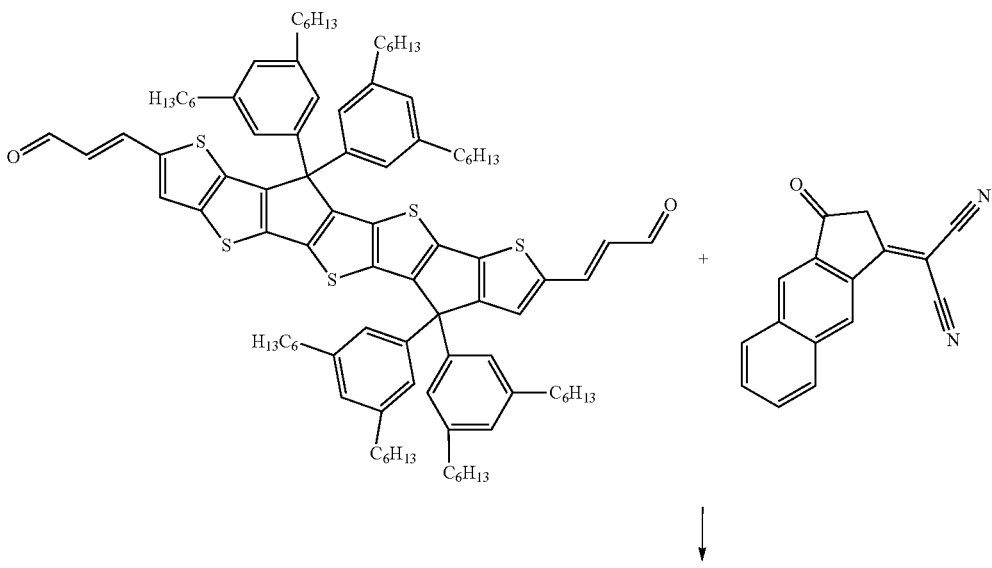

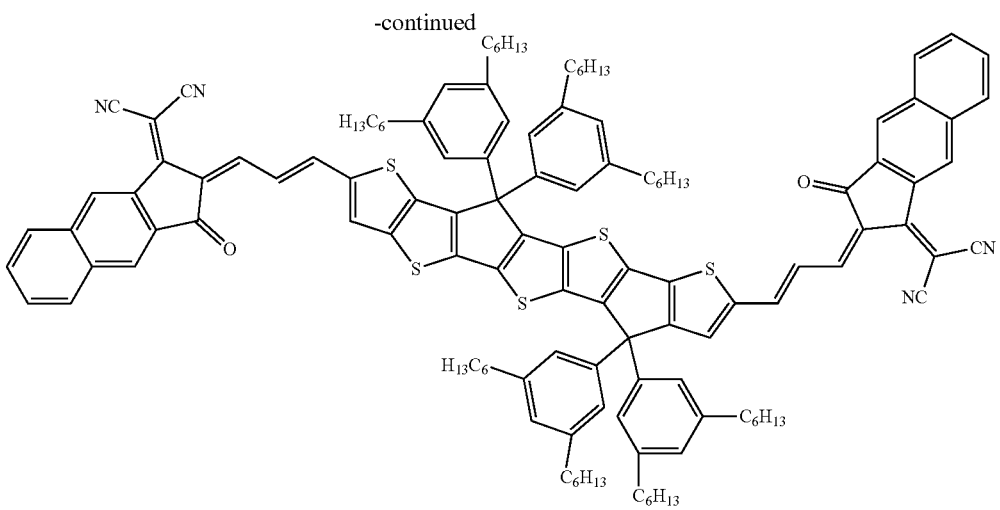

To a solution of intermediate 27 (120 mg, 0.082 mmol) in anhydrous chloroform (6.5 cm³) at 0° C. is added 2-(3-oxo-2,3-dihydro-cyclopenta[b]naphthalen-1-ylidene)-malononitrile (79.7 mg, 0.326 mmol) followed by pyridine (0.46 cm³). The resulting solution is then degassed for 15 minutes. The ice bath is removed and the mixture allowed to warm to 23° C. and stirred for 15 minutes. Acetonitrile (50 cm³) is added to form a heavy suspension and the solid collected by filtration to give compound 9 (145 mg, 92%) as a dark brown solid. $^1$H NMR (400 MHz, CD$_2$Cl$_2$) 9.07 (2H, d, J 5.4), 8.53-8.67 (2H, m), 8.36-8.44 (2H, m), 8.23-8.29 (2H, m), 7.94-8.05 (4H, m), 7.46-7.66 (7H, m), 7.34 (1H, s), 6.73-6.92 (12H, m), 2.35-2.48 (16H, m), 1.40-1.56 (16H, m), 1.17 (48H, d, J 2.4), 0.66-0.81 (24H, m).

Example 10

Intermediate 28

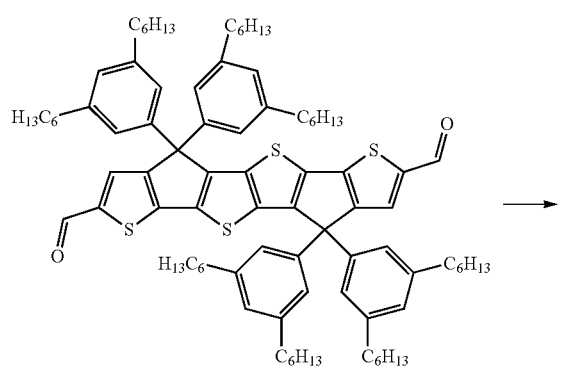

To a solution of tributyl(1,3-dioxolan-2-ylmethyl)-phosphonium bromide (1.03 g, 2.77 mmol) and intermediate 2 (1.72 g, 1.26 mmol) in anhydrous tetrahydrofuran (70 cm³) is added sodium hydride (303 mg, 7.57 mmol, 60% dispersion in mineral oil) and the reaction stirred for 17 hours. The reaction is cooled to 0° C. before addition of hydrochloric acid (11 cm³, 10% in water). The mixture is then stirred at 0° C. for 40 minutes and at 23° C. for 47 hours. Ethyl acetate (100 cm³) and water (100 cm³) are then added. The organic layer is then washed with water (100 cm³) and brine (25 cm³) before drying over anhydrous magnesium sulfate, filtered and the solvent removed in vacuo. The crude is then purified by column chromatography using a graded solvent system (40-60 petrol:dichloromethane; 1:0 to 3:7) to give intermediate 10 (1.53 g, 86%) as a dark oily solid. $^1$H NMR (400 MHz, CDCl$_3$) 9.57 (2H, d), 7.48-7.56 (2H, m), 7.24-7.26 (2H, m), 6.90 (4H, s), 6.78 (8H, s), 6.37-6.49 (2H, m), 2.42-2.55 (16H, m), 1.43-1.60 (16H, m), 1.17-1.30 (48H, m), 0.74-0.84 (24H, m).

Compound 10

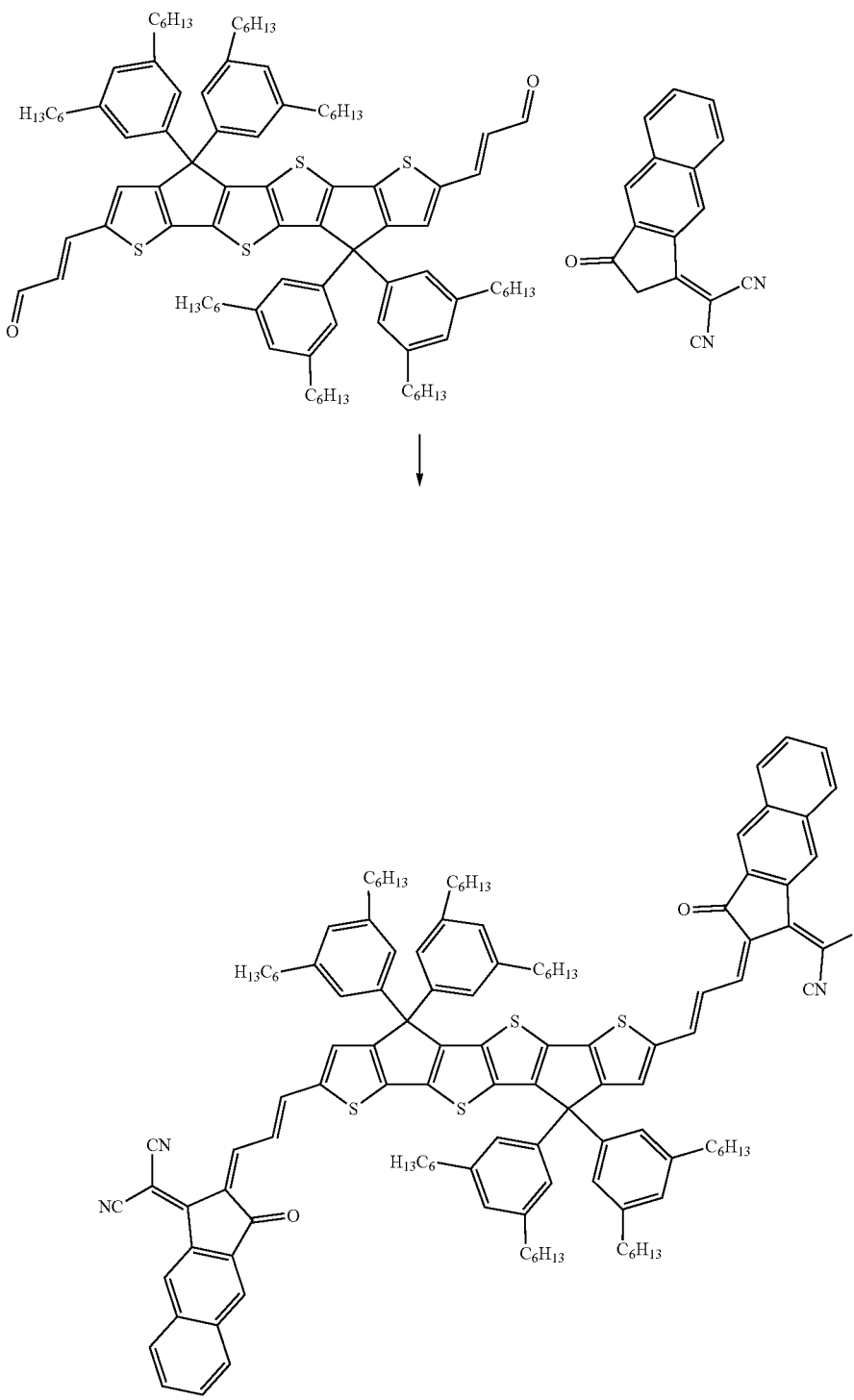

To a degassed solution of intermediate 28 (189 mg, 0.13 mmol) in anhydrous chloroform (10 cm³) and pyridine (0.76 cm³) at 0° C. is added 2-(3-oxo-2,3-dihydro-cyclopenta[b]naphthalen-1-ylidene)-malononitrile (131 mg, 0.535 mmol). The reaction mixture is stirred for 2.5 hours at 0° C. and then poured into stirred methanol (150 cm³). The mixture stirred for 25 minutes, the solid collected by filtration and washed with methanol (3×10 cm³), acetonitrile (3×10 cm³) and 40-60 petrol (3×10 cm³). The crude is then recrystallised (80-100 petrol:acetone) to give compound 10 (26 mg, 10%) as a black solid. $^1$H NMR (400 MHz, CDCl$_3$) 9.16 (2H, s), 8.69 (2H, dd, J 14.6, 11.9), 8.50 (2H, d, J 11.7), 8.35 (2H, s), 8.01-8.11 (4H, m), 7.66-7.73 (4H, m), 7.55 (2H, d, J 14.4), 7.38 (2H, s), 6.95 (4H, s), 6.81 (8H, d, J 1.2), 2.53 (16H, t, J 7.7), 1.49-1.66 (16H, m), 1.21-1.35 (48H, m), 0.81-0.89 (24H, m).

Example 11

Intermediate 29

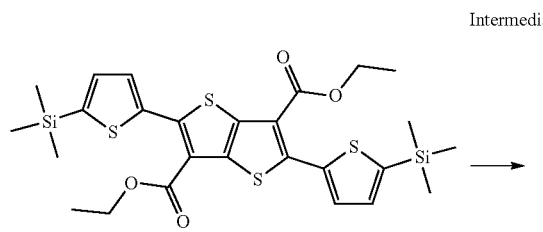

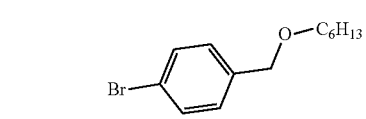

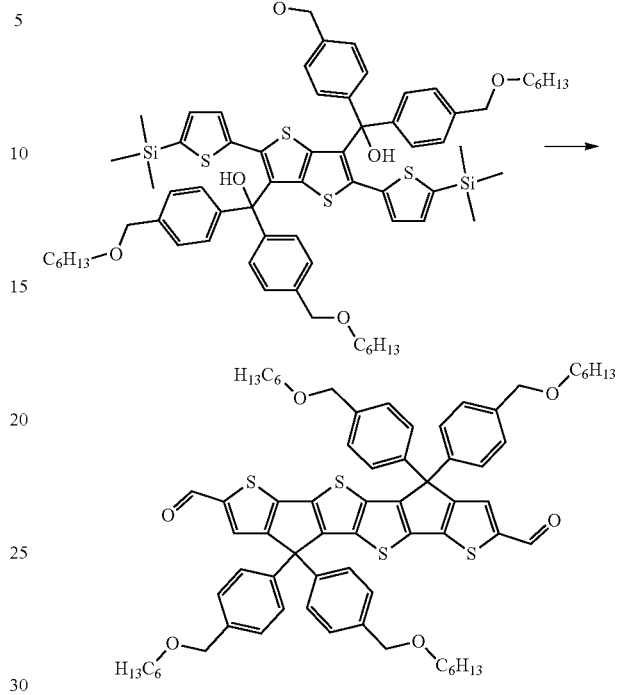

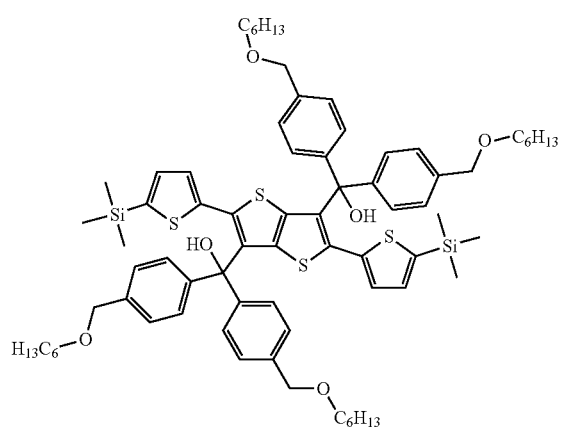

To a solution of 1-bromo-4-hexyloxymethyl-benzene (2.27 g, 8.37 mmol) in anhydrous tetrahydrofuran (68 cm$^3$) at −78° C. is slowly added t-butyllithium (9.9 cm$^3$, 17 mmol, 1.7 M in pentanes). The solution is stirred for 2 hours, warmed to −30° C. and then cooled again to −70° C. Intermediate 6 (993 mg, 1.67 mmol) is added, the reaction slowly warmed to 23° C. and stirred for 16 hours. Water (50 cm$^3$) and ether (100 cm$^3$) are added. The organic phase is washed with water (3×30 cm$^3$), dried over anhydrous magnesium sulphate, filtered and concentrated in vacuo. The resulting yellow oil (2.50 g) is taken through to the next step without further purification. $^1$H NMR (400 MHz, CDCl$_3$) 7.26-7.31 (16H, m), 6.83 (2H, d, J 3.4), 6.46 (2H, d, J 3.4), 4.53 (8H, s), 3.43-3.48 (10H, m), 1.54-1.70 (8H, m), 1.20-1.43 (24H, m), 0.83-0.97 (12H, m), 0.23 (18H, s).

Intermediate 30

To a nitrogen saturated solution of intermediate 29 (2.5 g) in toluene (100 cm$^3$) at 50° C. is added Amberlyst 15 strong acid (8.0 g). The suspension is purged with nitrogen for a further 5 minutes and stirred for 16 hours. The reaction mixture is filtered and washed with toluene (3×20 cm$^3$) and the combined filtrate concentrated in vacuo. The crude is purified by column chromatography (dichloromethane). The oil is dissolved in chloroform (50 cm$^3$) and cooled in an ice bath. N,N-Dimethylformamide (2.30 g, 31.5 mmol) and phosphorus oxychloride (4.52 g, 29.5 mmol) are slowly added. The reaction is stirred for 1 hour at 23° C., 60° C. for 8 hours and for 48 hours at 23° C. Water (20 cm$^3$) is slowly added and the biphasic solution is heated to 60° C. Saturated aqueous sodium acetate (20 cm$^3$) is added and the mixture stirred for a further 3 hours, then cooled to 23° C. The aqueous phase is extracted with dichloromethane (20 cm$^3$). The combined organics are washed with water (50 cm$^3$), dried over magnesium sulphate, filtered and concentrated in vacuo. The residue is purified by column chromatography using a graded solvent system (dichloromethane:acetone; 1:0 to 9:1) followed by trituration (80-100 petrol) to give intermediate 30 (380 mg, 17%) as an orange solid. $^1$H NMR (400 MHz, CDCl$_3$) 9.82 (2H, s), 7.66 (2H, s), 7.29-7.34 (8H, m), 7.19-7.24 (8H, m), 4.47 (8H, s), 3.49 (8H, t, J 6.6), 1.55-1.67 (8H, m), 1.24-1.41 (24H, m), 0.89 (12H, t, J 6.7).

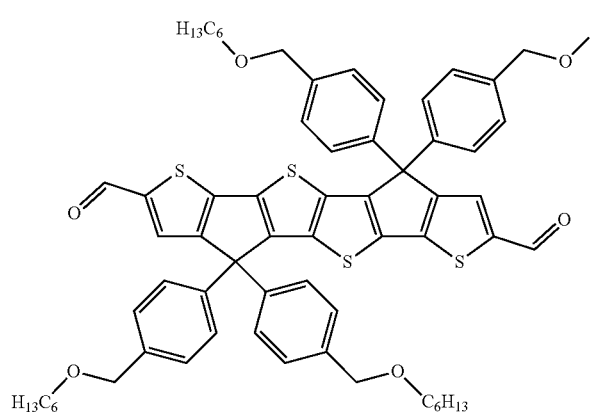
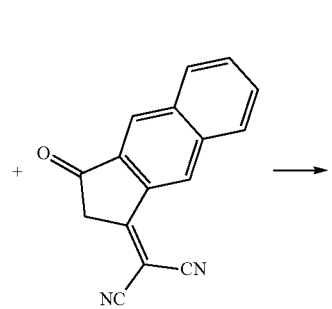

Compound 11

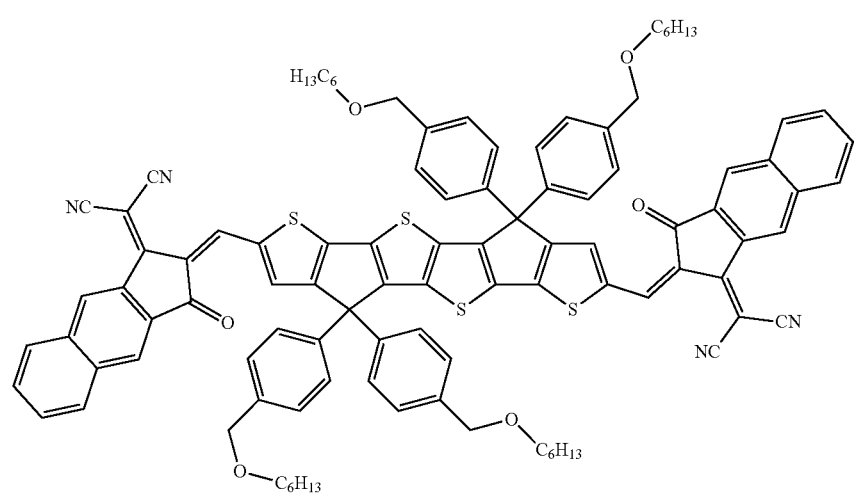

Intermediate 30 (100 mg, 0.09 mmol) and 2-(3-oxo-2,3-dihydro-cyclopenta[b]naphthalen-1-ylidene)-malononitrile (107 mg, 0.44 mmol) are suspended in chloroform (10 cm$^3$) and saturated with nitrogen. Pyridine (0.49 cm$^3$) is added and the solution stirred for 16 hours at 23° C. and at 60° C. for 1 hour. Methanol (25 cm$^3$) is added slowly over 15 minutes, the mixture stirred for 30 minutes and then cooled to 23° C., filtered and washed with methanol (2×25 cm$^3$). The crude is purified by column chromatography using a graded solvent system (dichloromethane:diethyl ether; 1:0 to 33:1) to give compound 11 (46 mg, 33%) as a green solid. $^1$H NMR (400 MHz, CDCl$_3$) 9.18 (2H, s), 8.93 (2H, s), 8.37 (2H, s), 8.02-8.11 (4H, m), 7.73 (2H, s), 7.63-7.71 (4H, m), 7.36 (8H, d, J 8.3), 7.26 (8H, d, J 8.4), 4.51 (8H, s), 3.51 (8H, t, J 6.6), 1.56-1.69 (8H, m), 1.19-1.44 (24H, m), 0.84-0.95 (12H, m).

Example 12

Intermediate 31

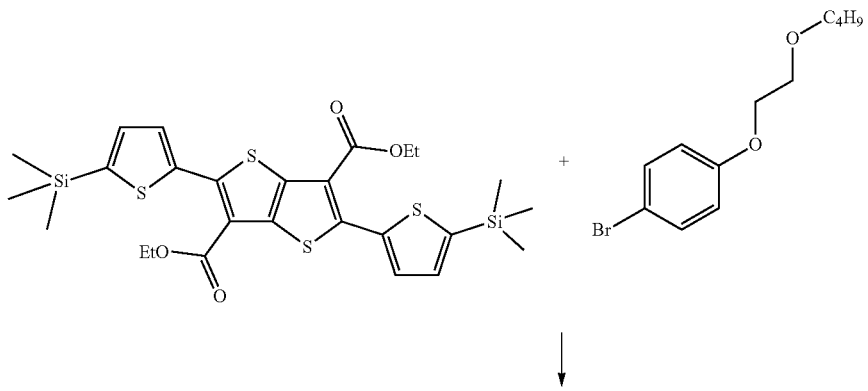

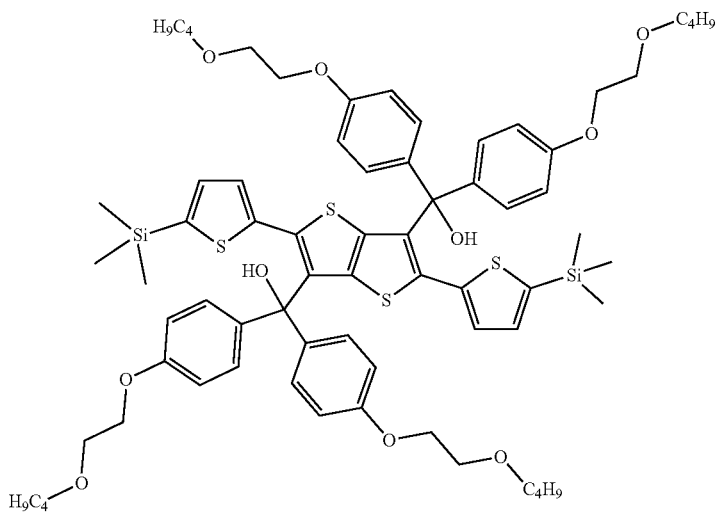

Anhydrous tetrahydrofuran (2 cm³) is added to a flask containing oven dried magnesium turnings (246 mg, 10.1 mmol) and an iodine crystal. The mixture is maintained at reflux while a solution of 1-bromo-4-(2-butoxy-ethoxy)-benzene (2.77 g, 10.1 mmol) in anhydrous tetrahydrofuran (5 cm³) is added portion wise over 10 minutes. The reaction is then heated at reflux for 2 hours. The resulting Grignard reagent is transferred over 5 minutes to a flask containing intermediate 6 (1.00 g, 1.69 mmol) dissolved in anhydrous tetrahydrofuran (10 cm³) and maintained at 65° C. The mixture is heated at 65° C. for 6 hours, followed by 16 hours at 23° C. The solution is partioned between water (30 cm³) and diethyl ether (30 cm³). Hydrochloric acid (2 N) is added slowly until the phases become clear. The organic phase is washed with water (2×20 cm³), dried over anhydrous magnesium sulphate, filtered and concentrated in vacuo. The residue is recrystallised (40-60 petrol) to give intermediate 31 (1.59 g, 74%) as a beige solid. $^1$H NMR (400 MHz, CDCl$_3$) 7.14-7.23 (8H, m), 6.88 (2H, d, J 3.4), 6.81-6.87 (8H, m), 6.48 (2H, d, J 3.4), 4.13 (8H, t, J 4.1), 3.79 (8H, t, J 4.1), 3.54 (8H, t, J 6.7), 3.39 (2H, s), 1.55-1.67 (8H, m), 1.32-1.47 (8H, m), 0.94 (12H, t, J 7.4), 0.25 (18H, s).

Intermediate 32

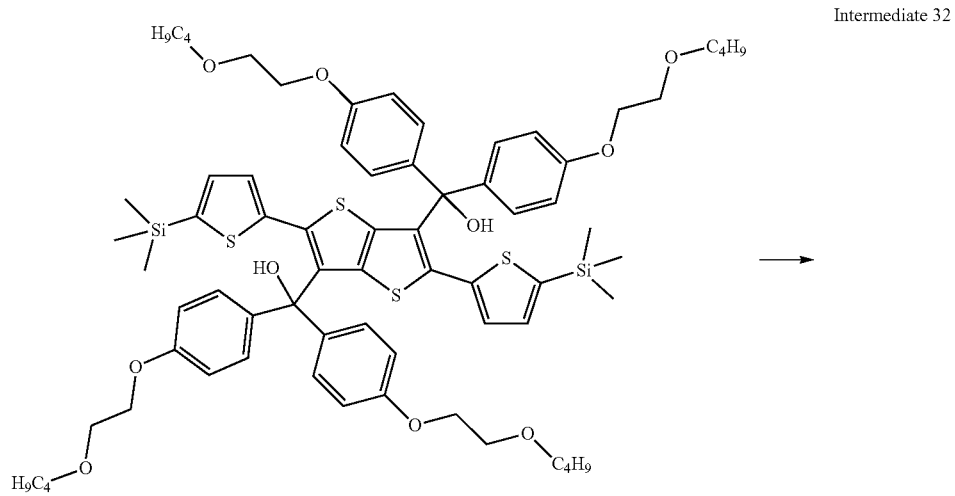

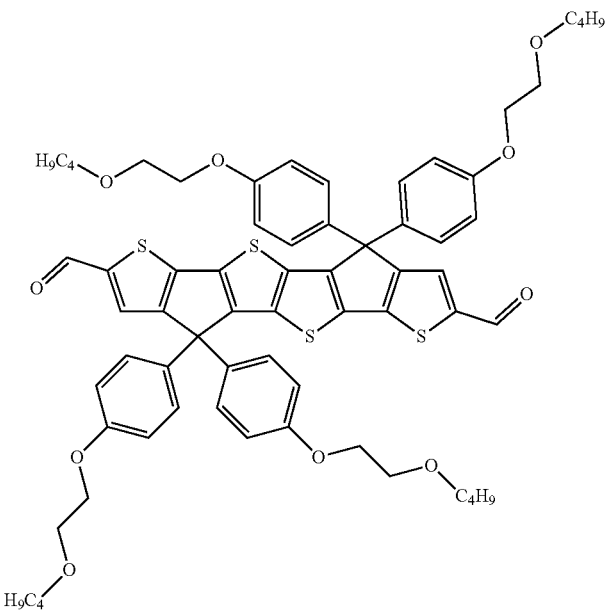

Intermediate 31 is dissolved in toluene (64 cm³). The solution is saturated with nitrogen and Amberlyst 15 strong acid (6.0 g) is added. Nitrogen is bubbled through the suspension for a further 10 minutes and the mixture is stirred for 16 hours. The reaction is filtered and the solid washed with hot toluene (3×10 cm³). The combined filtrates are concentrated in vacuo and purified by silica plug (dichloromethane). The intermediate is dissolved in chloroform (32 cm³), N,N-dimethylformamide (1.46 g) added and the solution cooled in an ice-bath. Phosphorus oxychloride (2.86 g, 18.7 mmol) is added over 5 minutes. The solution is warmed to 23° C. and then heated at 65° C. for 16 hours. Water (5 cm³) is slowly added followed by aqueous sodium acetate (50 cm³, 10 M) and the biphase is stirred for 1 hour at 65° C. The aqueous phase is extracted with dichloromethane (20 cm³) and the combined organics washed with water (2×20 cm³), dried over anhydrous magnesium sulphate, filtered and concentrated in vacuo. The residue is then triturated in boiling 40-60 petrol (15 cm³), filtered and washed with 40-60 petrol (2×5 cm³) to give intermediate 32 (670 mg, 47%) as an orange solid. $^1$H NMR (400 MHz, CDCl$_3$) 9.73 (2H, s), 7.58 (2H, s), 7.05 (8H, d, J 8.6), 6.78 (8H, d, J 8.7), 4.00 (8H, t, J 4.9), 3.68 (8H, t, J 4.7), 3.43 (8H, t, J 6.7), 1.43-1.56 (8H, m), 1.29 (8H, q, J 7.5), 0.83 (12H, t, J 7.3).

Compound 12

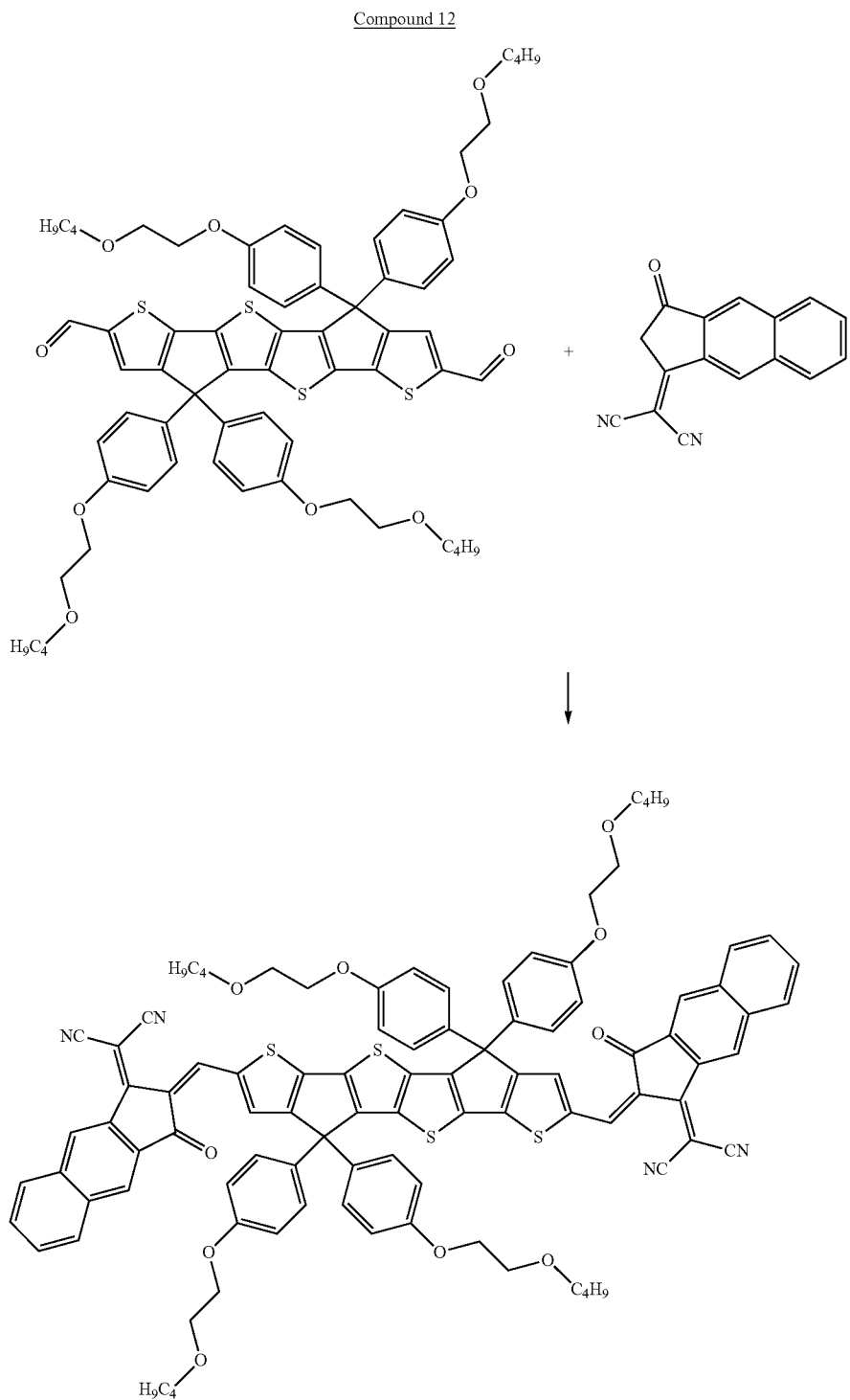

Intermediate 32 (100 mg, 0.09 mmol) and 2-(3-oxo-2,3-dihydro-cyclopenta[b]naphthalen-1-ylidene)-malononitrile (106 mg, 0.43 mmol) are dissolved in chloroform (2.5 cm$^3$). Nitrogen is bubbled through the suspension for 10 minutes. Pyridine (0.49 cm$^3$) is added and the nitrogen inlet removed after a further 10 minutes. The reaction is stirred for 18 hours, diluted with methanol (20 cm$^3$) and stirred for 10 minutes. The resulting suspension is filtered and washed with methanol (2×5 cm$^3$). The material is purified by column chromatography using a graded solvent system (dichloromethane:methanol; 10:0 to 49:1) followed by recrystallisation (chloroform:acetone) to give compound 12 (97 mg, 70%) as a green solid. $^1$H NMR (400 MHz, CDCl$_3$) 9.10 (2H, s), 8.87 (2H, s), 8.29 (2H, s), 7.94-8.05 (4H, m), 7.58-7.67 (6H, m), 7.05-7.14 (8H, m), 6.78-6.87 (8H, m), 4.03 (8H, t, J 4.6), 3.69 (8H, t, J 4.7), 3.44 (8H, t, J 6.7), 1.45-1.56 (8H, m), 1.23-1.35 (8H, m), 0.83 (12H, t, J 7.4).

Example 13

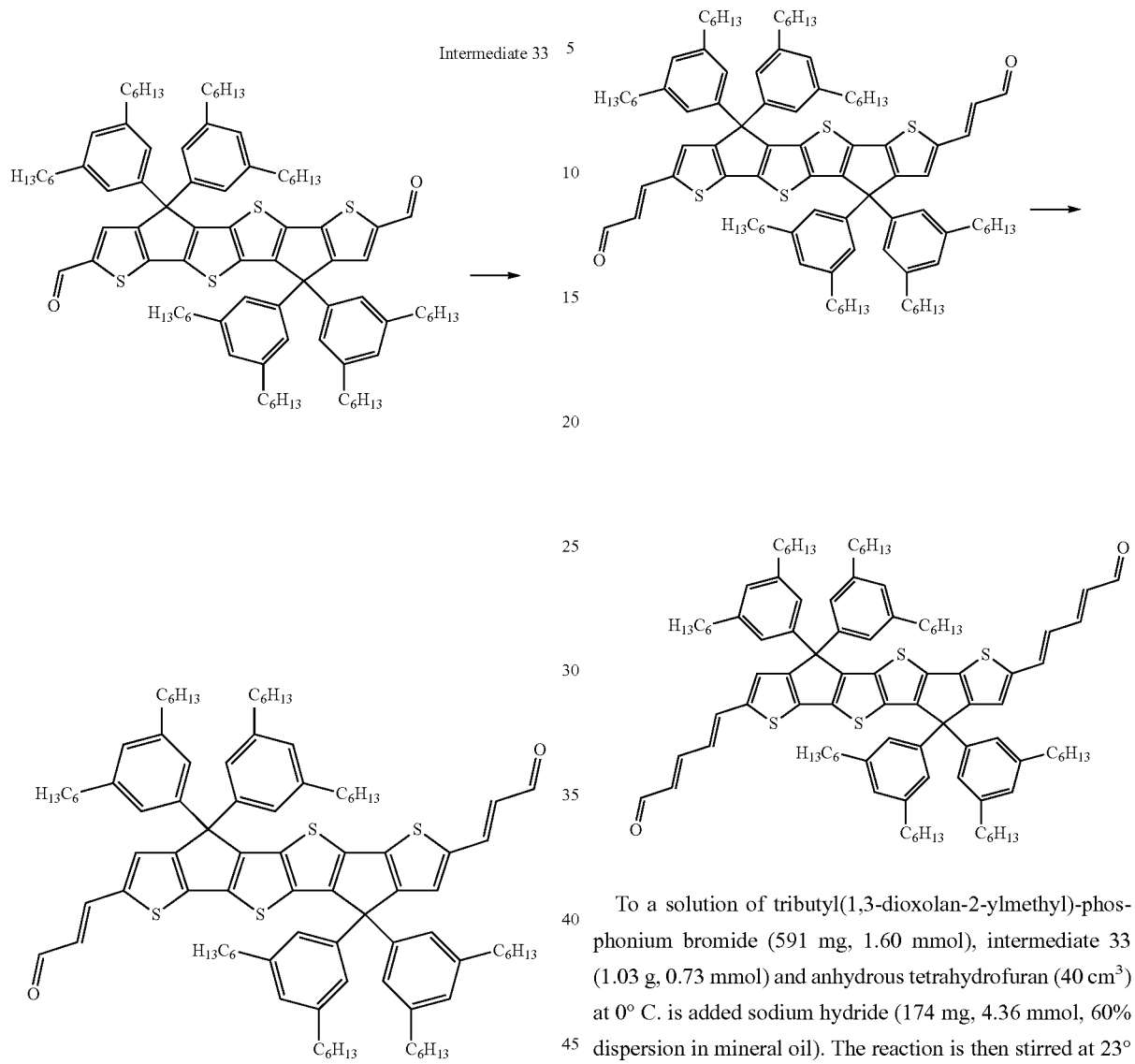

To a solution of tributyl(1,3-dioxolan-2-ylmethyl)-phosphonium bromide (1.03 g, 2.77 mmol) and intermediate 2 (1.72 g, 1.26 mmol) in anhydrous tetrahydrofuran (70 cm$^3$) is added sodium hydride (303 mg, 7.57 mmol, 60% dispersion in mineral oil) and the reaction stirred for 17 hours. The reaction is cooled to 0° C. before addition of hydrochloric acid (11 cm$^3$, 10% in water). The mixture is then stirred at 0° C. for 40 minutes and at 23° C. for 47 hours. Ethyl acetate (100 cm$^3$) and water (100 cm$^3$) are then added. The organic layer is washed with water (100 cm$^3$), brine (25 cm$^3$) before drying over anhydrous magnesium sulfate, filtered and the solvent removed in vacuo. The crude is then purified by column chromatography using a graded solvent system (40-60 petrol:dichloromethane; 1:0 to 3:7) to give intermediate 33 (1.53 g, 86%) as a dark oily solid. $^1$H NMR (400 MHz, CDCl$_3$) 9.54-9.60 (2H, m), 7.48-7.56 (2H, m), 7.24-7.26 (2H, m), 6.90 (4H, s), 6.78 (8H, s), 6.37-6.49 (2H, m), 2.42-2.55 (16H, m), 1.43-1.60 (16H, m), 1.17-1.30 (48H, m), 0.74-0.84 (24H, m).

To a solution of tributyl(1,3-dioxolan-2-ylmethyl)-phosphonium bromide (591 mg, 1.60 mmol), intermediate 33 (1.03 g, 0.73 mmol) and anhydrous tetrahydrofuran (40 cm$^3$) at 0° C. is added sodium hydride (174 mg, 4.36 mmol, 60% dispersion in mineral oil). The reaction is then stirred at 23° C. for 16 hours and then cooled to 0° C. before hydrochloric acid (10 cm$^3$, 10% in water) is added. The mixture is then stirred at 0° C. for 20 minutes and at 23° C. for 6 hours. Ethyl acetate (100 cm$^3$) and water (100 cm$^3$) are added and the organic layer washed with water (100 cm$^3$) and brine (100 cm$^3$) before drying over anhydrous magnesium sulfate, filtered and the solvent removed in vacuo. The crude is purified by column chromatography using a graded solvent system (40-60 petrol:ethyl acetate; 1:0 to 9:1) to give intermediate 34 (781 mg, 73%) as a purple/black oily solid. $^1$H NMR (400 MHz, CD$_2$Cl$_2$) 9.55 (2H, d, J 7.9), 7.20 (2H, dd, J 15.0, 11.1), 7.08-7.15 (4H, m), 6.91 (4H, s), 6.70-6.84 (10H, m), 6.16 (2H, dd, J 15.0, 7.9), 2.48 (16H, t, J 7.6), 1.45-1.57 (16H, m), 1.19-1.33 (48H, m), 0.80-0.87 (24H, m).

Compound 13

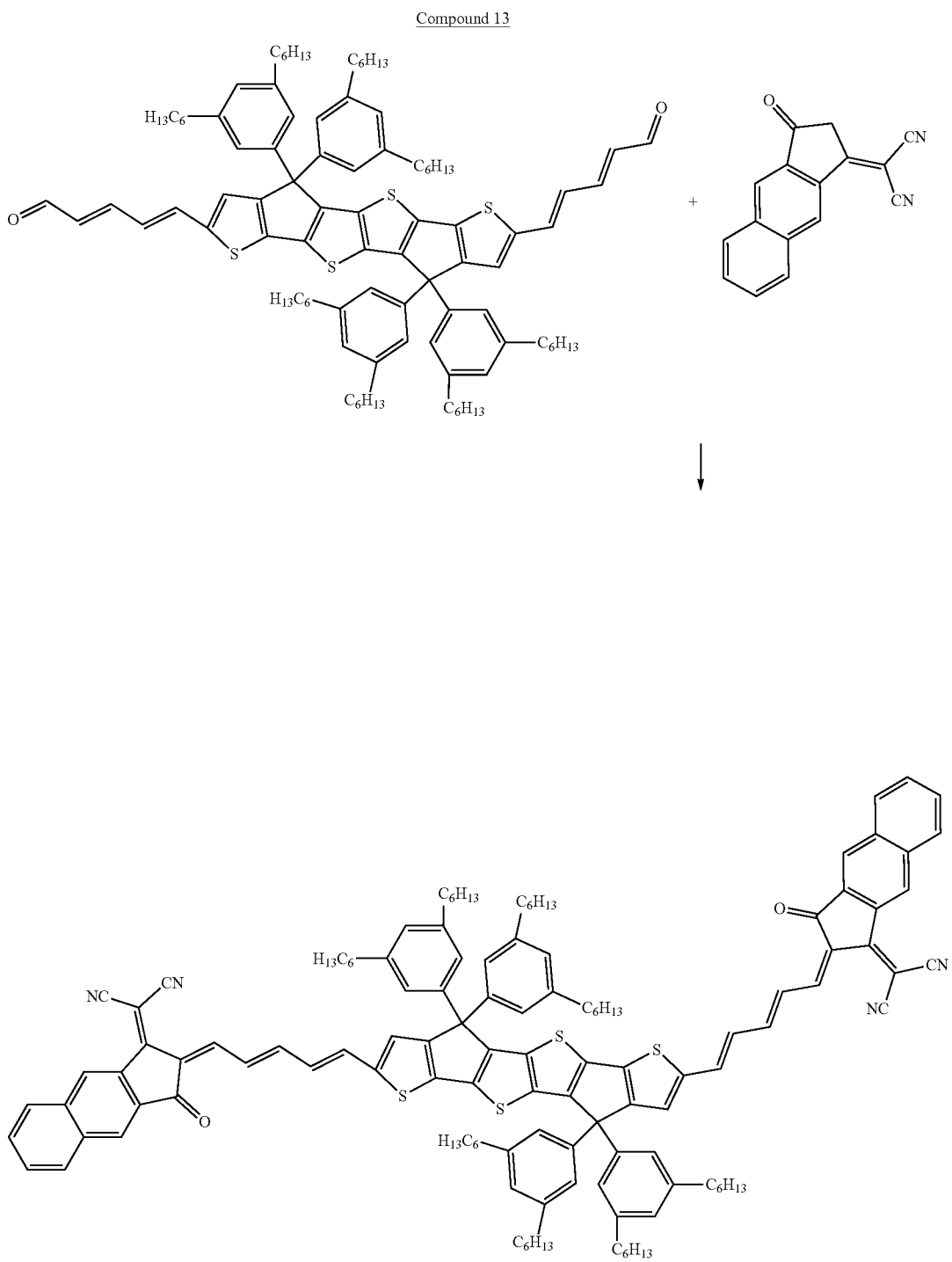

To a degassed solution of intermediate 34 (200 mg, 0.14 mmol), anhydrous chloroform (15 cm$^3$) and pyridine (0.77 cm$^3$, 9.6 mmol) at 0° C. is added 2-(3-oxo-2,3-dihydro-cyclopenta[b]naphthalen-1-ylidene)-malononitrile (133 mg, 0.55 mmol). The reaction mixture is then stirred at 0° C. for 110 minutes before adding to stirred methanol (150 cm$^3$) and the mixture stirred for 15 minutes at 23° C. The solid collected by filtration, washed with methanol (5×10 cm$^3$), acetonitrile (3×10 cm$^3$), 40-60 petrol (3×10 cm$^3$), cyclohexane (3×10 cm$^3$), ethyl acetate (3×10 cm$^3$), diethyl ether (3×10 cm$^3$), acetone (3×10 cm$^3$) and 2-butanone (3×10 cm$^3$). The solid is triturated with boiling ether (2×50 cm$^3$) and the collected solid washed with ether (2×50 cm$^3$) to give compound 13 (143 mg, 55%) as a black solid. $^1$H NMR (400 MHz, CD$_2$Cl$_2$) 9.15 (2H, s), 8.30-8.49 (6H, m), 8.03-8.13 (4H, m), 7.66-7.74 (4H, m), 7.18-7.34 (6H, m), 7.01 (2H, dd, J 14.6, 11.6), 6.93 (4H, s), 6.83 (8H, s), 2.50 (16H, t, J 7.5), 1.46-1.61 (16H, m), 1.18-1.36 (48H, m), 0.78-0.90 (24H, m).

Example 14

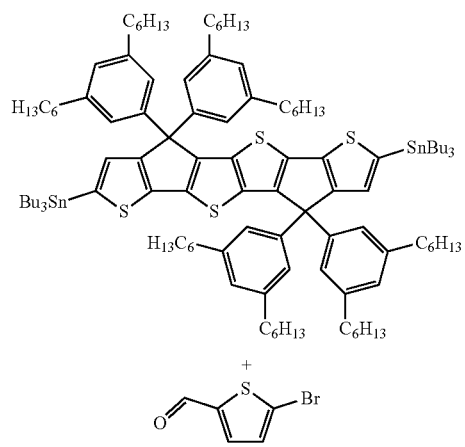

Intermediate 35

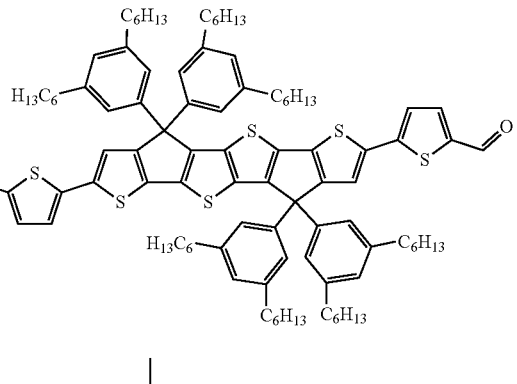

Intermediate 36

To a degassed solution of 5-bromo-thiophene-2-carbaldehyde (1.05 cm³, 8.83 mmol), anhydrous toluene (240 cm³) and intermediate 3 (7.56 g, 4.01 mmol) is added tris(dibenzylideneacetone)dipalladium(0) (294 mg, 0.32 mmol) and tris(o-tolyl)phosphine (366 mg, 1.20 mmol). The reaction mixture is then further degassed before heating at 80° C. for 45 hours. The reaction mixture is allowed to cool to 23° C. and the solvent removed in vacuo. The crude is purified by column chromatography using a graded solvent system (40-60 petrol:dichloromethane; 1:0 to 0:1) followed by trituration in acetonitrile (20 cm³) to give intermediate 35 (1.30 g, 21%) as a dark red solid. $^1$H NMR (400 MHz, CDCl$_3$) 9.82 (2H, s), 7.63 (2H, d, J 4.0), 7.29 (2H, s), 7.18 (2H, d, J 4.0), 6.90 (4H, s), 6.82 (8H, d, J 1.1), 2.49 (16H, t, J 7.6), 1.47-1.57 (16H, m), 1.19-1.32 (48H, m), 0.80-0.87 (24H, m).

To a mixture of tributyl(1,3-dioxolan-2-ylmethyl)-phosphonium bromide (692 mg, 1.87 mmol), intermediate 35 (1.30 g, 0.85 mmol) and anhydrous tetrahydrofuran (46 cm³) is added sodium hydride (204 mg, 5.11 mmol, 60% dispersion in mineral oil) and the reaction stirred at 23° C. for 70 hours. Hydrochloric acid (12 cm³, 10% in water) is added and the mixture stirred for 3 hours. Ethyl acetate (75 cm³) and water (75 cm³) are then added and the organic layer extracted with ethyl acetate (10 cm³). The combined organic layer is washed with water (75 cm³) and brine (75 cm³) before drying over anhydrous magnesium sulfate, filtered and the solvent removed in vacuo. The crude is triturated in warm acetonitrile (2×20 cm³) to give intermediate 36 (1.29 g, 96%) as a purple solid. $^1$H NMR (400 MHz, CDCl$_3$) 9.60 (2H, d, J 7.7), 7.50 (2H, d, J 15.5), 7.23 (2H, d, J 3.9), 7.20 (2H, s), 7.10 (2H, d, J 4.0), 6.89 (4H, s), 6.82 (8H, d, J 1.5), 6.40 (2H, dd, J 15.4, 7.7), 2.49 (16H, t, J 7.7), 1.47-1.56 (16H, m), 1.18-1.32 (48H, m), 0.78-0.87 (24H, m).

Compound 14

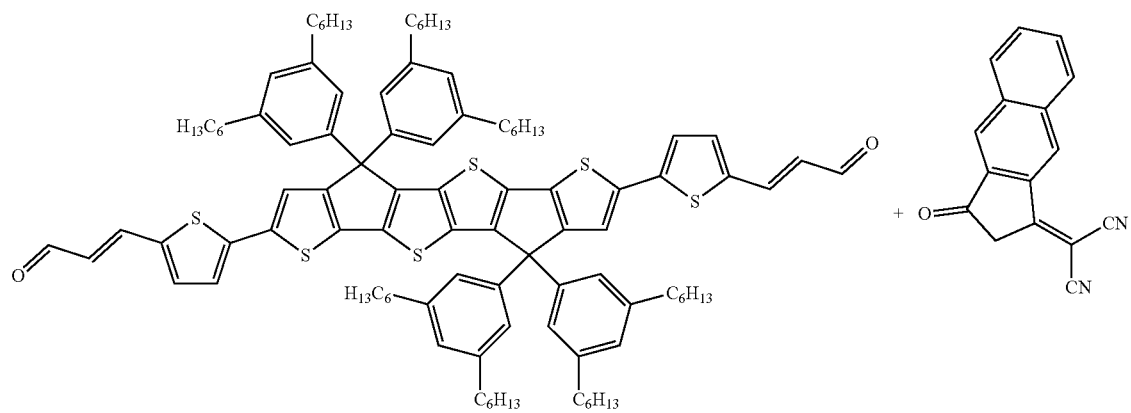

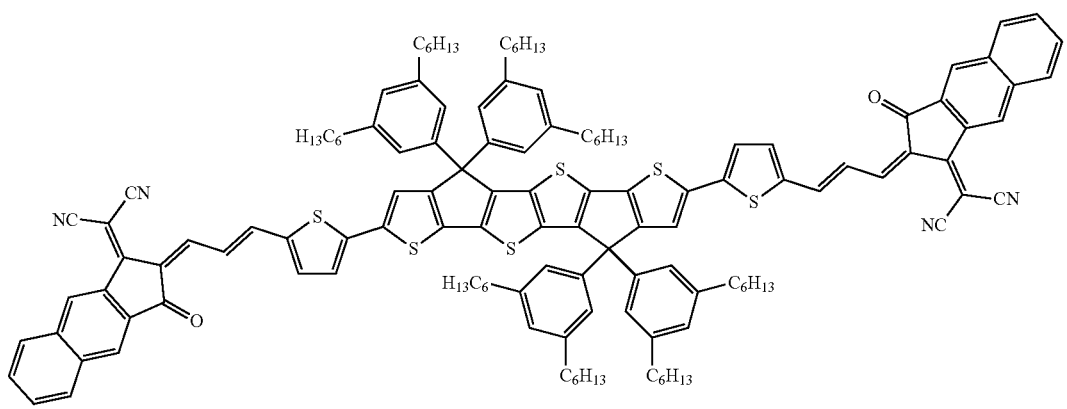

To a degassed solution of intermediate 36 (200 mg, 0.13 mmol), anhydrous chloroform (13 cm³) and pyridine (0.72 cm³) at 0° C. is added 2-(3-oxo-2,3-dihydro-cyclopenta[b]naphthalen-1-ylidene)-malononitrile (124 mg, 0.51 mmol). The reaction mixture is stirred for 165 minutes and then added to stirred acetonitrile (75 cm³) and the mixture stirred for 45 minutes. The solid is collected by filtration and washed with acetonitrile until the filtrate runs colourless. The solid is further washed with 40-60 petrol (2×10 cm³), cyclohexane (2×10 cm³), acetone (2×10 cm³) and ether (2×10 cm³) to give compound 14 (186 mg, 72%) as a black solid. ¹H NMR (400 MHz, 1,2-dichlorobenzene-d4, 100° C.) 9.02 (2H, s), 8.65 (2H, dd, J 14.7, 11.6), 8.39 (2H, d, J 11.5), 8.16 (2H, s), 7.68-7.79 (4H, m), 7.38-7.46 (6H, m), 7.10-7.15 (10H, m), 7.00 (2H, d, J 4.1), 6.96 (2H, d, J 4.0), 6.94 (4H, s), 2.51 (16H, t, J 7.5), 1.51-1.61 (16H, m), 1.18-1.30 (48H, m), 0.78-0.84 (24H, m).

Example 15

Intermediate 37

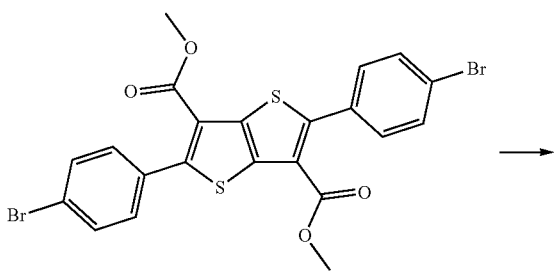

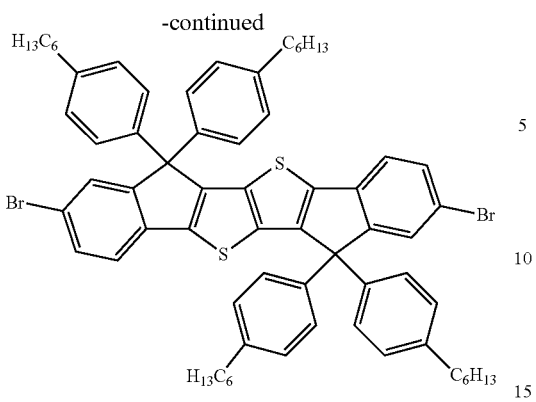

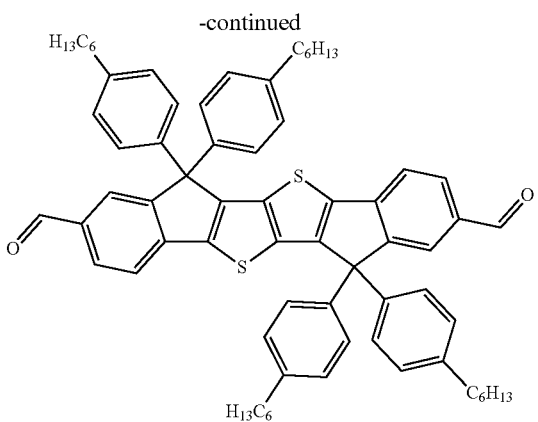

To a solution of 1-bromo-4-hexyl-benzene (10.0 g, 41.5 mmol) in anhydrous tetrahydrofuran (70 cm$^3$) at −78° C. is added n-butyllithium (16.6 cm$^3$, 41.5 mmol, 2.5 M in tetrahydrofuran) over 10 minutes. The reaction mixture is then stirred for 1 hour before methyl 5-bromo-2-[5-(4-bromo-2-methoxycarbonyl-phenyl)thieno[3,2-b]thiophen-2-yl]benzoate (4.70 g, 8.29 mmol) is added. The reaction mixture is then allowed to warm to 23° C. and stirred for 17 hours. Water (100 cm$^3$) is added and the mixture stirred for 1 hour. Ether (100 cm$^3$) is added and the organic washed with water (2×50 cm$^3$), brine (20 cm$^3$) and dried over anhydrous magnesium sulfate, filtered and the solvent removed in vacuo. The solid triturated in ice-cold 40-60 petrol (30 cm$^3$) to give a yellow solid. The solid is taken up in toluene (40 cm$^3$) and p-toluene sulfonic acid (2 g) is added. The reaction is stirred at 23° C. for 2 hours and at 50° C. for 1 hour. The mixture is filtered and the solvent removed in vacuo. The solid is triturated in acetone to give intermediate 37 (3.40 g, 37%) as a yellow solid. $^1$H NMR (400 MHz, CDCl$_3$) 7.44 (2H, s), 7.19 (2H, s), 7.12-7.14 (2H, m), 6.98-7.15 (16H, m), 2.42-2.53 (8H, m), 1.44-1.57 (8H, m), 1.12-1.28 (24H, m), 0.75-0.80 (12H, m).

To a solution of intermediate 37 (8.75 g, 7.85 mmol) in anhydrous tetrahydrofuran (95 cm$^3$) at −78° C. is added dropwise n-butyllithium (7.2 cm$^3$, 18 mmol, 2.5 M in hexanes). The reaction mixture is stirred for 1 hour before N,N-dimethylformamide (1.5 cm$^3$, 20 mmol) is added dropwise. The reaction mixture is allowed to warm to 23° C. and stirred for 17 hours. Water (100 cm$^3$) is added and the aqueous extracted with dichloromethane (2×100 cm$^3$). The combined organic layer is washed with brine (50 cm$^3$), dried over anhydrous magnesium sulfate, filtered and the solvent removed in vacuo. The crude is purified by column chromatography using a graded solvent system (heptane:ethyl acetate; 9:1 to 4:1) to give intermediate 38 (3.30 g, 42%) as a yellow solid. $^1$H NMR (400 MHz, CDCl$_3$) 9.95 (2H, s), 7.94 (2H, s), 7.81-7.83 (2H, m), 7.49-7.54 (2H, m), 7.05-7.21 (16H, m), 2.51-2.62 (8H, m), 1.52-1.67 (8H, m), 1.25-1.41 (24H, m), 0.84-0.91 (12H, m).

Intermediate 39

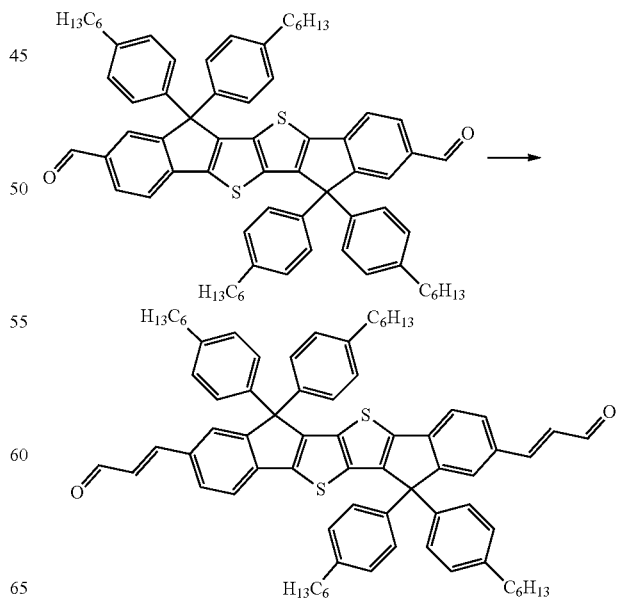

Intermediate 38

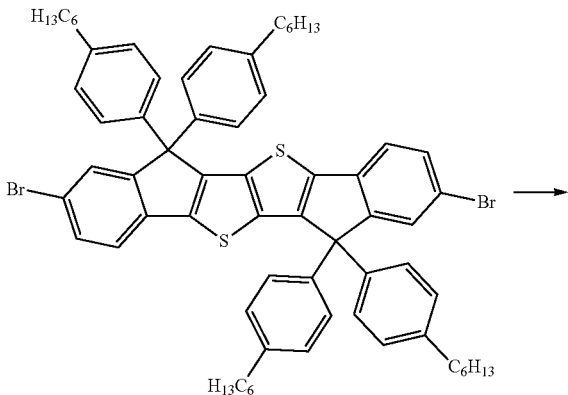

To a mixture of tributyl(1,3-dioxolan-2-ylmethyl)-phosphonium bromide (200 mg, 0.54 mmol), intermediate 38 (250 mg, 0.25 mmol) and anhydrous tetrahydrofuran (13 cm$^3$) at 0° C. is added sodium hydride (59 mg, 1.5 mmol, 60% dispersion in mineral oil). The reaction mixture is allowed to warm to 23° C. and stirred for 17 hours. Dichloromethane (20 cm$^3$) and hydrochloric acid (40 cm$^3$, 2N) are added and the mixture stirred for 30 minutes. The organic layer separated, washed with water (20 cm$^3$), dried over anhydrous magnesium sulfate, filtered and the solvent removed in vacuo. The crude is purified by column chromatography using a graded solvent system (40-60 petrol:dichloromethane; 9:11 to 7:13) to give intermediate 39 (228 mg, 87%) as a yellow solid. $^1$H NMR (400 MHz, CDCl$_3$) 9.68 (2H, d, J 7.7), 7.61 (2H, s), 7.39-7.56 (6H, m), 7.08-7.20 (16H, m), 6.68 (2H, dd, J 15.9, 7.6), 2.53-2.62 (8H, m), 1.56-1.66 (8H, m), 1.26-1.39 (24H, m), 0.84-0.92 (12H, m).

To a degassed mixture of 2-(3-oxo-2,3-dihydro-cyclopenta[b]naphthalen-1-ylidene)-malononitrile (115 mg, 0.469 mmol), intermediate 39 (100 mg, 0.094 mmol) and chloroform (10 cm$^3$) is added pyridine (520 mg) and the mixture further degassed. The reaction mixture is stirred for 17 hours and methanol (30 cm$^3$) added. The solid is collected by filtration and the filtrate concentrated in vacuo. To the filtrate is added methanol (30 cm$^3$) and the solid collected by filtration. The combined solids are then purified by column chromatography using a graded solvent system (40-60 petrol:dichloromethane; 2:3 to 1:4) to give compound 15 (66 mg, 46%) as a green solid. $^1$H NMR (400 MHz, CDCl$_3$) 9.13 (2H, s), 8.74-8.86 (2H, m), 8.48 (2H, d, J 11.6), 8.32 (2H, s), 7.96-8.05 (4H, m), 7.58-7.71 (8H, m), 7.33-7.42 (4H, m), 7.12 (8H, d, J 8.4), 7.06 (8H, d, J 8.4), 2.29-2.68 (8H, m), 1.53 (8H, t, J 7.5), 1.15-1.32 (24H, m), 0.72-0.84 (12H, m).

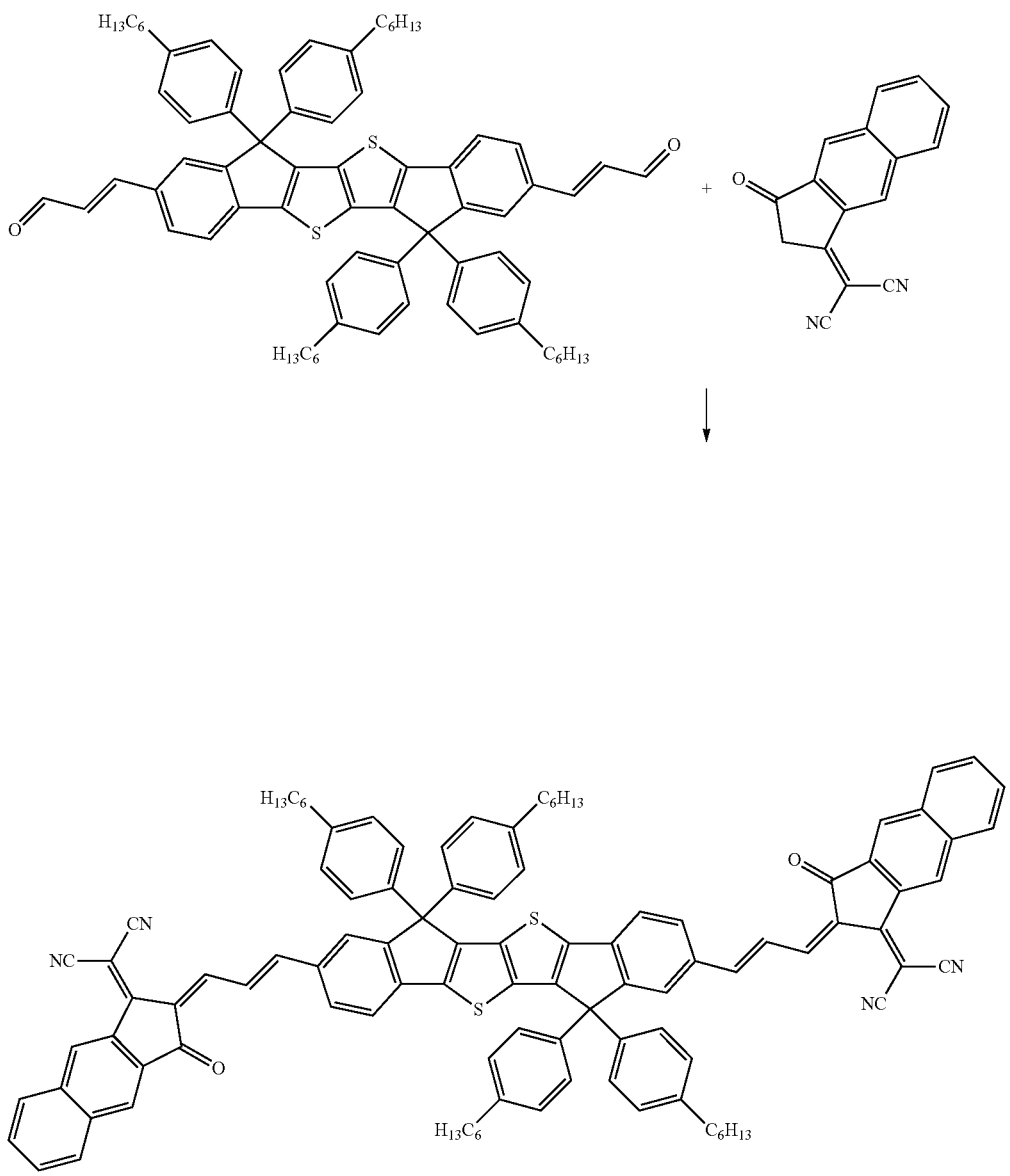

Compound 15

Example 16

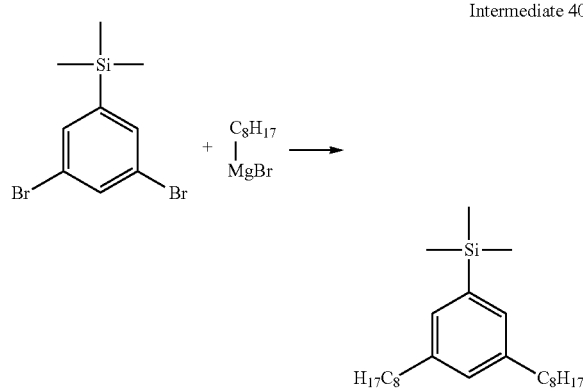

Intermediate 40

To octylmagnesium bromide solution (183 cm³, 365 mmol, 2.0 M in ether) and anhydrous tetrahydrofuran (450 cm³) is added (3,5-dibromophenyl)trimethylsilane (45.0 g, 146 mmol) and [1,1'-bis(diphenylphosphino)ferrocene]dichloropalladium (II) (1.60 g, 2.19 mmol). The reaction mixture is heated at 55° C. for 16 hours before it is cooled to 0° C. and water (250 cm³) added. The organics extracted with dichloromethane (2×250 cm³). The combined organics are washed with brine (100 cm³), dried over anhydrous magnesium sulfate, filtered and the solvent removed in vacuo. The crude is purified by column chromatography (heptane) to give intermediate 40 (22.2 g, 41%) as a colourless oil. $^1$H NMR (400 MHz, CDCl$_3$) 7.15 (2H, d, J 1.6), 7.00 (1H, s), 2.52-2.64 (4H, m), 1.55-1.68 (24H, m), 0.84-0.89 (6H, m), 0.22-0.31 (9H, m).

Intermediate 41

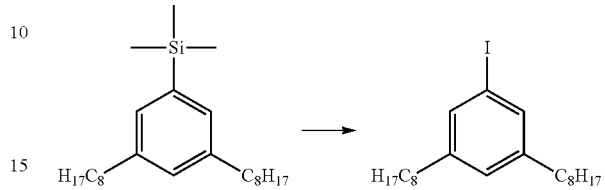

To a solution of intermediate 40 (10.0 g, 26.7 mmol), chloroform (100 cm³) and methanol (100 cm³), in the dark, is added silver(I) trifluoroacetate (12.4 g, 56.0 mmol). The mixture is cooled to 0° C., iodine (13.5 g, 53.4 mmol) added and the mixture stirred for 90 minutes. The reaction mixture is filtered through a plug of silica (dichloromethane) and the orgaic phase washed with saturated aqueous sodium bisulfate (100 cm³), water (100 cm³) and brine (100 cm³) before drying over anhydrous magnesium sulfate. The mixture is filtered, and the solvent removed in vacuo to give intermediate 41 (11.4 g, 99%) as a colourless liquid. $^1$H NMR (400 MHz, CDCl$_3$) 7.27 (2H, d, J 1.4), 6.85 (1H, d, J 1.5), 2.43 (4H, t, J 7.7), 1.07-1.34 (24H, m), 0.70-0.85 (6H, m).

Intermediate 42

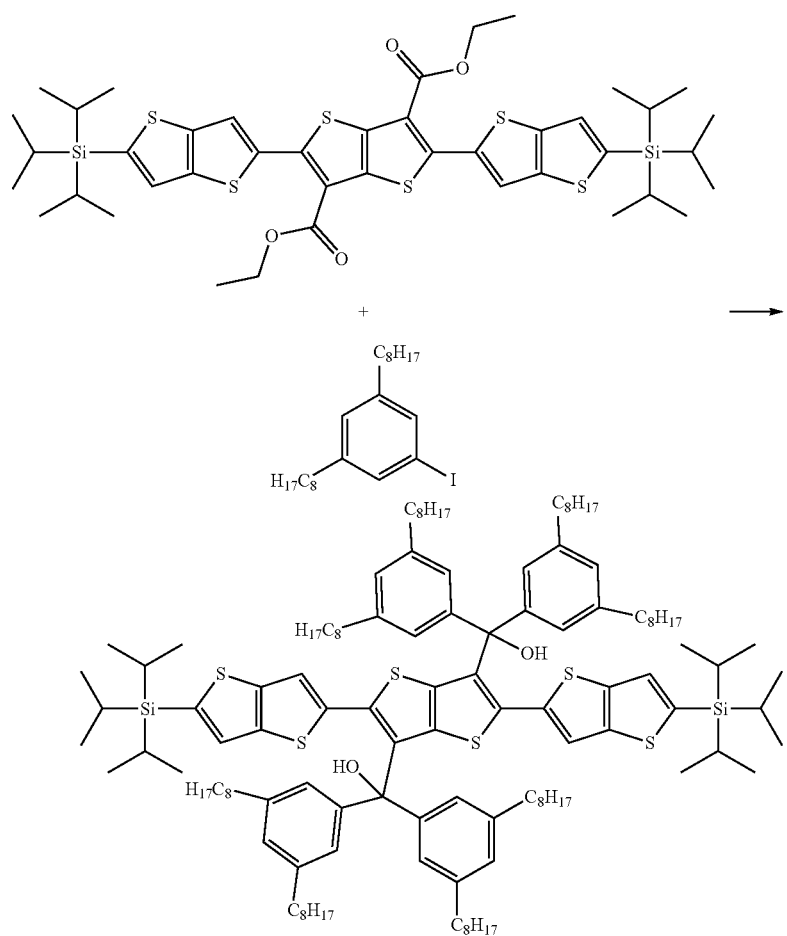

To a solution of intermediate 41 (4.99 g, 10.3 mmol) in anhydrous tetrahydrofuran (37 cm³) at −78° C. is added t-butyllithium (12.1 cm³, 20.6 mmol, 1.7 M in pentane) dropwise over 10 minutes. The solution is stirred for 1 hour; gently warmed to −25° C. for 6 minutes and re-cooled.

Intermediate 14 (1.50 g, 1.72 mmol) is added. The reaction is slowly warmed to 23° C. and stirred for 16 hours. Water (5 cm³) is slowly added and, after 10 minutes of stirring, the solution portioned between diethyl ether (100 cm³) and water (50 cm³). The organic phase is washed with water (3×20 cm³), dried over anhydrous magnesium sulphate and concentrated in vacuo. The crude is purified by column chromatography (40-60 petrol:dichloromethane; 9:1) to give intermediate 42 (2.76 g, 73%) as a yellow oil. ¹H NMR (400 MHz, CDCl₃) 7.17 (2H, s), 6.85-6.99 (12H, m), 6.46 (2H, s), 3.40 (2H, s), 2.48 (16H, dd, J 8.9, 6.3), 1.43-1.67 (16H, m), 1.21-1.41 (80H, m), 1.12 (36H, d, J 7.4), 0.81-0.92 (30H, m).

To a degassed solution of intermediate 42 (500 mg, 0.251 mmol) in toluene (30 cm³) at 50° C. is added Amberllyst 15 strong acid (2.0 g) and the reaction mixture heated at 50° C. for 17 hours. The mixture filtered and the solid washed with warm toluene (20 cm³) and the solvent removed in vacuo. To the crude is added N,N-dimethylformamide (310 mg, 4.3 mmol) and chloroform (8.8 cm³) and the mixture cooled to 0° C. Phosphorus oxychloride (620 mg, 4.02 mmol) is then added dropwise and, after addition, the reaction mixture is stirred for 30 minutes, and then heated at 60° C. for 26 hours. A saturated aqueous solution of potassium acetate (25 cm³) is added and the mixture stirred for 3 hours before cooling to 23° C. The aqueous phase is extracted with dichloromethane (20 cm³) and the combined organics washed with water (20 cm³), dried over anhydrous magnesium sulphate, filtered and concentrated in vacuo. The crude is purified by column chromatography using a graded solvent system (40-60 petrol:dichloromethane; 4:1 to 3:2) to give intermediate 43 (130 mg, 29%) as an orange solid. ¹H NMR (400 MHz, CDCl₃) 9.88 (2H, s), 7.94 (2H, s), 6.92 (4H, s), 6.80 (8H, s), 2.50 (16H, t, J 7.7), 1.41-1.71 (16H, m), 1.17-1.31 (90H, m), 0.67-1.04 (24H, m).

Intermediate 43

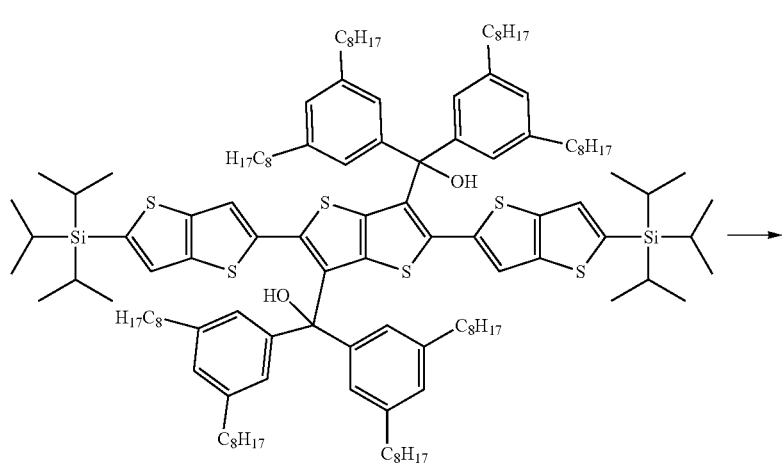

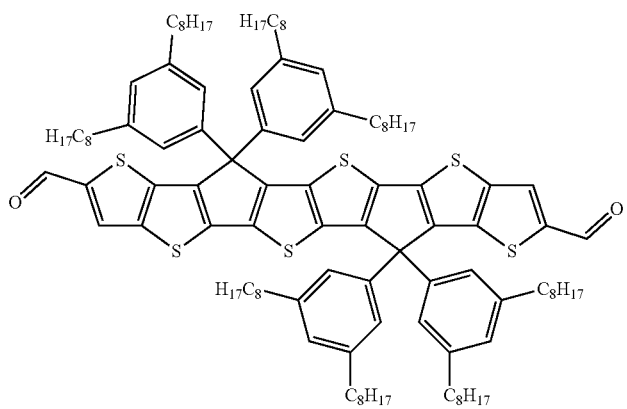

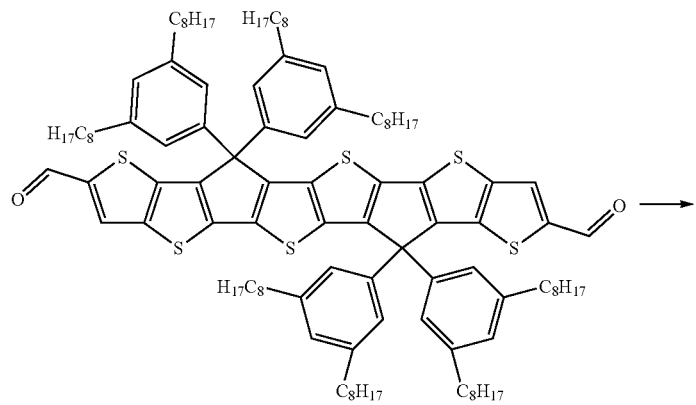

Compound 16

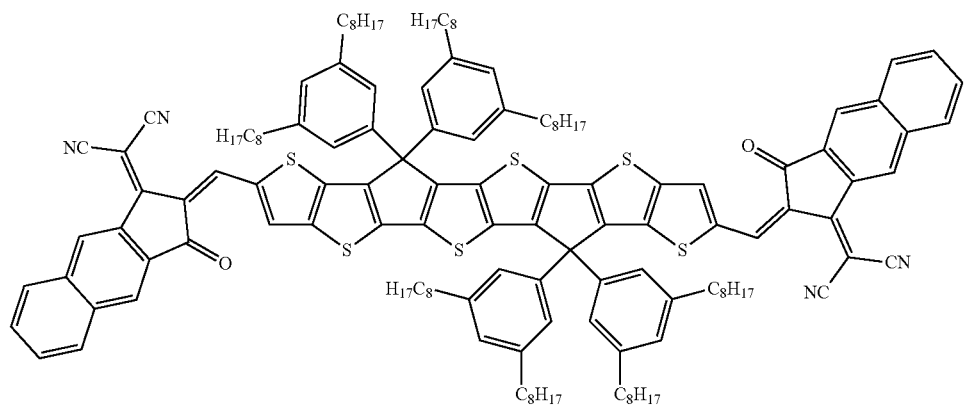

To a degassed solution of intermediate 43 (130 mg, 0.08 mmol) and 2-(3-oxo-2,3-dihydro-cyclopenta[b]naphthalen-1-ylidene)-malononitrile (93.5 mg, 0.38 mmol) in chloroform (3.3 cm³) is added pyridine (0.43 cm³, 5.4 mmol) and mixture further degassed. The reaction is stirred at 40° C. for 6 hours, then methanol (30 cm³) added. After cooling to 23° C. the precipitate is collected by filtration and washed with methanol (20 cm³). The crude is purified by column chromatography using a graded solvent system (40-60 petrol: dichloromethane; 7:3 to 1:1) to give compound 16 (43 mg, 26%) as a green solid. $^1$H NMR (400 MHz, CDCl$_3$) 9.20 (2H, s), 9.00 (2H, s), 8.34 (2H, s), 8.16 (2H, s), 8.10 (2H, dd, J 6.2, 3.4), 8.05 (2H, dd, J 6.2, 3.4), 7.71 (4H, dd, J 6.3, 3.2), 6.97 (4H, d, J 1.6), 6.91 (8H, d, J 1.7), 2.56 (16H, t, J 7.7), 1.58 (16H, s), 1.07-1.34 (80H, m), 0.78 (24H, t, J 6.9).

Example 17

Intermediate 44

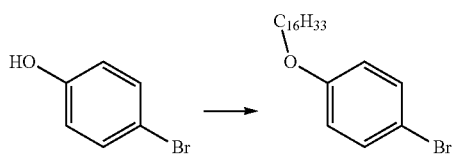

To a suspension of potassium carbonate (39.9 g, 289 mmol) in acetonitrile (160 cm³) is added 4-bromo-phenol (10.0 g, 57.8 mmol) and 1-bromohexadecane (16.8 g, 54.9 mmol) and the reaction mixture heated at 80° C. for 16 hours. The reaction is hot filtered and the solid washed with dichloromethane (150 cm³). The combined filtrate is concentrated to 200 cm³, cooled to 23° C. and then stirred in an ice bath for 10 minutes. The suspension is filtered and washed with ice-cool acetonitrile (50 cm³) to give intermediate 44 (12.6 g, 55%) as a white solid. ¹H NMR (400 MHz, CDCl₃) 7.37 (2H, d, J 9.0), 6.78 (2H, d, J 9.0), 3.92 (2H, t, J 6.6), 1.73-1.82 (2H, m), 1.39-1.50 (2H, m), 1.39-1.20 (24H, m), 0.82-0.95 (3H, m).

added over 5 minutes, the coolant is left to evaporate and the reaction is stirred at 23° C. overnight. Water (5 cm³) is slowly added and the solution stirred for 10 minutes before partitioning between diethyl ether (100 cm³) and water (50 cm³). The organic phase is washed with water (3×20 cm³), dried over anhydrous magnesium sulphate and concentrated in vacuo. The residue is purified by column chromatography Intermediate 45

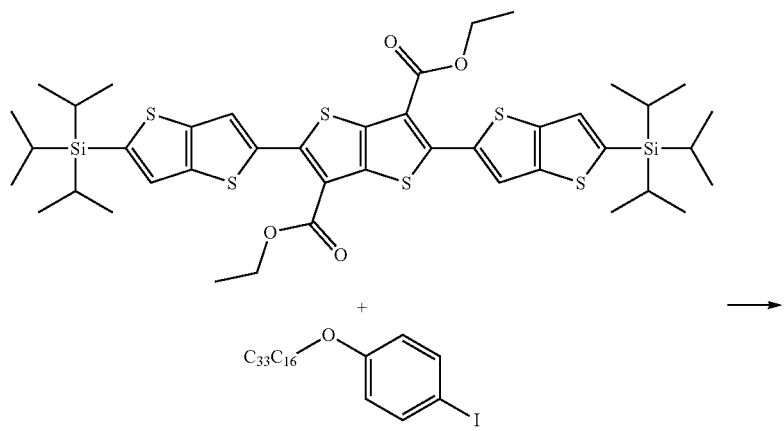

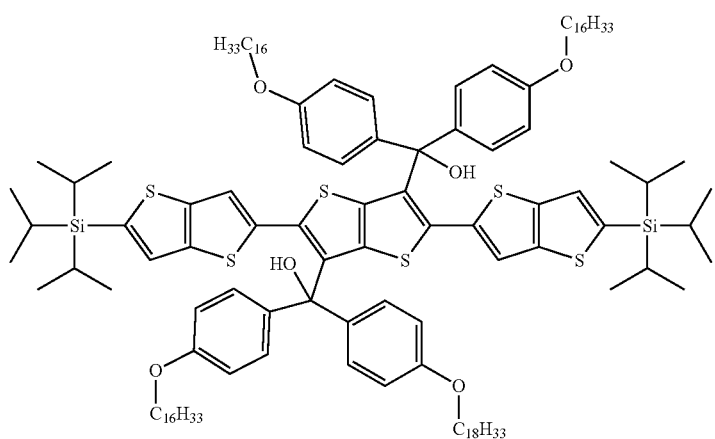

To a solution of intermediate 44 (2.73 g, 6.87 mmol) in anhydrous tetrahydrofuran (150 cm³) at −78° C. is added t-butyllithium (8.1 cm³, 14 mmol, 1.7 M in pentane) over 10 minutes. The resulting suspension is stirred for 90 minutes, warmed to −25° C. over 20 minutes and re-cooled to −70° C. Then a sonicated suspension of intermediate 14 (1.00 g, 1.14 mmol) in anhydrous tetrahydrofuran (150 cm³) is using a graded solvent system (40-60 petrol:dichloromethane; 1:0 to 0:1) to give intermediate 45 (1.8 g, 76%). ¹H NMR (400 MHz, CDCl₃) 7.22 (2H, s), 7.18-7.22 (8H, m), 6.80-6.84 (8H, m), 6.66 (2H, s), 3.96 (8H, t, J 6.6), 3.45 (2H, s), 1.79 (8H, p, J 6.8), 1.41-1.52 (8H, m), 1.31 (96H, s), 1.13 (36H, d, J 7.4), 0.84-0.94 (18H, m).

Intermediate 46

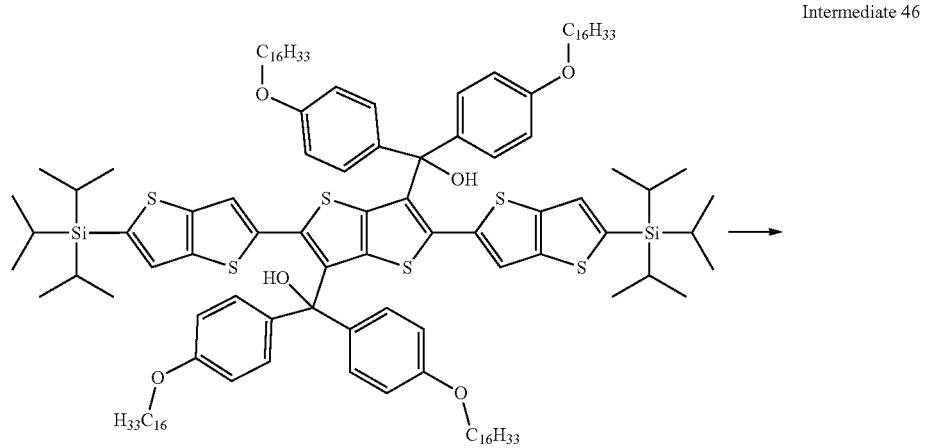

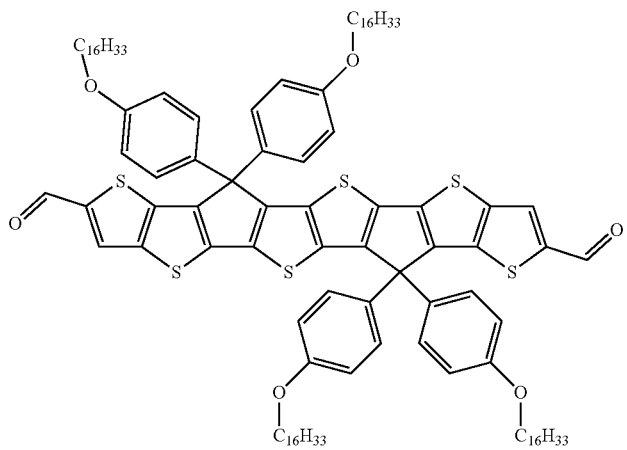

To a degassed mixture of intermediate 45 (1.79 g, 0.871 mmol) and toluene (72 cm$^3$), at 65° C., is added Amberlyst 15 strong acid (16 g) and the mixture stirred for 16 hours. The reaction mixture is filtered and the solid washed with hot toluene (2×30 cm$^3$). The combined organic phase is concentrated in vacuo and purified by column chromatography (40:60 petrol:dichloromethane; 4:1). The product is dissolved in chloroform (36 cm$^3$), N,N-dimethylformamide (1.02 g, 13.9 mmol) is added, followed by slow addition of phosphorus oxychloride (2.00 g, 13.1 mmol), over 5 minutes. The resulting solution is heated at 55° C. for 16 hours. To the solution is added a saturated aqueous solution of potassium acetate (50 cm$^3$) and mixture stirred for 2 hours before to cooling to 23° C. The aqueous phase is extracted with dichloromethane (50 cm$^3$). The combined organic phase is washed with water (50 cm$^3$), dried over anhydrous magnesium sulphate and concentrated in vacuo before purification by column chromatography using a graded solvent system (40-60 petrol:dichloromethane; 1:0 to 3:4) to give intermediate 46 (763 mg, 50%). $^1$H NMR (400 MHz, CDCl$_3$) 9.90 (2H, s), 7.94 (2H, s), 7.15 (8H, d, J 8.8), 6.84 (8H, d, J 8.8), 3.91 (8H, t, J 6.5), 1.66-1.85 (8H, m), 1.37-1.48 (8H, m), 1.20-1.37 (96H, m), 0.87-0.89 (12H, m).

Compound 17

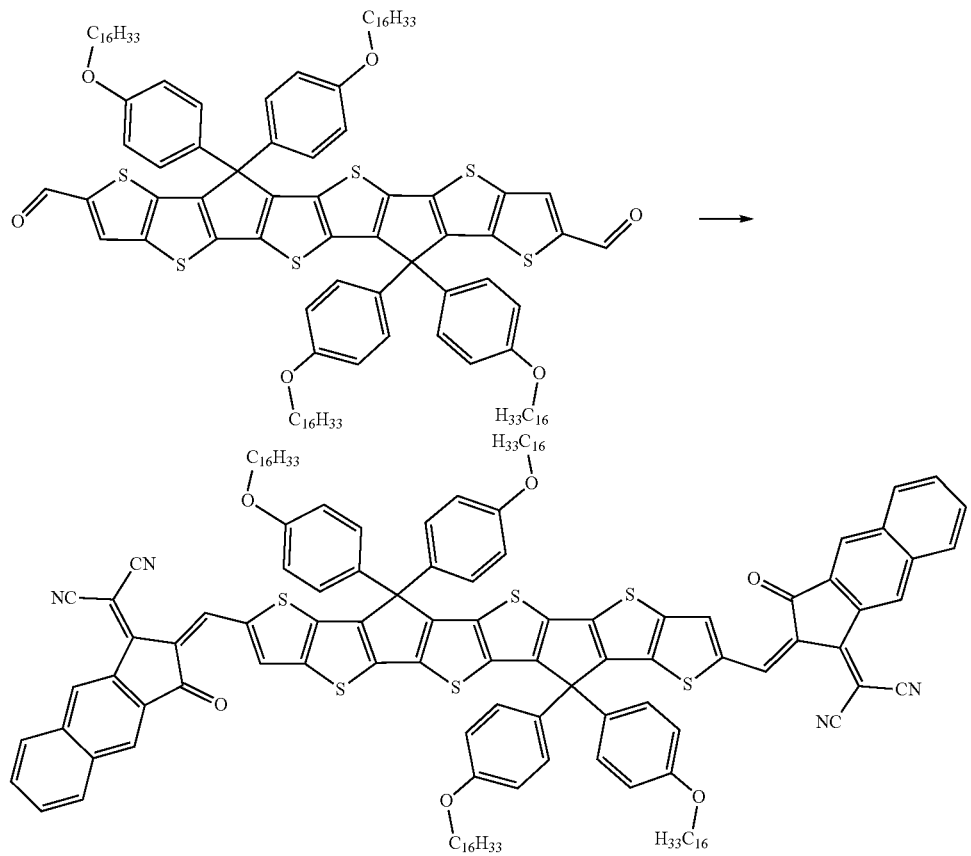

To a degassed solution of intermediate 46 (100 mg, 0.0567 mmol) and 2-(3-oxo-2,3-dihydro-cyclopenta[b]naphthalen-1-ylidene)-malononitrile (97 mg, 0.40 mmol) in chloroform (2.5 cm$^3$) is added pyridine (0.32 cm$^3$, 4.0 mmol). The reaction is further degassed and then stirred at 40° C. for 6 hours. Methanol (30 cm$^3$) is added and the resulting suspension cooled to 23° C., filtered and washed with methanol (20 cm$^3$). The resulting solid is purified by column chromatography using a graded solvent system (40-60 petrol:dichloromethane; 3:2 to 3:7). The material is precipitated from a hot mixture of chloroform (4 cm$^3$) and acetone (15 cm$^3$) to give, upon filtration, compound 17 (51 mg, 41%) as a green solid. $^1$H NMR (400 MHz, CDCl$_3$) 9.18 (2H, s), 8.95 (2H, s), 8.39 (2H, s), 8.19 (2H, s), 8.00-8.14 (4H, m), 7.78-7.66 (4H, m), 7.24 (8H, d, J 8.5), 6.91 (8H, d, J 8.2), 3.93 (8H, t, J 6.4), 1.67-1.85 (8H, m), 1.38-1.51 (8H, m), 1.17-1.38 (32H, m), 0.88 (12H, t, J 6.6).

Example 18

Intermediate 47

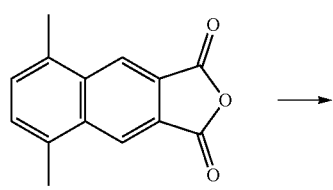

-continued

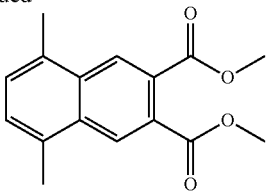

To a solution of 5,8-dimethyl-naphtho[2,3-c]furan-1,3-dione (10.0 g, 44.2 mmol) in methanol (50 cm$^3$) is added concentrated sulfuric acid (920 mg, 9.38 mmol) and the mixture heated at reflux for 12 hours. The reaction mixture is cooled to 23° C. and concentrated in vacuo. The residue is diluted with water (250 cm$^3$) and extracted with ethyl acetate (3×100 cm$^3$). The combined organic layer is washed with saturated aqueous sodium bicarbonate (3×100 cm$^3$), brine (200 cm$^3$), dried over anhydrous sodium sulphate, filtered and the solvent removed in vacuo to give intermediate 47 (10.0 g, 83%) as a yellow solid. $^1$H NMR (400 MHz, CDCl$_3$) 8.44 (2H, s), 7.34 (2H, s), 3.97 (6H, s), 2.70 (6H, s).

Intermediate 48

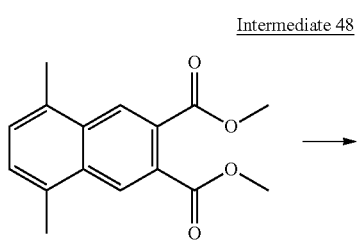

To a solution of intermediate 47 (12.0 g, 44.1 mmol) in anhydrous tetrahydrofuran (100 cm³) is added sodium hydride (14.1 g, 353 mmol, 60% dispersion in mineral oil) and anhydrous ethyl acetate (35 cm³). The reaction mixture is then heated at reflux for 12 hours. After cooling to 23° C. the mixture is concentrated in vacuo. The residue is triturated in ethyl acetate (100 cm³) and the solid collected by filtration to give intermediate 48 (30.0 g) as a yellow solid, which is used without further purification.

Intermediate 49

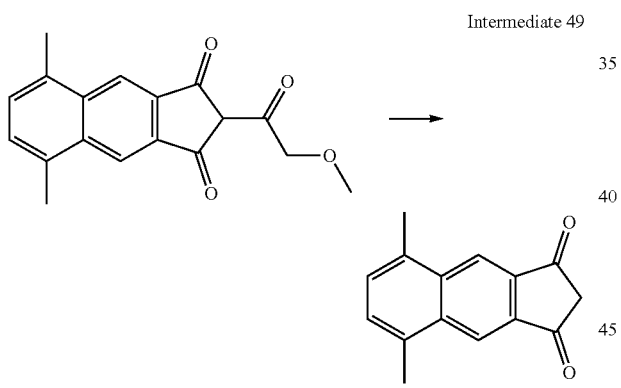

To a mixture of intermediate 48 (30.0 g) and water (200 cm³) is added hydrochloric acid (7.35 cm³, 12 M) and the reaction mixture heated at 80° C. for 12 hours. The mixture allowed to cool to 23° C. and the solid collected by filtration to give intermediate 49 (6.0 g) as a brown solid, which is used without any further purification.

Intermediate 50

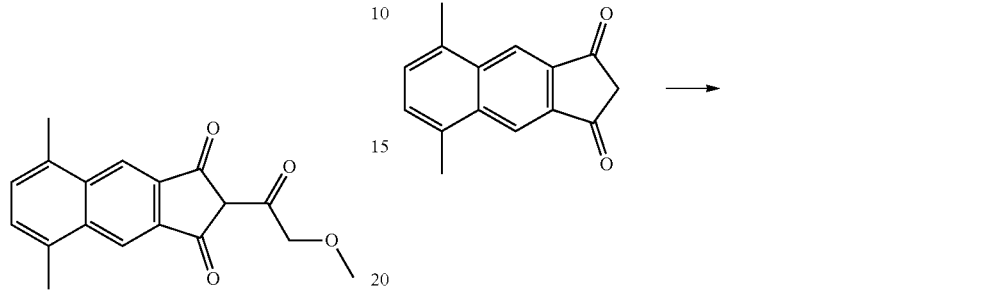

To a solution of intermediate 49 (4.5 g) and malononitrile (2.52 g, 38.1 mmol) in ethanol (20 cm³) is added sodium acetate (2.47 g, 30.1 mmol) and the mixture stirred for 12 hours. The reaction mixture is adjusted to pH=2 with aqueous hydrochloric acid (1 M) and extracted with dichloromethane (3×50 cm³). The combined organic layer is washed with water (2×50 cm³), brine (50 cm³), dried over anhydrous sodium sulfate, filtered and concentrated in vacuo. The residue is purified by column chromatography using a graded solvent system (dichloromethane:methanol; 1:0 to 9:1) to give intermediate 50 (1.7 g) as a red solid. ¹H NMR (400 MHz, CDCl₃) 9.38 (1H, s), 8.67 (1H, s), 7.51 (2H, s), 3.87 (2H, s), 2.81 (3H, s), 2.77 (3H, s).

Compound 18

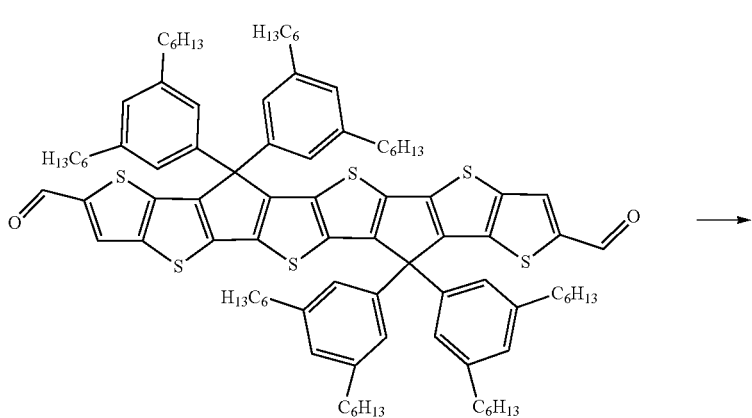

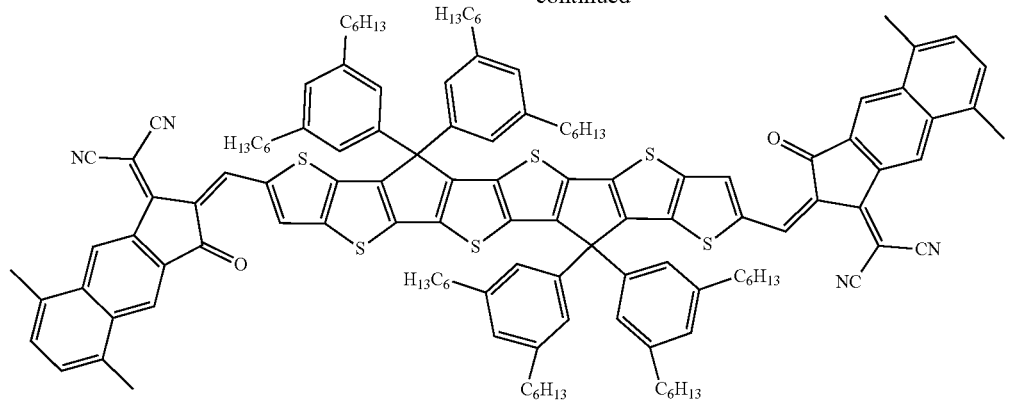

Intermediate 21 (75 mg, 0.05 mmol) and intermediate 50 (69 mg, 0.25 mmol) are dissolved in chloroform (30 cm³). Pyridine (0.3 cm³, 4 mmol) is added and the reaction stirred at 55° C. for 17 hours. The reaction mixture is cooled to 23° C. and the solvent removed in vacuo before addition of methanol (100 cm³). The solid is collected by filtration and purified by column chromatography (40-60 petrol:dichloromethane 3:2). The product is dissolved in chloroform (50 cm³), treated with acetonitrile (50 cm³) and collected by filtration to give compound 18 (67 mg, 66%). ¹H NMR (400 MHz, CD₂Cl₂) 9.28 (2H, s), 8.86 (2H, s), 8.44 (2H, s), 8.09 (2H,s), 7.36 (4H, s), 6.89 (4H, s), 6.83 (8H, d, J 1.5), 2.67 (12H, d, J 4.9), 2.45 (16H, t, J 7.7), 1.54-1.45 (8H, m), 1.26-1.05 (56H, m), 0.71-0.58 (24H, m).

Example 19

Intermediate 51

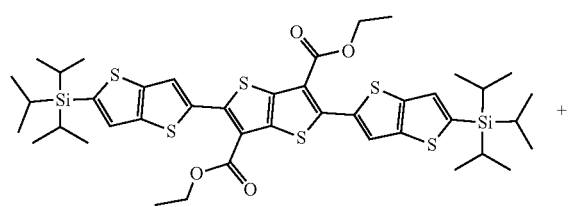

+

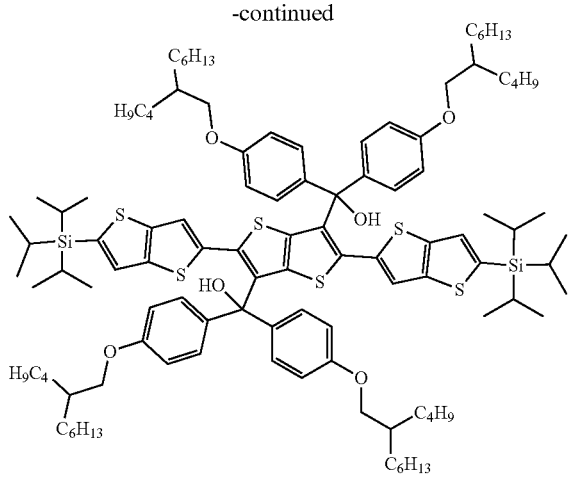

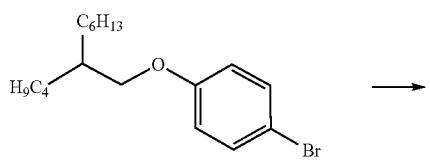

→

To a solution of 1-bromo-4-[(2-butyloctyl)oxy]benzene (3.52 g, 10.3 mmol) in anhydrous tetrahydrofuran (150 cm³) at −78° C. is added t-butyllithium (12.1 cm³, 20.6 mmol, 1.7 M in pentane) dropwise over 10 minutes. The reaction mixture is stirred for 1.5 hours and warmed to −25° C. A suspension of intermediate 14 (1.50 g, 1.72 mmol) in anhydrous tetrahydrofuran (50 cm³) is added and the reaction mixture stirred for 16 hours at 23° C. Water (100 cm³) is slowly added and the mixture stirred for 10 minutes before addition of ether (100 cm³). After phase separation the organic phase is washed with water (3×20 cm³), dried over anhydrous magnesium sulphate, filtered and the solvent removed in vacuo. The crude product is purified by column chromatography (40-60 petrol:dichloromethane; 4:1) to give intermediate 51 (1.77 g, 56%). ¹H NMR (400 MHz, CD₂Cl₂) 7.15 (2H, s), 7.08 (8H, d, J 8.7), 6.73 (8H, d, J 8.8), 6.56 (2H, s), 3.75 (8H, d, J 6.2), 3.33 (2H, s), 1.64-1.72 (4H, m), 0.97-1.39 (106H, m), 0.80 (24H, q, J 6.9, 5.8).

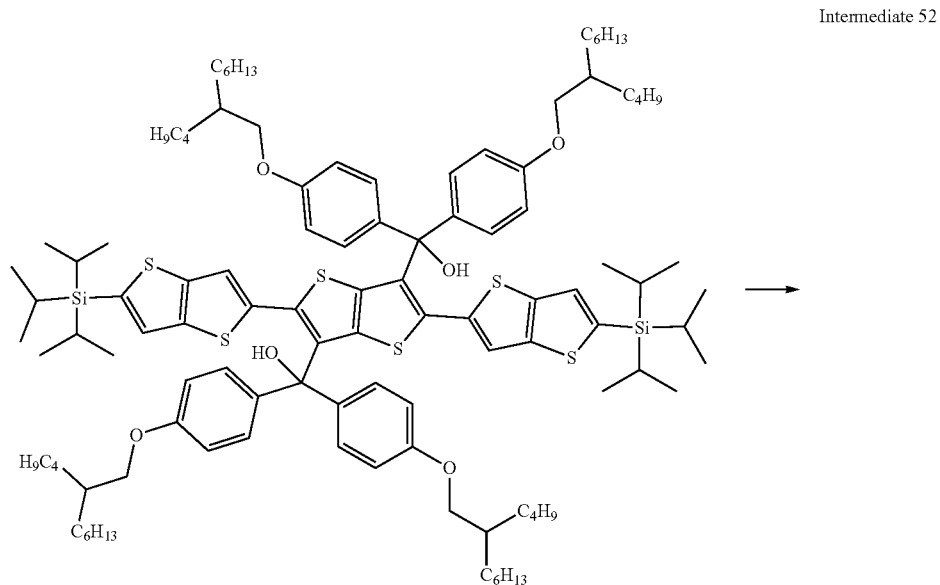
Intermediate 52
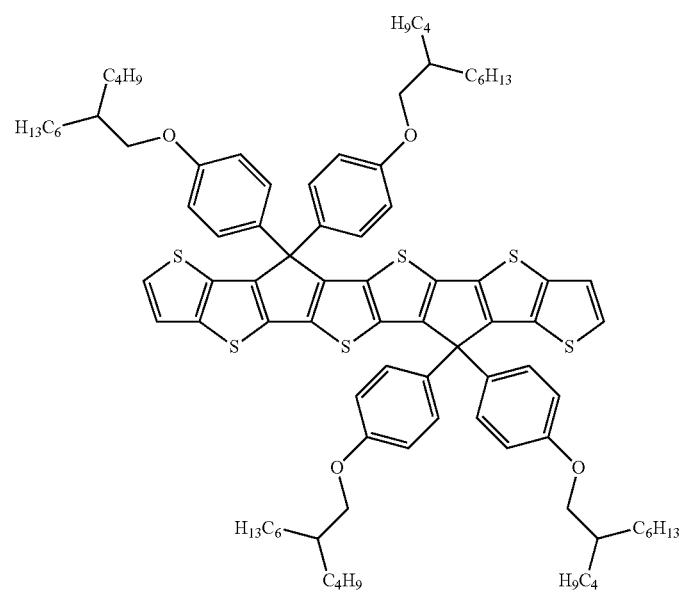

To a solution of intermediate 51 (1.68 g, 0.916 mmol) in toluene (150 cm$^3$) is added Amberlyst 15 strong acid (8.0 g) and the reaction mixture stirred at 50° C. for 17 hours. The hot reaction mixture is filtered and the filtrate washed with water (50 cm$^3$). The organic layer is dried over anhydrous magnesium sulphate, filtered and the solvent removed in vacuo. The crude is purified by column chromatography (40-60 petrol:dichloromethane; 19:1) to give intermediate 52 (1.13 g, 83%). $^1$H NMR (400 MHz, CD$_2$Cl$_2$) 7.22 (4H, dd, J 6.7), 7.07 (8H, d, J 8.8), 6.72 (8H, d, J 8.8), 3.69 (8H, d, J 5.6), 1.63 (4H, h, J 5.9), 1.10-1.38 (64H, m), 0.70-0.84 (24H, m).

Intermediate 53

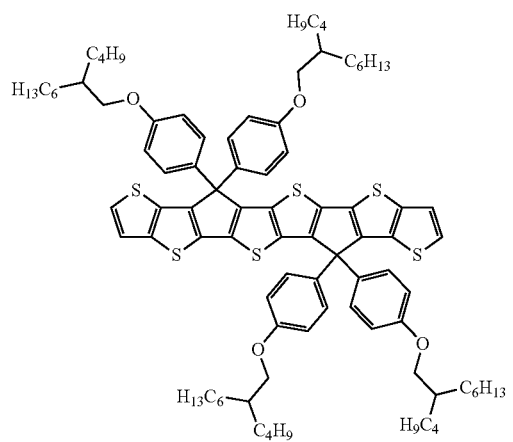

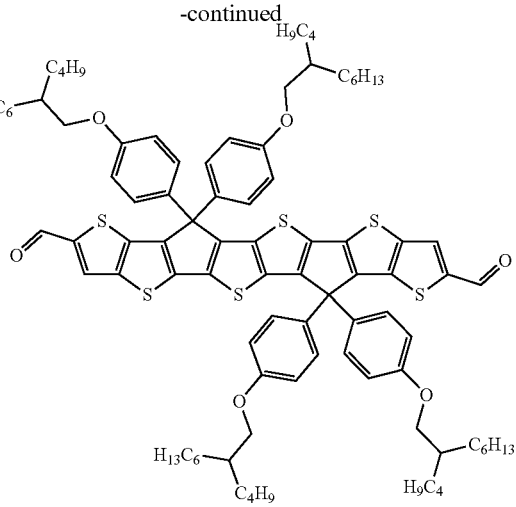

To a degassed solution of intermediate 52 (1.13 g, 0.762 mmol) in chloroform (30 cm$^3$) and N,N-dimethylformamide (0.70 cm$^3$, 9.1 mmol) is added phosphorus(V)oxychloride (0.7 cm$^3$, 8 mmol) and the reaction mixture heated at 60° C. for 17 hours. Saturated aqueous sodium acetate (10 cm$^3$) is added and the resulting mixture stirred at 50° C. for 1 hour. The resulting mixture is then cooled to 23° C. and the organic solvent removed in vacuo. The remaining aqueous phase and material are extracted with ether (3×100 cm$^3$). The combined organic layer is washed with water (2×25 cm$^3$), brine (30 cm$^3$) and dried over anhydrous magnesium sulphate. The solvent is removed in vacuo and the crude product purified by column chromatography (40-60 petrol: dichloromethane: 4:1) to give intermediate 53 (910 mg, 78%) as a red solid. $^1$H NMR (400 MHz, CD$_2$Cl$_2$) 9.78 (2H, s), 7.88 (2H, s), 7.06 (8H, d, J 8.8), 6.74 (8H, d, J 8.8), 3.69 (8H, d, J 5.6), 1.64 (4H, p, J 5.9), 1.09-1.39 (64H, m), 0.70-0.84 (24H, m).

Compound 19

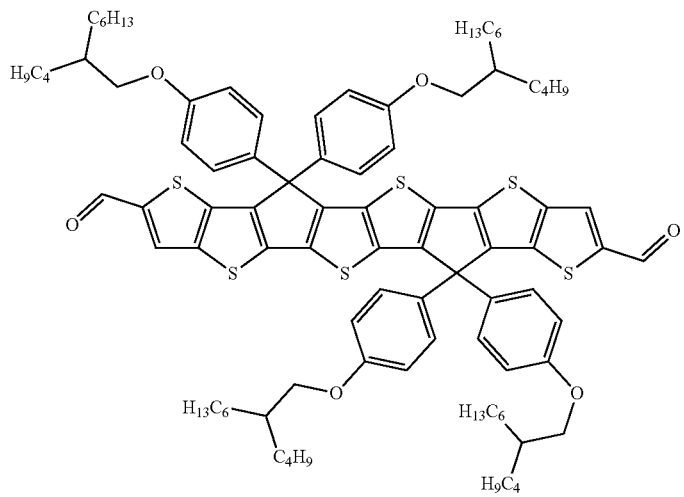

-continued

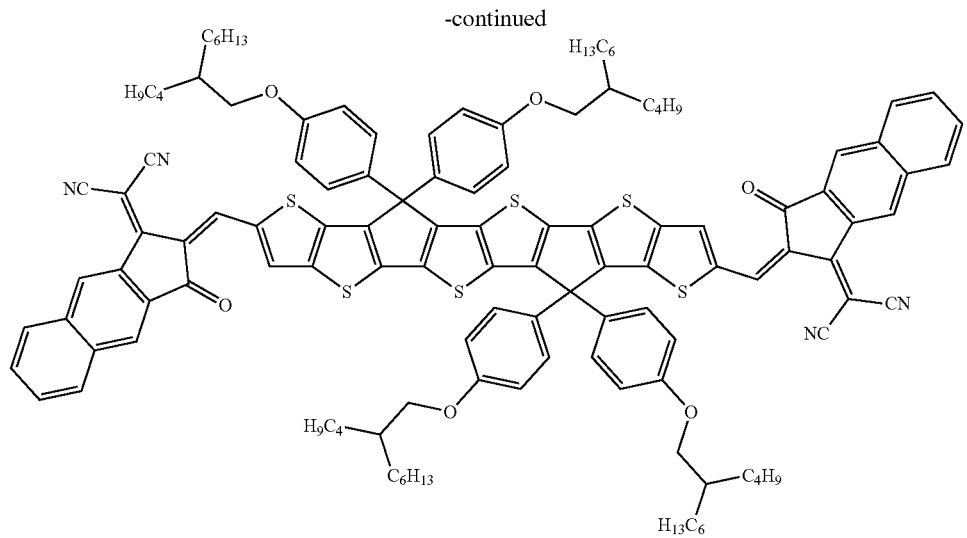

To a solution of intermediate 53 (100 mg, 0.065 mmol) and 2-{3-oxo-1H,2H,3H-cyclopenta[b]naphthalen-1-ylidene}propanedinitrile (79.4 mg, 0.325 mmol) in chloroform (30 cm$^3$) is added pyridine (0.4 cm$^3$, 5 mmol) and the reaction mixture stirred at 55° C. for 17 hours. The reaction mixture is cooled down to 23° C. and the solvent removed in vacuo. The crude product is purified by column chromatography (40-60 petrol:dichloromethane; 3:2). The product is dissolved in chloroform (50 cm$^3$), treated with acetonitrile (50 cm$^3$) and collected by filtration to give compound 19 (80 mg, 62%). $^1$H NMR (400 MHz, CD$_2$Cl$_2$) 9.08 (2H, s), 8.84 (2H, s), 8.28 (2H, s), 8.12 (2H, s), 8.01 (4H, d, J 7.4), 7.63 (4H, dd, J 6.6, 2.9), 7.15 (8H, d, J 8.8), 6.81 (8H, d, J 8.8), 3.73 (8H, d, J 5.6), 1.64 (4H, d, J 7.0), 1.08-1.39 (64H, m), 0.69-0.85 (24H, m).

Example 20

Intermediate 54

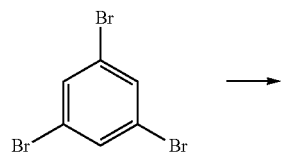

-continued

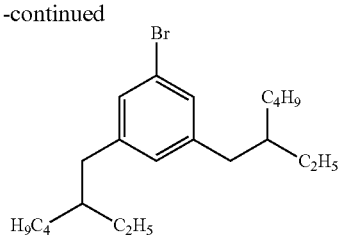

To a suspension of 1,3,5-tribromobenzene (10.0 g, 31.8 mmol) in anhydrous ether (400 cm$^3$) at −78° C. is added t-butyllithium (74.7 cm$^3$, 127 mmol, 1.7 M in pentane) dropwise over 25 minutes. The reaction mixture is then stirred for 2 hours and 2-ethylhexanal (15.0 g, 117 mmol) is added over 20 minutes. The reaction mixture is allowed to warm to 23° C. and stirred for 16 hours. Water (20 cm$^3$) is slowly added followed by a saturated aqueous ammonium chloride solution (100 cm$^3$). The organic is washed with water (2×50 cm$^3$), dried over anhydrous magnesium sulphate, filtered and the solvent removed in vacuo. The crude material is purified by column chromatography using a graded solvent system (40-60 petrol:dichloromethane; 1:1 to 0:1). The purified material is then taken up in dichloromethane (42 cm$^3$), triethylsilane (14.2 g, 122 mmol) added and the mixture cooled to 0° C. Boron trifluoride diethyl etherate (8.65 g, 61.0 mmol) is then added portion wise over 1 hour, the mixture allowed to warm to 23° C. and stirred for 16 hours. The reaction mixture is then heated at 40° C. for 10 minutes, cooled to 23° C. and a saturated aqueous solution of sodium bicarbonate is added to reach ph ~8. The aqueous solution is extracted with dichloromethane (10 cm$^3$) and the combined organics dried over anhydrous magnesium sulphate, filtered and the solvent removed in vacuo. The crude is purified by column chromatography (40-60 petrol) to give intermediate 54 (2.39 g, 62%) as a colourless oil. $^1$H NMR (400 MHz, CDCl$_3$) 7.12 (2H, s), 6.85 (1H, s), 2.48 (4H, d, J 7.1), 1.49-1.57 (2H, m), 1.18-1.36 (16H, m), 0.82-0.96 (12H, m).

Intermediate 55

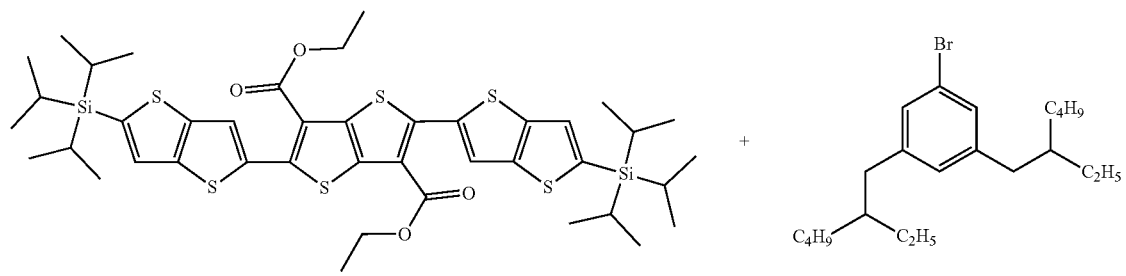

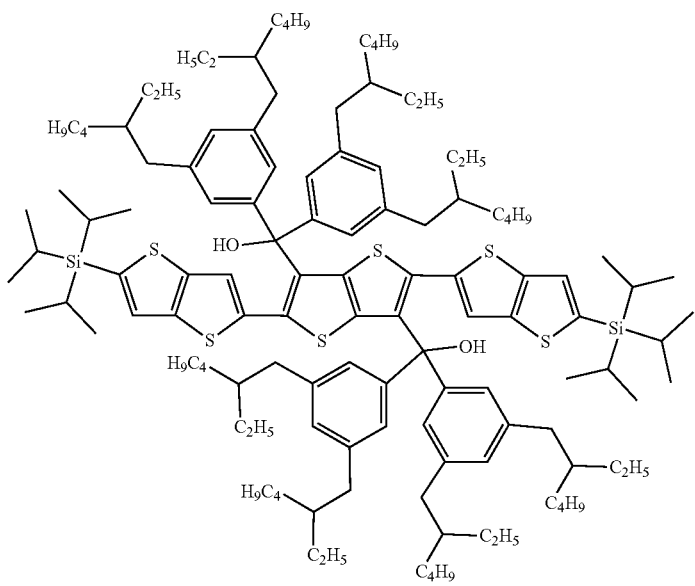

To a solution of intermediate 54 (2.25 g, 5.91 mmol) in anhydrous tetrahydrofuran (13 cm³) at −78° C. is added dropwise t-butyllithium (6.95 cm³, 11.8 mmol, 1.7 M in pentane). The reaction mixture is then stirred for 1 hour, warmed to −18° C. and then re-cooled to −78° C. A sonicated suspension of intermediate 14 (860 mg, 0.98 mmol) in anhydrous tetrahydrofuran (13 cm³) is then added, the reaction mixture allowed to warm to 23° C. and stirred for 16 hours. Water (10 cm³) is added and the biphasic mixture stirred for 5 minutes. Diethyl ether (100 cm³) is added and the organic phase washed with water (3×30 cm³), dried over anhydrous magnesium sulphate, filtered and the solvent removed in vacuo. The residue is purified by column chromatography using a graded solvent system (40-60 petrol:dichloromethane; 9:1 to 4:1) to give intermediate 55 (1.21 g, 62%) as an oil. $^1$H NMR (400 MHz, CDCl$_3$) 7.17 (2H, s), 6.89 (8H, s), 6.87 (4H, s), 6.58 (2H, s), 3.47-3.56 (2H, m), 2.34-2.53 (16H, m), 1.51 (4H, s), 1.05-1.41 (116H, m), 0.72-0.95 (48H, m).

Intermediate 56

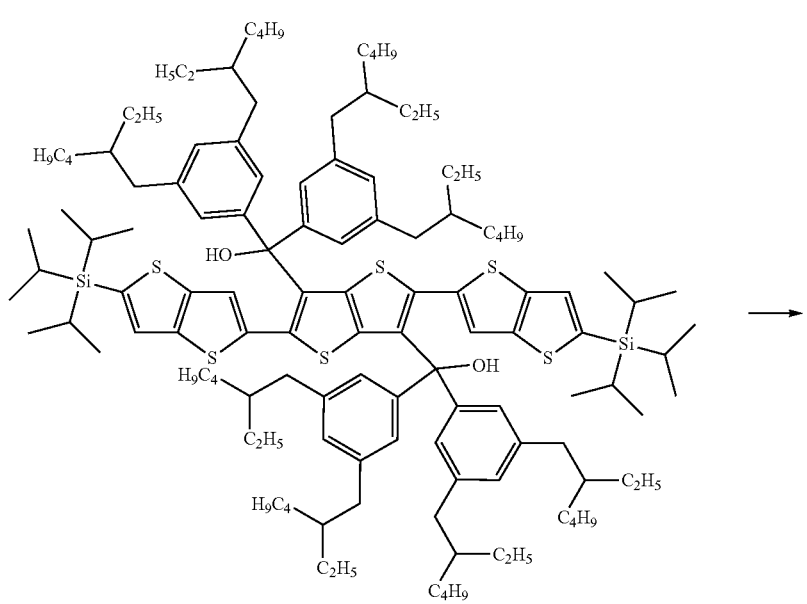

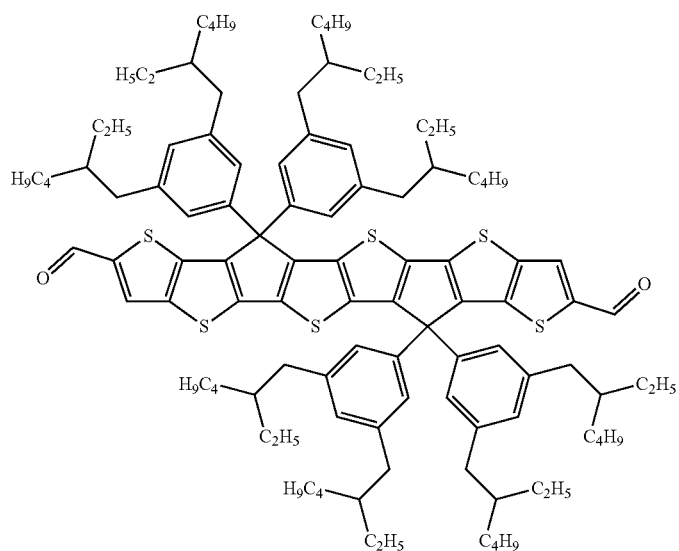

To a degassed mixture of intermediate 55 (1.20 g, 0.603 mmol) dissolved in toluene (48 cm³) at 50° C. is added Amberlyst 15 strong acid (4.0 g) and the reaction mixture stirred for 17 hours. The reaction mixture is filtered, the residue washed with hot toluene (2×20 cm³) and the combined organic phase concentrated in vacuo. The residue is dissolved in chloroform (24 cm³), N,N-dimethylformamide (0.70 g, 9.64 mmol) added and the reaction mixture cooled to 0° C. Phosphorus oxychloride (1.39 g, 9.04 mmol) is added over 5 minutes. The reaction mixture is warmed to 23° C. over 30 minutes and then heated at 55° C. for 16 hours before cooling to 23° C. Saturated aqueous potassium acetate (50 cm³) is added and the biphasic solution stirred for 2 hours. The aqueous phase is extracted with chloroform (20 cm³) and the combined organic phase washed with water (50 cm³), dried over anhydrous magnesium sulphate, filtered and the solvent removed in vacuo. The residue is purified by column chromatography using a graded solvent system (40-60 petrol:dichloromethane; 9:1 to 3:1) to give intermediate 56 (730 mg, 71%) as a dark solid. $^1$H NMR (400 MHz, CDCl$_3$) 9.88 (2H, s), 7.93 (2H, s), 6.86 (4H, s), 6.77 (8H, s), 2.37-2.45 (16H, m), 1.44-1.61 (8H, m), 1.11-1.39 (64H, m), 0.72-0.95 (48H, m).

Compound 20
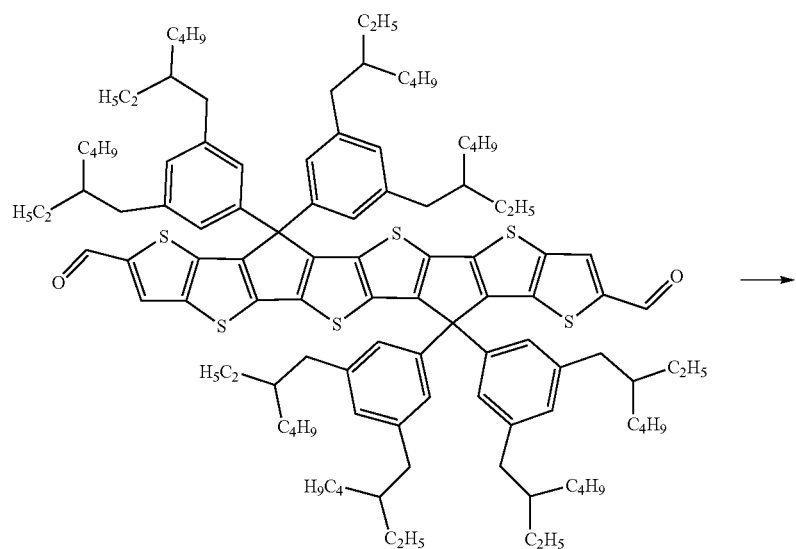
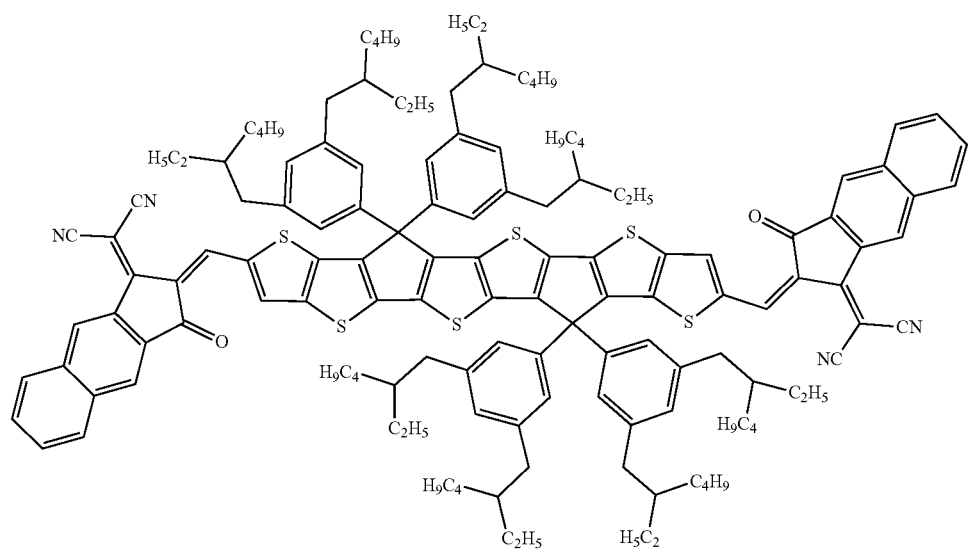

To a solution of intermediate 56 (100 mg, 0.06 mmol) and 2-(3-oxo-2,3-dihydro-cyclopenta[b]naphthalen-1-ylidene)-malononitrile (72 mg, 0.29 mmol) in chloroform (5.0 cm³) is added pyridine (0.33 cm³, 4.1 mmol) and the reaction mixture heated at 50° C. for 3 hours. Methanol (50 cm³) is added, the solid collected by filtration and washed with methanol (2×10 cm³). The crude is purified by column chromatography using a graded solvent system (40-60 petrol:dichloromethane; 3:2 to 1:1) to give compound 20 (94 mg, 74%) as a green solid. ¹H NMR (400 MHz, CDCl₃) 9.20 (2H, s), 8.96 (2H, s), 8.31 (2H, s), 8.20 (2H, s), 8.10 (2H, dd, J 6.2, 3.4), 8.04 (2H, dd, J 6.2, 3.3), 7.71 (4H, dd, J 6.3, 3.3), 6.89 (4H, s), 6.83-6.89 (8H, m), 2.36-2.58 (16H, m), 1.10-1.36 (72H, m), 0.71-0.88 (48H, m).

Example 21

Intermediate 57

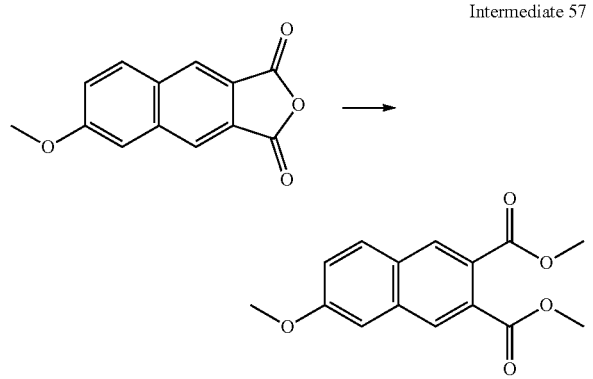

To a solution of 6-methoxy-naphtho[2,3-c]furan-1,3-dione (30.0 g, 131 mmol) in methanol (150 cm³) is added concentrated sulfuric acid (4.18 g, 42.6 mmol) and the mixture heated at reflux for 12 hours. The mixture is cooled to 23° C. and the solvent removed in vacuo. The residue is diluted with water (250 cm³) and extracted with ethyl acetate (3×100 cm³). The combined organic layer is washed with saturated aqueous sodium bicarbonate (3×100 cm³), brine (200 cm³), dried over anhydrous sodium sulfate, filtered and concentrated in vacuo. The residue is purified by column chromatography using a graded solvent system (40-60 petrol: ethyl acetate; 1:0 to 0:1) to give intermediate 57 (15.0 g, 42%) as a white solid. ¹H NMR (400 MHz, CDCl₃) 8.24 (1H, s), 8.08 (1H, s), 7.82 (1H, d, J 9.2), 7.26-7.29 (1H, m), 7.19 (1H, d, J 2.4), 3.96 (3H, s), 3.95 (6H, s).

Intermediate 58

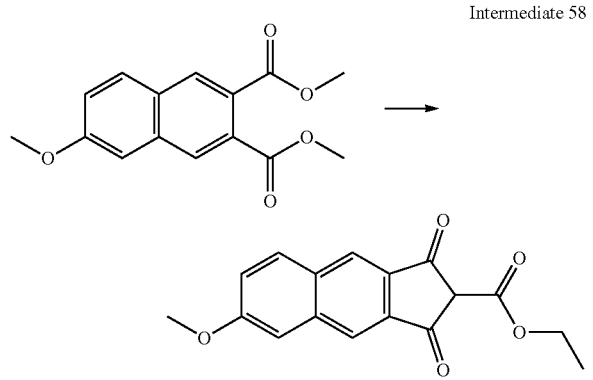

To a solution of sodium hydride (5.83 g, 146 mmol, 60% dispersion in mineral oil) in anhydrous tetrahydrofuran (300 cm³) is added anhydrous ethyl acetate (14 cm³) and the mixture stirred for 30 minutes. Intermediate 57 (5.00 g, 18.3 mmol) is then added and the mixture heated at reflux for 12 hours. After cooling to 23° C., the volatiles are removed in vacuo to give intermediate 58 (20.0 g) as a yellow solid, which is used without any further purification.

Intermediate 59

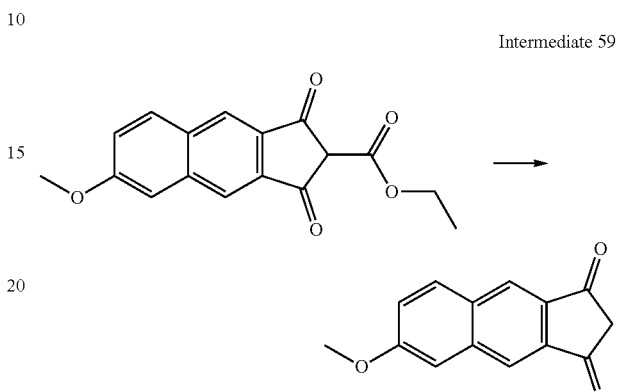

A mixture of intermediate 58 (10.0 g) in aqueous hydrochloric acid (100 cm³, 2 M) is stirred at 80° C. for 12 hours. The reaction mixture is cooled to 23° C. and the solid collected by filtration. The crude is triturated in ethyl acetate (30 cm³) and the solid collected by filtration to give intermediate 59 (8.0 g) as a yellow solid, which is used without any further purification.

Intermediate 60

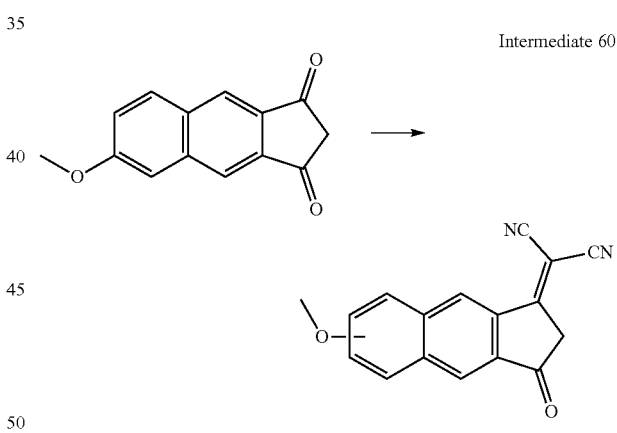

To a solution of intermediate 59 (8.00 g) in ethanol (100 cm³) is added sodium acetate (4.35 g, 53.0 mmol) and malononitrile (4.44 g, 67.2 mmol) and the mixture stirred for 12 hours. The reaction mixture is adjusted to pH ~1-2 with aqueous hydrochloric acid (1 M). The residue is diluted with water (100 cm³) and extracted with dichloromethane (3×100 cm³). The combined organic layer is washed with water (2×100 cm³), brine (100 cm³), dried over anhydrous sodium sulfate, filtered and concentrated in vacuo. The residue is purified by column chromatography using a graded solvent system (dichloromethane:methanol; 0:1 to 1:0) followed by trituration in acetonitrile. The solid is collected by filtration to give intermediate 60 (3.00 g) as a yellow solid. ¹H NMR (400 MHz CDCl₃) 9.04-9.10 (1H, m), 8.38-8.41 (1H, m), 7.98-8.06 (1H, m), 7.34-7.44 (2H, m), 4.02 (3H, s), 3.83 (2H, s).

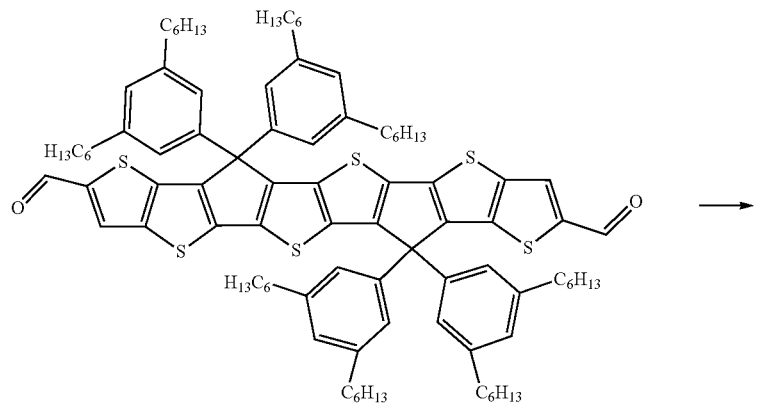

Compound 21

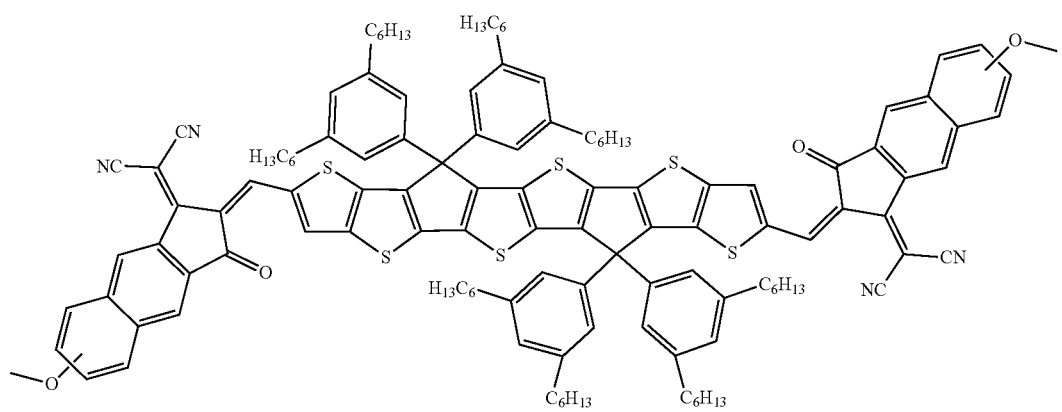

To a degassed solution of intermediate 21 (120 mg, 0.0814 mmol) and intermediate 60 (111 mg, 0.407 mmol) in chloroform (30 cm³) is added pyridine (0.5 cm³, 6 mmol) and the reaction mixture stirred at 55° C. for 16 hours. The solvent is removed in vacuo and the crude material purified by column chromatography using a graded solvent system (40-60 petrol:dichloromethane; 3:2 to 0:1). The product dissolved in a minimum dichloromethane, treated with acetonitrile and the solid collected by filtration to give compound 21 (132 mg, 82%) as a green solid. $^1$H NMR (400 MHz, CD$_2$Cl$_2$) 8.77-9.07 (4H, m), 8.05-8.17 (4H, m), 7.84-7.92 (2H, m), 7.21-7.34 (4H, m), 6.89 (4H, s), 6.83 (8H, s), 3.89 (6H, s), 2.45 (16H, t, J 7.7), 1.47 (16H, s), 1.06-1.28 (48H, m), 0.60-0.75 (24H, m).

Example 22

Compound 22

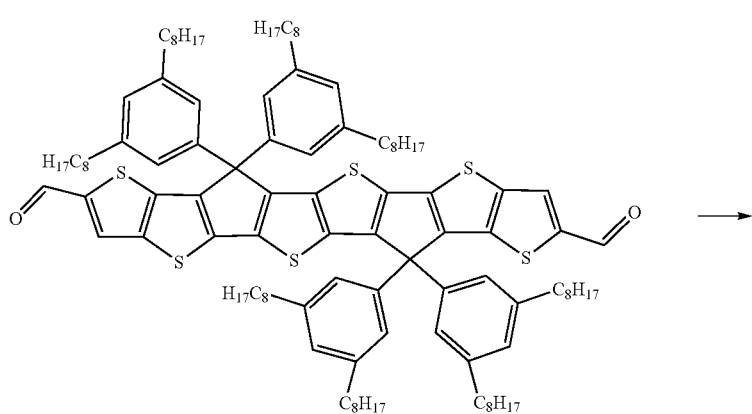

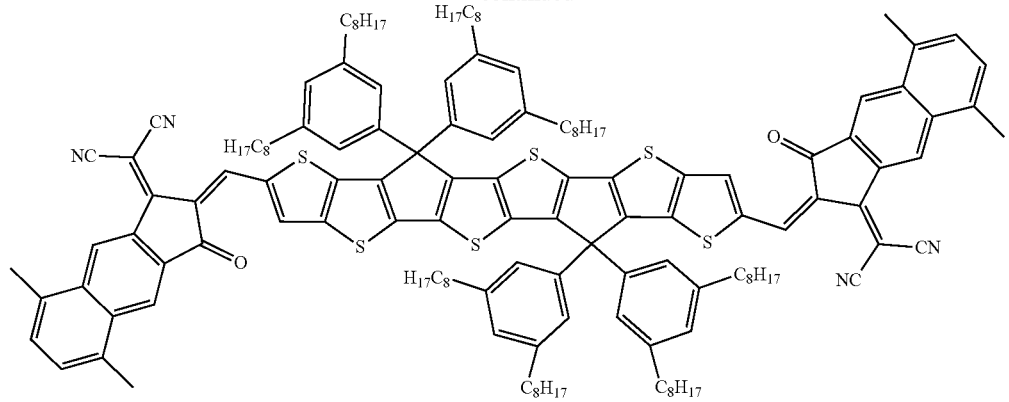

To a degassed solution of intermediate 43 (100 mg, 0.059 mmol) and intermediate 50 (80 mg, 0.29 mmol) in chloroform (30 cm³) is added pyridine (0.3 cm³, 4 mmol) and the reaction mixture stirred at 55° C. for 16 hours. The reaction mixture is cooled down to 23° C. and the solvent removed in vacuo. The crude product is purified by column chromatography (40-60 petrol:dichloromethane; 3:2) and the solid washed with ether (50 cm³) to give compound 22 (39 mg, 30%) as a dark solid. ¹H NMR (400 MHz, CD$_2$Cl$_2$) 9.28 (2H, s), 8.87 (2H, s), 8.44 (2H, s), 8.08 (2H, s), 7.35 (4H, s), 6.88 (4H, s), 6.83 (8H, s), 2.67 (12H, s), 2.45 (16H, t, J 7.7), 1.47-1.57 (16H, m), 0.91-1.28 (80H, m), 0.66 (24H, t, J 6.6).

Example 23

Compound 23

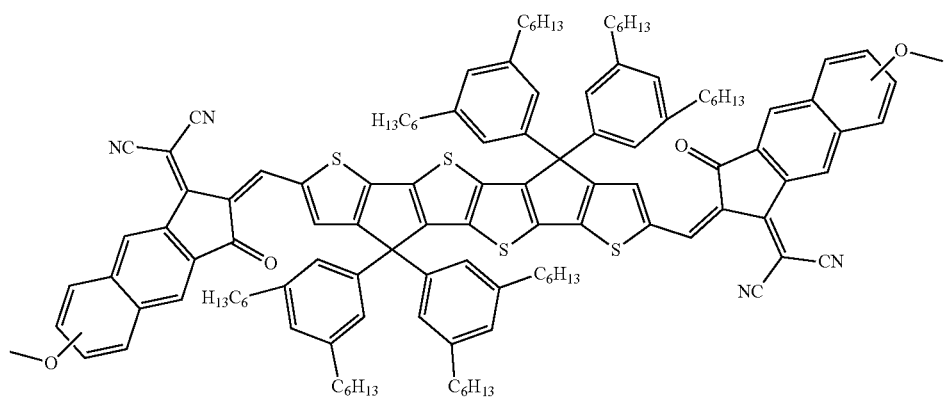

To a solution of intermediate 60 (101 mg, 0.367 mmol) and intermediate 2 (100 mg, 0.073 mmol) in chloroform (10 cm$^3$) is added pyridine (0.41 cm$^3$, 5.1 mmol) and the reaction mixture stirred for 16 hours. Methanol (50 cm$^3$) is slowly added over 15 minutes, the solid collected by filtration and washed with methanol (2×5 cm$^3$). The residue is purified by column chromatography using a graded solvent system (40-60 petrol:dichloromethane 7:3 to 1:1). The solid is triturated in methanol and collected by filtration to give compound 23 (98 mg, 71%). $^1$H NMR (400 MHz, CDCl$_3$) 9.01-9.16 (2H, m), 8.86-8.99 (2H, m), 8.19-8.33 (2H, m), 7.96 (2H, dd, J 15.2, 9.1), 7.73 (2H, d, J 3.2), 7.35 (4H, d, J 8.2), 6.97 (4H, d, J 1.9), 6.84 (8H, d, J 1.5), 3.98-4.04 (6H, m), 2.54 (16H, t, J 7.7), 1.57 (16H, d, J 13.9), 1.22-1.38 (48H, m), 0.77-0.96 (24H, m).

Example 24

To a solution of intermediate 50 (100 mg, 0.37 mmol) and intermediate 2 (100 mg, 0.073 mmol) in chloroform (10 cm$^3$) is added pyridine (0.41 cm$^3$, 5.1 mmol) and the reaction mixture stirred at 23° C. for 16 hours. Methanol (120 cm$^3$) is added slowly over 15 minutes, the solid collected by filtration and washed with methanol (2×5 cm$^3$). The residue is purified by column chromatography using a graded solvent system (40-60 petrol:dichloromethane 7:3 to 1:1) to give compound 24 (102 mg, 74%) as a dark solid. $^1$H NMR (400 MHz, CDCl$_3$) 9.38 (2H, s), 8.96 (2H, s), 8.56 (2H, s), 7.74 (2H, s), 7.41 (4H, s), 6.98 (4H, s), 6.85 (8H, d, J 1.4), 2.78 (6H, s), 2.77 (6H, s), 2.55 (16H, t, J 7.7), 1.53-1.64 (16H, m), 1.24-1.38 (48H, m), 0.79-0.92 (24H, m).

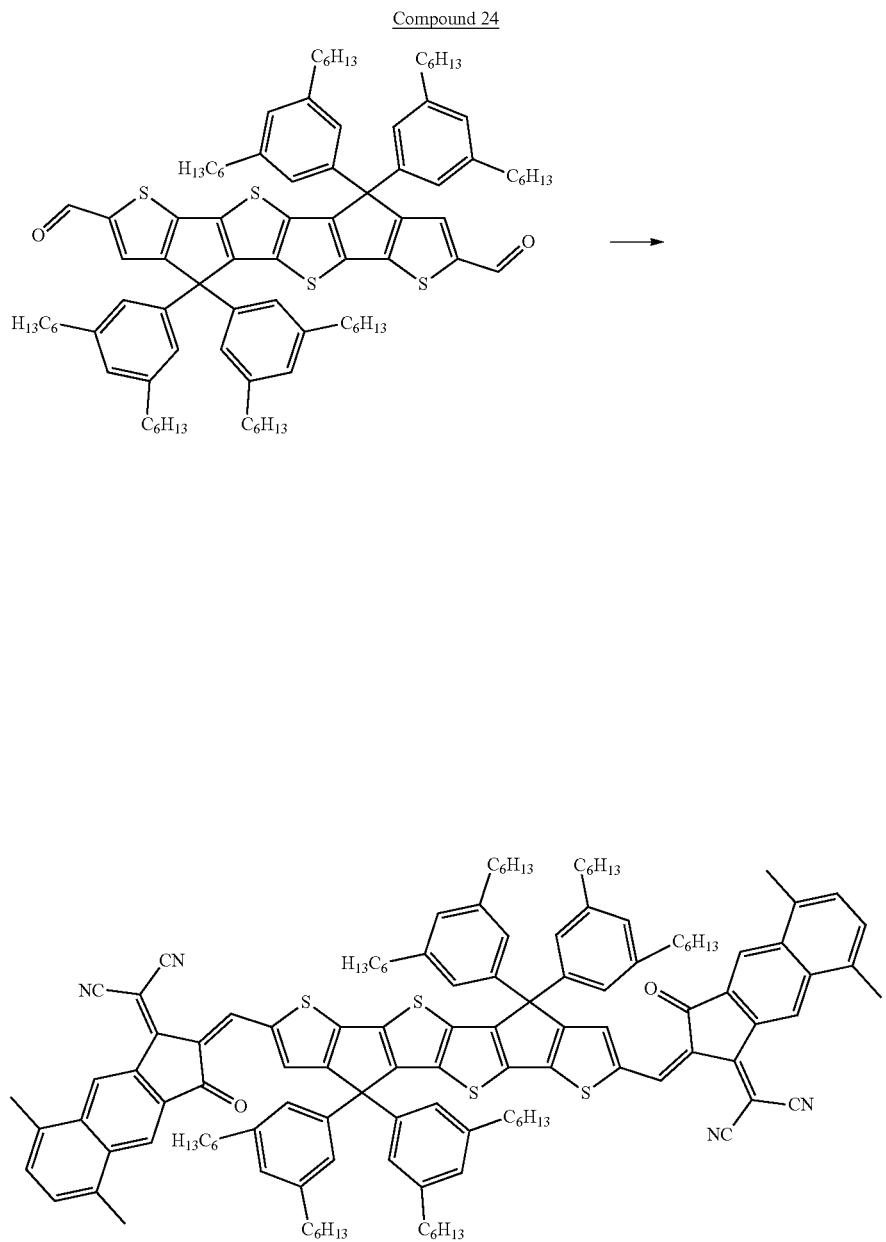

Compound 24

Example 25
Intermediate 61
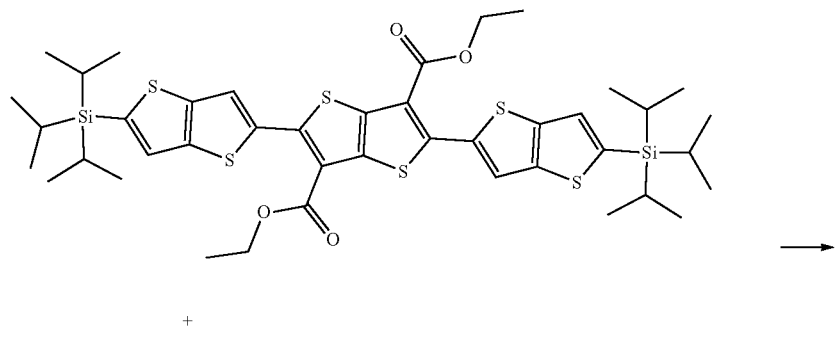
+
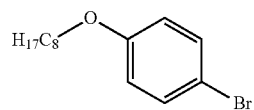
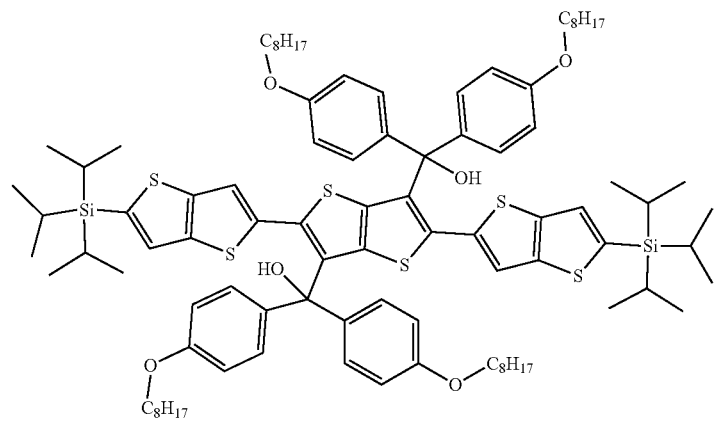

To a solution of 1-bromo-4-(octyloxy)benzene (1.57 g, 5.50 mmol) in anhydrous tetrahydrofuran (24 cm³) at −78° C. is added dropwise t-butyllithium (6.47 cm³, 11.0 mmol, 1.7 M in pentane). The solution is stirred for 2 hours, warmed to −30° C. and re-cooled to −78° C. A suspension of intermediate 14 (800 mg, 0.92 mmol) in anhydrous tetrahydrofuran (10 cm³) is then added. The reaction is slowly warmed to 23° C. and stirred for 16 hours. Water (10 cm³) is added and the mixture partitioned between ether (50 cm³) and water (50 cm³). The aqueous phase is extracted with ether (20 cm³), the combined organic phase is washed with water (3×20 cm³), dried over anhydrous magnesium sulphate, filtered and concentrated in vacuo. The residue is purified by column chromatography using a graded solvent system (40-60 petrol:dichloromethane 7:3 to 1:1) to give intermediate 61 (600 mg, 41%) as a pale brown solid. ¹H NMR (400 MHz, CDCl₃) 7.22 (2H, s), 7.17-7.22 (8H, m), 6.79-6.87 (8H, m), 6.66 (2H, s), 3.96 (8H, t, J 6.6), 3.45 (2H, s), 1.79 (8H, p, J 6.7), 1.41-1.51 (8H, m), 1.26-1.41 (38H, m), 1.13 (36H, d, J 7.4), 0.83-0.95 (12H, m).

7.07 (8H, d, J 8.8), 6.71 (8H, d, J 8.8), 3.79 (8H, t, J 6.6), 1.56-1.68 (8H, m), 1.31 (8H, t, J 7.4), 1.10-1.26 (32H, m), 0.68-0.84 (12H, m).

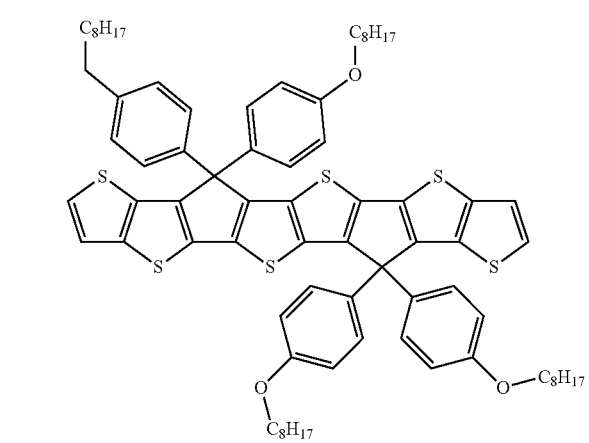

To a solution of intermediate 61 (561 mg, 0.349 mmol) in toluene (80 cm³) is added Amberlyst 15 strong acid (2.2 g) and the reaction mixture stirred at 50° C. for 16 hours. The hot reaction mixture is filtered and the filtrate washed with water (50 cm³). The organics dried over anhydrous magnesium sulphate, filtered and the solvent removed in vacuo. The crude is purified by column chromatography (40-60 petrol:dichloromethane; 4:1) to give intermediate 62 (335 mg, 76%). ¹H NMR (400 MHz, CD₂Cl₂) 7.20 (4H, d, J 6.7), To a degassed solution of intermediate 62 (335 mg, 0.266 mmol) in chloroform (30 cm³) and N,N-dimethylformamide (0.25 cm³, 3.2 mmol) is added phosphorus(V) oxychloride (0.25 cm³, 2.7 mmol) and the reaction mixture heated at 60° C. for 16 hours. Saturated aqueous sodium acetate solution (10 cm³) is added and the resulting mixture stirred at 50° C. for 1 hour. The mixture is then cooled down to 23° C. and the organic solvent removed in vacuo. The remaining aqueous phase and material are extracted with ether (3×100 cm³), the combined organic layer is washed with water (2×25 cm³), and brine (30 cm³), before drying over anhydrous magnesium sulphate. The mixture is filtered, the solvent removed in vacuo and the crude product purified by column chromatography using a graded solvent system (40-60 petrol:dichloromethane; 4:1 to 1:1) to give intermediate 63 (206 mg, 59%). ¹H NMR (400 MHz, CD₂Cl₂) 9.76 (2H, s), 7.85 (2H, s), 7.05 (8H, d, J 8.4), 6.71 (8H, d, J 8.5), 3.78 (8H, t, J 6.6), 1.61 (8H, q, J 6.9), 1.25-1.36 (8H, m), 1.10-1.25 (32H, m), 0.77 (12H, t, J 6.7).

Compound 25
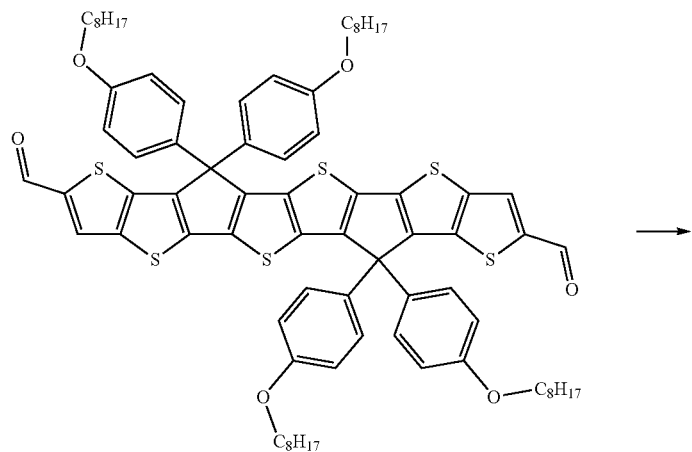
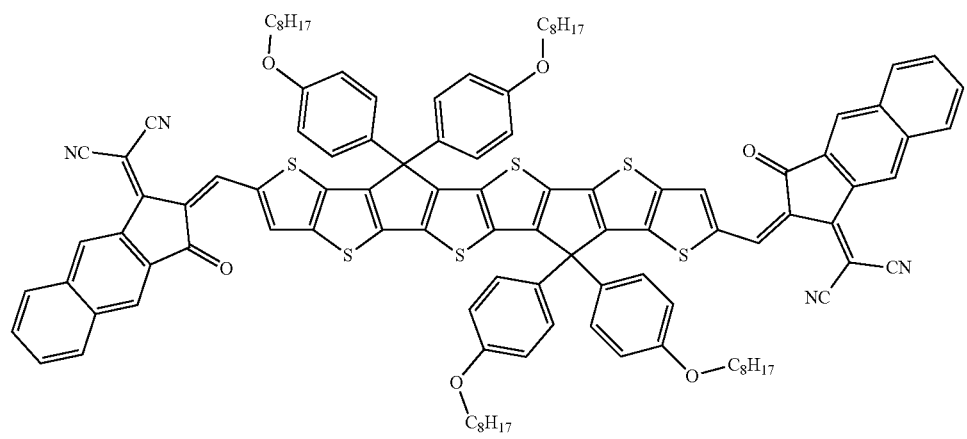

To a degassed solution of intermediate 63 (60 mg, 0.046 mmol) and 2-{3-oxo-1H,2H,3H-cyclopenta[b]naphthalen-1-ylidene}propanedinitrile (56 mg, 0.23 mmol) in chloroform (30 cm³) is added pyridine (0.3 cm³) and the reaction mixture stirred at 55° C. for 16 hours. The solvent is removed in vacuo, and the crude purified by column chromatography (chloroform). The product is dissolved in the minimum chloroform, treated with acetonitrile (50 cm³) and the solid collected by filtration to give compound 25 (40 mg, 50%) as a dark solid. $^1$H NMR (400 MHz, CDCl$_3$) 9.09 (2H, s), 8.86 (2H, s), 8.30 (2H, s), 8.10 (2H, s), 7.98 (4H, ddd, J 10.5, 6.1, 3.3), 7.62 (4H, dd, J 6.3, 3.2), 7.15 (8H, d, J 8.9), 6.77-6.85 (8H, d, J 8.9), 3.84 (8H, t, J 6.5), 1.67 (8H, p, J 6.7), 1.30-1.39 (8H, m), 1.10-1.28 (32H, m), 0.70-0.83 (12H).

Example 26

Intermediate 64

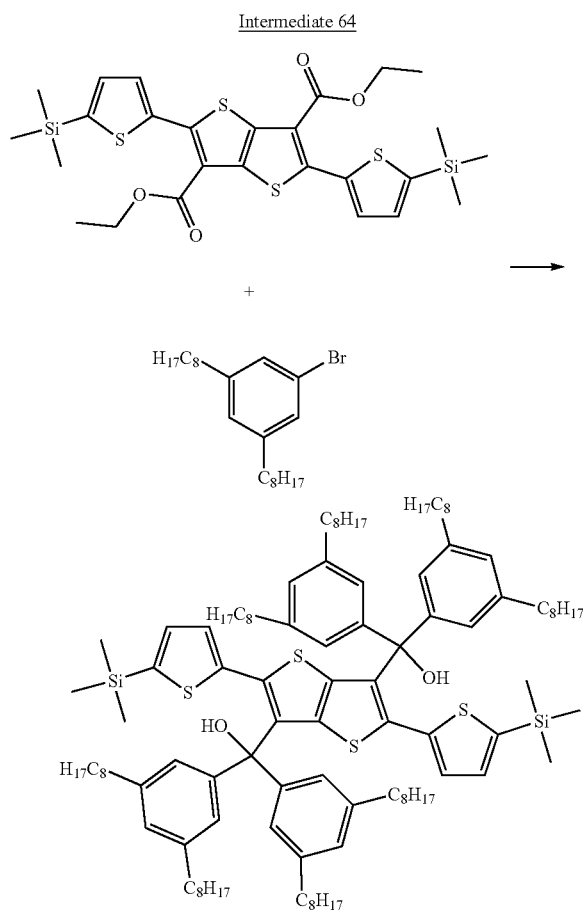

To a solution of 1-bromo-3,5-dioctyl-benzene (3.1 g, 8.1 mmol) in anhydrous tetrahydrofuran (12 cm³) at −78° C. is added t-butyllithium (9.5 cm³, 16 mmol, 1.7 M in pentane) over 10 minutes and the solution stirred for 2 hours. The cooling is removed for 5 minutes and the reaction mixture is re-cooled to −78° C. A solution of 2,5-bis-(5-trimethylsilanyl-thiophen-2-yl)-thieno[3,2-b]thiophene-3,6-dicarboxylic acid diethyl ester (0.80 g, 1.35 mmol) in anhydrous tetrahydrofuran (10 cm³) is added over 5 minutes, the coolant is left to evaporate and the reaction stirred for 16 hours. Water (5 cm³) is added and the mixture stirred for 5 minutes. The reaction is partitioned between ether (100 cm³) and water (50 cm³), the organic phase is washed with water (3×20 cm³), dried over anhydrous magnesium sulphate, filtered and concentrated in vacuo. The residue is purified by column chromatography using a graded solvent system (40-60 petrol:dichloromethane; 9:1 to 4:1) to give intermediate 64 (2.1 g, 89%). $^1$H NMR (400 MHz, CDCl$_3$) 6.93 (8H, d, J 1.5), 6.90 (4H, d, J 1.7), 6.79 (2H, d, J 3.4), 6.43 (2H, d, J 3.4), 3.35 (2H, s), 2.50 (16H, t, J 7.7), 1.48-1.56 (16H, m), 1.20-1.36 (80H, m), 0.80-0.94 (24H, m), 0.22 (18H, s).

Intermediate 65

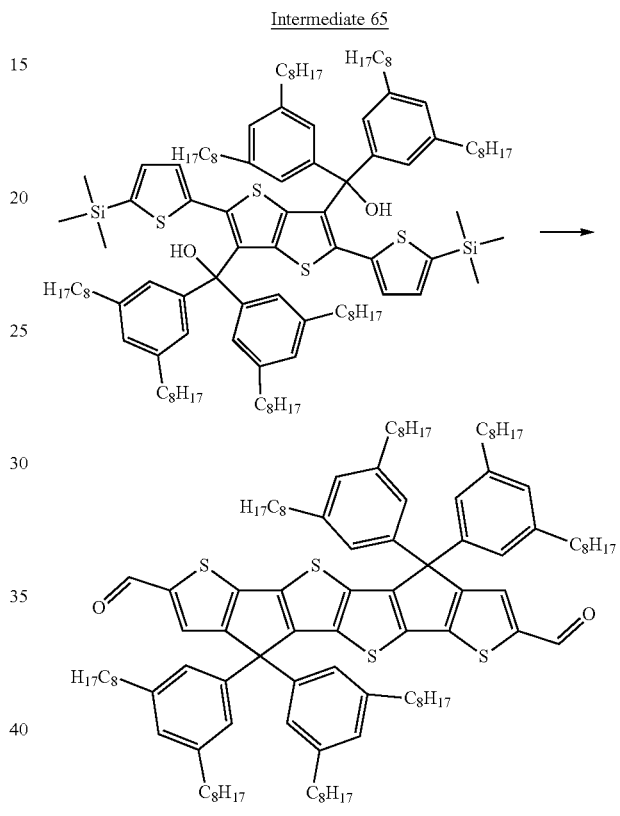

To a degassed solution of intermediate 64 (2.00 g, 1.17 mmol) in toluene (30 cm³) at 50° C. is added Amberlyst 15 strong acid (8 g). The reaction is stirred for 16 hours, filtered and the solid extracted with toluene (3×50 cm³). The combined organic phase is concentrated in vacuo and passed through a silica plug using a graded solvent system (40-60 petrol:dichloromethane; 1:0 to 19:1). Crude material (1.20 g) is dissolved in chloroform (24 cm³) and N,N-dimethylformamide (0.92 g, 13 mmol), and the solution cooled to 0° C. Phosphorus(V) oxychloride (1.80 g, 11.8 mmol) is added over 5 minutes, stirred at 23° C. for 30 minutes and heated at 55° C. for 16 hours. Saturated aqueous potassium acetate (50 cm³) is added and the biphasic solution stirred at 55° C. for 1 hour. The aqueous phase is extracted with dichloromethane (20 cm³) and the combined organics washed with water (20 cm³), dried over anhydrous magnesium sulphate, filtered and concentrated in vacuo. The residue is purified by column chromatography using a graded solvent system (40-60 petrol:dichloromethane; 4:1 to 3:1) to give intermediate 65 (545 mg, 44%). $^1$H NMR (400 MHz, CDCl$_3$) 9.82 (2H, s), 7.66 (2H, s), 6.93 (4H, t, J 1.5), 6.80 (8H, d, J 1.5), 2.50 (16H, t, J 7.7), 1.53 (16H, t, J 7.7), 1.26 (80H, t, J 7.5), 0.83-0.91 (24H, m).

Compound 26

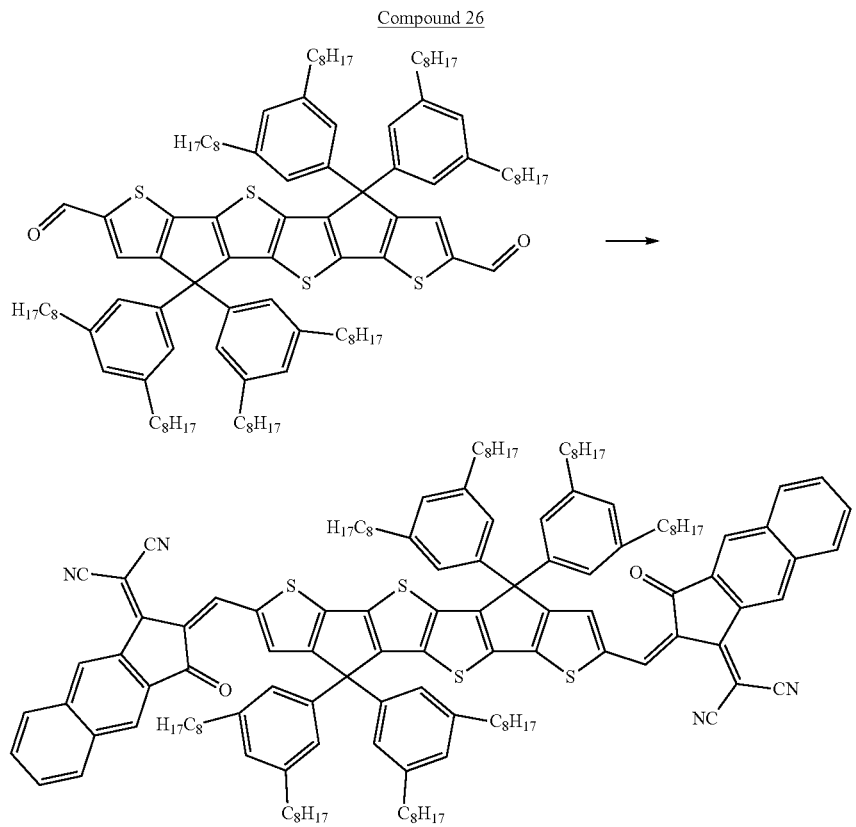

To a solution of intermediate 65 (100 mg, 0.063 mmol) and 2-{3-oxo-1H,2H,3H-cyclopenta[b]naphthalen-1-ylidene}propanedinitrile (100 mg, 0.410 mmol) in chloroform (10 cm$^3$) is added pyridine (0.36 cm$^3$, 4.4 mmol) and the reaction stirred at 55° C. for 6 hours. Methanol (30 cm$^3$) is added, the suspension cooled to 23° C., filtered and the solid washed with methanol (5 cm$^3$). The solid is purified by column chromatography using a graded solvent system (40-60 petrol:dichloromethane; 7:3 to 11:9) to give compound 26 (56 mg, 44%) as a green solid. $^1$H NMR (400 MHz, CDCl$_3$) 9.19 (2H, s), 8.98 (2H, s), 8.36 (2H, s), 8.05-8.11 (4H, m), 7.68-7.78 (6H, m), 6.98 (4H, s), 6.83 (8H, d, J 1.5), 2.54 (16H, t, J 7.8), 1.45-1.70 (8H, m), 1.21-1.32 (88H, m), 0.81-0.90 (24H, m).

Example 27

Intermediate 66

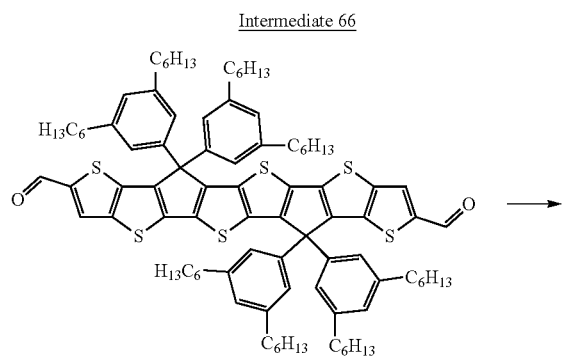

-continued

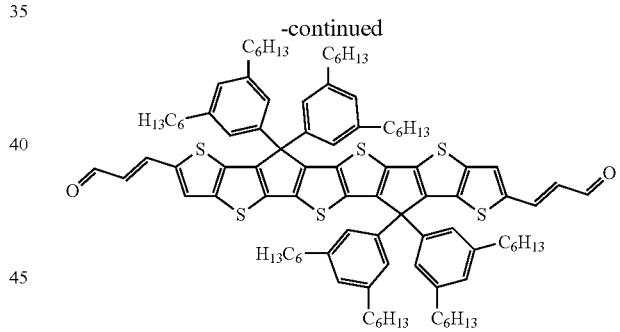

To a solution of intermediate 21 (500 mg, 0.34 mmol) and tributyl(1,3-dioxolan-2-ylmethyl)-phosphonium bromide (276 mg, 0.75 mmol) in tetrahydrofuran (19 cm$^3$) at 0° C. is added sodium hydride (81.4 mg, 2.03 mmol, 60% dispersion in mineral oil). The reaction is slowly warmed to 23° C. and stirred for 16 hours. Aqueous hydrochloric acid (60 cm$^3$, 10%) is added and the reaction mixture heated at 45° C. for 24 hours. The mixture allowed to cool, and the organics extracted with ether (40 cm$^3$). The organic layer is then washed with water (2×20 cm$^3$), dried over anhydrous magnesium sulphate, filtered and the solvent removed in vacuo. Purification by column chromatography using a graded solvent system (40-60 petrol:dichloromethane; 5:1 to 3:2) gives intermediate 66 (480 mg, 93%) as a purple solid. $^1$H NMR (400 MHz, CDCl$_3$) 9.62 (2H, d, J 7.6), 7.58 (2H, d, J 15.4), 7.54 (2H, s), 6.93 (4H, d, J 1.5), 6.82 (8H, d, J 1.5), 6.41 (2H, dd, J 15.4, 7.6), 2.51 (16H, t, J 7.6), 1.53 (16H, q, J 7.6, 7.0), 1.19-1.34 (48H, m), 0.80-0.88 (24H, m).

Compound 27

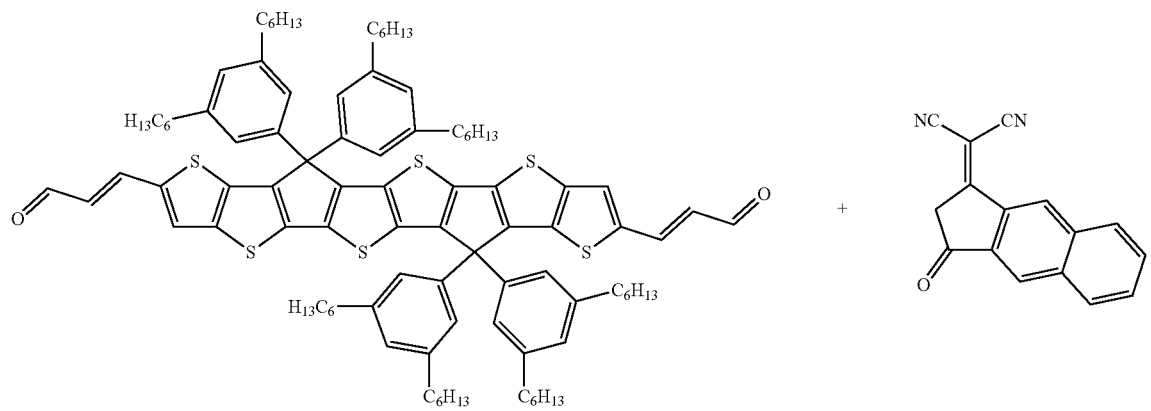

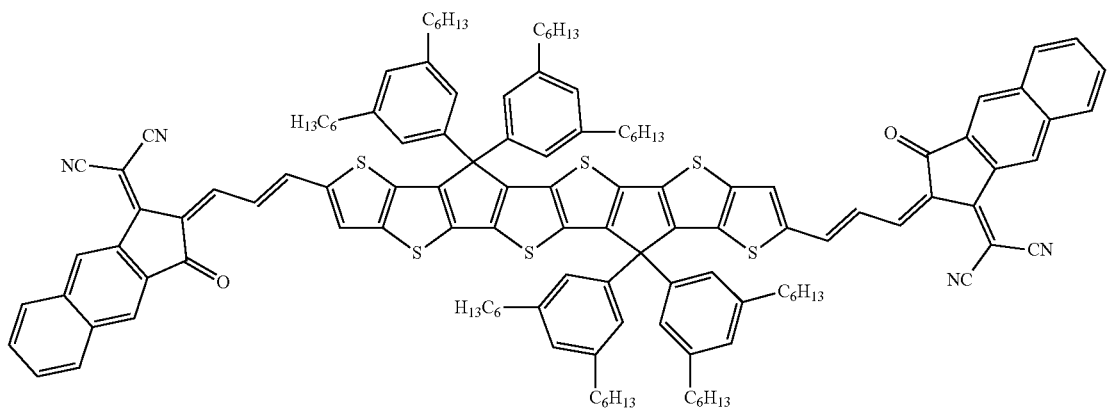

Intermediate 66 (100 mg, 0.066 mmol) and 2-(3-oxo-2,3-dihydro-cyclopenta[b]naphthalen-1-ylidene)-malononitrile (35.2 mg, 0.144 mmol) are suspended in chloroform (5.0 cm$^3$), pyridine (0.37 cm$^3$, 4.6 mmol) added and the reaction mixture stirred at 23° C. for 16 hours. Methanol (30 cm$^3$) is added, the solid collected by filtration and washed with methanol (10 cm$^3$). The crude is purified by column chromatography using a graded solvent system (40-60 petrol:dichloromethane; 5:1 to 3:7) to give compound 27 (68 mg, 53%) as a dark solid. $^1$H NMR (400 MHz, CDCl$_3$) 9.20 (2H, s), 8.72 (2H, s), 8.53 (2H, d, J 11.7), 8.35 (2H, s), 8.00-8.18 (4H, m), 7.67-7.77 (4H, m), 7.65 (2H, s), 7.57 (2H, d, J 14.3), 6.96 (4H, s), 6.86 (8H, s), 2.56 (16H, t, J 7.6), 1.54-1.65 (16H, m), 1.19-1.40 (48H, m), 0.79-0.86 (24H, m).

Example 28

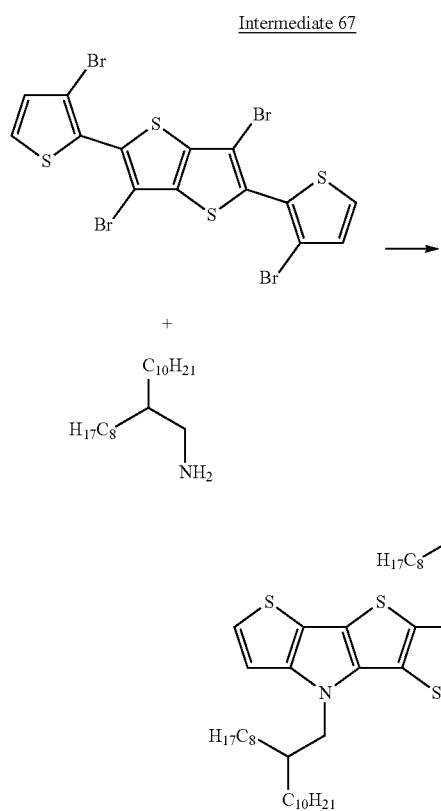

Intermediate 67

To a degassed solution of 3,6-dibromo-2,5-bis(3-bromo-2-thienyl)-thieno[3,2-b]thiophene (1.00 g, 1.61 mmol), sodium 2-methylpropan-2-olate (3.10 g, 32.3 mmol), 1,1′-bis(diphenylphosphino)ferrocene (358 mg, 0.645 mmol) and tris(dibenzylideneacetone)dipalladium(0) (148 mg, 0.161 mmol) in anhydrous toluene (30 cm³) is added 2-octyl-1-dodecylamine (1.44 g, 4.838 mmol). The reaction mixture is then heated at 110° C. for 20 hours. The mixture is cooled to 23° C. and water (50 cm³) added. The aqueous phase is extracted with cyclohexane (2×25 cm³) and the combined organics dried over anhydrous magnesium sulfate, filtered and the solvent removed in vacuo. The crude is purified by column chromatography (40-60 petrol:dichloromethane; 19:1) to give intermediate 67 (606 mg, 42%) as an orange solid. $^1$H NMR (400 MHz, CD$_2$Cl$_2$) 7.17 (2H, d, J 5.3), 7.07 (2H, d, J 5.3), 4.21 (4H, d, J 7.6), 2.12-2.23 (2H, m), 1.19-1.48 (64H, m), 0.83-0.96 (12H, m).

Intermediate 68

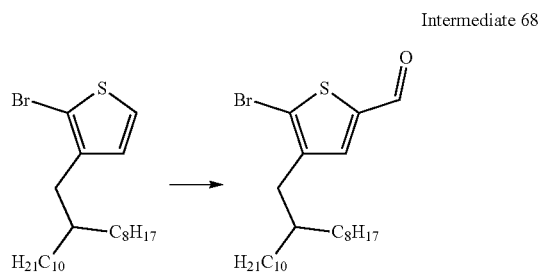

To a solution of 2-bromo-3-(2-octyldodecyl)thiophene (5.90 g, 13.3 mmol) in anhydrous tetrahydrofuran (50 cm³) at −78° C. is added lithium diisopropylamine (9.98 cm³, 20.0 mmol, 2.0 M in tetrahydrofuran) and the mixture stirred for 90 minutes. Anhydrous N,N-dimethylformamide (1.5 cm³, 20 mmol) is added and the cooling bath removed. The mixture is stirred at 23° C. for 1 hour and then cooled back to −78° C. Saturated aqueous ammonium chloride solution (20 cm³) is added and the mixture allowed to warm to 23° C. where the solvent is removed in vacuo. The organic residue is taken into 40-60 petrol (100 cm³), dried over anhydrous magnesium sulfate, filtered and the solvent removed in vacuo. The crude is purified by column chromatography using a graded solvent system (40-60 petrol:dichloromethane; 9:1 to 7:3) to give intermediate 68 (6.01 g, 96%) as a pale yellow liquid. $^1$H NMR (400 MHz, CDCl$_3$) 9.78 (1H, s), 7.44 (1H, s), 2.55 (2H, d, J 7.1), 1.63-1.73 (1H, m), 1.20-1.38 (32H, m), 0.87-0.94 (6H, m).

Intermediate 69

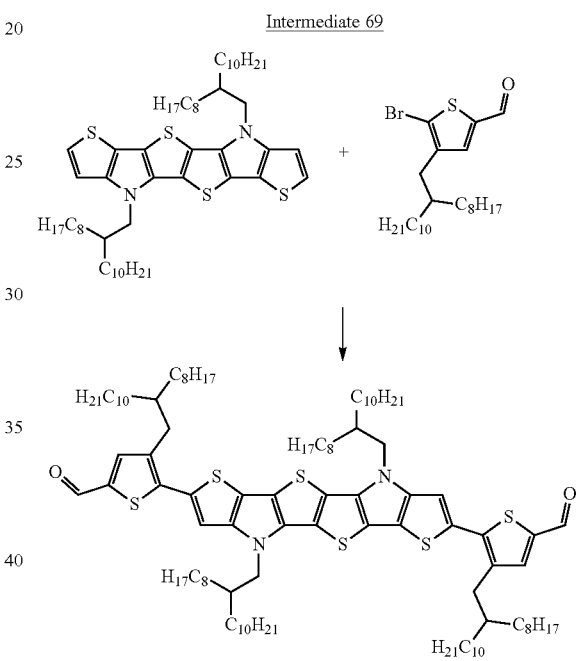

To a solution of intermediate 67 (710 mg, 0.796 mmol) in anhydrous tetrahydrofuran (15 cm³) at −78° C. is added t-butyllithium (1.4 cm³, 2.4 mmol, 1.7 M in pentane) batchwise over 10 minutes. The mixture is stirred for 6 hours. Chlorotrimethylstannane (4.8 cm³, 4.8 mmol) is added, the reaction mixture allowed to warm to 23° C. and stirred for 17 hours. The solvent removed in vacuo, the residue triturated in 40-60 petrol (40 cm³) and then passed through a plug of celite. The solid is taken up in anhydrous toluene (25 cm³) and anhydrous N,N-dimethylformamide (5.0 cm³) and intermediate 68 (970 mg, 2.1 mmol) added. The solution is degassed followed by addition of tris(dibenzylideneacetone)dipalladium(0) (75 mg, 0.082 mmol) and tri(o-tolyl)phosphine (100 mg, 0.33 mmol). The reaction mixture is then stirred at 120° C. (external) for 2 hours. The mixture is allowed to cool to 23° C. and the solvent removed in vacuo. The crude is purified by column chromatography using a graded solvent system (40-60 petrol:dichloromethane; 7:3 to 1:1) followed by trituration in methanol to give intermediate 69 (860 mg, 63%) as a brown-red solid. 1H NMR (400 MHz, CD$_2$Cl$_2$) 9.73 (2H, s), 7.49 (2H, s), 7.12 (2H, s), 4.08 (4H, d, J 7.6), 2.75 (4H, d, J 7.2), 2.00-2.13 (2H, m), 1.63-1.76 (2H, m), 1.00-1.39 (128H, m), 0.71-0.83 (24H, m).

Compound 28

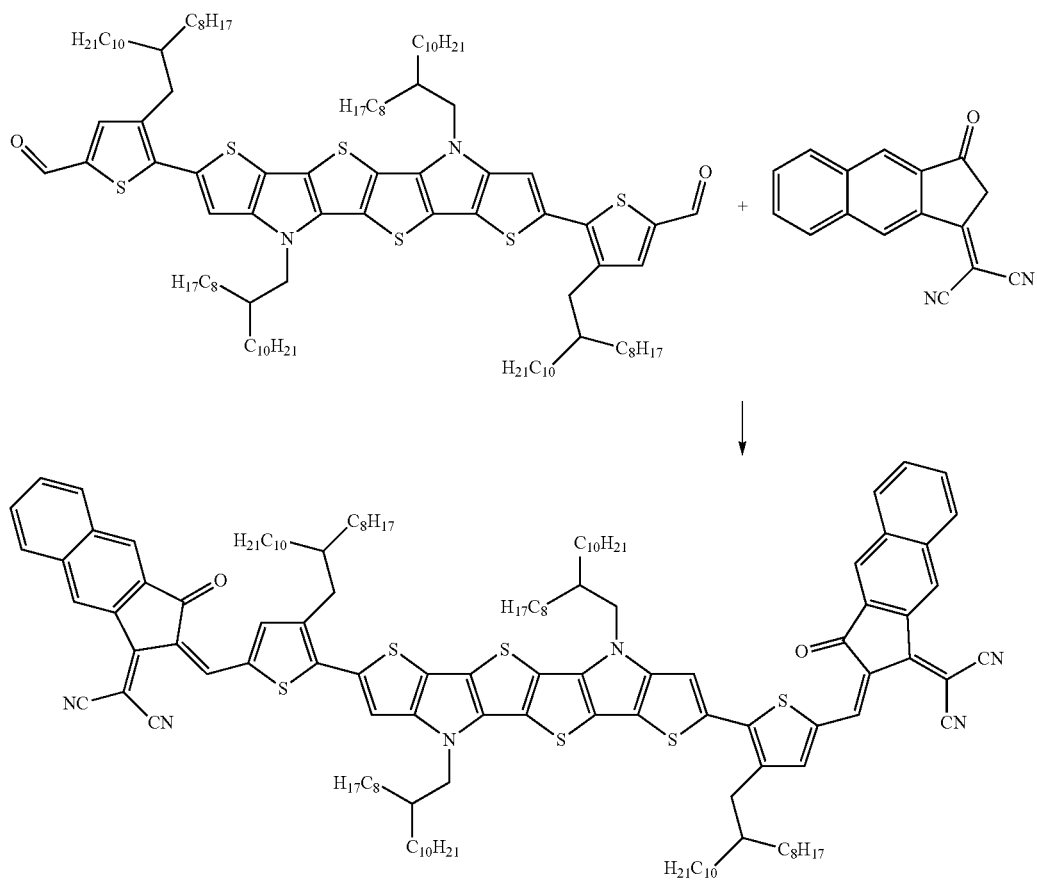

To a solution of intermediate 69 (250 mg, 0.149 mmol) in chloroform (20 cm³) and ethanol (5 cm³) is added pyridine (20 mg, 0.25 mmol) and 2-{3-oxo-1H,2H,3H-cyclopenta[b]naphthalen-1-ylidene}propanedinitrile (110 mg, 0.448 mmol). The solution is stirred for 48 hours before the volatiles are removed in vacuo. The crude is purified by column chromatography using a graded solvent system (cyclohexane:chloroform; 2:3 to 0:1) to give compound 28 (281 mg, 89%) as a brown solid. ¹H NMR (400 MHz, tetrahydrofuran-d8) 8.90 (2H, s), 8.66 (2H, s), 8.14 (2H, s), 7.86-7.96 (4H, m), 7.68 (2H, br. s), 7.51-7.60 (4H, m), 7.44 (2H, s), 4.26 (4H, d, J 7.6), 2.91 (4H, d, J 7.2), 2.12-2.25 (2H, m), 1.91-2.04 (2H, m), 1.08-1.59 (128H, m), 0.76-0.93 (24H, m).

Example 29

Intermediate 70

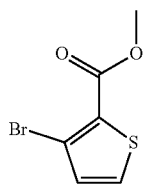

-continued

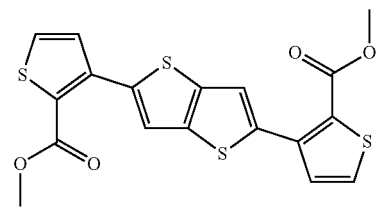

To a degassed solution of 3-bromothiophene-2-carboxylate (10.4 g, 47.2 mmol), toluene (500 cm³) and trimethyl [5-(trimethylstannyl)thieno[3,2-b]thiophen-2-yl]stannane (10.0 g, 21.5 mmol) is added tris(dibenzylideneacetone)dipalladium(0) (983 mg, 1.07 mmol) and 2-dicyclohexylphosphino-2',4',6'-triisopropylbiphenyl (2.05 g, 4.29 mmol). The reaction is then degassed for a further 15 minutes before heating to 80° C. for 45 minutes. The reaction is then heated at 110° C. for a further 15 minutes before cooling to 23° C. and stirring for 17 hours. The solid is collected by filtration, washed with ether (4×50 cm³) and 40-60 petrol (3×70 cm³) to give intermediate 70 (8.76 g, 97%) as a beige solid. ¹H NMR (400 MHz, CDCl₃) 8.19 (2H, s), 7.56 (2H, d, J 5.2), 7.47 (2H, d, J 5.2), 4.02 (6H, s).

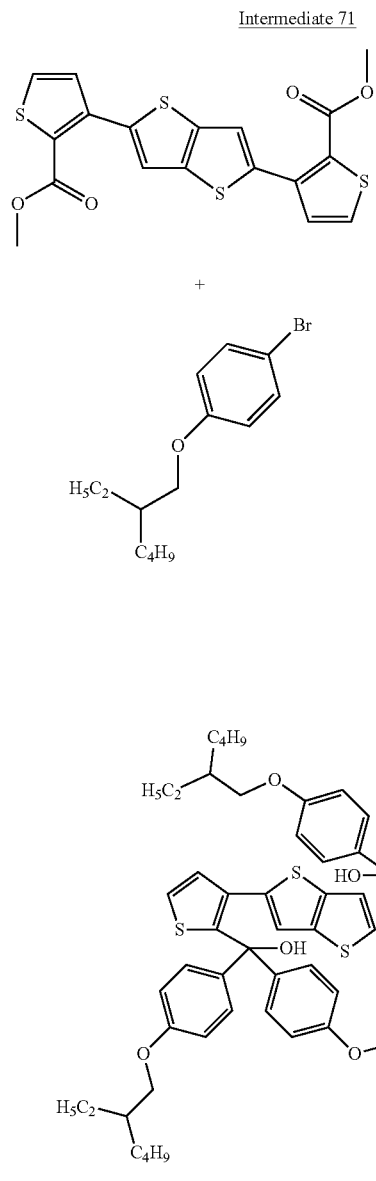

Intermediate 71

To a solution of 1-bromo-4-[(2-ethylhexyl)oxy]benzene (10.2 g, 35.7 mmol) in anhydrous tetrahydrofuran (127 cm³) at −78° C. is added dropwise t-butyllithium (35.0 cm³, 59.4 mmol, 1.7 M in pentane) over 35 minutes keeping the reaction temperature below −50° C. Once the addition is finished the reaction mixture is stirred for 2 hours. The ice-bath is then removed and the reaction is allowed to warm to about −40° C. and stirred for 15 minutes. The reaction mixture is then cooled to −78° C., intermediate 70 (2.50 g, 5.95 mmol) added and the reaction mixture stirred for 1 hour. The cooling is then removed and the resulting suspension stirred at 23° C. for 17 hours. Water (100 cm³) is added and the mixture stirred for 1 hour. The organics are extracted with ether (3×100 cm³) and the combined organics washed with water (100 cm³), brine (100 cm³), dried over anhydrous magnesium sulfate, filtered and the solvent removed in vacuo. The crude product is suspended in acetonitrile (150 cm³) and stirred for 1 hour. The mixture is then let stand for 10 minutes and the upper solution decanted. The crude is further purified by column chromatography using a graded solvent system (40-60 petrol:dichloromethane; 9:1 to 1:1) to give intermediate 71 (3.72 g, 53%) as a pale brown oil. ¹H NMR (400 MHz, CDCl₃) 7.17-7.25 (8H, m), 7.15 (2H, d, J 5.1), 7.09 (2H, d, J 5.1), 6.79-6.86 (8H, m), 6.61 (2H, s), 3.85 (8H, d, J 5.9), 3.54 (2H, s), 1.73 (4H, quin, J 6.1), 1.25-1.55 (32H, m), 0.87-0.99 (24H, m).

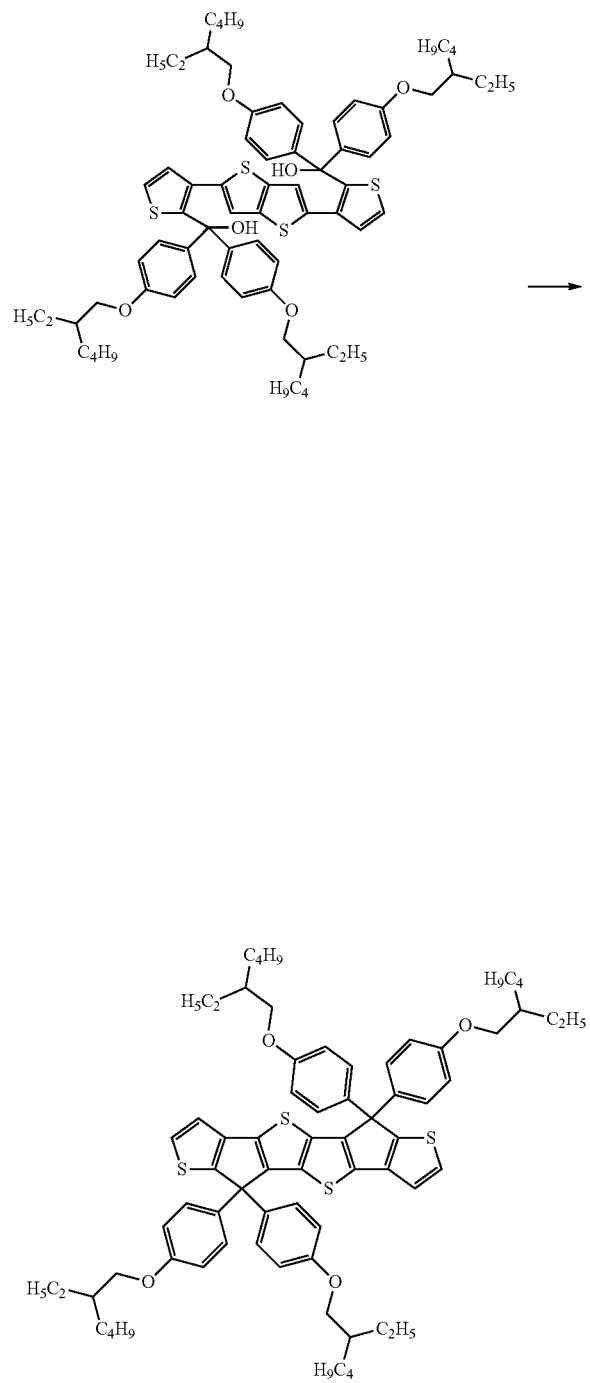

Intermediate 72

To a solution of p-toluene sulfonic acid monohydrate (1.32 g, 6.96 mmol) in chloroform (75 cm³) at 70° C. is added a solution of compound 71 (1.50 g, 1.16 mmol) in chloroform (75 cm³). The reaction mixture is heated at 70° C. for 65 hours. The reaction mixture is then cooled to 23° C. and the solvent removed in vacuo before water (50 cm³) is added. The organics are then extracted with ether (3×50 cm³). The combined organic layer is washed with brine (50 cm³), dried over anhydrous magnesium sulfate, filtered and the solvent removed in vacuo. Purification by column chromatography using a graded solvent system (40-60 petrol: dichloromethane: 9:1 to 7:3) gives intermediate 72 (585 mg, 44%) as a pale cream solid. ¹H NMR (400 MHz, CDCl₃) 7.36 (2H, d, J 4.9), 7.14-7.24 (8H, m), 7.01 (2H, d, J 4.9), 6.76-6.87 (8H, m), 3.74-3.87 (8H, m), 1.63-1.77 (4H, m), 1.20-1.57 (32H, m), 0.81-0.96 (24H, m).

Intermediate 73

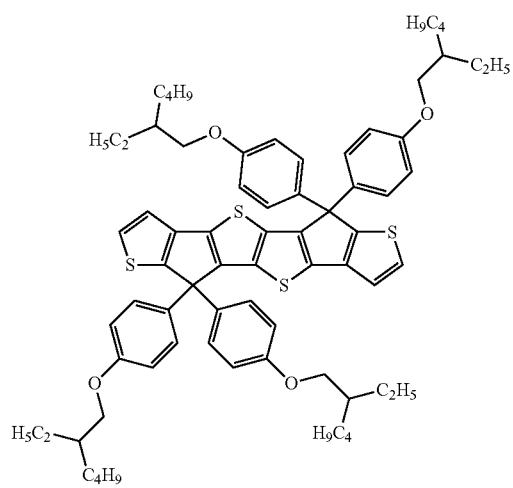

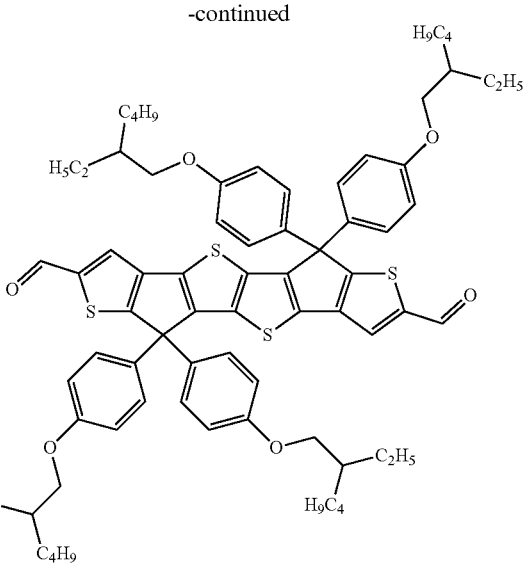

To a solution of N,N-dimethylformamide (0.22 cm³) in anhydrous chloroform (80 cm³) at 0° C. is added dropwise phosphorus(V) oxychloride (0.22 cm³, 2.40 mmol). After 15 minutes at 0° C., the reaction is stirred at 23° C. for 30 minutes. Intermediate 72 (550 mg, 0.480 mmol) is then added and the reaction heated at reflux for 48 hours. Saturated aqueous sodium acetate solution (50 cm³) is then added and the resulting mixture heated at 50° C. for 1 hour. The solution is cooled to 23° C. and the solvent removed in vacuo. The organics extracted with ether (3×80 cm³) and the combined organics washed with brine (30 cm³), dried over anhydrous magnesium sulfate, filtered and the solvent removed in vacuo. The crude is purified by column chromatography using a graded solvent system (40-60 petrol: dichloromethane; 1:1 to 1:4) to give intermediate 73 (480 mg, 83%) as pale yellow solid. ¹H NMR (400 MHz, CDCl₃) 9.72-9.88 (2H, m), 7.50-7.62 (2H, m), 7.01-7.14 (8H, m), 6.66-6.82 (8H, m), 3.62-3.84 (8H, m), 1.60 (4H, dq, J 12.1, 5.8), 1.09-1.46 (32H, m), 0.71-0.92 (24H, m).

Compound 29

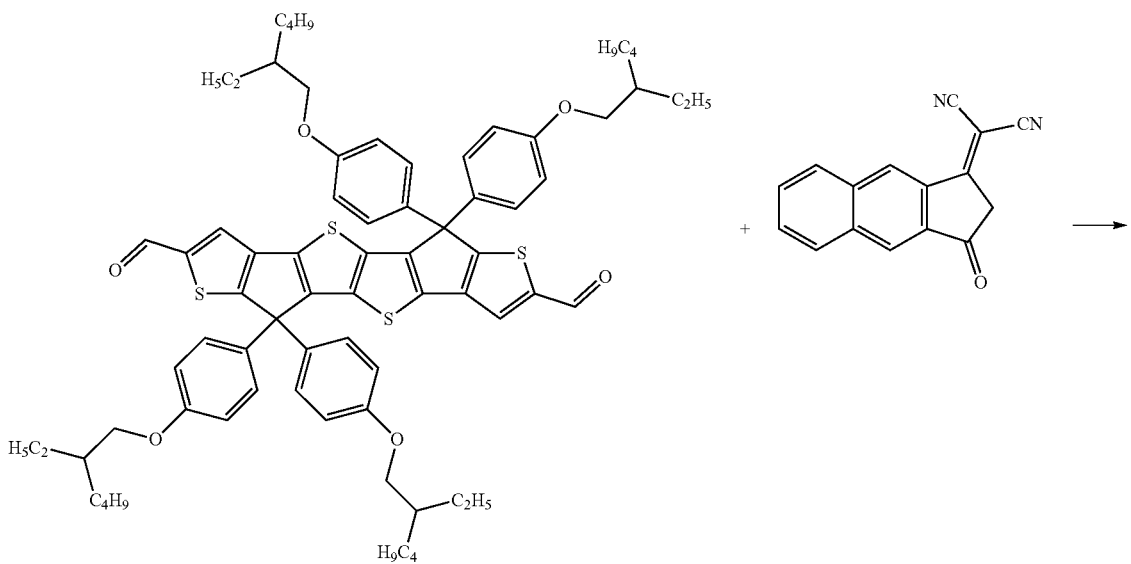

-continued

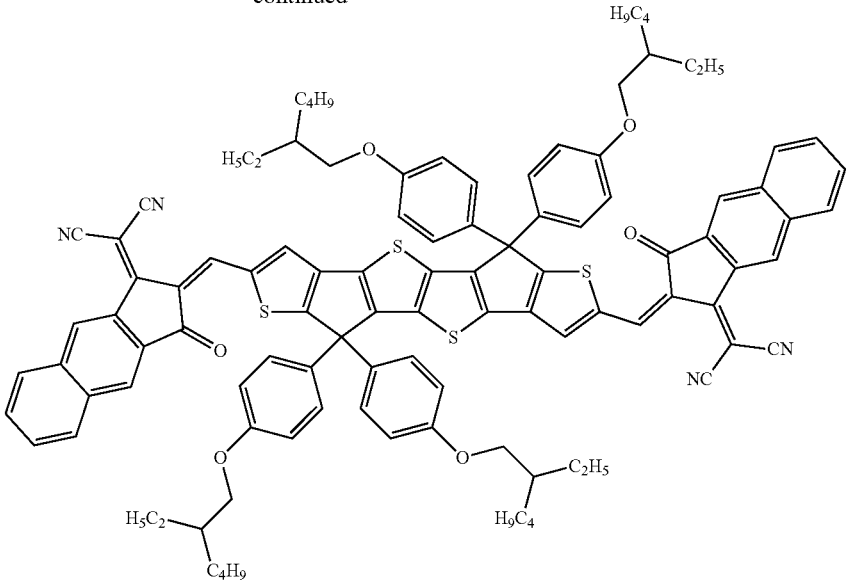

A degassed solution of intermediate 73 (150 mg, 0.13 mmol), pyridine (0.71 cm³), 2-(3-oxo-2,3-dihydro-cyclopenta[b]naphthalen-1-ylidene)-malononitrile (152 mg, 0.624 mmol) in anhydrous chloroform (10 cm³) is stirred for 17 hours. The reaction mixture is diluted with methanol (150 cm³) and stirred for 1 hour. The solid is collected by filtration and washed with acetonitrile (100 cm³). The crude is triturated in ether (100 cm³) and the solid collected by filtration to give compound 29 (205 mg, 99%) as a dark solid. ¹H NMR (400 MHz, CDCl₃) 9.11 (2H, s), 8.88 (2H, s), 8.24-8.37 (2H, m), 7.97 (4H, ddd, J 12.2, 6.0, 3.6), 7.72-7.81 (2H, m), 7.56-7.68 (4H, m), 7.11-7.23 (8H, m), 6.75-6.86 (8H, m), 3.67-3.81 (8H, m), 1.57-1.68 (4H, m), 1.11-1.45 (32H, m), 0.76-0.87 (24H, m).

Example 30

Intermediate 74

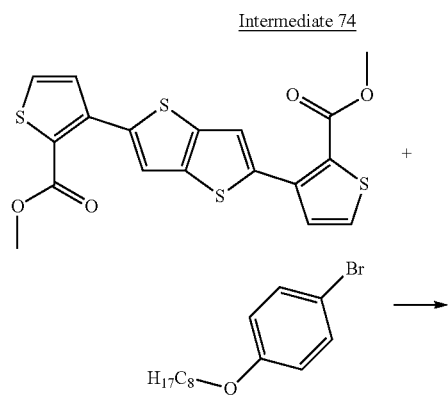

-continued

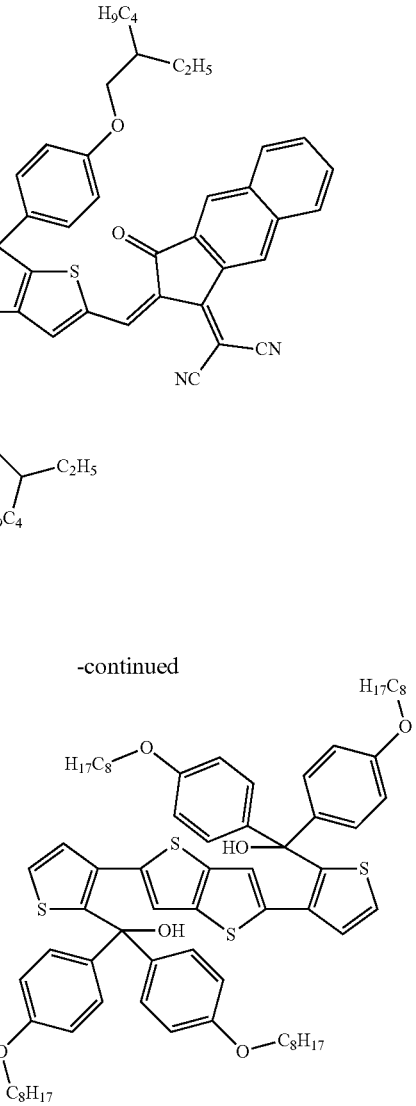

To a solution of 1-bromo-4-(octyloxy)benzene (6.06 g, 21.3 mmol) in anhydrous tetrahydrofuran (90 cm³) at −78° C. is added dropwise t-butyllithium (25.0 cm³, 42.5 mmol, 1.7 M in pentane) keeping the reaction temperature below −60° C. After 20 minutes stirring at −78° C. the reaction is allowed to warm to −40° C. over 10 minutes before re-cooling to −78° C. After stirring at −78° C. for 15 minutes, additional 1-bromo-4-octyloxybenzene (606 mg, 2.13 mmol) is added to the reaction mixture and the reaction stirred for a further 15 minutes before addition of intermediate 71 (1.79 g, 4.25 mmol). The reaction mixture is stirred at −78° C. for 25 minutes before removing the cooling and allowing the reaction to warm to 23° C. over 17 hours. Water (10 cm³) is then added before the reaction mixture is added to a separating funnel with ether (100 cm³) and additional water (100 cm³). The organic layer is then washed with water (100 cm³), brine (100 cm³), dried over anhydrous magnesium sulfate, filtered and the solvent removed in vacuo. The crude is purified by column chromatography using a graded solvent system (40-60 petrol:dichloromethane; 1:0 to 1:3) to give intermediate 74 (4.20 g, 84%) as a brown/green glassy oil. ¹H NMR (400 MHz, CDCl₃) 7.17-7.22 (8H, m), 7.14 (2H, d, J 5.2), 7.08 (2H, d, J 5.2), 6.77-6.83 (8H, m), 6.60 (2H, s), 3.95 (8H, t, J 6.6), 3.52 (2H, s), 1.78 (8H, p, J 6.7), 1.45 (8H, p, J 6.8), 1.23-1.39 (32H, m), 0.85-0.91 (12H, m).

Intermediate 75

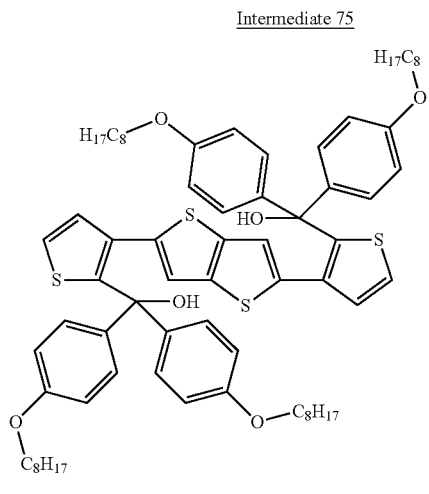

Intermediate 76

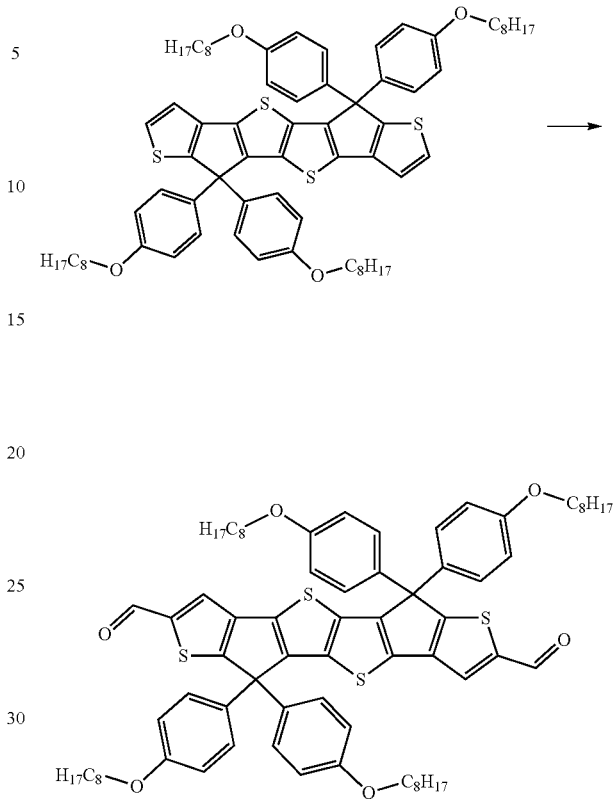

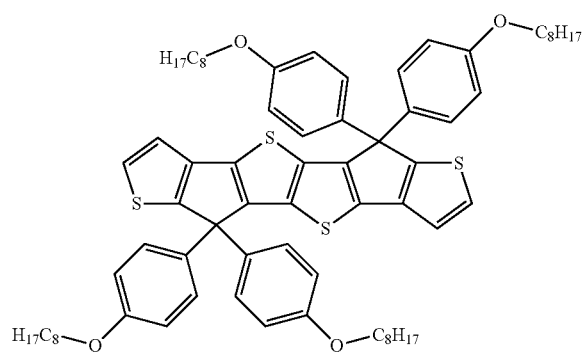

To a degassed solution of intermediate 74 (3.85 g, 3.26 mmol) in toluene (250 cm³) is added p-toluene sulfonic acid monohydrate (1.24 g, 6.51 mmol) and the mixture degassed for a further 10 minutes before stirring for 50 minutes and then heating at 50° C. for 16 hours. The reaction mixture is cooled to 23° C. and concentrated in vacuo. Water (100 cm³) and ether (100 cm³) are then added. The organic layer is washed with water (100 cm³), brine (100 cm³) and dried over anhydrous magnesium sulfate, filtered and the solvent removed in vacuo. The crude is purified by column chromatography using a graded solvent system (40-60 petrol:dichloromethane; 1:0 to 7:3) to give intermediate 75 (1.03 g, 28%) as a yellow/brown oil. ¹H NMR (400 MHz, CDCl₃) 7.34 (2H, d, J 5.0), 7.14-7.19 (8H, m), 6.98 (2H, d, J 5.0), 6.76-6.82 (8H, m), 3.89 (8H, t, J 6.5), 1.68-1.77 (8H, m), 1.36-1.45 (8H, m), 1.18-1.36 (32H, m), 0.84-0.92 (12H, m).

To a solution of N,N-dimethylformamide (0.41 cm³, 5.25 mmol) in anhydrous chloroform (30 cm³) at 0° C. is added dropwise phosphorous(V) oxychloride (0.41 cm³, 4.4 mmol). The mixture is then stirred for 10 minutes at 0° C. and at 23° C. for 30 minutes. A solution of intermediate 75 (1.00 g, 0.87 mmol) in chloroform (20 cm³) is then added to the reaction mixture which is then stirred at 23° C. for 35 minutes before heating at 65° C. for 66 hours. The reaction is then cooled to 23° C. before adding N,N-dimethylformamide (0.82 cm³, 10.5 mmol). After 5 minutes the reaction is cooled to 0° C. before adding phosphorous(V) oxychloride (0.82 cm³, 8.8 mmol). The reaction is stirred at 0° C. for 15 minutes before heating at reflux for 6 hours. The reaction is then cooled to 23° C. before adding N,N-dimethylformamide (0.82 cm³, 10.5 mmol). After 5 minutes the reaction is cooled to 0° C. before adding phosphorous(V) oxychloride (0.82 cm³, 8.8 mmol). The reaction is stirred at 0° C. for 10 minutes before heating at reflux for 19 hours. Saturated aqueous sodium acetate solution (20 cm³) is then added slowly. After a further 40 minutes at 75° C. the reaction is then cooled to 23° C. Water (100 cm³) and dichloromethane (50 cm³) are added. The organic layer is washed with water (100 cm³) and dried over anhydrous magnesium sulfate, filtered and the solvent removed in vacuo. The crude product is purified by column chromatography using a graded solvent system (40-60 petrol:dichloromethane; 1:0 to 3:7) to give intermediate 76 (763 mg, 73%) as a glassy yellow/brown solid. ¹H NMR (400 MHz, CDCl₃) 9.87 (2H, s), 7.63 (2H, s), 7.11-7.17 (8H, m), 6.78-6.84 (8H, m), 3.90 (8H, t, J 6.5), 1.74 (8H, p, J 6.6), 1.37-1.45 (8H, m), 1.22-1.36 (32H, m), 0.84-0.89 (12H, m).

Compound 30

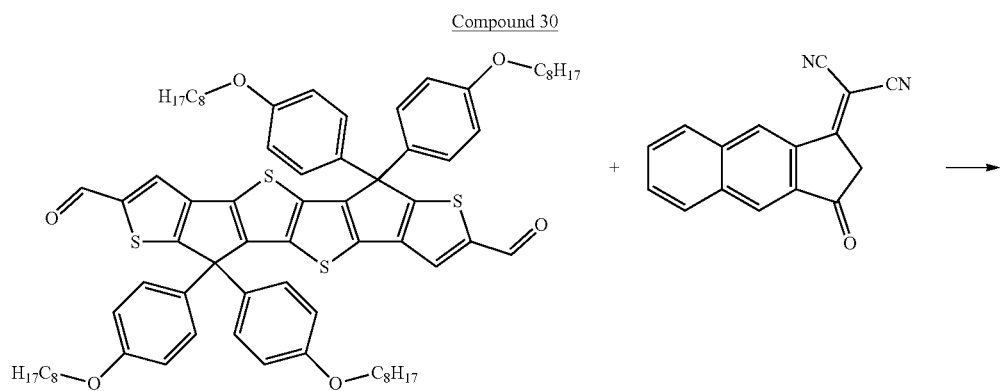

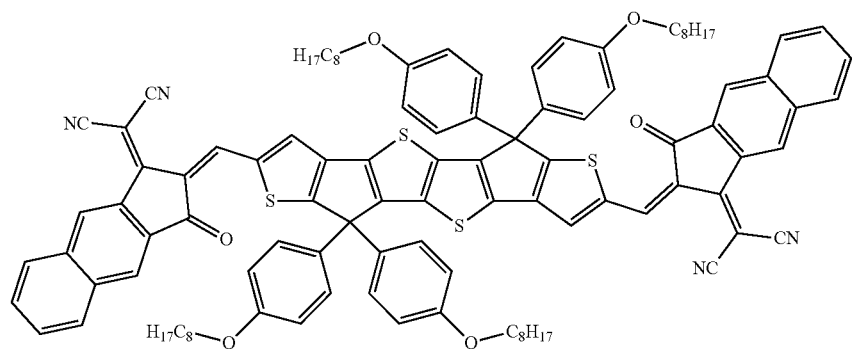

To a degassed solution of intermediate 76 (160 mg, 0.13 mmol), anhydrous chloroform (40 cm$^3$) and pyridine (0.75 cm$^3$) at 0° C. is added 2-(3-oxo-2,3-dihydro-cyclopenta[b] naphthalen-1-ylidene)-malononitrile (130 mg, 0.53 mmol). The reaction is stirred at 0° C. for 70 minutes, 23° C. for 85 minutes and at 40° C. for 110 minutes. The reaction mixture is then stirred at 23° C. for 10 minutes before the reaction mixture is poured into stirred methanol (150 cm$^3$). The solid is collected by filtration and washed with methanol (4×10 cm$^3$). The solid is then triturated in acetone (75 cm$^3$) and the collected solid washed with acetone (2×10 cm$^3$) and ether (3×10 cm$^3$). The solid is then triturated in boiling acetone (50 cm$^3$) and the collected solid washed with acetone (2×10 cm$^3$) to give compound 30 (89 mg, 40%) as a black solid. $^1$H NMR (400 MHz, CDCl$_3$) 9.19 (2H, s), 8.97 (2H, s), 8.37 (2H, s), 8.00-8.11 (4H, m), 7.84 (2H, m), 7.66-7.74 (4H, m), 7.18-7.25 (8H, m), 6.82-6.90 (8H, m), 3.92 (8H, t, J 6.5), 1.75 (8H, p, J 6.6), 1.37-1.47 (8H, m), 1.19-1.37 (32H, m), 0.81-0.91 (12H, m).

Example 31

Intermediate 77

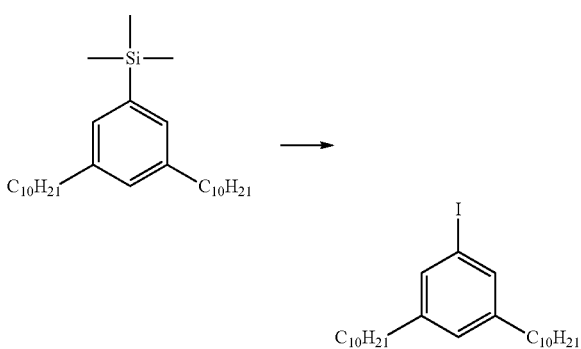

To a solution of 3,5-bis(decyl)phenyl]trimethylsilane (7.28 g, 16.9 mmol) in chloroform (10 cm$^3$) and methanol (10 cm³), in the dark, is added silver trifluoroacetate (7.84 g, 35.5 mmol). The mixture cooled to 0° C., iodine (8.58 g, 33.8 mmol) added and the mixture stirred for 90 minutes. The mixture is filtered through a plug of silica (40-60 petrol) and the organic phase washed with saturated aqueous sodium thiosulfate (100 cm³), water (100 cm³) and brine (100 cm³). The organics are dried over anhydrous magnesium sulfate, filtered and the solvent removed in vacuo to give intermediate 77 (6.98 g, 85%) as a white solid. ¹H NMR (400 MHz, CDCl₃) 7.27 (2H, s), 6.85 (1H, s), 2.43 (4H, t, J 7.8), 1.44-1.55 (4H, m), 1.13-1.29 (28H, m), 0.78-0.84 (6H, m).

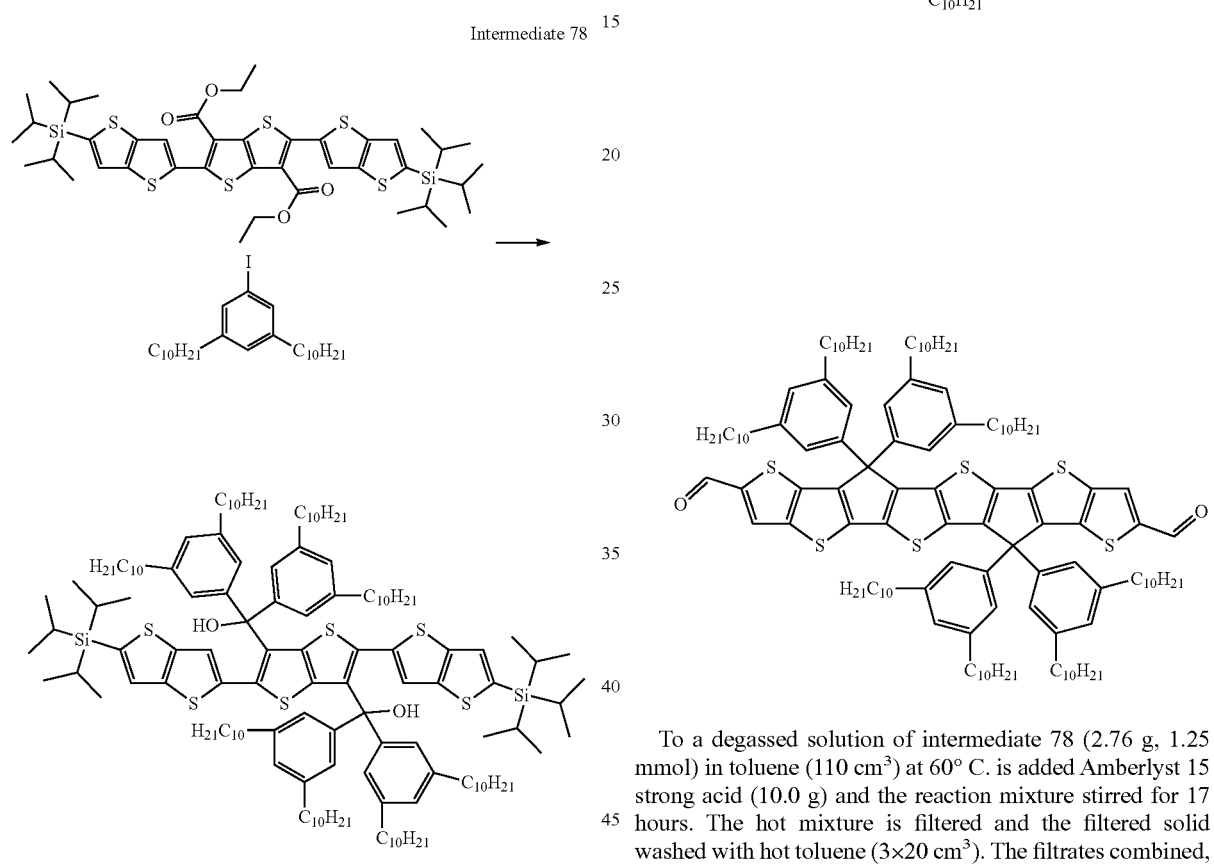

To a solution of intermediate 77 (4.99 g, 10.3 mmol) in anhydrous tetrahydrofuran (37.5 cm³) at −78° C. is added dropwise t-butyllithium (12.1 cm³, 20.6 mmol, 1.7 M in pentane) over 10 minutes. The reaction mixture is then stirred for 1 hour before the cooling is removed for 6 minutes and then the mixture cooled back to −78° C. Intermediate 14 (1.50 g, 1.71 mmol) is then added and the reaction mixture allowed to warm to 23° C. and stirred for 17 hours. Water (5 cm³) is added and the mixture stirred for a further 10 minutes. Ether (100 cm³) and water (50 cm³) are added and the organic layer washed with water (3×20 cm³), dried over anhydrous magnesium sulfate, filtered and the solvent removed in vacuo. The crude is purified by column chromatography using a graded solvent system (40-60 petrol:dichloromethane; 1:0 to 3:1) to give intermediate 78 (2.76 g, 73%) as a pale brown oil. ¹H NMR (400 MHz, CDCl₃) 7.17 (2H, s), 6.93 (8H, s), 6.88 (4H, s), 6.45 (2H, s), 3.39 (2H, s), 2.42-2.53 (16H, m), 1.48-1.61 (16H, m), 1.07-1.41 (118H, m), 0.83-0.94 (60H, m).

To a degassed solution of intermediate 78 (2.76 g, 1.25 mmol) in toluene (110 cm³) at 60° C. is added Amberlyst 15 strong acid (10.0 g) and the reaction mixture stirred for 17 hours. The hot mixture is filtered and the filtered solid washed with hot toluene (3×20 cm³). The filtrates combined, and the solvent removed in vacuo. The intermediate is then purified by column chromatography using a graded solvent system (40-60 petrol:dichloromethane; 1:0 to 17:3). The solid is then dissolved in chloroform (55.2 cm³) and N,N-dimethylformamide (1.46 g, 19.9 mmol) added. Phosphorus (V) oxychloride (2.86 g, 18.7 mmol) is then added slowly over 5 minutes and then the reaction mixture stirred for 30 minutes and heated at 55° C. for 17 hours. The reaction mixture is allowed to cool to 23° C. and aqueous potassium acetate (150 cm³, 3 M) is added and the mixture stirred for 1 hour. The organics are extracted with dichloromethane (2×200 cm³) and the combined organics washed with water (50 cm³), dried over anhydrous magnesium sulfate, filtered and the solvent removed in vacuo. The crude is purified by column chromatography using a graded solvent system (40-60 petrol:dichloromethane; 9:1 to 3:1) to give intermediate 79 (1.37 g, 57%) as a red oil. ¹H NMR (400 MHz, CDCl₃) 9.89 (2H, s), 7.93 (2H, s), 6.92 (4H, s), 6.80 (8H, s), 2.50 (16H, t, J 7.7), 1.52 (16H, q, J 7.2), 1.09-1.40 (112H, m), 0.87 (24H, t, J 6.8).

Compound 31

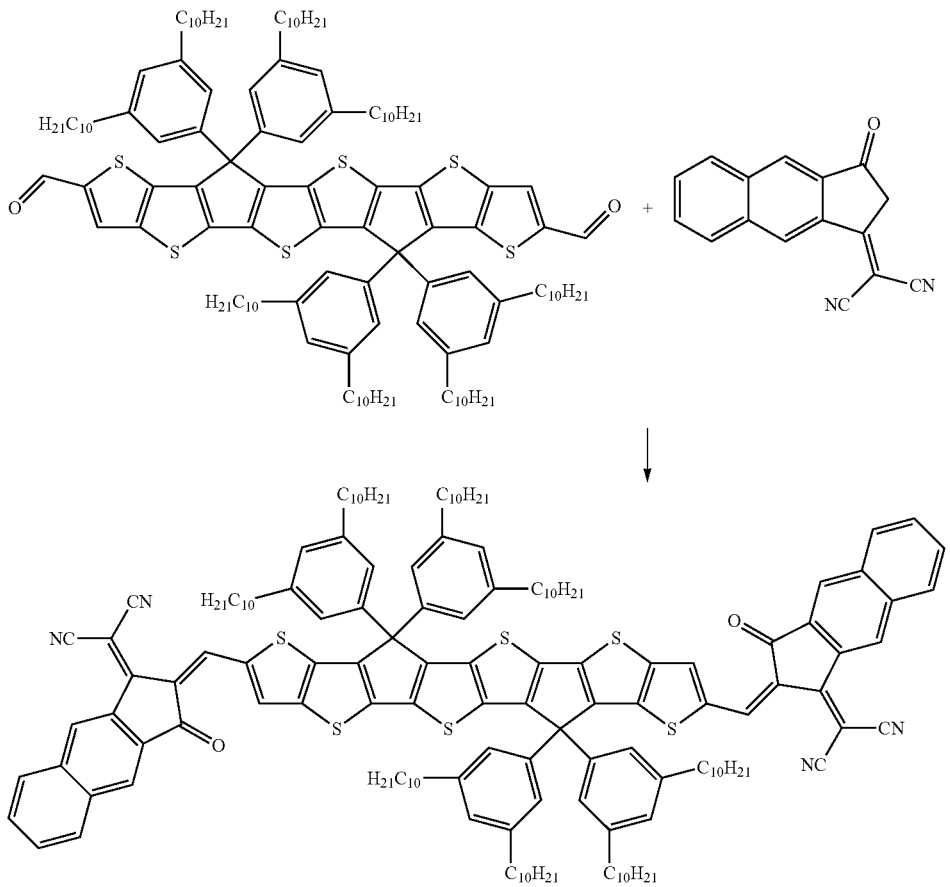

To a degassed mixture of intermediate 79 (100 mg, 0.05 mmol) and 2-(3-oxo-2,3-dihydro-cyclopenta[b]naphthalen-1-ylidene)-malononitrile (51 mg, 0.21 mmol) in chloroform (2.5 cm$^3$) is added pyridine (0.29 cm$^3$, 3.6 mmol) and the mixxture degassed for a further 10 minutes. The solution is heated at 40° C. for 6 hours and then cooled to 23° C. before methanol (30 cm$^3$) is added. The solid is collected by filtration and washed with methanol (20 cm$^3$). The crude is purified by column chromatography using a graded solvent system (40-60 petrol:dichloromethane; 3:2 to 1:1) to give compound 31 (51 mg, 41%). $^1$H NMR (400 MHz, CDCl$_3$) 9.20 (2H, s), 9.00 (2H, s), 8.33 (2H, s), 7.98-8.22 (6H, m), 7.63-7.80 (4H, m), 6.96 (4H, s), 6.90 (8H, s), 2.55 (16H, t, J 7.7), 1.51-1.63 (16H, m), 0.99-1.41 (112H, m), 0.82 (24H, t, J 7.0).

Example 32

To a solution of bromo(octyl)magnesium (183 cm$^3$, 365 mmol, 2.0 M in tetrahydrofuran) in anhydrous tetrahydrofuran (450 cm$^3$) is added (3,5-dibromophenyl)trimethylsilane (45.0 g, 146 mmol) and [1,1'-bis(diphenylphosphino)ferrocene]dichloropalladium (II) (1.60 g, 2.19 mmol) and the reaction mixture heated at reflux for 17 hours. The reaction mixture is then cooled to 0° C., water (250 cm$^3$) added and the mixture stirred for 1 hour. The organics are extracted with dichloromethane (2×250 cm$^3$). The combined organics are washed with brine (100 cm$^3$), dried over anhydrous magnesium sulfate, filtered and the solvent removed in vacuo. The crude is purified by column chromatography (heptane) to give intermediate 80 (22.2 g, 41%) as a colourless oil. $^1$H NMR (400 MHz, CDCl$_3$) 7.15 (2H, s), 7.00 (1H, s), 2.53-2.65 (4H, m), 1.56-1.70 (4H, m), 1.20-1.43 (16H, m), 0.82-0.96 (6H, m), 0.27 (9H, s).

Intermediate 80

Intermediate 81

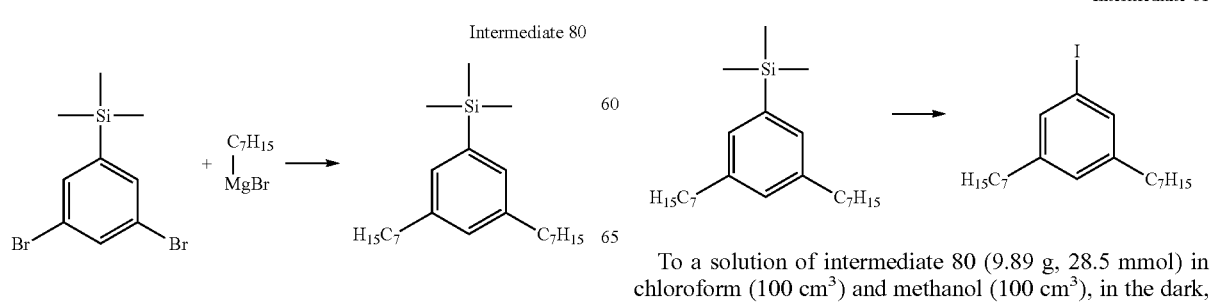

To a solution of intermediate 80 (9.89 g, 28.5 mmol) in chloroform (100 cm$^3$) and methanol (100 cm$^3$), in the dark, is added silver(I) trifluoroacetate (13.2 g, 59.9 mmol) and the mixture cooled to 0° C. Iodine (14.5 g, 57.0 mmol) is added and the mixture stirred for 1.5 hours. The mixture is filtered through a silica plug (dichloromethane) and the filtrate washed with saturated aqueous sodium bisulfite (200 cm³), water (200 cm³) and brine (200 cm³). The solution is then dried over anhydrous magnesium sulfate, filtered and the solvent removed in vacuo to give intermediate 81 (9.51 g, 83%). ¹H NMR (400 MHz, CD₂Cl₂) 7.27 (2H, s), 6.88 (1H, s), 2.43 (4H, t, J 7.5), 1.43-1.53 (4H, m), 1.15-1.28 (16H, m), 0.76-0.83 (6H, m).

Intermediate 82

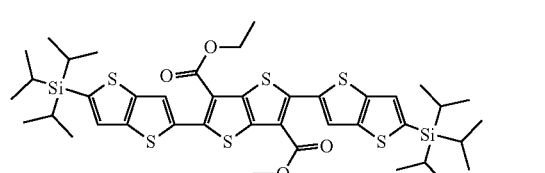

+

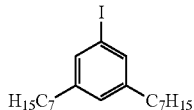

To a solution of intermediate 81 (4.13 g, 10.3 mmol) in anhydrous tetrahydrofuran (38 cm³) at −78° C. is added t-butyllithium (12.1 cm³, 20.6 mmol, 1.7 M in pentane) over 10 minutes. The reaction mixture is then stirred for 1 hour, the cooling bath removed for 6 minutes and then the mixture cooled back to −78° C. Intermediate 14 (1.50 g, 1.72 mmol) is added, the reaction mixture allowed to warm to 23° C. and stirred for 17 hours. Water (5 cm³) is slowly added and the mixture stirred for 10 minutes. Ether (100 cm³) is then added, the mixture washed with water (3×50 cm³) and then dried over anhydrous magnesium sulfate, filtered and the solvent removed in vacuo. The crude is then purified by column chromatography using a graded solvent system (40-60 petrol:dichloromethane; 1:0 to 17:3) to give intermediate 82 (1.83 g, 57%).

¹H NMR (400 MHz, CDCl₃) 7.17 (2H, s), 6.92-6.96 (8H, m), 6.87-6.90 (4H, m), 6.46 (2H, s), 3.42 (2H, s), 2.44-2.54 (16H, m), 1.49-1.61 (16H, m), 1.20-1.36 (70H, m), 1.12 (36H, d, J 7.4), 0.83-0.93 (24H, m).

Intermediate 83

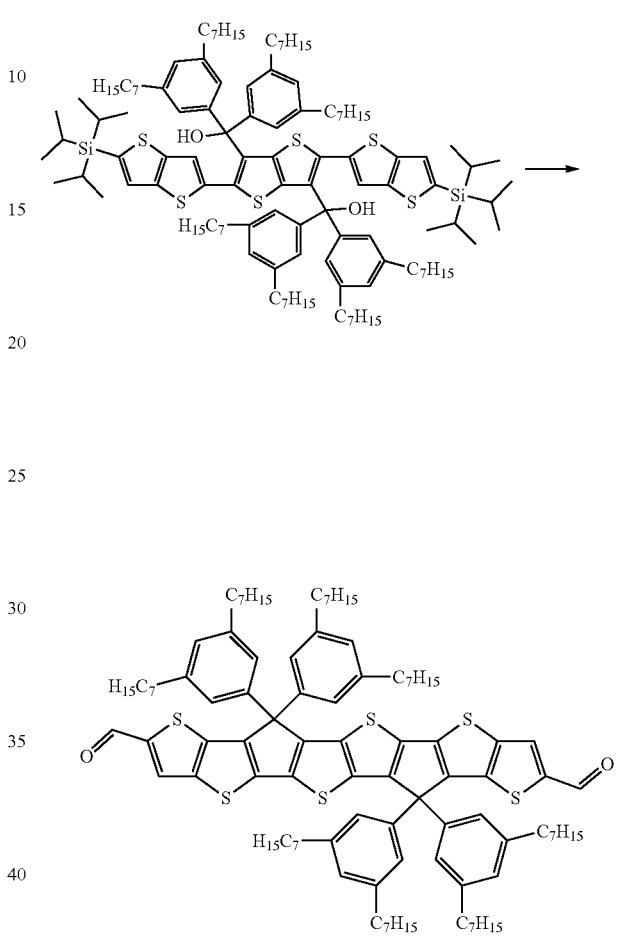

To a degassed solution of intermediate 82 (1.83 g, 0.975 mmol) in toluene (73 cm³) at 60° C. is added Amberlyst 15 strong acid (6.0 g) and the reaction mixture stirred for 17 hours. The hot reaction mixture is filtered and the solid washed with hot toluene (3×20 cm³). The filtrate is then concentrated in vacuo. The crude is purified by column chromatography using a graded solvent system (40-60 petrol:dichloromethane; 19:1 to 3:1). The purified material is then taken up in chloroform (37 cm³) and N,N-dimethylformamide (1.14 g, 15.6 mmol) added followed by phosphorus (V) oxychloride (2.24 g, 14.6 mmol) over 5 minutes. The reaction mixture is then stirred for 30 minutes and then heated at 55° C. for 17 hours. The mixture is allowed to cool to 23° C., aqueous potassium acetate (150 cm³, 3 M) added and the mixture stirred for 1 hour. The organics are extracted with dichloromethane (20 cm³) and the organic layer washed with water (50 cm³), dried over anhydrous magnesium sulfate, filtered and the solvent removed in vacuo. The crude is purified by column chromatography using a graded solvent system (40-60 petrol:dichloromethane; 9:1 to 7:3) to give intermediate 83 (890 mg, 58) as an orange/red solid. ¹H NMR (400 MHz, CDCl₃) 9.89 (2H, s), 7.93 (2H, s), 6.90-6.94 (4H, m), 6.79-6.82 (8H, m), 2.50 (16H, t, J 7.7), 1.47-1.59 (16H, m), 1.16-1.33 (64H, m), 0.83-0.92 (24H, m).

Compound 32

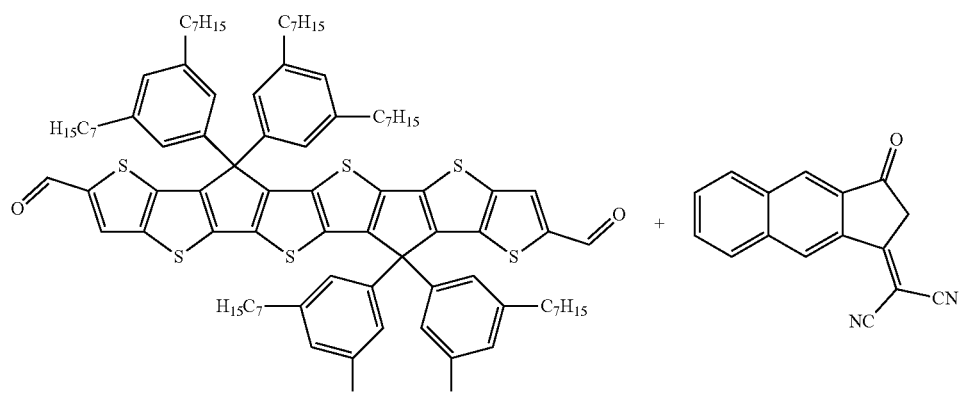

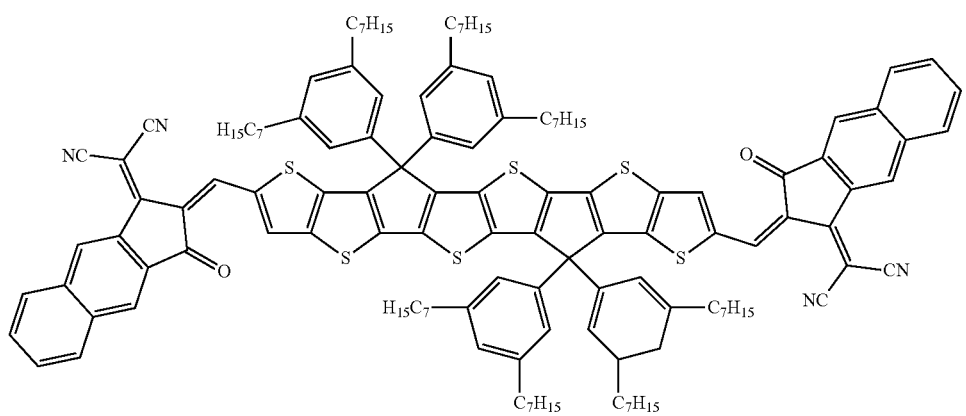

To a degassed mixture of intermediate 83 (100 mg, 0.06 mmol) and 2-(3-oxo-2,3-dihydro-cyclopenta[b]naphthalen-1-ylidene)-malononitrile (62 mg, 0.25 mmol) in chloroform (3 cm³) is added pyridine (0.36 cm³, 4.4 mmol) and the solution further degassed. The reaction mixture is stirred for 6 hours and then heated at 50° C. for a further 1 hour. The reaction is cooled to 23° C., methanol (30 cm³) added and the solid is collected by filtration which is then washed with methanol (20 cm³). The crude is purified by column chromatography using a graded solvent system (40-60 petrol: dichloromethane; 1:1 to 2:3) to give compound 32 (74 mg, 57%) as a dark solid. $^1$H NMR (400 MHz, CDCl$_3$) 9.19 (2H, s), 8.99 (2H, s), 8.33 (2H, s), 8.16 (2H, s), 8.01-8.14 (4H, m), 7.67-7.76 (4H, m), 6.97 (4H, d, J 1.7), 6.90 (8H, d, J 1.5), 2.56 (16H, t, J 7.7), 1.48-1.65 (16H, m), 1.12-1.34 (64H, m), 0.74-0.82 (24H, m).

Example 33

Intermediate 84

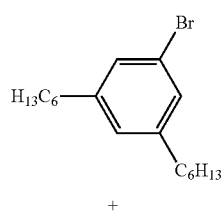

+

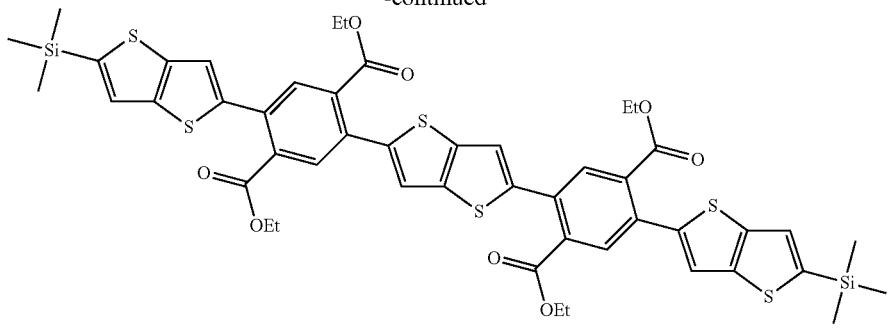

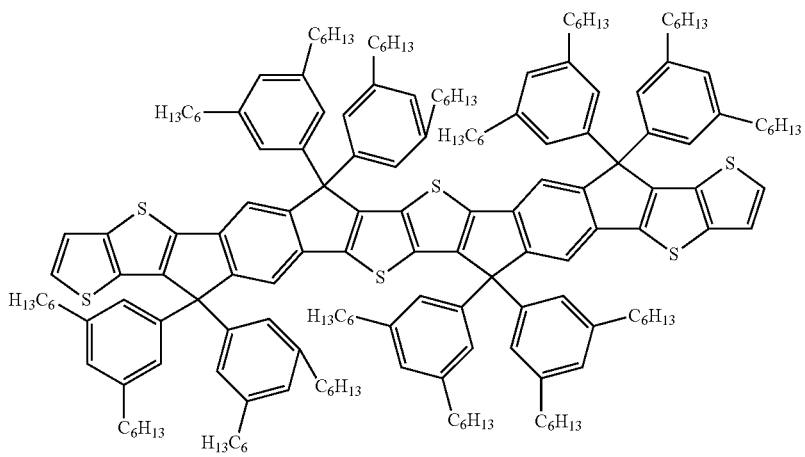

To a solution of 1-bromo-3,5-dihexylbenzene (5.06 g, 14.9 mmol) in anhydrous tetrahydrofuran (50 cm³) at −78° C. is added t-butyllithium (8.8 cm³, 15 mmol, 1.7 M in pentane) over 20 minutes. The solution is then stirred at −78° C. for 2 hours. 1,1',4,4'-Tetraethyl ester-2,2'-thieno[3,2-b] thiophene-2,5-diylbis[5-[5-(trimethylsilyl)thieno[3,2-b]thien-2-yl]-1,4-benzenedicarboxylic acid (1.50 g, 1.49 mmol) is added and the reaction mixture stirred for 17 hours in the cooling bath allowing the temperature to slowly rise to 23° C. The solution is then heated at 50° C. for 1 hour before cooling to 23° C. Water (10 cm³) is added and the mixture stirred for 5 minutes. The volatiles are removed in vacuo and the residue extracted with ether (2×25 cm³). The combined organics are dried over anhydrous magnesium sulfate, filtered and the solvent removed in vacuo. The crude is purified by column chromatography using a graded solvent system (40-60 petrol:dichloromethane; 1:0 to 1:1). The purified material is taken up in anhydrous dichloromethane (50 cm³) and a solution of p-toluenesulfonic acid monohydrate (100 mg, 0.526 mmol) in acetic acid (2 cm³) is added. The solution is stirred for 1 hour and the volatiles removed in vacuo. The residue is triturated in methanol, the solid collected by filtration and washed with methanol (100 cm³). The solid is purified by column chromatography using a graded solvent system (40-60 petrol:dichloromethane; 19:1 to 9:1) to give intermediate 84 (1.86 g, 48%) as a pale orange solid. $^1$H NMR (400 MHz, CD$_2$Cl$_2$) 7.38 (2H, s), 7.30 (2H, s), 7.17-7.22 (4H, m), 6.77-6.82 (16H, m), 6.73-6.76 (8H, m), 2.29-2.43 (32H, m), 1.33-1.50 (32H, m), 1.03-1.23 (96H, m), 0.67-0.77 (24H, m), 0.58-0.67 (24H, m).

Intermediate 85

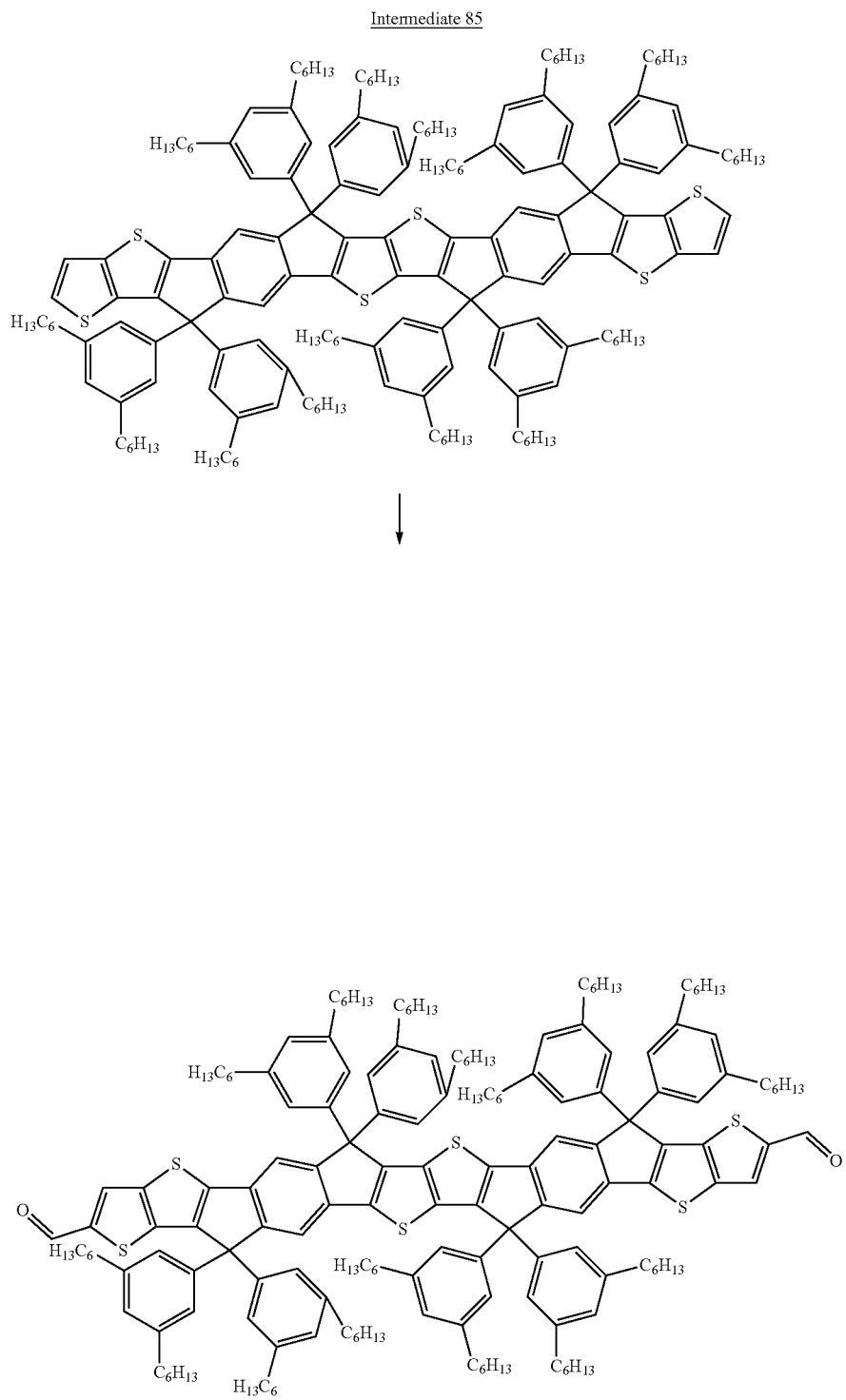

To a solution of intermediate 84 (1.60 g, 0.622 mmol) and anhydrous N,N-dimethylformamide (0.5 cm³) in anhydrous chloroform (50 cm³) at 0° C. is added phosphorus (V) oxychloride (0.60 cm³, 6.4 mmol). The mixture is stirred at 0° C. for 30 minutes and then at 23° C. for 1 hour and finally at 60° C. for 24 hours. The reaction mixture allowed to cool to 23° C. and saturated aqueous sodium acetate solution (20 cm³) added and the mixture stirred for 30 minutes. The mixture is then concentrated in vacuo and the solid collected by filtration. The solid is then washed with water (50 cm³) and methanol (50 cm³) to give intermediate 85 (1.60 g, 98%) as a red/orange solid. $^1$H NMR (400 MHz, CDCl$_3$) 9.87 (2H, s), 7.92 (2H, s), 7.52 (2H, s), 7.39 (2H, s), 6.86-6.92 (16H, m), 6.78-6.82 (8H, m), 2.48 (32H, dt, J 10.5, 7.6), 1.45-1.63 (32H, m), 1.13-1.33 (96H, m), 0.77-0.88 (24H, m), 0.69-0.77 (24H, m).

Compound 33

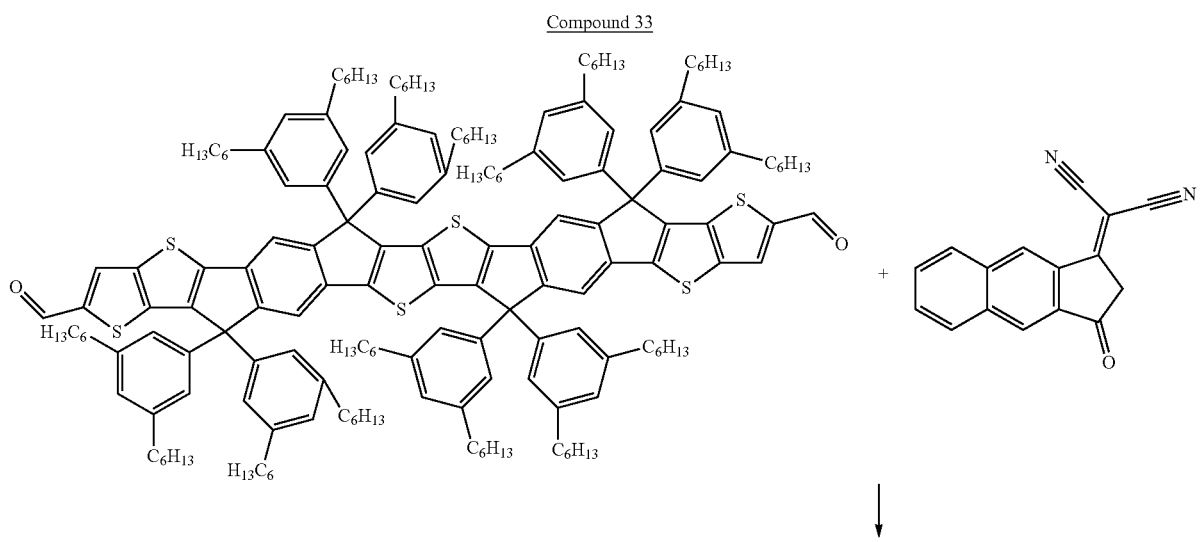

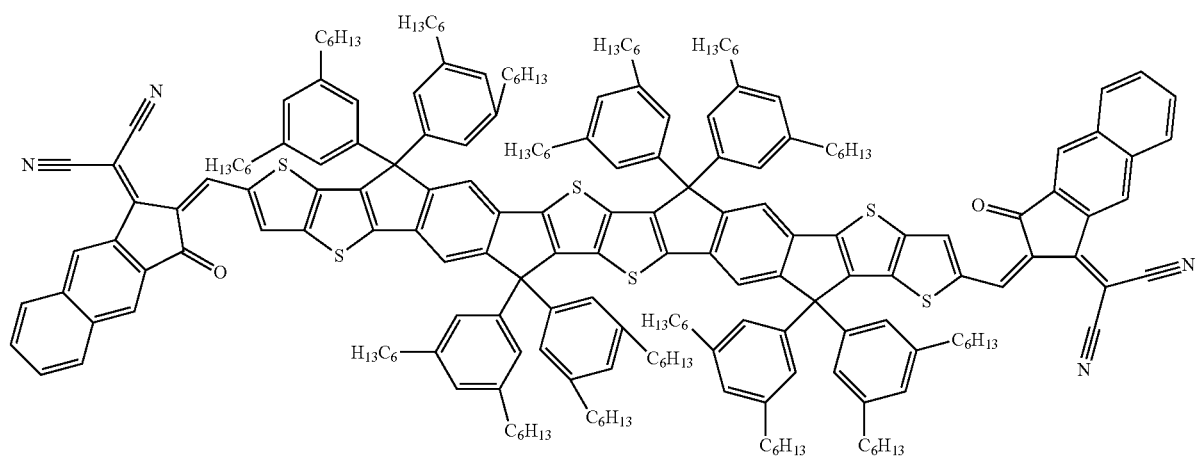

To a solution of intermediate 85 (200 mg, 0.076 mmol) in chloroform (10 cm³) and ethanol (0.50 cm³) is added pyridine (0.1 cm³, 1 mmol) and 2-{3-oxo-1H,2H,3H-cyclopenta[b]naphthalen-1-ylidene}propanedinitrile (56 mg, 0.23 mmol). The reaction mixture is then stirred for 12 hours and the volatiles removed in vacuo. The residue is triturated in methanol, the solid collected by filtration and washed with methanol until the filtrate runs colourless. The crude is purified by column chromatography using a graded solvent system (40-60 petrol:dichloromethane; 7:3 to 1:1) to give compound 33 (209 mg, 89%) as a dark green solid. $^1$H NMR (400 MHz, CDCl$_3$) 9.19 (2H, s), 8.97 (2H, s), 8.33 (2H, s), 8.14-8.23 (2H, m), 8.07-8.13 (2H, m), 7.99-8.06 (2H, m), 7.68-7.74 (4H, m), 7.54-7.60 (2H, m), 7.36-7.47 (2H, m), 6.85-6.96 (24H, m), 2.45-2.56 (32H, m), 1.48-1.61 (32H, m), 1.14-1.34 (96H, m), 0.69-0.80 (48H, m).

Example 34

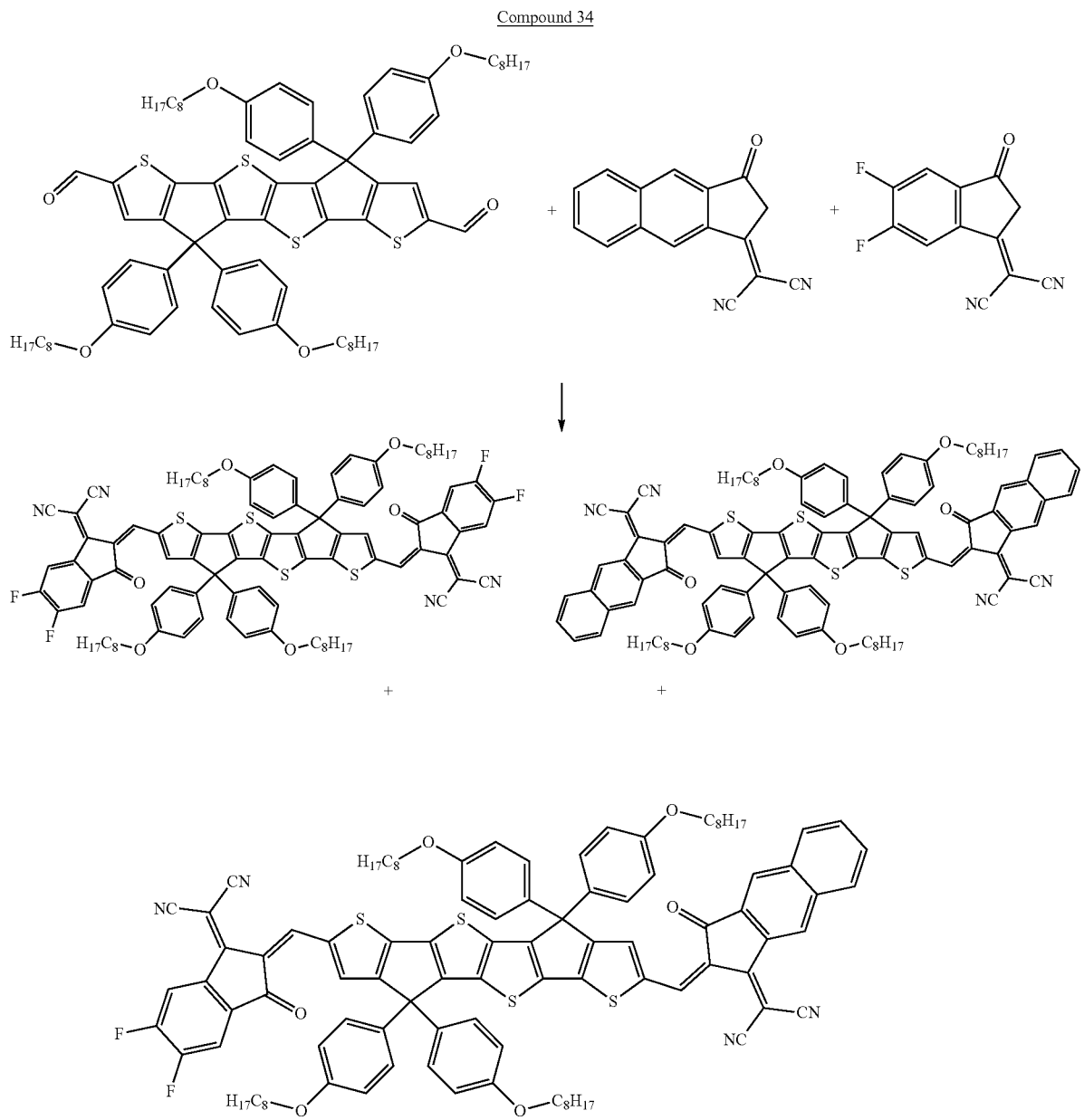

Compound 34

To a degassed solution of intermediate 8 (100 mg, 0.08 mmol), 2-{3-oxo-1H,2H,3H-cyclopenta[b]naphthalen-1-ylidene}propanedinitrile (41 mg, 0.17 mmol) and 2-(5,6-difluoro-3-oxo-indan-1-ylidene)-malononitrile (38 mg, 0.17 mmol) in chloroform (2.5 cm$^3$) is added pyridine (0.47 cm$^3$, 5.8 mmol) and the mixture degassed for a further 20 minutes. The solution is stirred for 6 hours before addition of methanol (35 cm$^3$). The solid is collected by filtration and washed with methanol (2 cm$^3$). The crude is purified by column chromatography using a graded solvent system (40-60 petrol:dichloromethane; 3:2 to 1:1) to give compound 34 (56 mg, 41%) as a mixture of 3 compounds. $^1$H NMR (400 MHz, CDCl$_3$) 9.20 (1H, s), 8.96 (1H, s), 8.86 (1H, s), 8.52-8.59 (1H, m), 8.38 (1H, s), 8.04-8.12 (2H, m), 6.65-7.77 (5H, m), 7.12-7.22 (8H, m), 6.82-6.92 (8H, m), 3.91-3.98 (8H, m), 1.73-1.83 (8H, m), 1.40-1.50 (8H, m), 1.21-1.40 (32H, m), 0.83-0.93 (12H, m).

Example 35

Intermediate 86

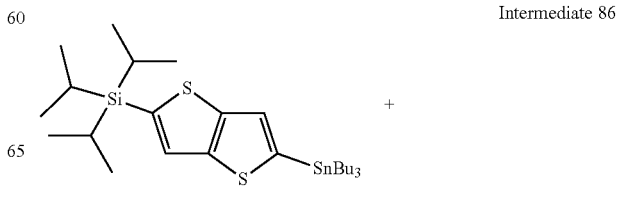

+

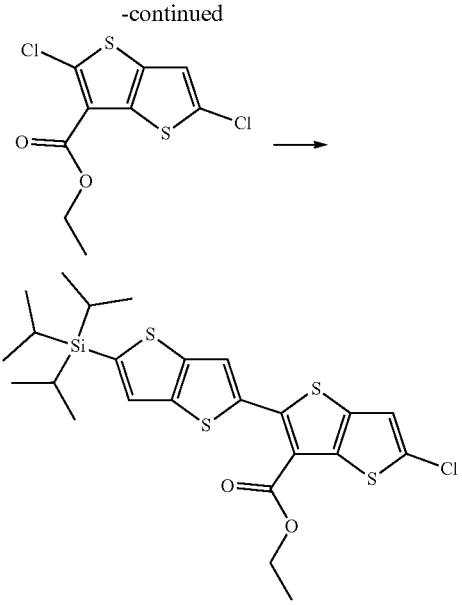

To a degassed solution of ethyl 2,5-dichlorothieno[3,2-b]thiophene-3-carboxylate (25.0 g, 88.9 mmol) in anhydrous toluene (650 cm³) at 110° C. is added tris(dibenzylideneacetone)dipalladium (0) (0.81 g, 0.89 mmol), dicyclohexyl-(2,4,6-triisoprpopyl-biphenyl-2-yl-phosphane (0.85 g, 1.8 mmol) and a solution of tris(propan-2-yl)[5-(tributylstannyl)thieno[3,2-b]thiophen-2-yl]silane (41.3 g, 59.2 mmol) in anhydrous toluene (50 cm³). The reaction mixture is stirred for 2 hours at 120° C. before allowing it to cool to 23° C. Water (750 cm³) is added and the organic phase is separated, washed with brine (100 cm³), dried over anhydrous magnesium sulfate and filtered off. Solvent is then removed in vacuo and the residue passed through a silica plug (heptane:dichloromethane; 1:5) to give intermediate 86 (28 g, 87%) as a yellow solid. ¹H NMR (400 MHz, CDCl₃) 7.76 (1H, s), 7.36 (1H, s), 7.12 (1H, s), 4.38-4.50 (2H, m), 1.34-1.45 (3H, m), 1.10-1.22 (21, H).

Intermediate 87

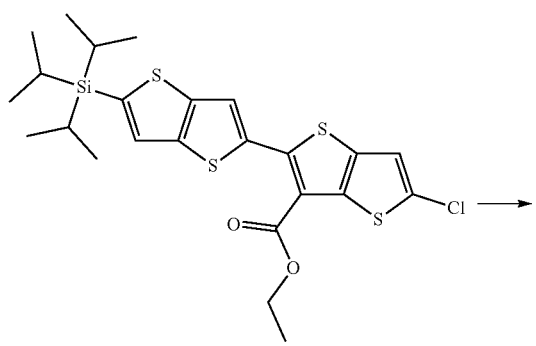

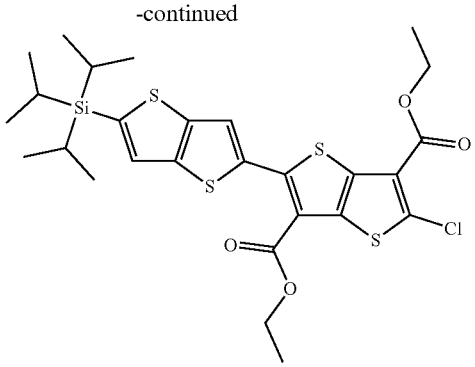

To a solution of intermediate 86 (51.2 g, 94.6 mmol) in anhydrous tetrahydrofuran (512 cm³) at −8° C. is added tetramethylpiperidinylmagnesium chloride lithium chloride complex (142 cm³, 142 mmol, 1.0 M in tetrahydrofuran/toluene) dropwise over 50 minutes. The reaction mixture is stirred for 1 hour and then ethyl chloroformate (13.6 cm³, 142 mmol) is added dropwise over 10 minutes. The reaction mixture is left stirring for 16 hours, warming up slowly to 23° C. Water (250 cm³) is added followed by dichloromethane (250 cm³). The aqueous layer is extracted with dichloromethane (2×250 cm³) and then the combined organic layer is washed with brine (100 cm³), dried over anhydrous magnesium sulfate and filtered off. Removal of the solvent in vacuo followed by repeated trituration in heptane gives intermediate 87 (41.8 g, 72%) as an orange solid. ¹H NMR (400 MHz, CDCl₃) 7.80 (1H, s), 7.36 (1H, s), 4.32-4.52 (4H, m), 1.34-1.50 (6H, m), 1.10-1.22 (21, H).

Intermediate 88

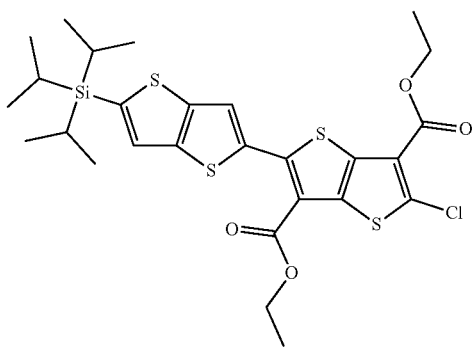

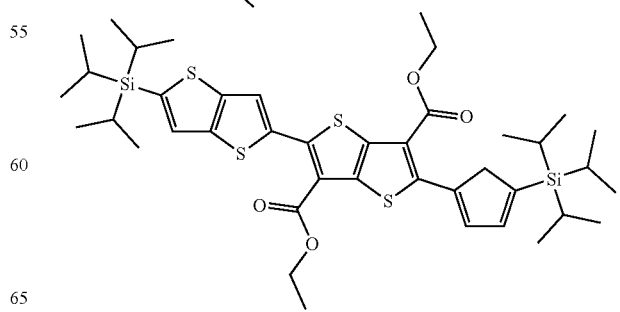

To intermediate 87 (48.0 g, 78.3 mmol) and toluene (480 cm³) is added tris(propan-2-yl)[5-(tributylstannyl)thiophen-2-yl]silane (54.4 g, 82.2 mmol). The mixture is degassed for 1 hour before it is heated to 105° C. Then, tris (dibenzylideneacetone)dipalladium (0) (1.79 g, 1.96 mmol) and dicyclohexyl-(2', 4',6'-triisopropylbiphenyl-2yl)-phosphane (1.87 g, 3.91 mmol) are added and the reaction mixture heated at 120° C. for 2 hours. After cooling down to 23° C., water (500 cm³) is added and the aqueous layer is extracted with dichloromethane (3×250 cm³). The combined organic layer is washed with brine (100 cm³), dried over anhydrous magnesium sulfate and filtered off. The removal of the solvent in vacuo followed by column chromatography (heptane:dichloromethane; 7:3) and trituration (heptane) gives intermediate 88 (41.5 g, 65%) as an orange solid. ¹H NMR (400 MHz, CDCl₃) 7.82 (1H, s), 7.68-7.72 (1H, d, J 3.5), 7.38 (1H, s), 7.25-7.29 (1H, m), 4.35-4.48 (4H, m), 1.34-1.50 (12H, m), 1.10-1.22 (36H, m).

rated, and the aqueous layer extracted with ether (2×100 cm³). The combined organics washed with water (2×50 cm³), dried over anhydrous magnesium sulfate, filtered and the solvent removed in vacuo. The crude is purified by column chromatography (40-60 petrol) to give intermediate 89 (7.2 g, 86%) as a pale cream oil. ¹H NMR (400 MHz, CDCl₃) 7.19-7.25 (8H, m), 7.17 (1H, s), 7.06-7.12 (8H, m), 6.90 (1H, d, J 3.5), 6.52-6.56 (2H, m), 3.54 (1H, s), 3.48 (1H, s), 2.47-2.60 (8H, m), 1.53-1.69 (4H, m), 0.99-1.42 (108H, m), 0.80-0.94 (24H, m).

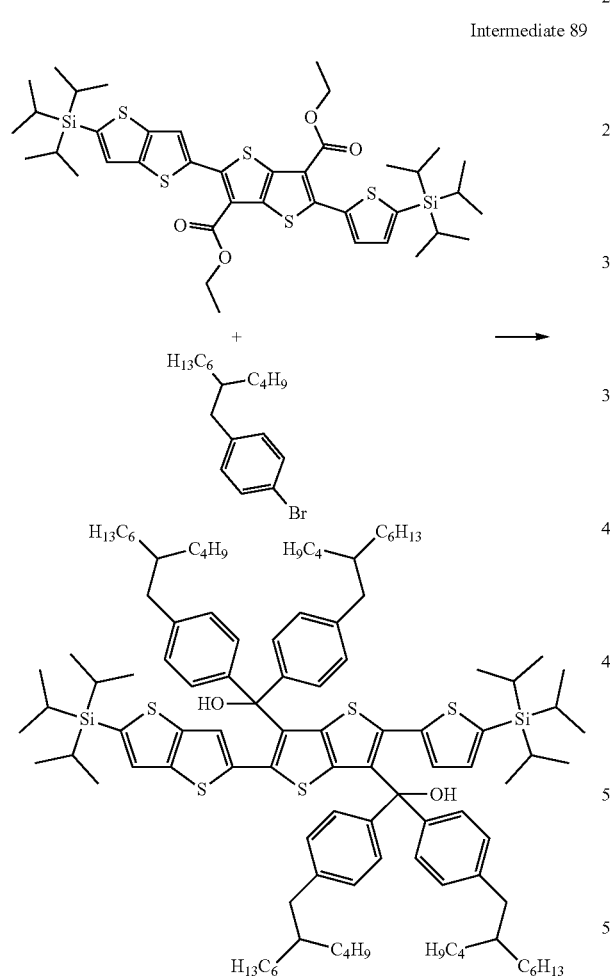

Intermediate 89

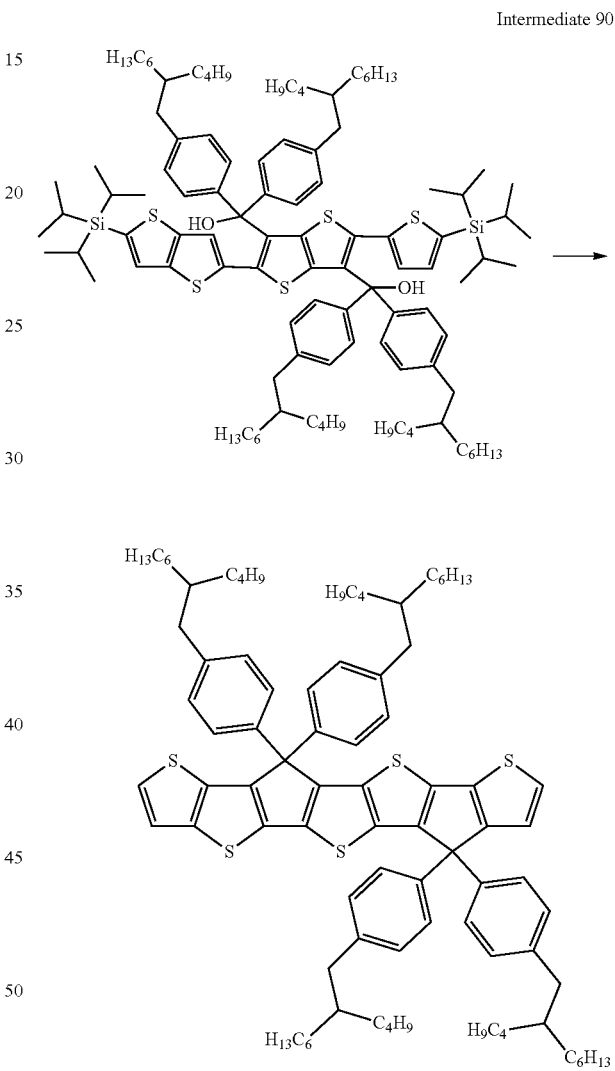

Intermediate 90

To a solution of 1-bromo-4-(2-butyloctyl)benzene (7.97 g, 0.024 mol) in anhydrous tetrahydrofuran (100 cm³) at −78° C. is added dropwise t-butyllithium (29 cm³, 0.049 mol, 1.7 M in pentane) over 70 minutes. The reaction mixture is then stirred for 2 hours. Intermediate 88 (4.00 g, 4.90 mmol) is then added and the reaction mixture allowed to warm to 23° C. and stirred for 17 hours. Water (100 cm³) is added and the mixture stirred for a further 1 hour. Ether (100 cm³) is added to the mixture, the organic layer sepa- To a solution of 4-methylbenzene-1-sulfonic acid hydrate (4.27 g, 22.4 mmol) in dichloromethane (250 cm³) at 0° C. is added a solution of intermediate 89 (6.40 g, 3.74 mmol) in dichloromethane (50 cm³). The reaction mixture is allowed to warm to 23° C. and stirred for 17 hours. The solvent is removed in vacuo and the residue passed through a celite plug (pentane). The crude is purified by column chromatography (40-60 petrol) to give intermediate 90 (1.8 g, 35%) as a red oil. ¹H NMR (400 MHz, CDCl₃) 7.19 (1H, d, 5.3), 7.15 (1H, d, 5.3), 7.09 (1H, d, 4.9), 7.04-7.08 (8H, m), 7.01 (1H, d, 4.9), 6.94-7.00 (8H, m), 2.35-2.43 (8H, m), 1.42-1.55 (4H, m), 1.06-1.28 (64H, m), 0.70-0.85 (24H, m).

Intermediate 91

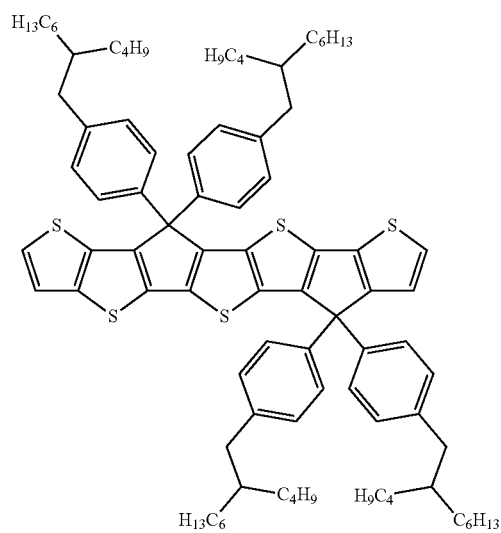

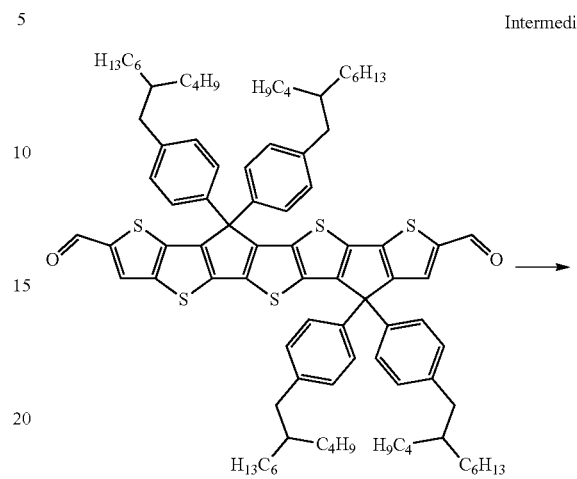

Intermediate 92

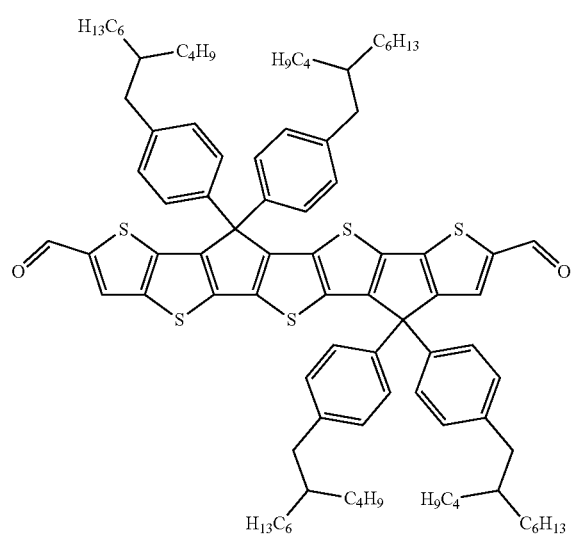

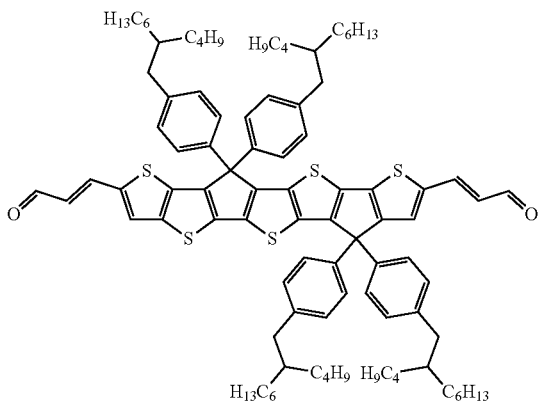

To a mixture of N,N-dimethylformamide (0.6 cm³) and chloroform (100 cm³) at 0° C. is added phosphor(V) oxychloride (1.01 g, 6.61 mmol). The reaction mixture is allowed to warm to 23° C. and stirred for 1 hour before cooling to 0° C. Intermediate 90 (1.80 g, 1.32 mmol) is added, the reaction mixture allowed to warm to 23° C. and stirred for 72 hours. The reaction mixture is poured onto saturated aqueous sodium acetate (100 cm³) and stirred for 30 minutes before heating to 50° C. and stirring for an additional 30 minutes. The aqueous layer is extracted with dichloromethane (100 cm³). The organic layer is washed with water (100 cm³), dried over anhydrous magnesium sulfate, filtered and the solvent removed in vacuo. The crude is purified by column chromatography using a graded solvent system (40-60 petrol:dichloromethane; 7:3 to 1:1) to give intermediate 91 (1.8 g, 96%) as an orange solid. $^1$H NMR (400 MHz, CDCl$_3$) 9.90 (1H, s), 9.82 (1H, s), 7.94 (1H, s), 7.71 (1H, s), 7.04-7.18 (16H, m), 2.50 (8H, t, J 6.7), 1.52-1.62 (4H, m), 1.16-1.33 (64H, m), 0.79-0.91 (24H, m).

To a solution of intermediate 91 (1.40 g, 0.99 mmol) and tributyl(1,3-dioxolan-2-ylmethyl)-phosphonium bromide (802 mg, 2.17 mmol) in tetrahydrofuran (72 cm³) is added sodium hydride (237 mg, 5.92 mmol, 60% dispersion in mineral oil) and the reaction mixture stirred at 23° C. for 18 hours. The reaction mixture is cooled to 0° C. and aqueous hydrochloric acid (20 cm³, 10%) added. The reaction mixture is stirred at 0° C. for 40 minutes and then at 23° C. for 2 hours. Water (100 cm³) is added and the organics extracted with ether (3×100 cm³). The combined organics washed with brine (100 cm³), dried over anhydrous magnesium sulfate, filtered and the solvent removed in vacuo. The crude is triturated (acetonitrile), the solid collected by filtration and washed with methanol (100 cm³) to give intermediate 92 (1.2 g, 83%) as a red solid. $^1$H NMR (400 MHz, CDCl$_3$) 9.53 (1H, d, J 7.6), 9.50 (1H, d, J 7.6), 7.40-7.52 (3H, m), 7.24 (1H, s), 6.96-7.10 (8H, m), 6.30-6.41 (2H, m), 2.35-2.47 (8H, m), 1.43-1.55 (4H, m), 1.04-1.27 (64H, m), 0.68-0.84 (24H, m).

Compound 35

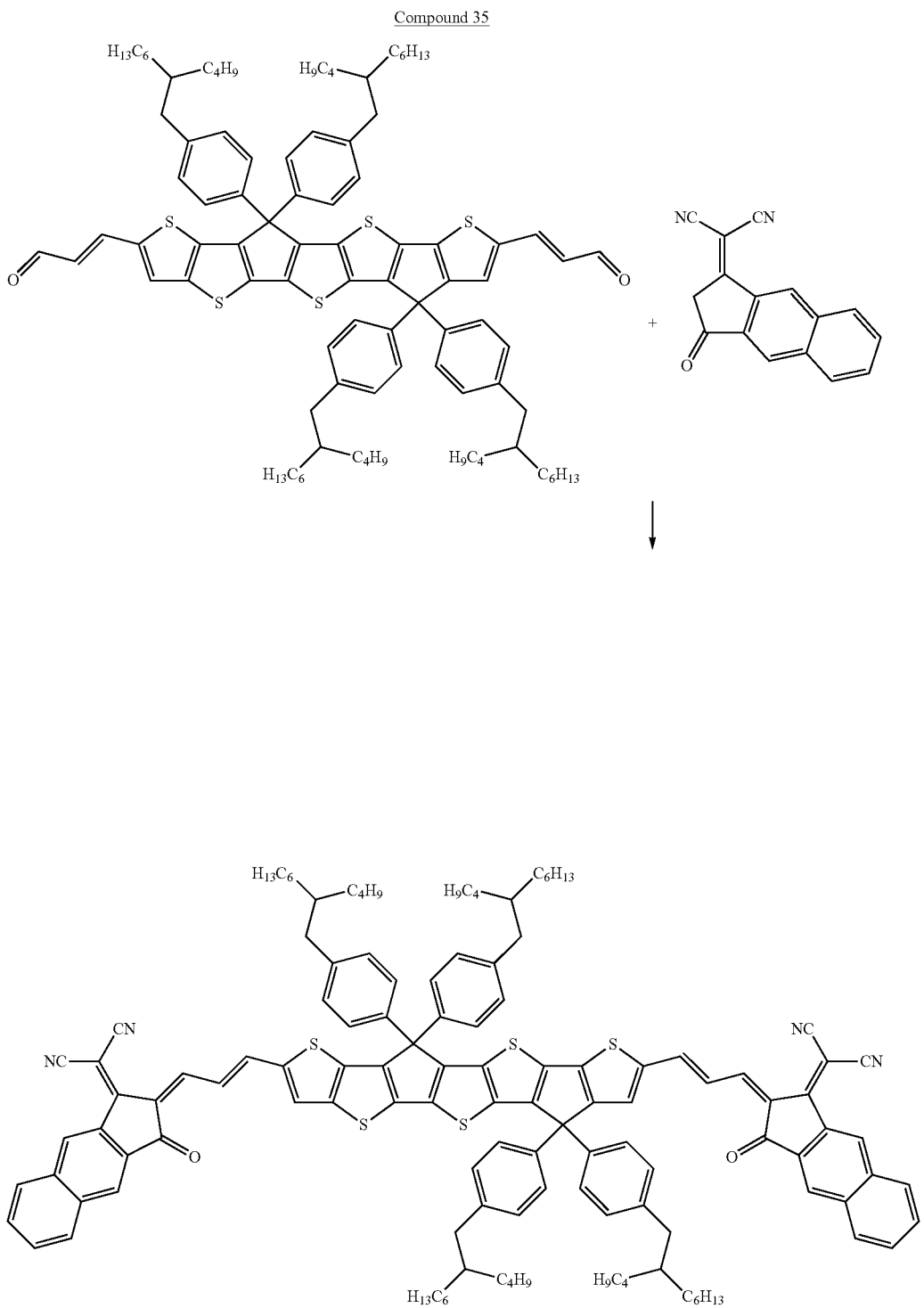

To a solution of intermediate 92 (250 mg, 0.17 mmol) in anhydrous chloroform (10 cm³) is added 2-{3-oxo-1H,2H,3H-cyclopenta[b]naphthalen-1-ylidene}propanedinitrile (125 mg, 0.510 mmol) followed by pyridine (0.1 cm³, 1 mmol). The resulting solution is stirred for 4 hours at 40° C. The mixture is allowed to cool to 23° C. and the volatiles removed in vacuo. The residue is triturated in methanol and the solid washed with further methanol until the filtrate runs colourless. The crude is purified by column chromatography (cyclohexane:chloroform; 7:13) to give compound 35 (94 mg, 29%) as a brown/green solid. $^1$H NMR (400 MHz, CDCl$_3$) 9.05-9.11 (2H, m), 8.50-8.67 (2H, m), 8.38-8.47 (2H, m), 8.24-8.31 (2H, m), 7.93-8.04 (2H, m), 7.57-7.68 (4H, m), 7.36-7.54 (4H, m), 6.99-7.16 (16H, m), 2.37-2.51 (8H, m), 1.45-1.60 (4H, m), 1.08-1.27 (64H, m), 0.69-0.82 (24H, m).

Example 36

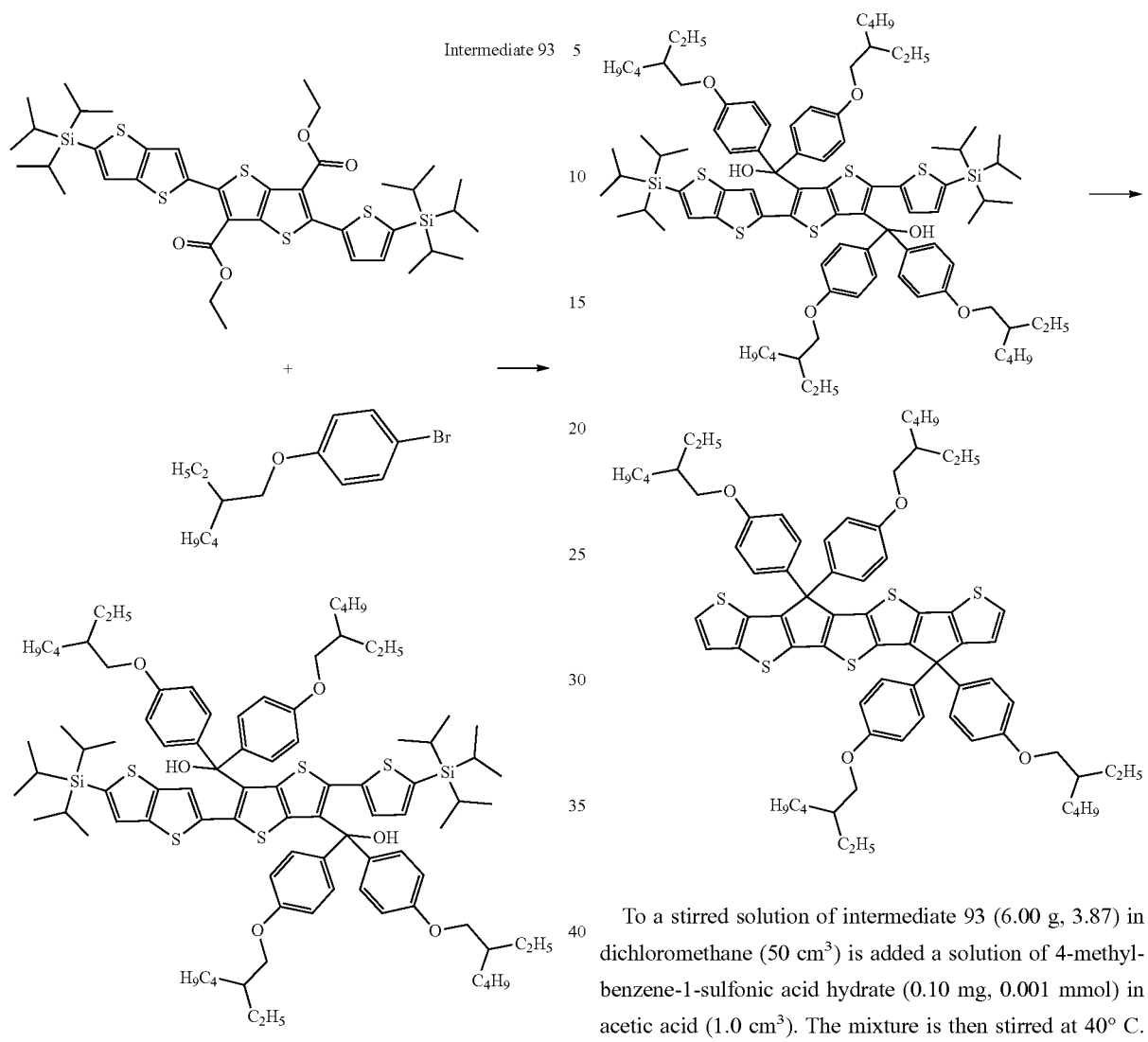

To a solution of 1-bromo-4-[(2-ethylhexyl)oxy]benzene (6.98 g, 24.5 mmol) in anhydrous tetrahydrofuran (100 cm³) at −78° C. is added dropwise t-butyllithium (28.8 cm³, 48.9 mmol, 1.7 M in pentane) over 70 minutes. The reaction mixture is then stirred for 2 hours. Intermediate 88 (4.00 g, 4.89 mmol) is then added as a single portion and the reaction mixture allowed to warm to 23° C. and stirred for 17 hours. Water (100 cm³) is added and the mixture stirred for a further 1 hour. Ether (100 cm³) is added and the aqueous layer extracted with ether (2×100 cm³). The combined organic layer is washed with water (2×50 cm³), dried over anhydrous magnesium sulfate, filtered and the solvent removed in vacuo. The crude is purified by column chromatography using a graded solvent system (pentane:dichloromethane; 1:0 to 0:1) to give intermediate 93 (6.70 g, 88%) as a yellow oil. ¹H NMR (400 MHz, CD₂Cl₂) 7.14 (1H, s), 7.04-7.12 (8H, m), 6.86 (1H, d, J 3.5), 6.69-6.75 (8H, m), 6.61 (1H, d, J 3.5), 6.54 (1H, m), 3.68-3.82 (8H, m), 3.30 (1H, s), 3.25 (1H, s), 1.56-1.68 (4H, m), 1.53-1.69 (4H, m), 1.11-1.42 (38H, m), 0.99-1.04 (18H, m), 0.92-0.97 (18H, m), 0.77-0.86 (24H, m).

To a stirred solution of intermediate 93 (6.00 g, 3.87) in dichloromethane (50 cm³) is added a solution of 4-methylbenzene-1-sulfonic acid hydrate (0.10 mg, 0.001 mmol) in acetic acid (1.0 cm³). The mixture is then stirred at 40° C. for 12 hours. The mixture allowed to cool to 23° C. and the volatiles removed in vacuo. The residue taken up in ether (50 cm³) and the solution washed with saturated aqueous potassium carbonate until the solution is basic. The solution is then dried over potassium carbonate, filtered and the solvent removed in vacuo. The residue is taken up in tetrahydrofuran (40 cm³) and tetrabutylammonium fluoride (10 cm³, 10 mmol, 1.0 M in tetrahydrofuran) is added. The mixture is stirred for 15 minutes and then the solvent removed in vacuo. The crude is purified by column chromatography using a graded solvent system (40-60 petrol:dichloromethane; 19:1 to 17:3) to give intermediate 94 (2.15 g, 46%) as a pale orange solid. ¹H NMR (400 MHz, CDCl₃) 7.29 (1H, d, J 5.2), 7.25 (1H, d, J 5.2), 7.16-7.21 (9H, m), 7.06 (1H, d, J 4.9), 6.80-6.85 (8H, m), 3.76-3.83 (8H, m), 1.64-1.75 (4H, m), 1.24-1.54 (32H, m), 0.84-0.96 (24H, m).

301

Intermediate 95

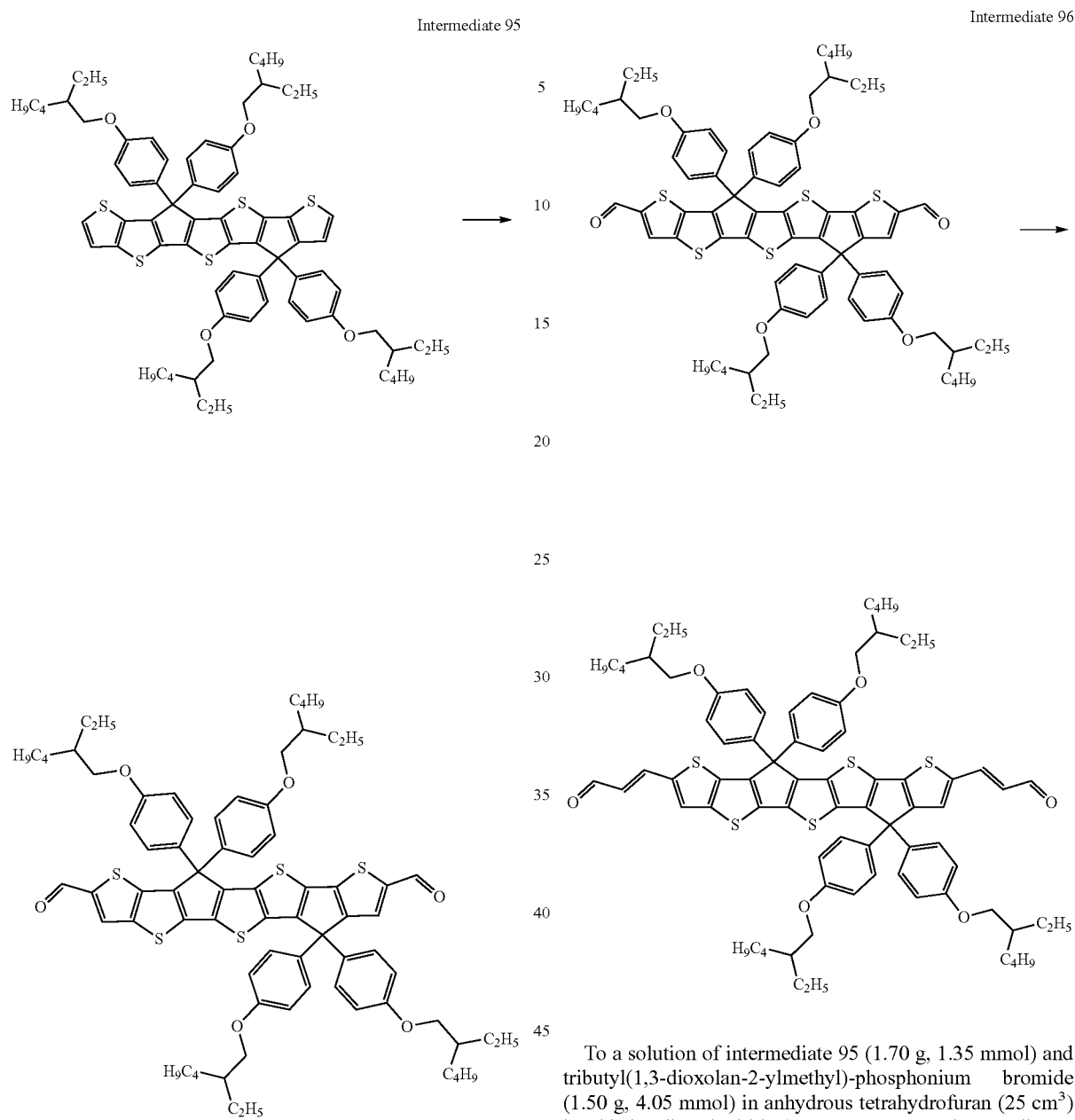

Intermediate 96

To a solution of intermediate 94 (1.98 g, 1.65 mmol), anhydrous N,N-dimethylformamide (0.65 cm³, 8.4 mmol) and anhydrous chloroform (50 cm³) at 0° C. is added phosphorus(V) oxychloride (0.80 cm³, 8.6 mmol). The mixture is then stirred at 0° C. for 30 minutes and at 50° C. for 16 hours before allowing to cool to 23° C. The volatiles are removed in vacuo and tetrahydrofuran (25 cm³) and water (5 cm³) are added. The mixture is then stirred for 30 minutes before the volatiles are removed in vacuo. The residue is triturated (methanol), the solid collected by filtration and washed with methanol (50 cm³) to give intermediate 95 (2.0 g, 99%) as an orange solid. ¹H NMR (400 MHz, CD$_2$Cl$_2$) 9.91 (1H, s), 9.83 (1H, s), 8.01 (1H, s), 7.72 (1H, s), 7.13-7.23 (8H, m), 6.81-6.91 (8H, m), 3.78-3.88 (8H, m), 1.69-1.79 (4H, m), 1.24-1.57 (32H, m), 0.85-1.00 (24H, m).

To a solution of intermediate 95 (1.70 g, 1.35 mmol) and tributyl(1,3-dioxolan-2-ylmethyl)-phosphonium bromide (1.50 g, 4.05 mmol) in anhydrous tetrahydrofuran (25 cm³) is added sodium hydride (270 mg, 6.76 mmol, 60% dispersion in mineral oil) and the reaction mixture stirred for 4 hours and then heated at 40° C. for 2 hours. The reaction mixture is cooled to 0° C. and aqueous hydrochloric acid (4.6 cm³, 10%) added. The reaction mixture is stirred at 0° C. for 10 minutes. The volatiles are removed in vacuo, the aqueous phase decanted, and the residue washed with water (2×10 cm³). The crude is triturated in methanol, the solid collected by filtration and washed with methanol (50 cm³). The product is further purified by column chromatography using a graded solvent system (40-60 petrol:dichloromethane; 3:17 to 0:1) followed by recrystallisation (chloroform:acetonitrile) to give intermediate 96 (1.63 g, 92%) as a red solid. ¹H NMR (400 MHz, CD$_2$Cl$_2$) 9.50 (1H, d, J 7.6), 9.48 (1H, d, J 7.6), 7.41-7.54 (3H, m), 7.22 (1H, s), 7.00-7.10 (8H, m), 6.69-6.78 (8H, m), 6.26-6.39 (2H, m), 3.64-3.77 (8H, m), 1.52-1.65 (4H, m), 1.11-1.45 (32H, m), 0.72-0.86 (24H, m).

Compound 36

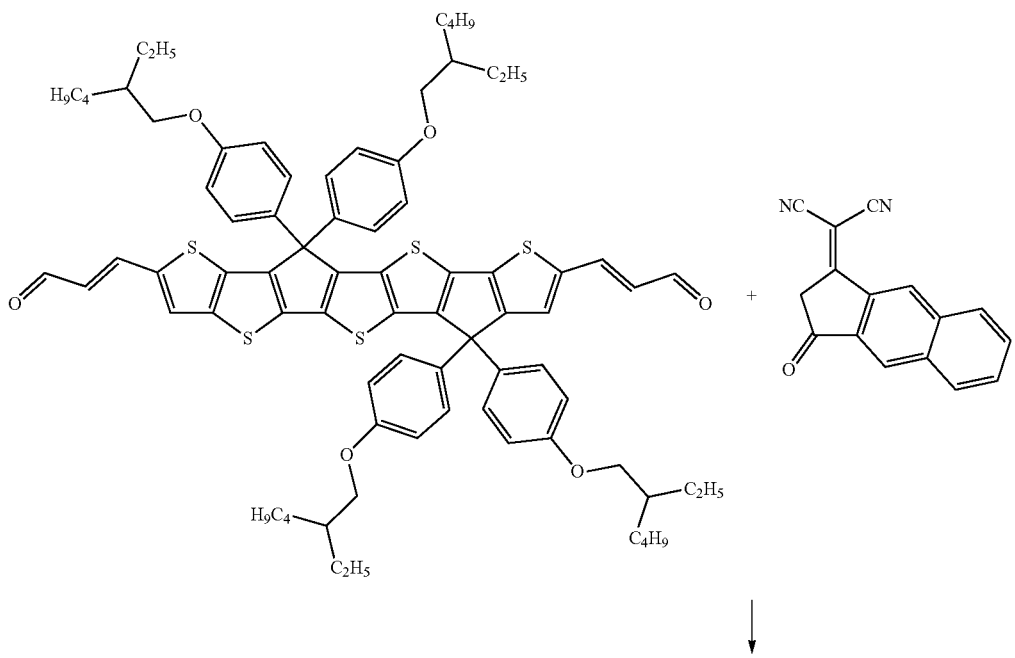

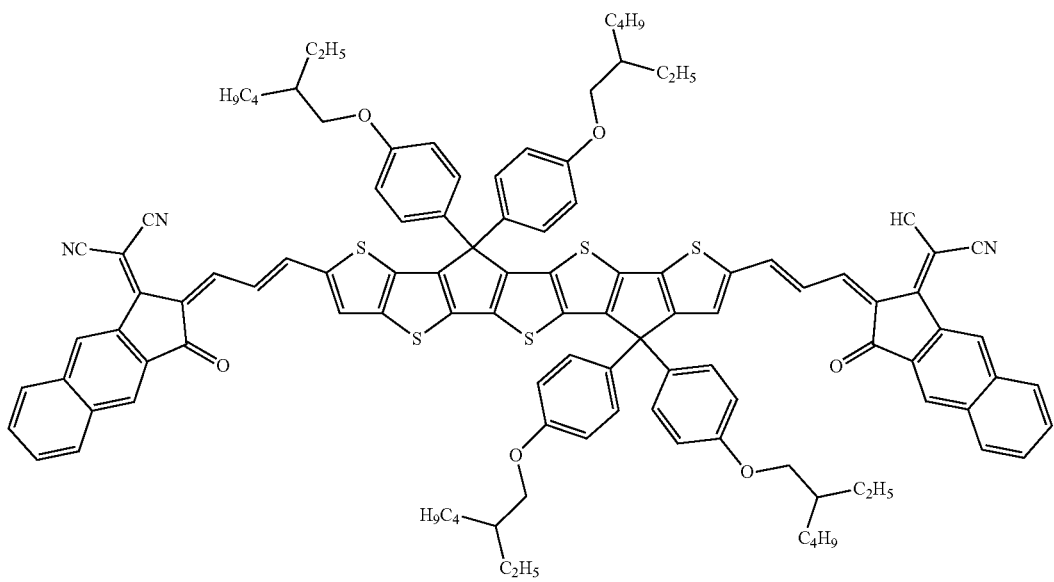

To a solution of intermediate 96 (250 mg, 0.191 mmol) in anhydrous chloroform (10 cm³) and ethanol (0.5 cm³) is added 2-{3-oxo-1H,2H,3H-cyclopenta[b]naphthalen-1-ylidene}propanedinitrile (140 mg, 0.573 mmol) followed by pyridine (0.1 cm³, 1.2 mmol). The resulting solution is stirred for 12 hours at 40° C. The mixture is allowed to cool to 23° C. and the volatiles removed in vacuo. The residue is triturated in methanol and the solid washed with further methanol until the filtrate runs colourless. The crude is purified by column chromatography using a graded solvent system (40-60 petrol:chloroform; 3:17 to 1:19) to give compound 36 (138 mg, 41%) as a dark green solid. $^1$H NMR (400 MHz, CDCl$_3$) 9.15-9.19 (2H, m), 8.61-8.74 (2H, m), 8.47-8.54 (2H, m), 8.34-8.39 (2H, m), 8.03-8.11 (4H, m), 7.66-7.75 (4H, m), 7.49-7.63 (3H, m), 7.42 (1H, s), 7.14-7.22 (8H, m), 6.83-6.96 (8H, m), 3.77-3.90 (8H, m), 1.64-1.77 (4H, m), 1.23-1.59 (32H, m), 0.83-0.97 (24H, m).

Example 37

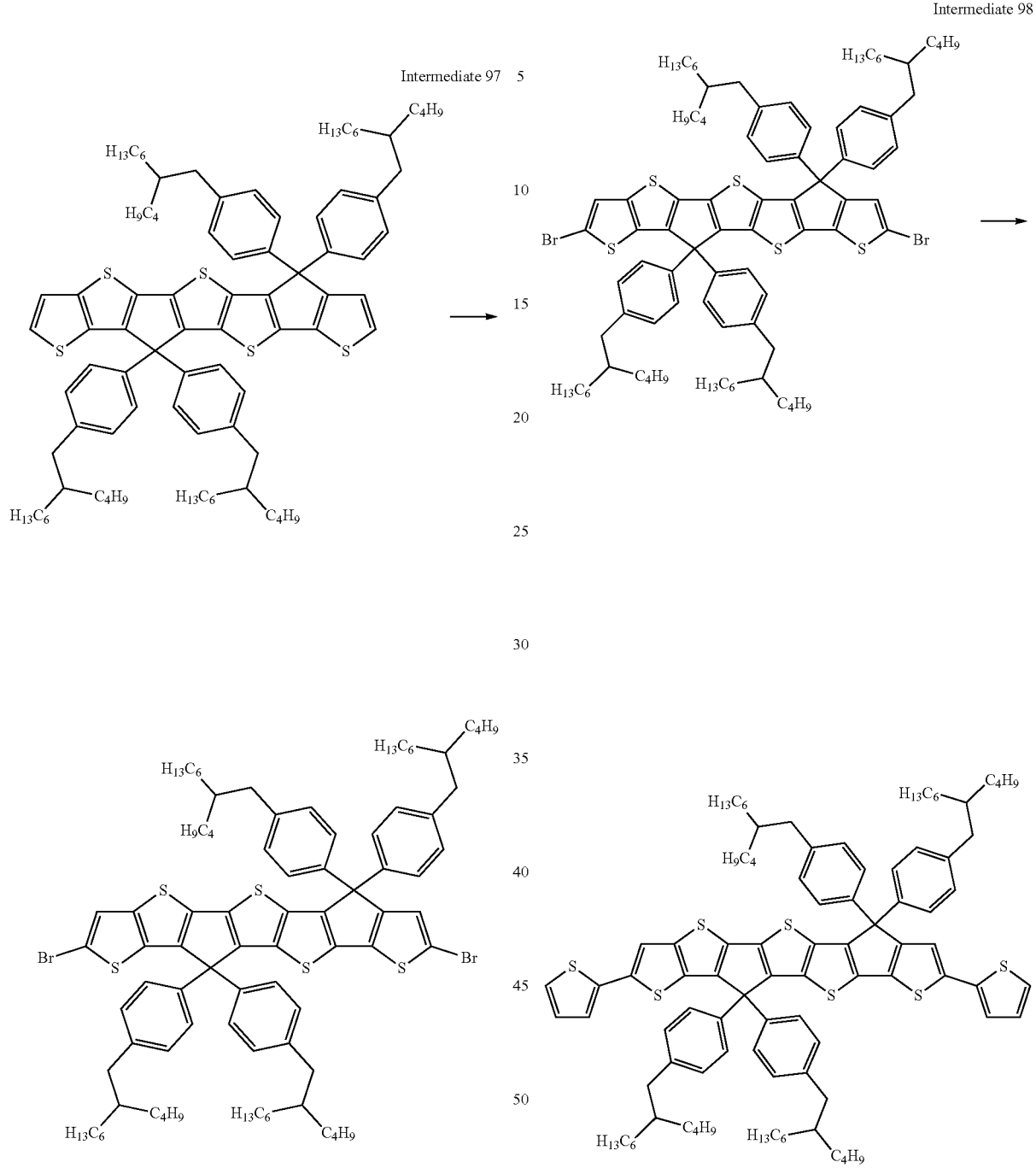

Intermediate 97

Intermediate 98

To a solution of intermediate 90 (1.10 g, 0.807 mmol) in tetrahydrofuran (50 cm$^3$) at 0° C. is added N-bromosuccinimide (302 mg, 1.70 mmol) in two portions over 10 minutes. The reaction mixture is then stirred at 23° C. for 17 hours. Dichloromethane (25 cm$^3$) and water (75 cm$^3$) are added and the aqueous layer extracted with dichloromethane (25 cm$^3$). The combined organic extracts are washed with water (50 cm$^3$) and brine (50 cm$^3$) before drying over anhydrous magnesium sulfate, filtered and the solvent removed in vacuo, to give intermediate 97 (1.0 g, 82%) as a brown oily solid. $^1$H NMR (400 MHz, CD$_2$Cl$_2$) 6.89-7.31 (18H, m), 2.39 (8H, dd, J 6.9), 1.42-1.57 (4H, m), 1.07-1.26 (64H, m), 0.67-0.83 (24H, m).

To a degassed mixture of intermediate 97 (1.00 g, 0.658 mmol), toluene (80 cm$^3$), tributyl(thiophen-2-yl)stannane (0.46 cm$^3$, 1.4 mmol) and tris(o-tolyl)phosphine (40 mg, 0.13 mmol) is added tris(dibenzylideneacetone)dipalladium (0) (30 mg, 0.033 mmol). The reaction is then heated at 110° C. for 4 hours before cooling to 23° C. The volatiles are removed in vacuo, ethanol (100 cm$^3$) added and the mixture stirred for 17 hours. The solid is collected by filtration and washed with ethanol (100 cm$^3$) to give intermediate 98 (905 mg, 90%) as a light yellow solid. $^1$H NMR (400 MHz, CD$_2$Cl$_2$) 7.30 (1H, s), 6.88-7.21 (23H, m), 2.40 (8H, t, J 7.2), 1.46 (4H, br. s.), 1.01-1.26 (64H, m), 0.65-0.84 (24H, m).

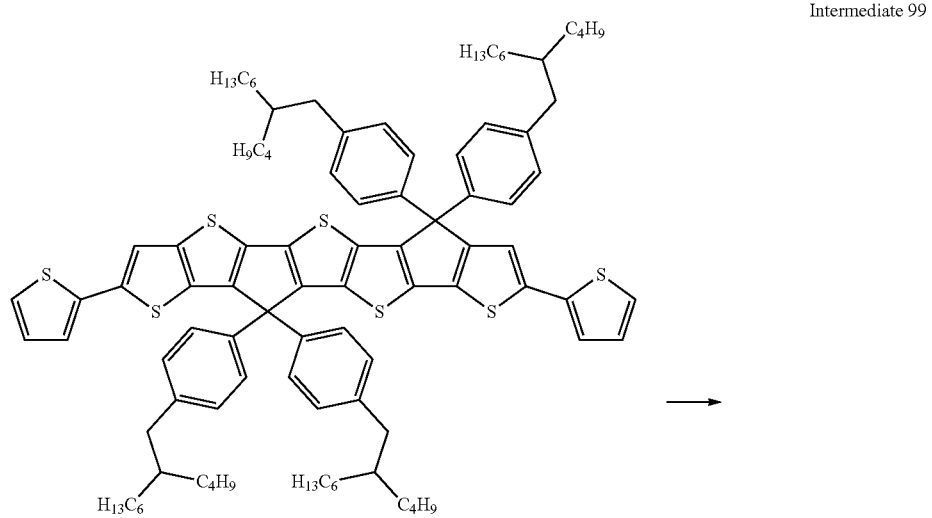

Intermediate 99

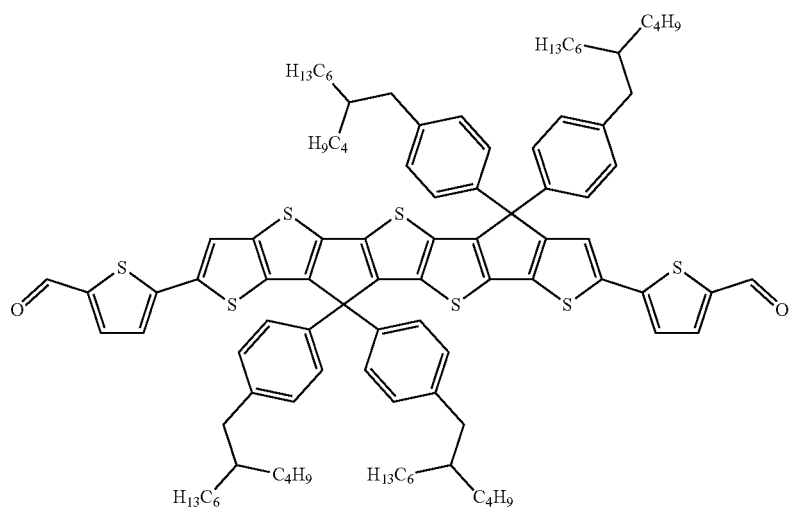

To a solution of N,N-dimethylformamide (0.4 cm³) in anhydrous chloroform (80 cm³) at 0° C. is added dropwise phosphorus(V) oxychloride (0.41 cm³, 4.4 mmol). After 10 minutes at 0° C., the reaction mixture is stirred at 23° C. for 30 minutes before intermediate 98 (900 mg, 0.590 mmol) is added. The reaction mixture is stirred for 17 hours at 23° C. and then heated at reflux for 17 hours. After cooling to 23° C., saturated aqueous sodium sulphate solution (50 cm³) is then added and the resulting mixture heated at 50° C. for 1 hour. The mixture allowed to cool to 23° C. and the volatiles removed in vacuo. The organics are extracted with ether (3×100 cm³) and the combined organics washed with water (2×25 cm³), brine (30 cm³) and dried over anhydrous magnesium sulfate. Filtration and removal of the solvent in vacuo gives the crude product which is purified by column chromatography using a graded solvent system (40-60 petrol:dichloromethane; 4:1 to 2:3) to give intermediate 99 (750 mg, 80%) as a dark red solid. $^1$H NMR (400 MHz, CDCl$_3$) 9.83 (1H, s), 9.82 (1H, s), 7.65 (1H, d, J 3.7), 7.66 (1H, d J 3.7), 7.58 (1H, s), 7.32 (1H, s), 7.23 (1H, d, J 3.9), 6.95-7.17 (17H, m), 2.49 (4H, d, J 6.9), 2.45 (4H, d, J 7.0), 1.47-1.63 (4H, m), 1.05-1.37 (64H, m), 0.73-0.89 (24H, m).

Compound 37

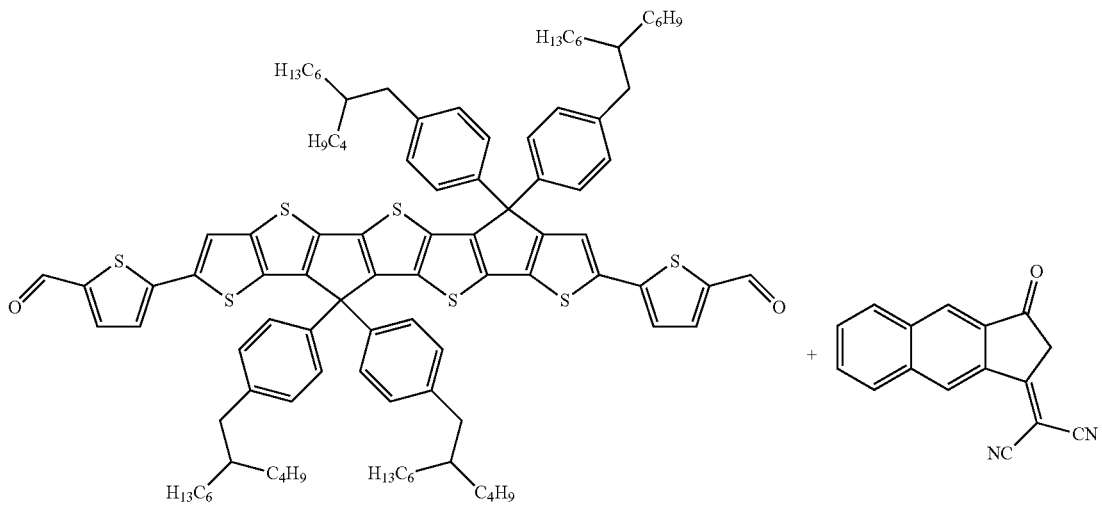

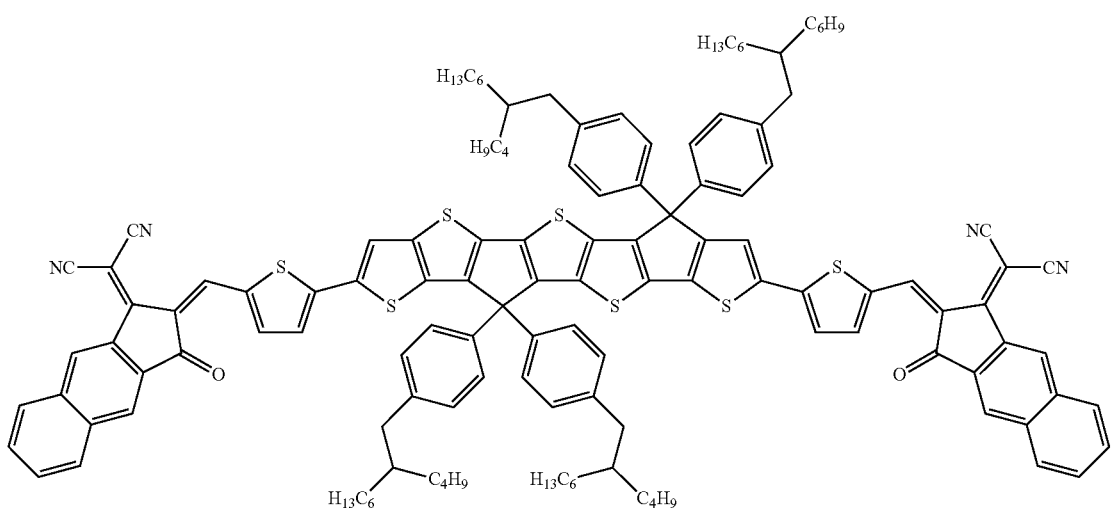

To a degassed solution of intermediate 99 (190 mg, 0.120 mmol) and 2-{3-oxo-1H,2H,3H-cyclopenta[b]naphthalen-1-ylidene}propanedinitrile (176 mg, 0.720 mmol) in anhydrous chloroform (40 cm³) at 10° C. is added pyridine (0.68 cm³, 8.4 mmol). The resulting solution is then degassed for a further 30 minutes. The reaction mixture is warmed to 23° C. and stirred for 3 hours. Acetonitrile (500 cm³) is added and the mixture stirred for 1 hour. The solid collected by filtration, washed with acetone (20 cm³) and ether (20 cm³) to give compound 37 (224 mg, 92%) as a dark grey solid. $^1$H NMR (400 MHz, CDCl$_3$) 9.08 (2H, d, J 18.9), 8.85 (2H, d, J 10.5), 8.33 (2H, s), 7.91-8.02 (3H, m), 7.82 (1H, d, J 8.1), 7.67-7.73 (2H, m), 7.50-7.65 (6H, m), 7.00-7.29 (18H, m), 2.48-2.61 (8H, m), 1.57-1.69 (4H, m), 1.14-1.36 (64H, m), 0.78-0.92 (24H, m).

Example 38

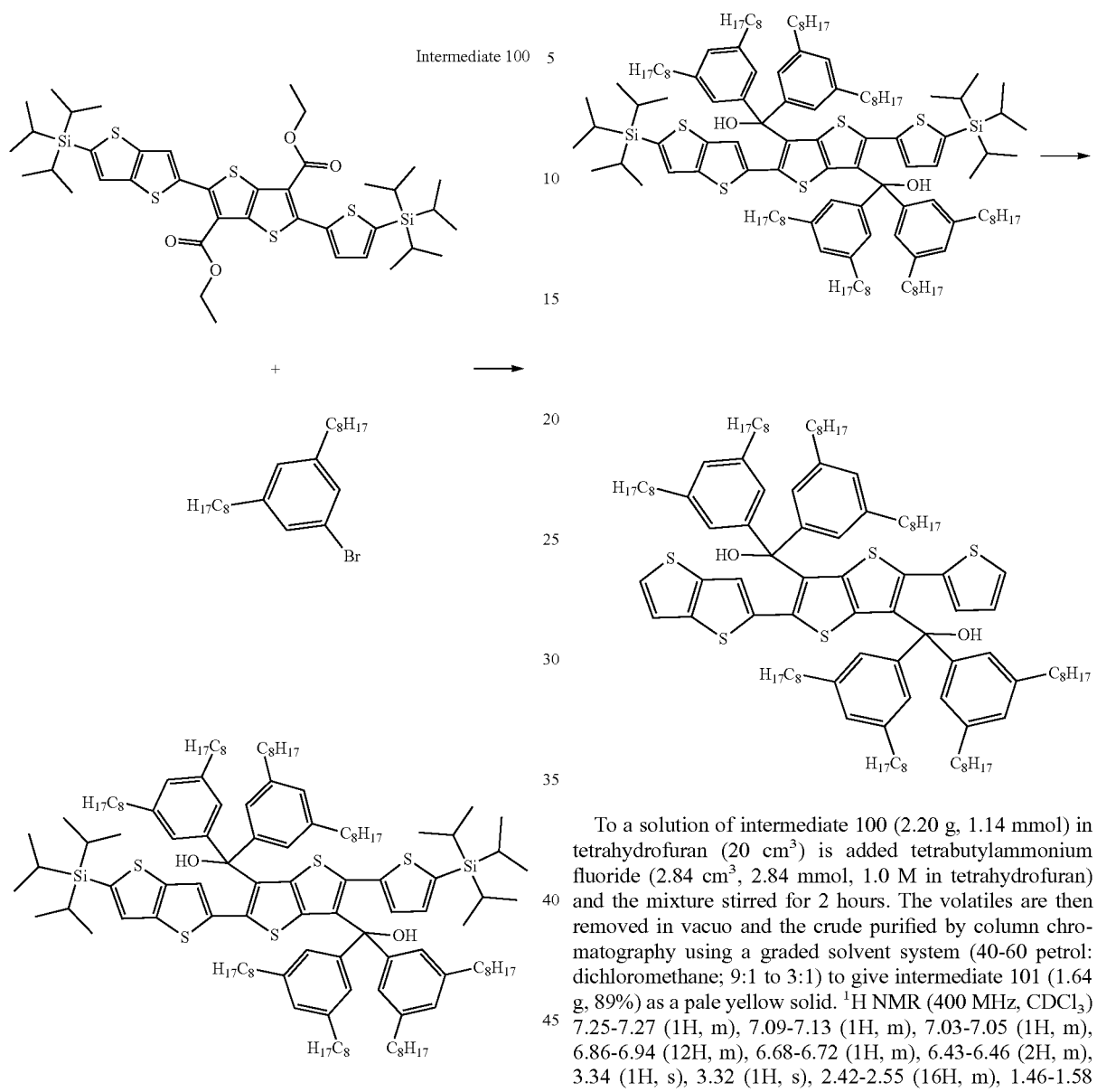

Intermediate 100

Intermediate 101

To a mixture of intermediate 88 (5.72 g, 15.0 mmol) and anhydrous tetrahydrofuran (40 cm$^3$) at −78° C. is added t-butyllithium (17.6 cm$^3$, 30.0 mmol, 1.7 M in pentane) over 10 minutes The mixture is then stirred for 2 hours before intermediate 43 (2.45 g, 3.00 mmol) is added, the mixture allowed to warm to 23° C. and stirred for 17 hours. Water (25 cm$^3$) is added and the mixture stirred for a further 1 hour. The aqueous layer is extracted with ether (2×50 cm$^3$) and the combined organics dried over anhydrous magnesium sulfate. Filtration and removal of the solvent in vacuo followed by column chromatography using a graded solvent system (40-60 petrol:dichloromethane; 1:0 to 17:3) gives intermediate 100 (3.03 g, 52%) as a yellow oil. $^1$H NMR (400 MHz, CDCl$_3$) 7.15 (1H, s), 6.95-7.00 (4H, m), 6.89-6.94 (6H, m), 6.89 (1H, d, J 3.4), 6.84-6.88 (2H, m), 6.62 (1H, d, J 3.4), 6.37 (1H, s), 3.50 (1H, s), 3.34 (1H, s), 2.40-2.59 (16H, m), 1.46-1.63 (16H, m), 1.19-1.42 (86H, m), 1.10-1.15 (18H, m), 1.02-1.07 (18H, m), 0.81-0.95 (24H, m).

To a solution of intermediate 100 (2.20 g, 1.14 mmol) in tetrahydrofuran (20 cm$^3$) is added tetrabutylammonium fluoride (2.84 cm$^3$, 2.84 mmol, 1.0 M in tetrahydrofuran) and the mixture stirred for 2 hours. The volatiles are then removed in vacuo and the crude purified by column chromatography using a graded solvent system (40-60 petrol: dichloromethane; 9:1 to 3:1) to give intermediate 101 (1.64 g, 89%) as a pale yellow solid. $^1$H NMR (400 MHz, CDCl$_3$) 7.25-7.27 (1H, m), 7.09-7.13 (1H, m), 7.03-7.05 (1H, m), 6.86-6.94 (12H, m), 6.68-6.72 (1H, m), 6.43-6.46 (2H, m), 3.34 (1H, s), 3.32 (1H, s), 2.42-2.55 (16H, m), 1.46-1.58 (16H, m), 1.14-1.34 (80H, m), 0.82-0.92 (24H, m).

Intermediate 102

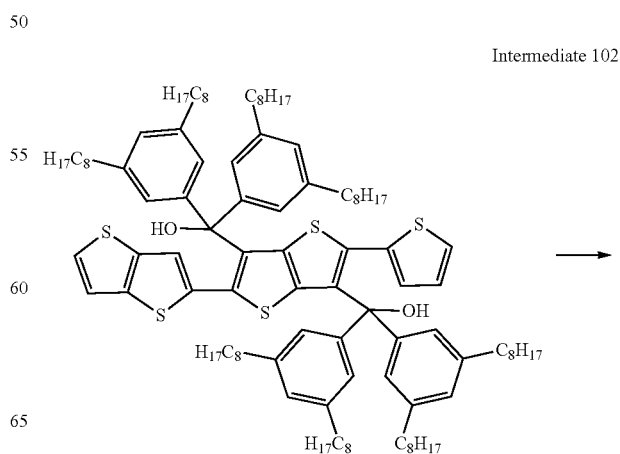

-continued

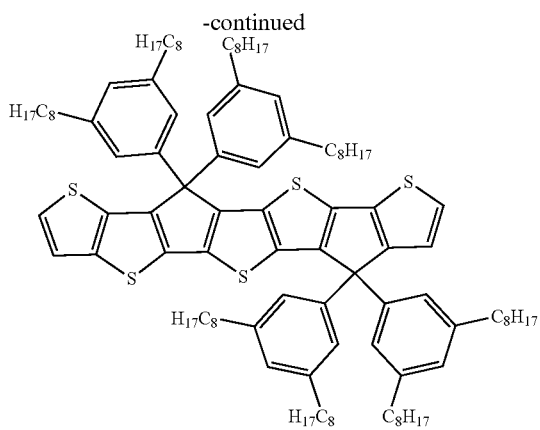

To a solution of intermediate 101 (910 mg, 0.560 mmol) in cyclohexane (50 cm³) is added Amberlyst 15 strong acid (3.5 g). The mixture is then heated at 50° C. for 25 minutes and the solution filtered. The volatiles are removed from the filtrate in vacuo and the residue purified by column chromatography (40-60 petrol) to give intermediate 102 (600 mg, 67%) as an orange oil. ¹H NMR (400 MHz, CD$_2$Cl$_2$) 7.21 (1H, d, 5.2), 7.17 (1H, d, 5.2), 7.13 (1H, d, 4.9), 6.98 (1H, d, 4.9), 6.78-6.82 (4H, m), 6.72-6.76 (8H, m), 2.33-2.44 (16H, m), 1.35-1.50 (16H, m), 1.04-1.27 (80H, m), 0.71-0.84 (24H, m).

Intermediate 103

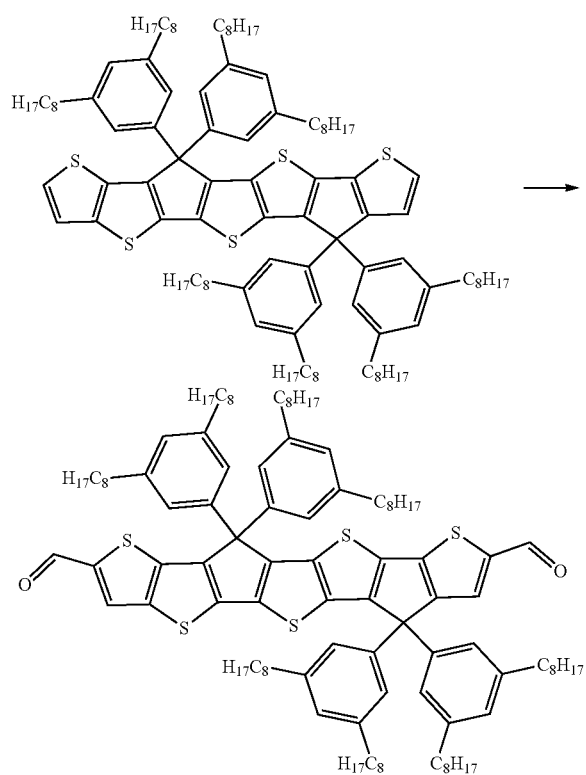

To a solution of intermediate 102 (590 mg, 0.372 mmol), anhydrous N,N-dimethylformamide (0.25 cm³, 3.2 mmol) and anhydrous chloroform (20 cm³) at 0° C. is added phosphorus (V) oxychloride (0.25 cm³, 2.7 mmol). The mixture is then stirred at 0° C. for 30 minutes and at 60° C. for 16 hours before allowing to cool to 23° C. The volatiles are removed in vacuo and tetrahydrofuran (10 cm³) and water (2 cm³) are added. The mixture is then stirred for 15 minutes before the volatiles are removed in vacuo. The aqueous is decanted and the residue purified by column chromatography using a graded solvent system (cyclohexane:dichloromethane; 3:1 to 13:7) to give intermediate 103 (590 mg, 97%) as an orange solid. ¹H NMR (400 MHz, CD$_2$Cl$_2$) 9.78 (1H, s), 9.71 (1H, s), 7.88 (1H, s), 7.58 (1H, s), 6.84 (4H, s), 6.74 (4H, s), 6.70 (4H, s), 2.32-2.47 (16H, m), 1.30-1.50 (16H, m), 1.04-1.25 (80H, m), 0.67-0.83 (24H, m).

Intermediate 104

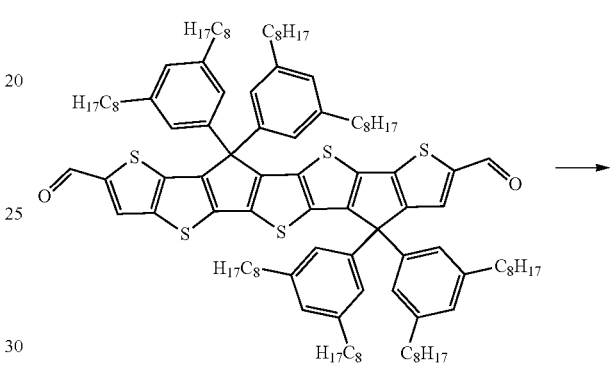

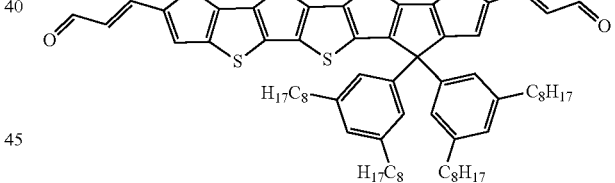

To a solution of intermediate 103 (630 mg, 0.384 mmol) and tributyl(1,3-dioxolan-2-ylmethyl)-phosphonium bromide (425 mg, 1.15 mmol) in anhydrous tetrahydrofuran (10 cm³) is added sodium hydride (77 mg, 1.9 mmol, 60% dispersion in mineral oil) and the reaction mixture stirred for 4 hours. The reaction mixture is cooled to 0° C. and aqueous hydrochloric acid (1.8 cm³, 10%) added. The reaction mixture is stirred at 0° C. for 10 minutes. The volatiles are removed in vacuo, the aqueous phase decanted, and the residue washed with water (2×10 cm³). The crude is then purified by column chromatography using a graded solvent system (40-60 petrol:dichloromethane; 11:9 to 2:3) to give intermediate 104 (460 mg, 71%) as an orange solid. ¹H NMR (400 MHz, CD$_2$Cl$_2$) 9.50 (1H, d, J 7.6), 9.47 (1H, d, J 7.6), 7.42-7.54 (3H, m), 7.21 (1H, s), 6.81-6.85 (4H, m), 6.69-6.75 (8H, m), 6.25-6.37 (2H, m), 2.34-2.45 (16H, m), 1.37-1.49 (16H, m), 1.05-1.23 (80H, m), 0.69-0.81 (24H, m).

315 316
Compound 38
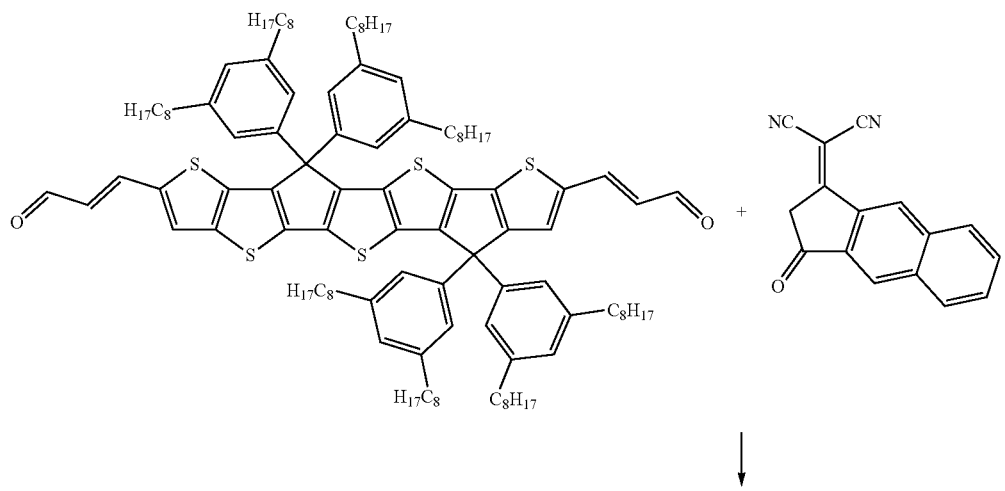
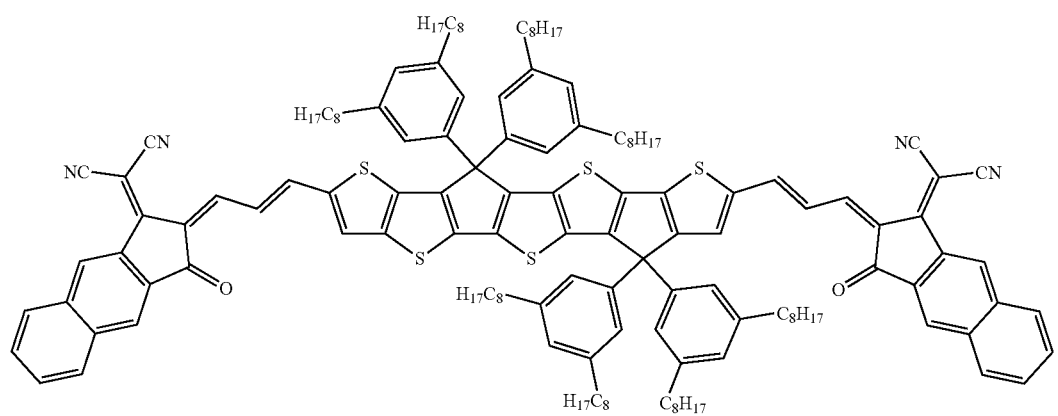

317

To a solution of intermediate 104 (139 mg, 0.082 mmol) in chloroform (10 cm³) is added pyridine (0.1 cm³, 1 mmol) and 2-{3-oxo-1H,2H,3H-cyclopenta[b]naphthalen-1-ylidene}propanedinitrile (59.0 mg, 0.241 mmol). The solution is stirred for 12 hours and then heated at 40° C. for 3 hours and then allowed to cool to 23° C. The volatiles are removed in vacuo and the residue triturated with methanol. The solid is collected by filtration and washed with methanol until the filtrate is colourless. The crude is then further purified by column chromatography (chloroform) to give compound 38 (133 mg, 76%) as a green solid. ¹H NMR (400 MHz, CDCl₃) 9.06-9.13 (2H, m), 8.56-8.70 (2H, m), 8.39-8.47 (2H, m), 8.23-8.29 (2H, m), 7.92-8.07 (4H, m), 7.58-7.66 (4H, m), 7.55 (1H, s), 7.43-7.53 (2H, m), 7.30 (1H, s), 6.71-6.93 (12H, m), 2.39-2.51 (16H, m), 1.40-1.56 (16H, m), 1.00-1.28 (80H, m), 0.65-0.80 (24H, m).

Example 39

Intermediate 105

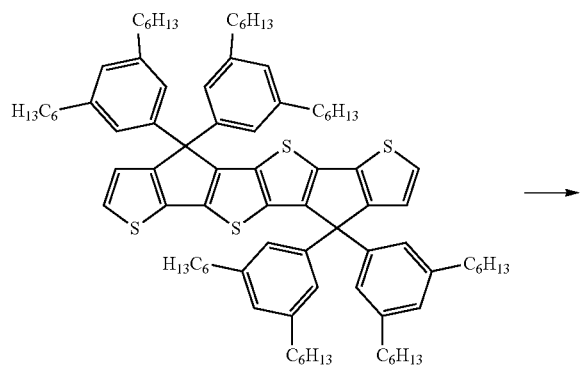

→

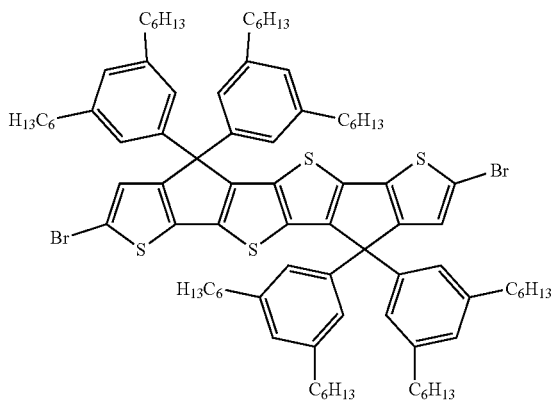

Intermediate 106

To a stirred solution of intermediate 1 (620 mg, 0.475 mmol) in tetrahydrofuran (30 cm³), in the dark, is added N-bromosuccinimide (175 mg, 0.973 mmol). The reaction mixture is stirred for 15 hours and the solvent removed in vacuo. The crude is purified by column chromatography (cyclohexane) to give intermediate 105 (690 mg, 99%) as an orange-yellow solid. ¹H NMR (400 MHz, CD₂Cl₂) 7.09 (2H, s), 6.92-6.94 (4H, m), 6.82 (8H, d, J 1.6), 2.51 (16H, t, J 7.7), 1.50-1.61 (16H, m), 1.22-1.36 (48H, m), 0.84-0.93 (24H, m).

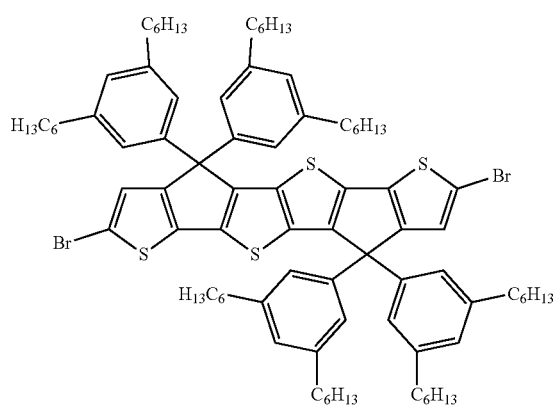

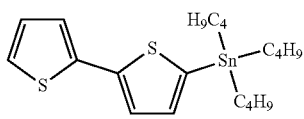

→

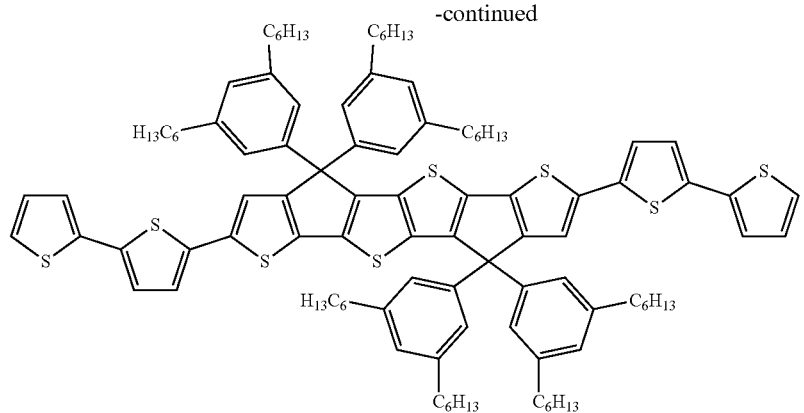

A mixture of intermediate 105 (900 mg, 0.615 mmol), {[2,2'-bithiophen]-5-yl}tributylstannane (729 mg, 1.54 mmol), tris(dibenzylideneacetone)dipalladium(0) (11 mg, 0.012 mmol), tris(o-tolyl)phosphine (15 mg, 0.049 mmol), anhydrous toluene (25 cm³) and anhydrous N,N-dimethylformamide (5 cm³) is stirred at 110° C. for 90 minutes. The mixture allowed to cool to 23° C. and the volatiles removed in vacuo. Methanol (20 cm³) is added, the solid collected by filtration and washed with methanol (20 cm³). The crude is purified by column chromatography using a graded solvent system (cyclohexane:chloroform; 49:1 to 19:1) to give intermediate 106 (990 mg, 99%) as a dark-red solid. ¹H NMR (400 MHz, CD$_2$Cl$_2$) 7.16 (2H, dd, J 5.1, 1.2), 7.09 (2H, dd, J 3.6, 1.2), 7.07 (2H, s), 6.97-7.02 (4H, m), 6.94 (2H, dd, J 5.1, 3.6), 6.80-6.84 (4H, m), 6.76-6.79 (8H, m), 2.41 (16H, t, J 7.7), 1.39-1.51 (16H, m), 1.10-1.25 (48H, m), 0.71-0.80 (24H, m).

Intermediate 107

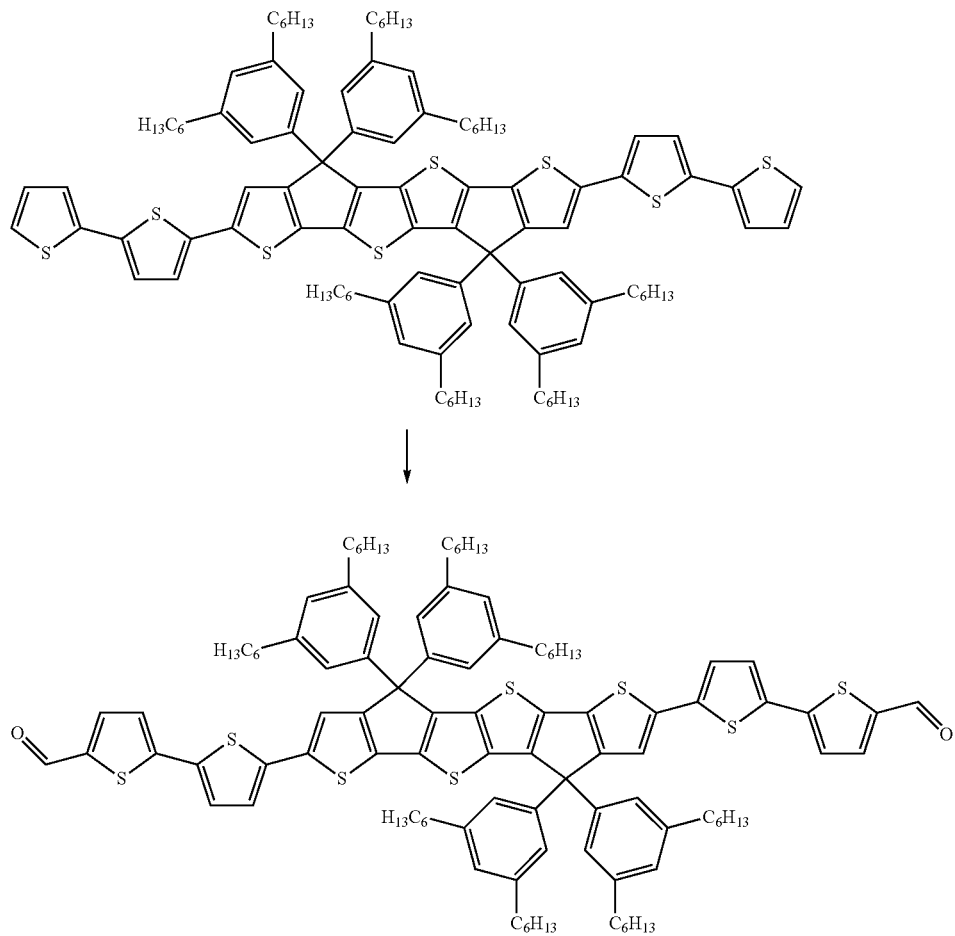

To a solution of intermediate 106 (990 mg, 0.606 mmol) and anhydrous N,N-dimethylformamide (0.30 cm$^3$, 3.9 mmol) in anhydrous chloroform (30 cm$^3$) at 0° C. is added phosphorus(V) oxychloride (0.35 cm$^3$, 3.8 mmol). The mixture is then stirred at 0° C. for 30 minutes and at 60° C. for 16 hours. The mixture is cooled to 23° C. and the volatiles removed in vacuo. Tetrahydrofuran (25 cm$^3$) and water (5 cm$^3$) are added and the mixture stirred for 30 minutes. The volatiles are removed in vacuo and the residue triturated with acetonitrile. The solid is collected by filtration and washed with acetonitrile (50 cm$^3$). The crude is purified by column chromatography using a graded solvent system (40-60 petrol:dichloromethane; 1:1 to 7:13), followed by trituration in acetonitrile. The solid is collected by filtration and washed with acetonitrile (50 cm$^3$) to give intermediate 107 (610 mg, 60%) as a red/brown solid. $^1$H NMR (400 MHz, CD$_2$Cl$_2$) 9.75 (2H, s), 7.60 (2H, d, J 4.0), 7.21 (2H, d, J 3.9), 7.16 (2H, d, J 3.9), 7.13 (2H, s), 7.04 (2H, d, J 4.0), 6.82-6.84 (4H, m), 6.76-6.79 (8H, m), 2.42 (16H, t, J 7.6), 1.40-1.52 (16H, m), 1.10-1.25 (48H, m), 0.70-0.81 (24H, m).

To a solution of intermediate 107 (200 mg, 0.118 mmol) in chloroform (10 cm$^3$) is added pyridine (0.1 cm$^3$, 1 mmol) and 2-{3-oxo-1H,2H,3H-cyclopenta[b]naphthalen-1-ylidene}propanedinitrile (86.7 mg, 0.355 mmol). The reaction mixture is stirred for 4 hours and then heated at 40° C. for 12 hours. The mixture allowed to cool to 23° C., the volatiles removed in vacuo and the residue triturated in methanol. The solid is collected by filtration, washed with methanol until the eluent is colourless. The crude is then purified by column chromatography (chloroform) to give compound 39 (230 mg, 91%) as a brown solid. $^1$H NMR (400 MHz, CDCl$_3$) 9.07 (2H, s), 8.81 (2H, s), 8.29 (2H, s), 7.91-7.98 (4H, m), 7.67-7.73 (2H, m), 7.53-7.60 (4H, m), 7.33-7.41 (2H, m), 7.09-7.23 (6H, m), 6.83-6.88 (4H, m), 6.75-6.82 (8H, m), 2.46 (16H, t, J 7.6), 1.42-1.55 (16H, m), 1.13-1.28 (48H, m), 0.72-0.83 (24H, m).

Compound 39

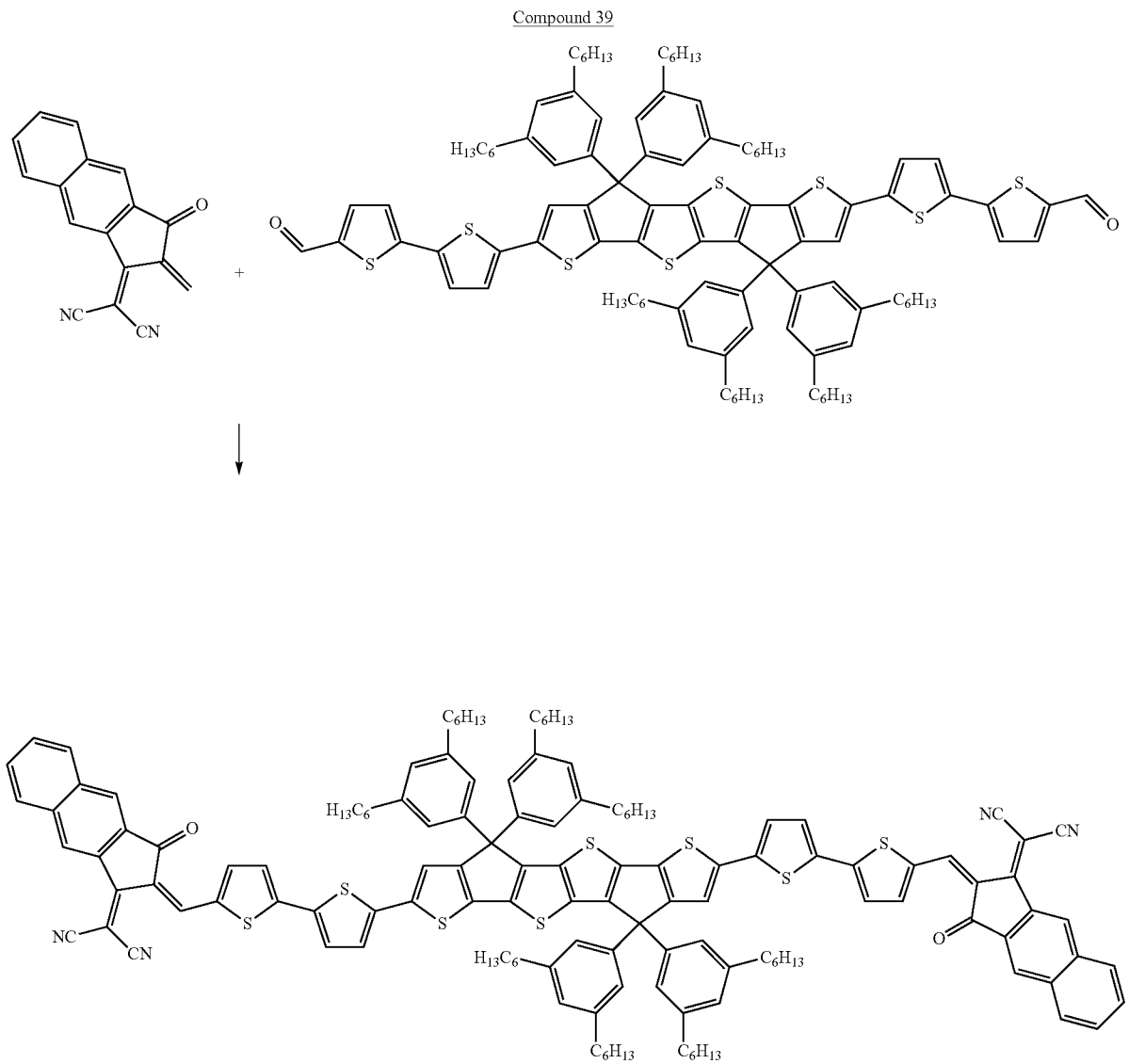

Example 39

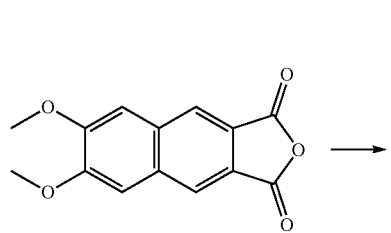

Intermediate 108

Sulphuric acid (2 cm³) is added to a solution of 6,7-dimethoxy-naphtho[2, 3-c]furan-1,3-dione (40.0 g, 155 mmol) in methanol (200 cm³). The mixture is stirred at 70° C. for 12 hours before cooling to 23° C. and the volatiles removed in vacuo. Water (200 cm³) is added and the organics extracted with ethyl acetate (3×200 cm³). The combined organic layer is washed with saturated aqueous sodium carbonate solution (2×200 cm³) and brine (200 cm³), dried over anhydrous sodium sulphate, filtered and concentrated in vacuo. The residue is purified by column chromatography using a graded solvent system (40-60 petrol:ethyl acetate; 1:0 to 0:1) to give intermediate 108 (28.0 g, 59%) as a yellow solid. ¹HNMR (400 MHz, CDCl₃) 8.08 (2H, s), 7.17 (2H, s), 4.02 (6H, s), 3.95 (6H, s).

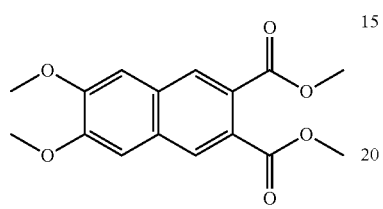

Intermediate 109

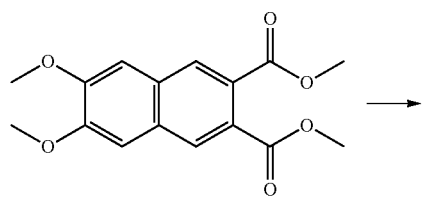

Intermediate 108 (20.0 g, 65.7 mmol) is added to a solution of sodium hydride (21.0 g, 525 mmol, 60% dispersion in mineral oil) in anhydrous ethyl acetate (51 cm³) and anhydrous tetrahydrofuran (400 cm³), and the mixture stirred at reflux for 12 hours. Upon cooling to 23° C. the mixture is concentrated in vacuo to give intermediate 109 (25 g) as a yellow solid, which is used without further purification.

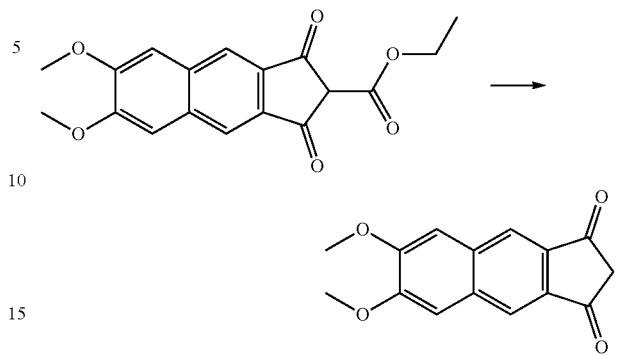

Intermediate 110

Intermediate 109 (25 g, 76 mmol) is dissolved in hydrochloric acid (333 cm³, 2.0 M) and the mixture stirred at 80° C. for 1 hour. The reaction mixture is filtered, and resulting solid, is triturated with ethyl acetate (30 cm³). Filtration gives intermediate 110 (10.0 g) as a yellow solid, which is used without further purification.

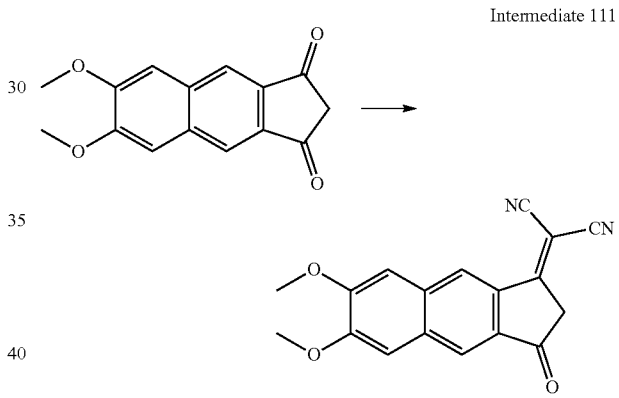

Intermediate 111

Sodium acetate (4.80 g, 58.5 mmol) and malononitrile (4.90 g, 74.1 mmol) are added to a solution of intermediate 110 (10.0 g, 39.0 mmol) in ethanol (100 cm³). The mixture is stirred at 25° C. for 12 hours before the reaction mixture is acidified (pH=1-2) by addition of hydrochloric acid (1 M). Water (100 cm³) is added and the organics extracted with dichloromethane (3×100 cm³). The combined organic layer is washed with water (2×100 cm³) and brine (100 cm³), dried over anhydrous sodium sulphate, filtered and concentrated in vacuo. The crude is purified by column chromatography using a graded solvent system (dichloromethane:methanol; 1:0 to 0:1) to give intermediate 111 (3.80 g) as a brown solid. ¹H NMR (400 MHz, CDCl₃) 8.98 (1H, s), 8.30 (1H, s), 7.36 (1H, s), 7.31 (1H, s), 4.09 (6H, s), 3.80 (2H, s).

Use Example 1

Current-voltage characteristics are measured using a Keithley 2400 SMU while the solar cells are illuminated by a Newport Solar Simulator at 100 mW·cm⁻² white light. The solar simulator is equipped with AM1.5G filters.

The illumination intensity is calibrated using a Si photodiode. All the device preparations and characterizations are carried out in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics are obtained for a composition, which contains Polymer 1 or Polymer 2 as shown below and an acceptor that is a compound of formula I, and is coated from an organic solution. Details of the solution composition are shown in Table 1.

achieve active layer thicknesses between 50 and 800 nm as measured using a profilometer. A short drying period follows to ensure removal of any residual solvent.

Typically, blade-coated films are dried at 60° C. for 2 minutes on a hotplate. Next the devices are transferred into an air atmosphere. On top of the active layer 0.18 mL of a conducting polymer poly(ethylene dioxythiophene) doped with poly(styrene sulfonic acid) [PEDOT:PSS Clevios P VP Al 4083 (Heraeus)] is spread and uniformly coated by doctor blade at 70° C. Afterwards Ag (100 nm) cathodes are thermally evaporated through a shadow mask to define the cells.

Table 1 shows the characteristics of the individual photoactive formulations.

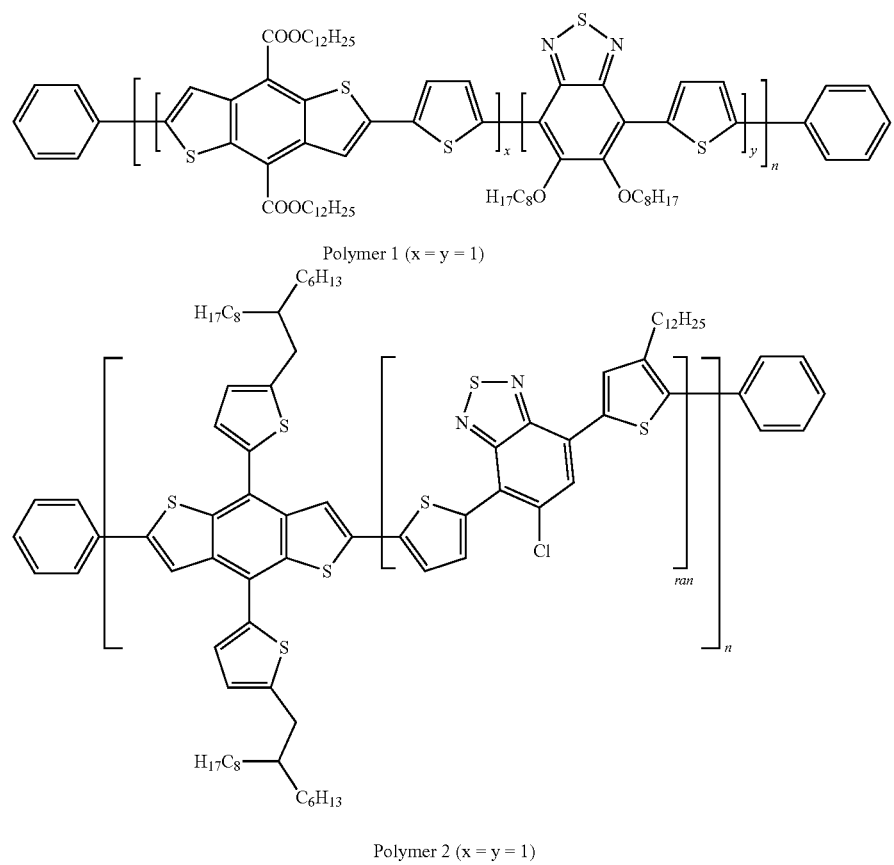

Polymer 1 (x = y = 1)

Polymer 2 (x = y = 1)

A1: Inverted Bulk Heterojunction Organic Photovoltaic Devices

Organic photovoltaic (OPV) devices are fabricated on pre-patterned ITO-glass substrates (13 Ω/sq.) purchased from LUMTEC Corporation. Substrates are cleaned using common solvents (acetone, iso-propanol, deionized-water) in an ultrasonic bath. A layer of commercially available aluminium zinc oxide (AlZnO, Nanograde) is applied as a uniform coating by doctor blade at 40° C. The AlZnO Films are then annealed at 100° C. for 10 minutes in air. Active material solutions (i.e. polymer+acceptor) are prepared to fully dissolve the solutes at a 23 mg·cm$^{-3}$ solution concentration. Thin films are blade-coated in air atmosphere to

TABLE 1

Formulation characteristics

| No. | Acceptor | Polymer | Ratio Polymer: Acceptor | Concentration g/L | Solvent |
|---|---|---|---|---|---|
| 1 | 1 | 1 | 1:1.3 | 23 | o-xylene |
| 2 | 1 | 2 | 1:1.3 | 23 | o-xylene |
| 3 | 3 | 1 | 1:1.3 | 23 | o-xylene |
| 4 | 3 | 2 | 1:1.3 | 23 | o-xylene: 3-phenoxytoluene (97:3) |

TABLE 1-continued

Formulation characteristics

| No. | Acceptor | Polymer | Ratio Polymer: Acceptor | Concentration g/L | Solvent |
|---|---|---|---|---|---|
| 5 | 4 | 1 | 1:1.3 | 23 | o-xylene |
| 6 | 4 | 2 | 1:1.3 | 23 | o-xylene |
| 7 | 5 | 1 | 1:1.3 | 23 | o-xylene |
| 8 | 5 | 2 | 1:1.3 | 23 | o-xylene |
| 9 | 6 | 1 | 1:1.3 | 23 | o-xylene |
| 10 | 6 | 2 | 1:1.3 | 23 | o-xylene |
| 11 | 7 | 1 | 1:1.3 | 23 | o-xylene |
| 12 | 7 | 2 | 1:1.3 | 23 | o-xylene |
| 13 | 8 | 1 | 1:1.3 | 23 | o-xylene |
| 14 | 8 | 2 | 1:1.3 | 23 | o-xylene |
| 15 | 9 | 1 | 1:1.3 | 23 | o-xylene: 3-phenoxytoluene (97:3) |
| 16 | 9 | 2 | 1:1.3 | 23 | o-xylene: 3-phenoxytoluene (97:3) |
| 17 | 11 | 1 | 1:1.3 | 23 | o-xylene |
| 18 | 11 | 2 | 1:1.3 | 23 | o-xylene |
| 19 | 12 | 1 | 1:1.3 | 23 | o-xylene |
| 20 | 12 | 2 | 1:1.3 | 23 | o-xylene |
| 21 | 15 | 1 | 1:1.3 | 23 | o-xylene |
| 22 | 16 | 1 | 1:1.3 | 23 | o-xylene |
| 23 | 16 | 2 | 1:1.3 | 23 | o-xylene |
| 24 | 17 | 1 | 1:1.3 | 23 | o-xylene |
| 25 | 17 | 2 | 1:1.3 | 23 | o-xylene |
| 26 | 18 | 1 | 1:1.3 | 23 | o-xylene |
| 27 | 19 | 1 | 1:1.3 | 23 | o-xylene |
| 28 | 19 | 2 | 1:1.3 | 23 | o-xylene |
| 29 | 20 | 1 | 1:1.3 | 23 | o-xylene |
| 30 | 20 | 2 | 1:1.3 | 23 | o-xylene |
| 31 | 21 | 1 | 1:1.3 | 23 | o-xylene |
| 32 | 21 | 2 | 1:1.3 | 23 | o-xylene |
| 33 | 22 | 1 | 1:1.3 | 23 | o-xylene |
| 34 | 22 | 2 | 1:1.3 | 23 | o-xylene |
| 35 | 23 | 1 | 1:1.3 | 23 | o-xylene |
| 36 | 23 | 2 | 1:1.3 | 23 | o-xylene |
| 37 | 24 | 1 | 1:1.3 | 23 | o-xylene |
| 38 | 26 | 1 | 1:1.3 | 23 | o-xylene |
| 39 | 26 | 2 | 1:1.3 | 23 | o-xylene |
| 40 | 27 | 1 | 1:1.3 | 23 | o-xylene |
| 41 | 31 | 1 | 1:1.3 | 23 | o-xylene |
| 42 | 31 | 2 | 1:1.3 | 23 | o-xylene |
| 43 | 32 | 1 | 1:1.3 | 23 | o-xylene |
| 44 | 32 | 2 | 1:1.3 | 23 | o-xylene |
| 45 | 34 | 1 | 1:1.3 | 23 | o-xylene |
| 46 | 35 | 2 | 1:1.3 | 23 | o-xylene |
| 47 | 36 | 2 | 1:1.3 | 23 | o-xylene |

TABLE 2

Photovoltaic cell characteristics under simulated solar irradiation at 1 sun (AM 1.5 G)

| | | | Average Performance | | | |
|---|---|---|---|---|---|---|
| No. | Acceptor | Polymer | Voc mV | Jsc mA cm$^{-2}$ | FF % | PCE % |
| 1 | 1 | 1 | 705 | 14.5 | 54.8 | 5.6 |
| 2 | 1 | 2 | 690 | 17.7 | 52.0 | 6.5 |
| 3 | 3 | 1 | 730 | 10.5 | 39.2 | 3.0 |
| 4 | 3 | 2 | 688 | 5.9 | 33.3 | 1.4 |
| 5 | 4 | 1 | 733 | 12.6 | 51.9 | 4.8 |
| 6 | 4 | 2 | 746 | 11.3 | 46.8 | 4.0 |
| 7 | 5 | 1 | 721 | 11.8 | 50.3 | 4.3 |
| 8 | 5 | 2 | 695 | 11.9 | 44.3 | 3.7 |
| 9 | 6 | 1 | 763 | 14.2 | 47.2 | 5.1 |
| 10 | 6 | 2 | 748 | 11.2 | 42.5 | 3.6 |
| 11 | 7 | 1 | 851 | 7.6 | 39.7 | 2.6 |
| 12 | 7 | 2 | 776 | 13.5 | 51.3 | 5.4 |
| 13 | 8 | 1 | 750 | 13.2 | 56.6 | 5.6 |
| 14 | 8 | 2 | 700 | 15.2 | 54.8 | 5.8 |
| 15 | 9 | 1 | 674 | 7.4 | 48.0 | 2.4 |
| 16 | 9 | 2 | 669 | 11.9 | 52.9 | 4.2 |
| 17 | 11 | 1 | 765 | 12.4 | 56.1 | 5.2 |
| 18 | 11 | 2 | 745 | 11.5 | 54.7 | 4.3 |
| 19 | 12 | 1 | 775 | 2.6 | 43.8 | 0.8 |
| 20 | 12 | 2 | 760 | 2.3 | 40.4 | 0.7 |
| 21 | 15 | 1 | 830 | 4.8 | 49 | 1.4 |
| 22 | 16 | 1 | 745 | 19 | 53 | 7.08 |
| 23 | 16 | 2 | 730 | 19.5 | 45.2 | 6.18 |
| 24 | 17 | 1 | 775 | 13.8 | 49 | 4.77 |
| 25 | 17 | 2 | 755 | 15 | 53.3 | 4.58 |
| 26 | 18 | 1 | 800 | 12.7 | 42 | 4.05 |
| 27 | 19 | 1 | 750 | 13.9 | 43.2 | 4.26 |
| 28 | 19 | 2 | 735 | 13.8 | 47.8 | 4.71 |
| 29 | 20 | 1 | 715 | 17.3 | 55.3 | 6.73 |
| 30 | 20 | 2 | 685 | 18.1 | 52.9 | 6.38 |
| 31 | 21 | 1 | 790 | 7.9 | 52.8 | 3.06 |
| 32 | 21 | 2 | 765 | 10 | 50.5 | 3.53 |
| 33 | 22 | 1 | 795 | 15.6 | 50.1 | 5.75 |
| 34 | 22 | 2 | 770 | 16 | 52.7 | 6.23 |
| 35 | 23 | 1 | 750 | 13 | 56.4 | 5.42 |
| 36 | 23 | 2 | 740 | 17.1 | 55.7 | 6.7 |
| 37 | 24 | 1 | 780 | 8.6 | 58.2 | 3.53 |
| 38 | 26 | 1 | 780 | 13.4 | 56 | 4.7 |
| 39 | 26 | 2 | 735 | 18.5 | 56 | 6.6 |
| 40 | 27 | 2 | 705 | 12.3 | 56 | 4.5 |
| 41 | 31 | 1 | 820 | 14.7 | 45 | 4.8 |
| 42 | 31 | 2 | 785 | 17.7 | 40 | 5 |
| 43 | 32 | 1 | 745 | 17 | 50 | 6.2 |
| 44 | 32 | 2 | 715 | 17.7 | 50 | 6.5 |
| 45 | 34 | 1 | 655 | 15.3 | 55.7 | 5.36 |
| 46 | 35 | 2 | 655 | 19.8 | 47.1 | 5.09 |
| 47 | 36 | 2 | 665 | 12.7 | 55 | 3.35 |

Light stability of synthesised compounds is shown in Table 3.

TABLE 3

Light stability of Example devices under constant illumination at 1 Sun

| No. | Acceptor | Donor | Initial PCE | PCE after 200 h constant illumination |
|---|---|---|---|---|
| 1 | 16 | 2 | 6.6% | 4.6% |
| 2 | 1 | 2 | 6.4% | 4.8% |
| 3 | PC61BM | 2 | 6.9% | 4.0% |

A1: Bulk Heterojunction Organic Photodetector Devices (OPDs)

Devices are fabricated onto glass substrates with six pre-patterned ITO dots of 5 mm diameter to provide the bottom electrode. The ITO substrates are cleaned using a standard process of ultrasonication in Decon90 solution (30 minutes) followed by washing with de-ionized water (x3) and ultrasonication in de-ionized water (30 minutes). The ZnO ETL layer was deposited by spin coating a ZnO nanoparticle dispersion onto the substrate and drying on a hotplate for 10 minutes at a temperature between 100 and 140° C. A formulation of Polymer 2, Polymer 3 (sourced from Merck KGaA) or Polymer 4 (Lisicon PV-D4650 (sourced from Merck KGaA)) and compound as disclosed herein was prepared at a ratio of 1:1 in o-xylene at a concentration of 20 mg/ml, and stirred for 17 hours at a temperature of between 23° C. and 60° C. The active layer was deposited using blade coating (K101 Control Coater System from RK). The stage temperature was set to between 20-60° C., the blade gap set between 2-200 μm and the speed set between 2-8 m/min targeting a final dry film thickness of 500-1000 nm. Following coating the active layer was annealed at 100° C. for 10 minutes. The MoO₃ HTL layer was deposited by E-beam vacuum deposition from MoO₃ pellets at a rate of 1 Å/s, targeting 15 nm thickness. Finally, the top silver electrode was deposited by thermal evaporation through a shadow mask, to achieve Ag thickness between 30-80 nm.

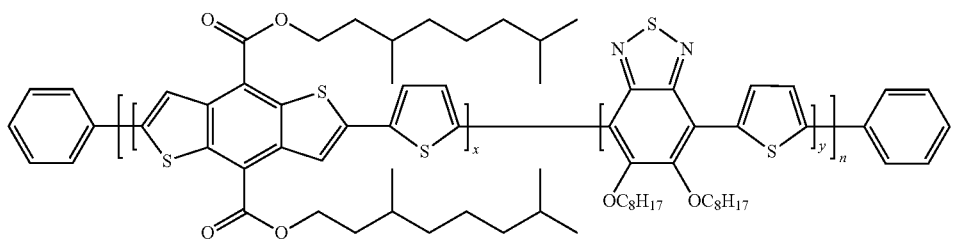

Polymer 3 (x = y = 1)

The J-V curves are measured using a Keithley 4200 system under light and dark conditions at a bias from +5 to −5 V. The light source was a 580 nm LED with power 0.5 mW/cm².

The EQE of OPD devices are characterized between 400 and 1100 nm under −2V bias, using an External Quantum Efficiency (EQE) Measurement System from LOT-QuantumDesign Europe.

Table 4 shows the characteristics of the individual formulations.

TABLE 4

Formulation characteristics

| No. | Acceptor | Polymer |
|---|---|---|
| 1 | Compound 1 | 3 |
| 2 | Compound 1 | 4 |
| 3 | Compound 2 | 2 |
| 4 | Compound 2 | 3 |
| 5 | Compound 9 | 2 |
| 6 | Compound 9 | 3 |
| 7 | Compound 10 | 2 |
| 8 | Compound 10 | 3 |
| 9 | Compound 30 | 4 |

Tables 5, 6 and 7 show the EQE values for the individual OPD devices comprising a photoactive layer with a BHJ formed from the photoactive acceptor/polymer formulations of Table 4.

TABLE 5

EQEs for the devices at 650 nm

| No. | EQE % |
|---|---|
| 1 | 42 |
| 2 | 49 |
| 3 | 15 |
| 4 | 14 |
| 5 | 29 |

TABLE 5-continued

EQEs for the devices at 650 nm

| No. | EQE % |
|---|---|
| 6 | 14 |
| 7 | 42 |
| 8 | 23 |
| 9 | 18 |

TABLE 6

EQEs for the devices at 850 nm

| No. | EQE % |
|---|---|
| 1 | 41 |
| 2 | 46 |
| 5 | 23 |
| 6 | 9 |
| 7 | 36 |
| 8 | 17 |

TABLE 7

EQEs for the devices at 940 nm

| No. | EQE % |
|---|---|
| 5 | 15 |
| 7 | 32 |
| 8 | 15 |

The invention claimed is:

1. A compound of formula I

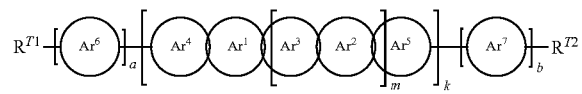

I wherein the individual radicals, independently of each other and on each occurrence identically or differently, have the following meanings Ar¹, Ar² are a group selected from the following formulae
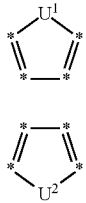
A1
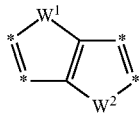
A2
Ar³ is a group selected from the following formulae and their mirror images
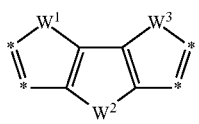
A3a
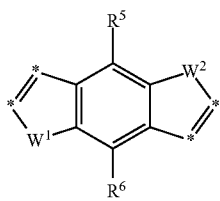
A3b
A3c
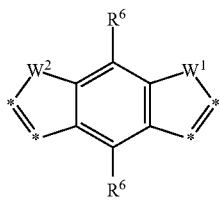
A3d
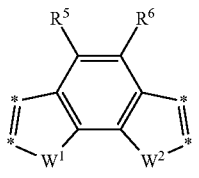
A3e
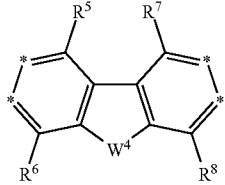
A3f
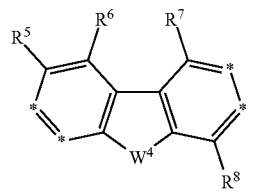
A3g
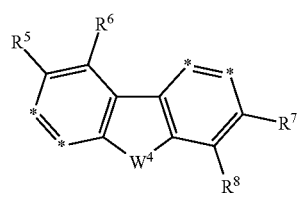
A3h
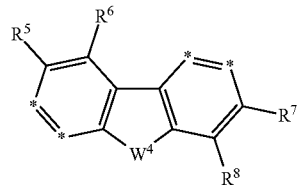
A3i
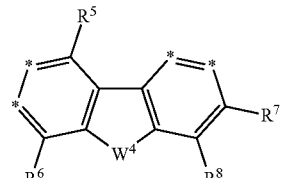
A3j
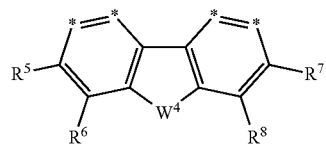
A3k
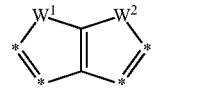
A3l
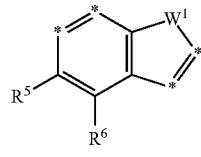
A3m
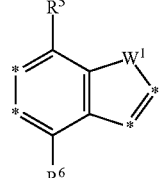
A3n
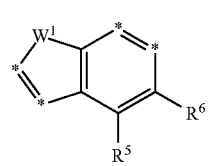
A3o
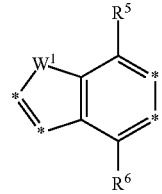
A3p -continued
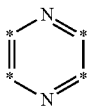
A3q
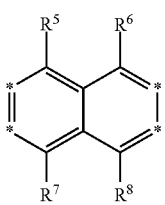
A3r
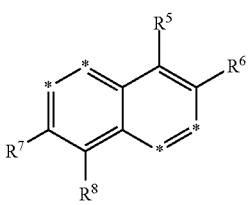
A3s
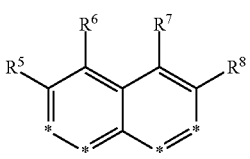
A3t
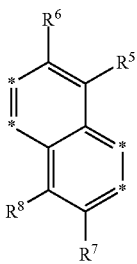
A3u
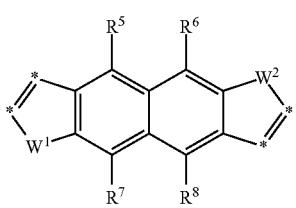
A3v
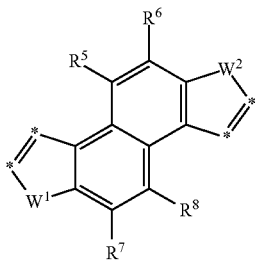
A3w
Ar⁴ is a group selected from the following formulae and their mirror images
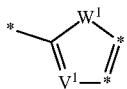
A4a
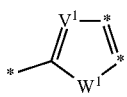
A4b
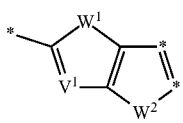
A4c
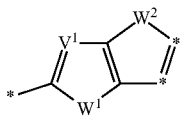
A4d
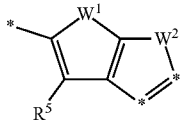
A4e
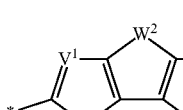
A4f
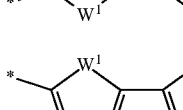
A4g
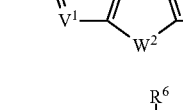
A4h
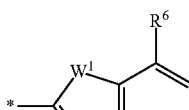
A4i
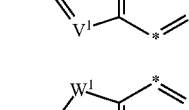
A4j
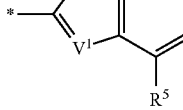
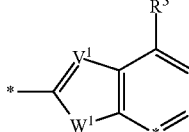
A4k
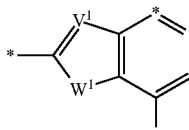

-continued
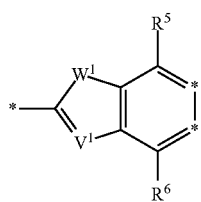
A4l
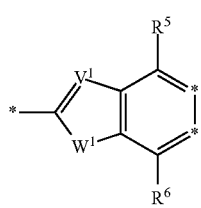
A4m
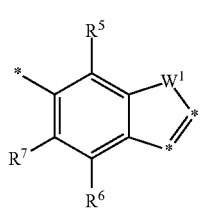
A4n
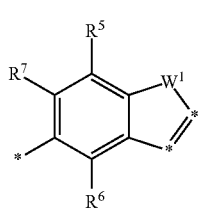
A4o
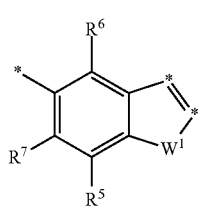
A4p
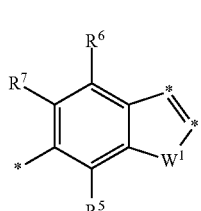
A4q
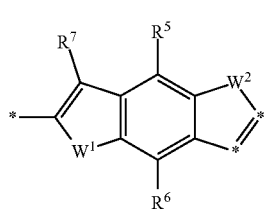
A4r
-continued
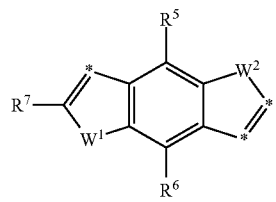
A4s
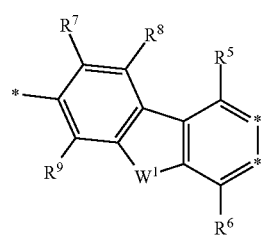
A4t
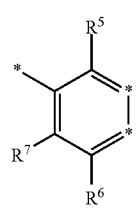
A4u
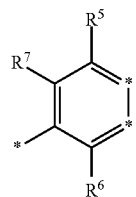
A4v
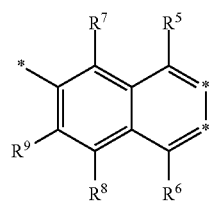
A4w
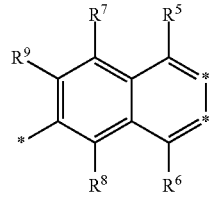
A4x
$Ar^5$ is a group selected from the following formulae and their mirror images
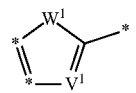
A5a
A5b

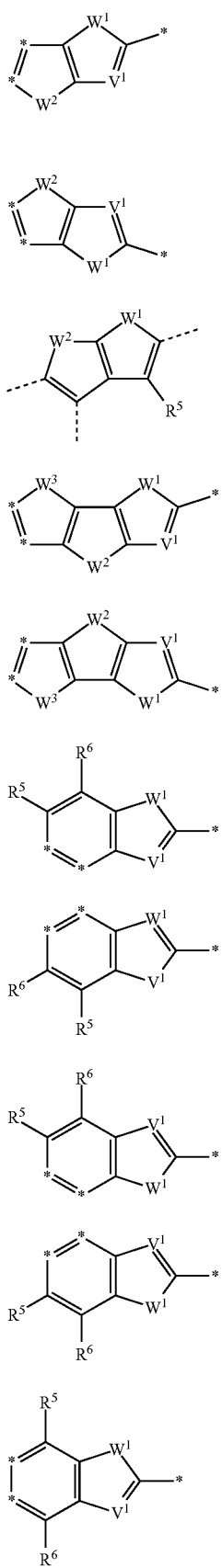
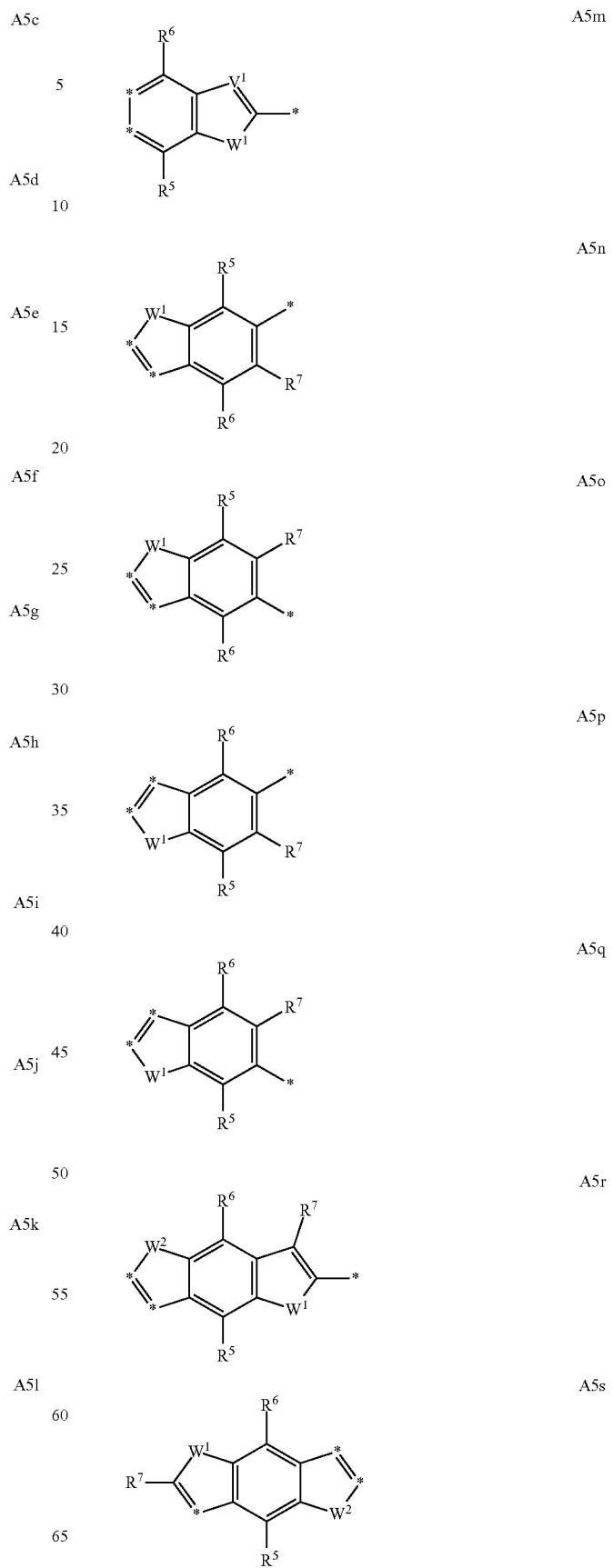

-continued

A5t
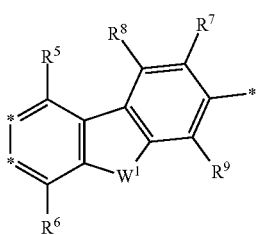

A5u
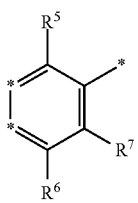

A5v
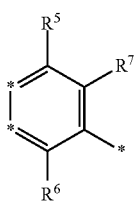

A5w
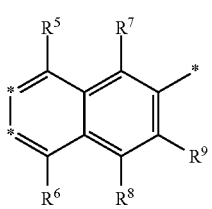

A5x
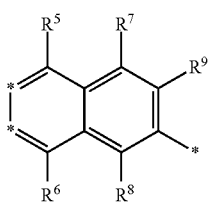

Ar$^{6,7}$ are arylene or heteroarylene that has from 5 to 20 ring atoms, is mono- or polycyclic, optionally contains fused rings, and is unsubstituted or substituted by one or more identical or different groups R$^1$ or L$^S$, or CY$^1$=CY$^2$ or —C≡C—, U$^1$, U$^2$ are CR$^1$R$^2$, SiR$^1$R$^2$, GeR$^1$R$^2$, C=CR$^1$R$^2$, NR$^1$ or C=O, V$^1$ is CR$^3$ or N, W$^1$, W$^2$, W$^3$ are S, O, Se or C=O, W$^4$ is S, O, Se, C=O or NR$^1$, R$^{1-9}$ is H, F, Cl, CN, or straight-chain, branched or cyclic alkyl with 1 to 30 C atoms, in which one or more CH$_2$ groups are optionally replaced by —O—, —S—, —C(=O)—, —C(=S)—, —C(=O)—O—, —O—C(=O)—, —NR$^o$—, —SiR$^o$R$^{oo}$—, —CF$_2$—, —CR$^o$=CR$^{oo}$—, —CY$^1$=CY$^2$— or —C≡C— in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L$^S$, and the pair of R$^1$ and R$^2$, together with the C, Si or Ge atom to which they are attached, may also form a spiro group with 5 to 20 ring atoms which is mono- or polycyclic, does optionally contain fused rings, and is unsubstituted or substituted by one or more identical or different groups L$^S$, R$^{T1}$, R$^{T2}$ are an electron withdrawing group, Y$^1$, Y$^2$ are H, F, Cl or CN, L$^S$ is F, Cl, —NO$_2$, —CN, —NC, —NCO, —NCS, —OCN, —SCN, R$^o$, OR$^o$, SR$^o$, —C(=O)X$^o$, —C(=O)R$^o$, —C(=O)—OR$^o$, —O—C(=O)—R$^o$, —NH$_2$, —NHR$^o$, —NR$^o$R$^{oo}$, —C(=O)NHR$^o$, —C(=O)NR$^o$R$^{oo}$, —SO$_3$R$^o$, —SO$_2$R$^o$, —OH, —NO$_2$, —CF$_3$, —SF$_5$, or optionally substituted silyl, or carbyl or hydrocarbyl with 1 to 30 C atoms that is optionally substituted and optionally comprises one or more hetero atoms, R$^o$, R$^{oo}$ are H or straight-chain or branched alkyl with 1 to 20 C atoms that is optionally fluorinated, X$^o$ is halogen, a, b are 0 or an integer from 1 to 10, k is an integer from 1 to 10, m is 0 or an integer from 1 to 10, wherein at least one of R$^{T1}$ and R$^{T2}$ is an electron withdrawing group of formula TG TG
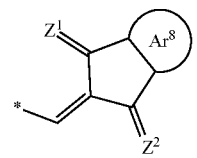

Ar$^8$ is bi- or polycyclic arylene or heteroarylene having from 5 to 20 ring atoms which is optionally substituted with one or more groups L, L is F, Cl, —NO$_2$, —CN, —NC, —NCO, —NCS, —OCN, —SCN, R$^o$, OR$^o$, SR$^o$, —C(=O)X$^o$, —C(=O)R$^o$, —C(=O)—OR$^o$, —O—C(=O)—R$^o$, —NH$_2$, —NHR$^o$, —NR$^o$R$^{oo}$, —C(=O)NHR$^o$, —C(=O)NR$^o$R$^{oo}$, —SO$_3$R$^o$, —SO$_2$R$^o$, —OH, —NO$_2$, —CF$_3$, —SF$_5$, Z$^1$, Z$^2$ are O or C(CN)$_2$, and wherein at least one group Ar$^3$ denotes thieno[3,2-b]thiophene and/or at least one of the groups Ar$^4$ and Ar$^5$ denotes thieno[3,2-b]thiophene that is optionally substituted with R$^3$.

2. The compound according to claim 1, characterized in that it is selected from the following subformulae

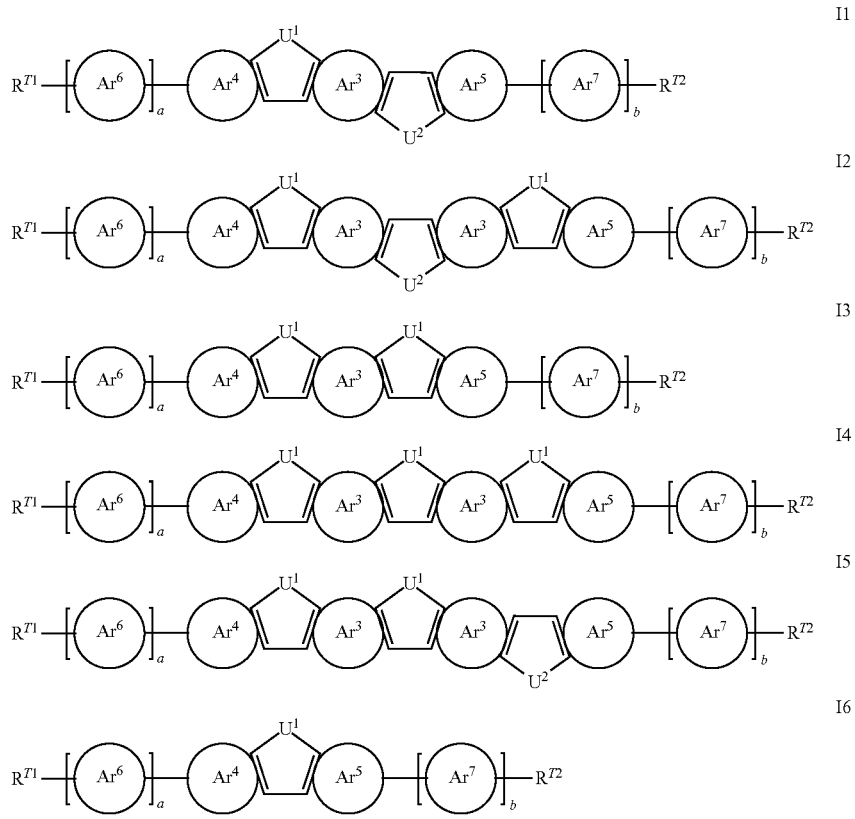

wherein $U^1$, $U^2$, $Ar^3$, $Ar^4$, $Ar^5$, $Ar^6$, $Ar^7$, $R^{T1}$, $R^{T2}$, a and b, independently of each other and on each occurrence identically or differently, have the meanings given in claim 1.

3. The compound according to claim 1, characterized in that the groups $Ar^3$ are on each occurrence identically or differently selected from the following formulae and their mirror images

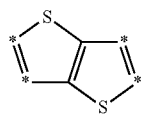

A3a1

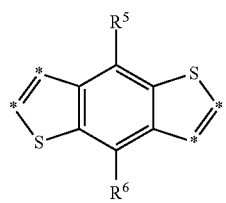

A3b1

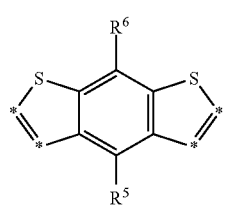

A3c1

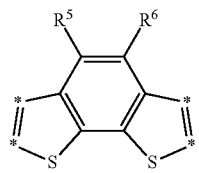

-continued

A3d1

A3e1

A3f1

-continued
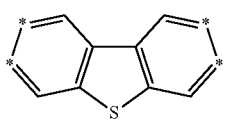 A3g1
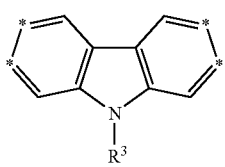 A3g2
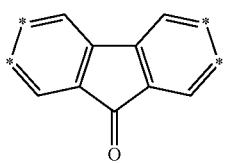 A3g3
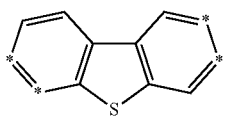 A3h1
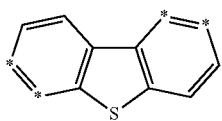 A3i1
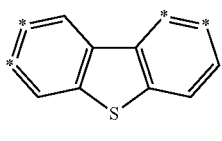 A3j1
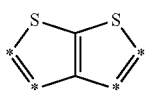 A3k1
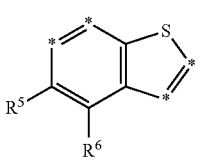 A3l1
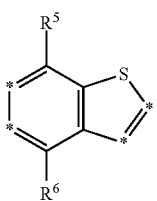 A3m1
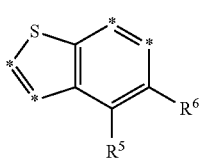 A3n1
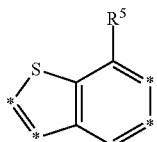 A3o1
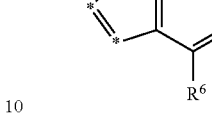 A3p
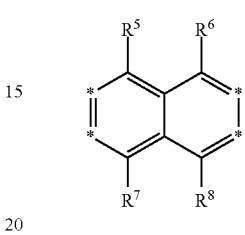 A3q
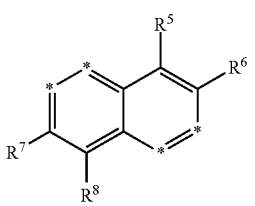 A3r
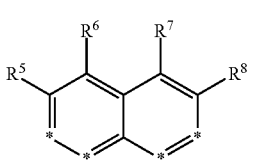 A3s
wherein $R^{5-8}$ have the meanings given in claim 1.
4. The compound according to claim 1, characterized in that the groups $Ar^4$ are on each occurrence identically or differently selected from the following formulae and their mirror images
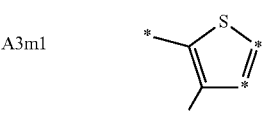 A4a1
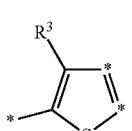 A4b1
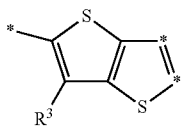 A4c1

-continued
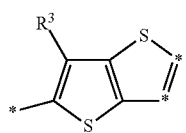
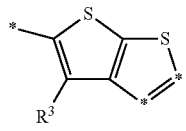
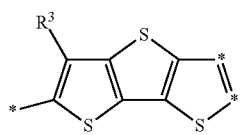
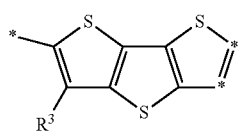
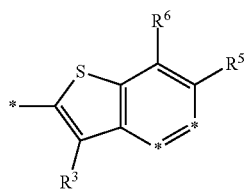
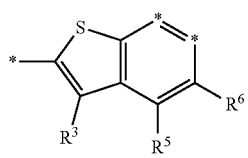
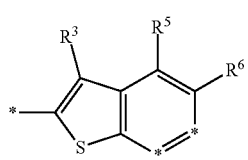
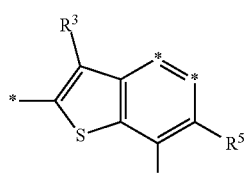
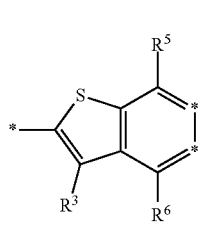
-continued
A4d1
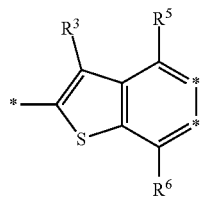
A4e1
A4f1
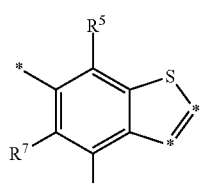
A4g1
A4h1
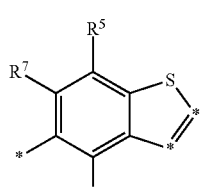
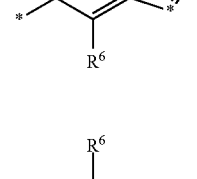
A4i1
A4j1
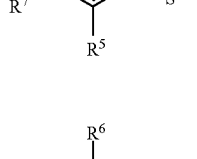
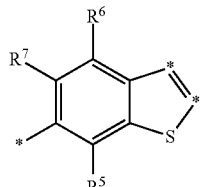
A4k1
A4l1
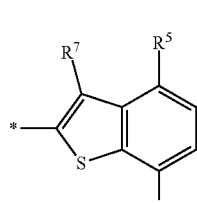
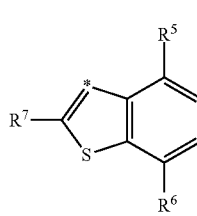
A4m1
A4n1
A4o1
A4p1
A4q1
A4r1
A4s1

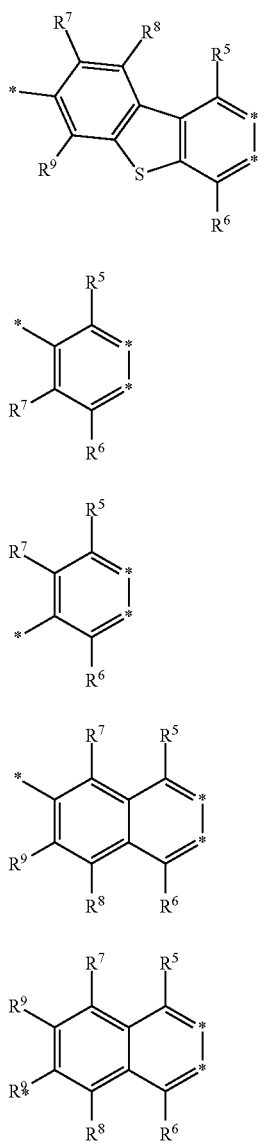
wherein R³⁻⁹ have the meanings given in claim 1.
5. The compound according to claim 1, characterized in that the groups Ar⁵ are on each occurrence identically or differently selected from the following formulae and their mirror images
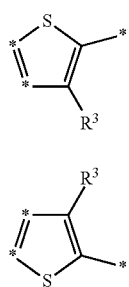
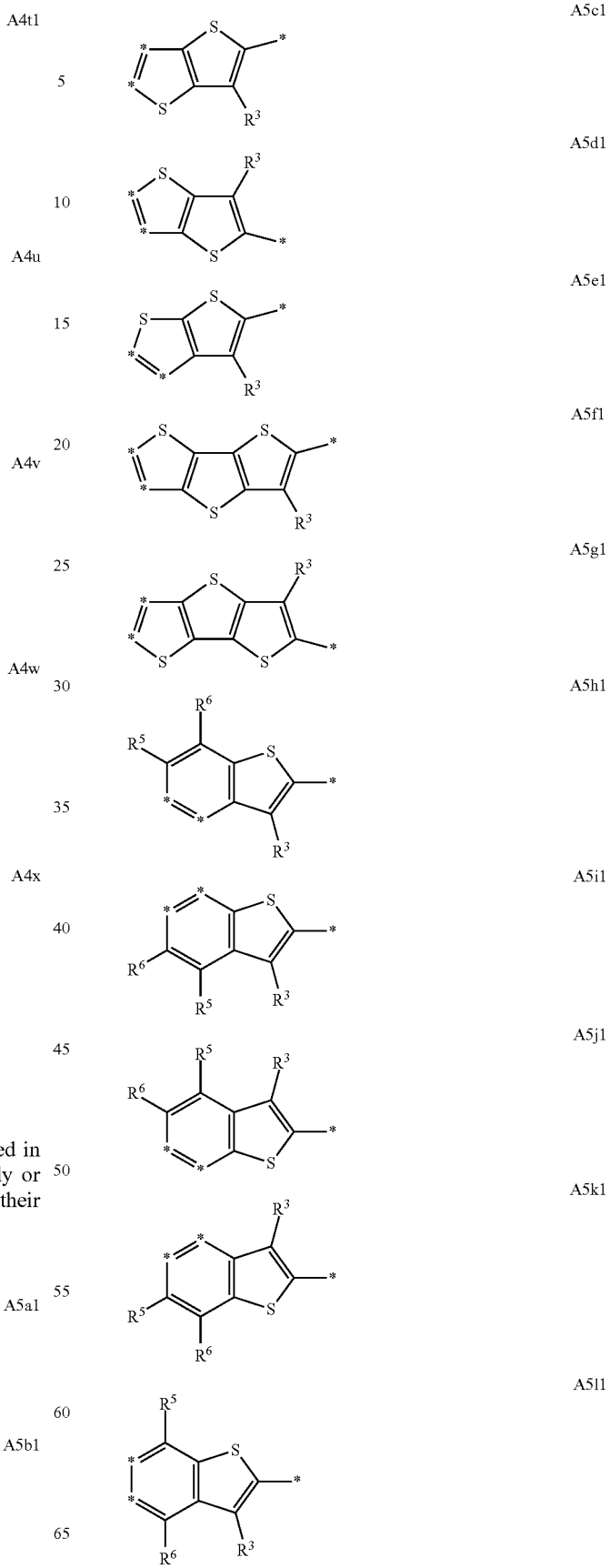

349
-continued
A5m1 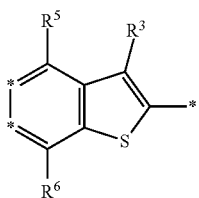
A5n1 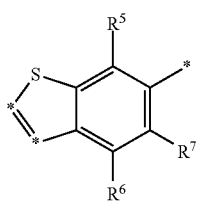
A5o1 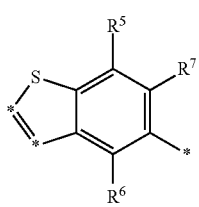
A5p1 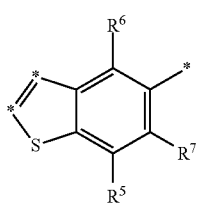
A5q1 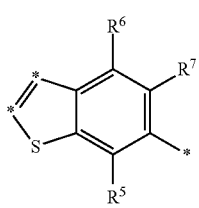
A5r1 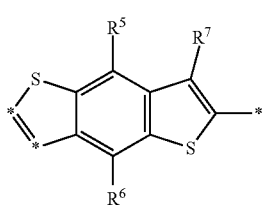
A5s1 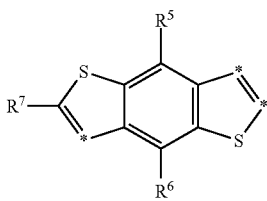
350
-continued
A5t1 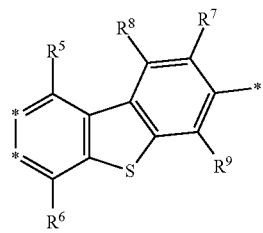
A5u1 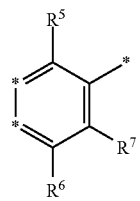
A5v1 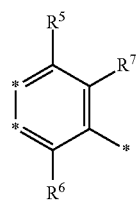
A5w1 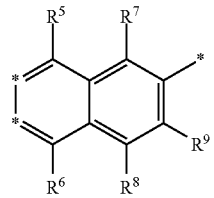
A5x1 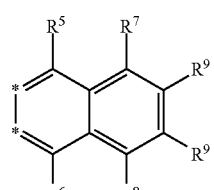
wherein $R^{3-9}$ have the meanings given in claim 1.
6. The compound according to claim 1, characterized in that the groups $Ar^6$ and $Ar^7$ are on each occurrence identically or differently selected from the following formulae and their mirror images
AR1 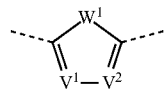
AR2 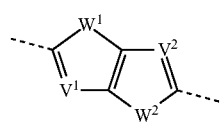

-continued

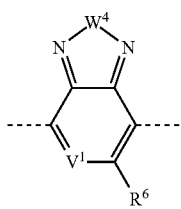
AR3

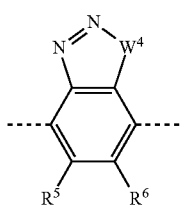
AR4

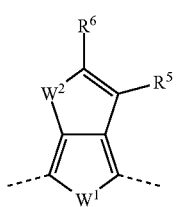
AR5

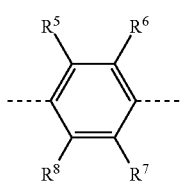
AR6

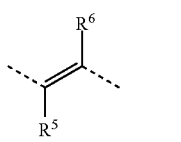
AR7 wherein, independently of each other and on each occurrence identically or differently, $V^2$ is $CR^4$ or N.

7. The compound according to claim 1, characterized in that the groups $Ar^6$ and $Ar^7$ are on each occurrence identically or differently selected from the following formulae and their mirror images

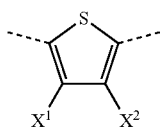
AR1-1

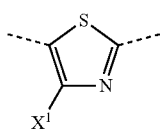
AR1-2

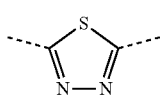
AR1-3

-continued

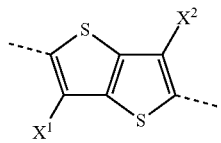
AR2-1

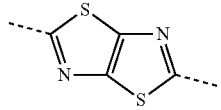
AR2-2

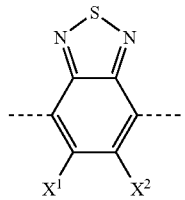
AR3-1

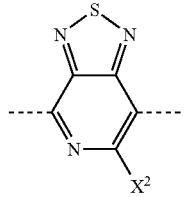
AR3-2

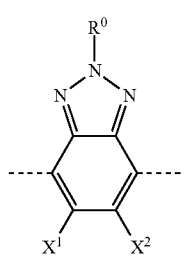
AR3-3

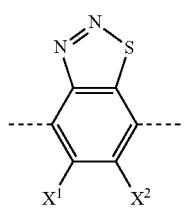
AR4-1

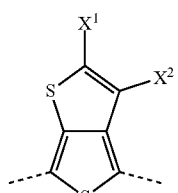
AR5-1

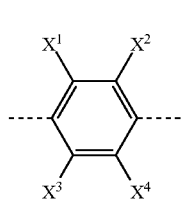
AR6-1

-continued
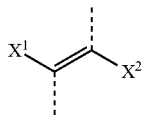
AR7-1
wherein $X^1$, $X^2$, $X^3$ and $X^4$ have one of the meanings given for $R^1$ in claim 1, and $R^0$ is as defined in claim 1.
8. The compound according to claim 1, characterized in that group $Ar^8$ in formula TG is on each occurrence identically or differently selected from the following formulae and their mirror images
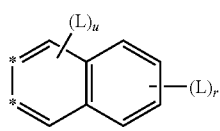
A8-1
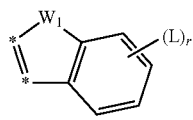
A8-2
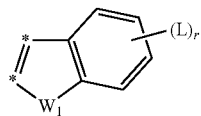
A8-3
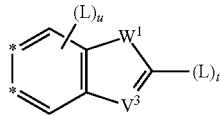
A8-4
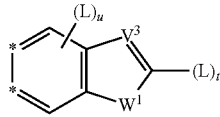
A8-5
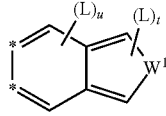
A8-6
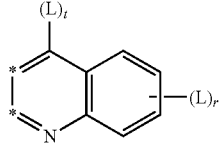
A8-7
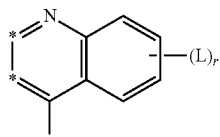
A8-8
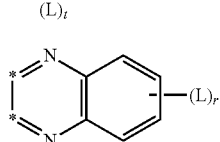
A8-9
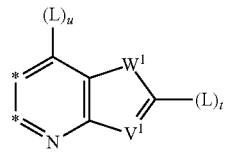
A8-10
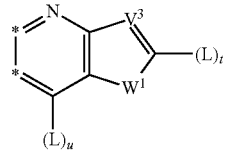
A8-11
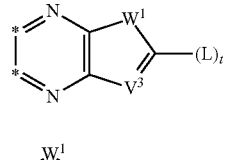
A8-12
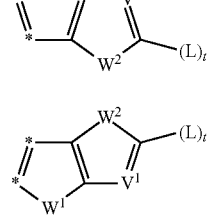
A8-13
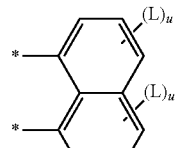
A8-14
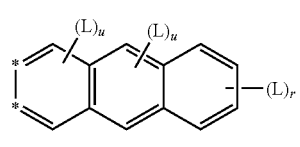
A8-15
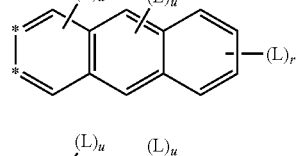
A8-16
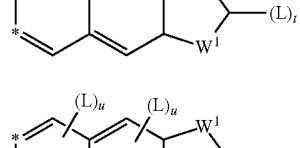
A8-17
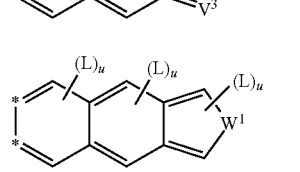
A8-18
A8-19
A8-20

-continued

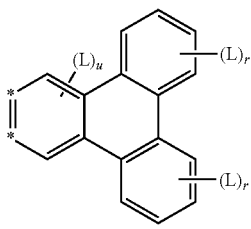
A8-21

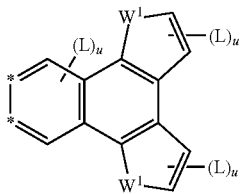
A8-22

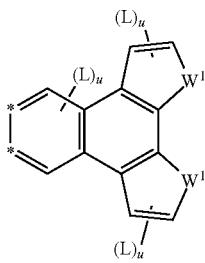
A8-23

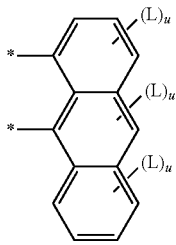
A8-24 wherein, independently of each other and on each occurrence identically or differently, W¹ and L have the meanings given in claim 1, V³ is N or C(L)$_t$, r is 0, 1, 2, 3 or 4, u is 0, 1 or 2, and t is 0 or 1.

9. The compound according to claim 1, characterized in that group Ar⁸ in formula TG is on each occurrence identically or differently selected from the following formulae and their mirror images

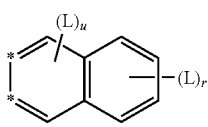
A8-1a

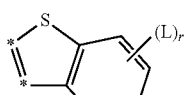
A8-2a

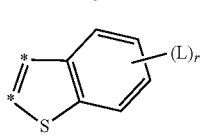
A8-3a

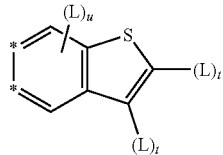
A8-4a

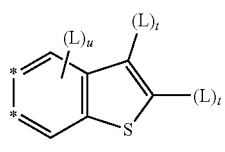
A8-5a

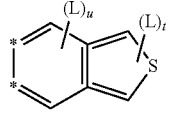
A8-6a wherein L, r, t and u, independently of each other and on each occurrence identically or differently, have the meanings given in claim 8.

10. The compound according to claim 1, characterized in that $R^{T1}$ and $R^{T2}$ in formula I are selected from the following subformulae

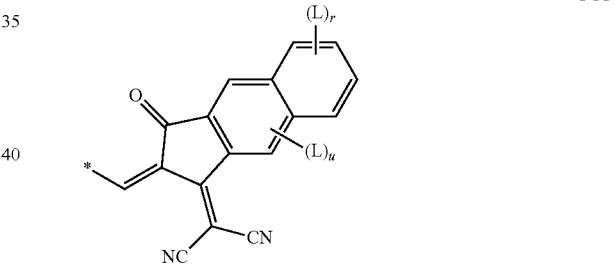
TG1

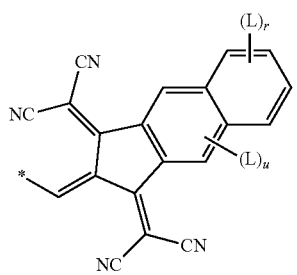
TG2

TG3

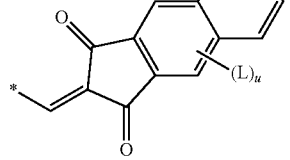

357
-continued
TG4
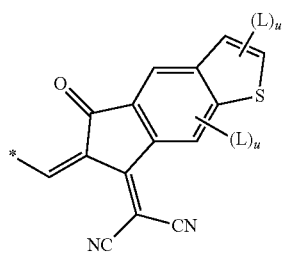
TG5
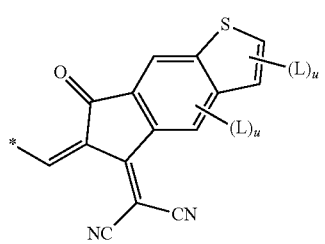
TG6
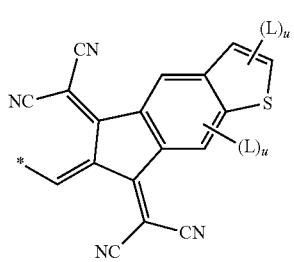
TG7
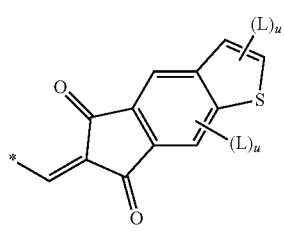
TG8
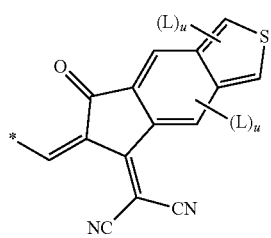
TG9
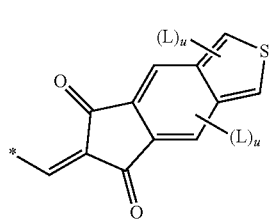
358
-continued
TG10
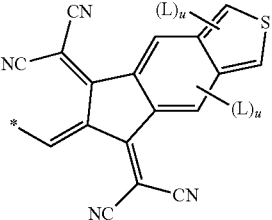
TG11
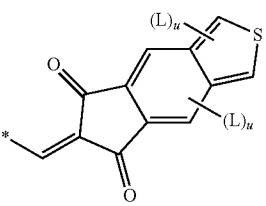
TG12
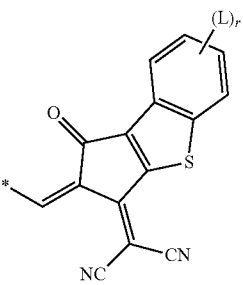
TG13
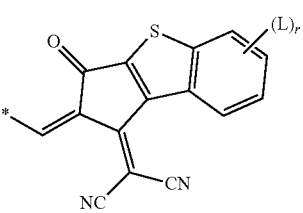
TG14
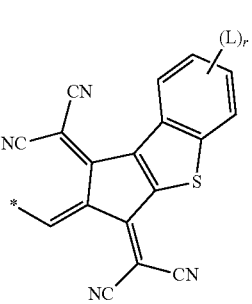
TG15
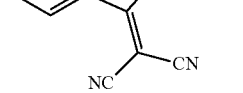
wherein L, u and r have the meanings given in claim 8.
11. The compound according to claim 1, characterized in that both $R^{T1}$ and $R^{T2}$ are selected from formula TG as defined in claim 1.

12. The compound according to claim 1, characterized in that it is selected of the following subformula

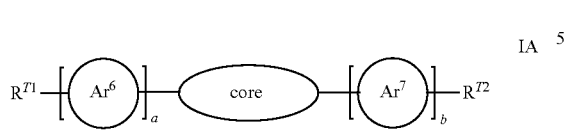

IA wherein $Ar^6$, $Ar^7$, $R^{T1}$, $R^{T2}$, a and b, independently of each other and on each occurrence identically or differently, have the meanings given in claim 1, and "Core" is, on each occurrence identically or differently, a polycyclic divalent group selected from the following formulae

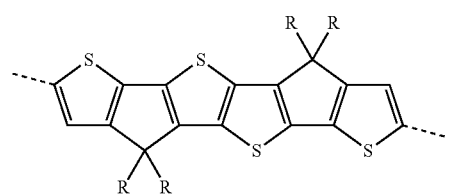

C1

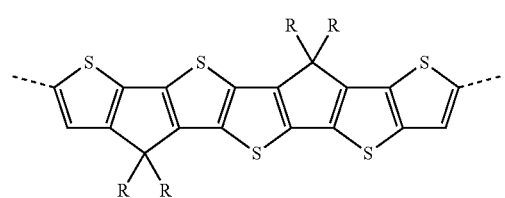

C2

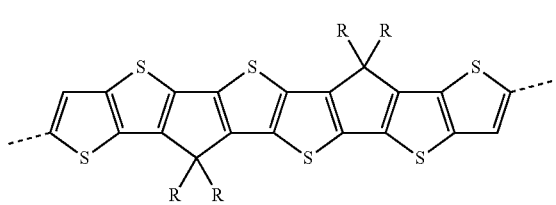

C3

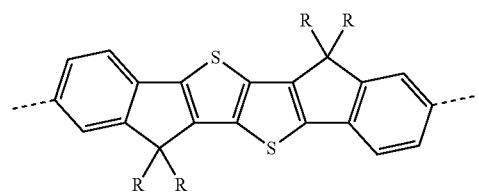

C4

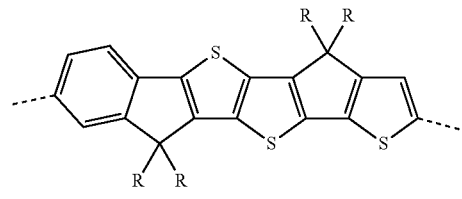

C5

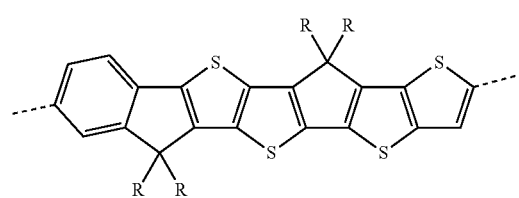

C6

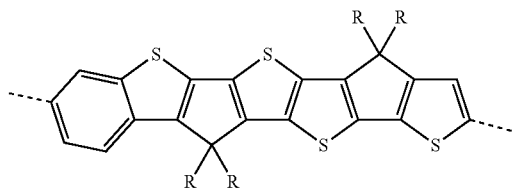

C7

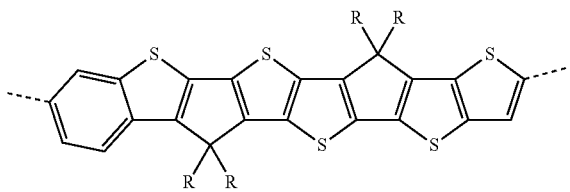

C8

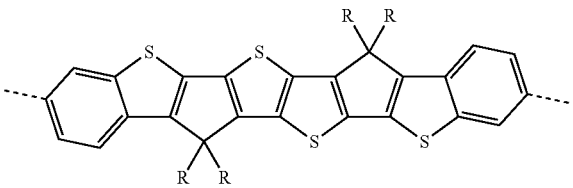

C9

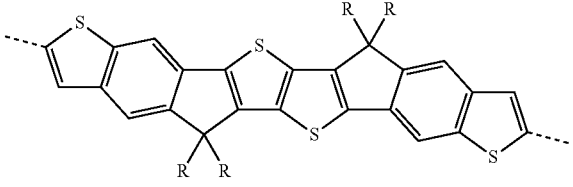

C10

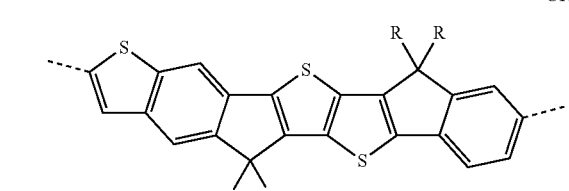

C11

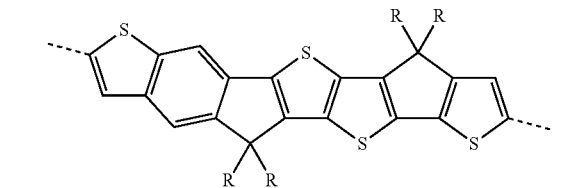

C12

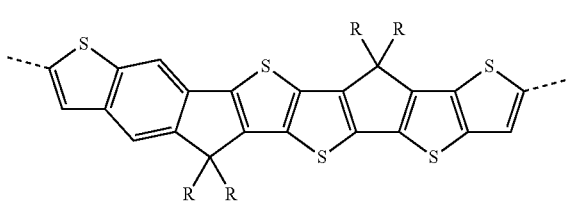

C13

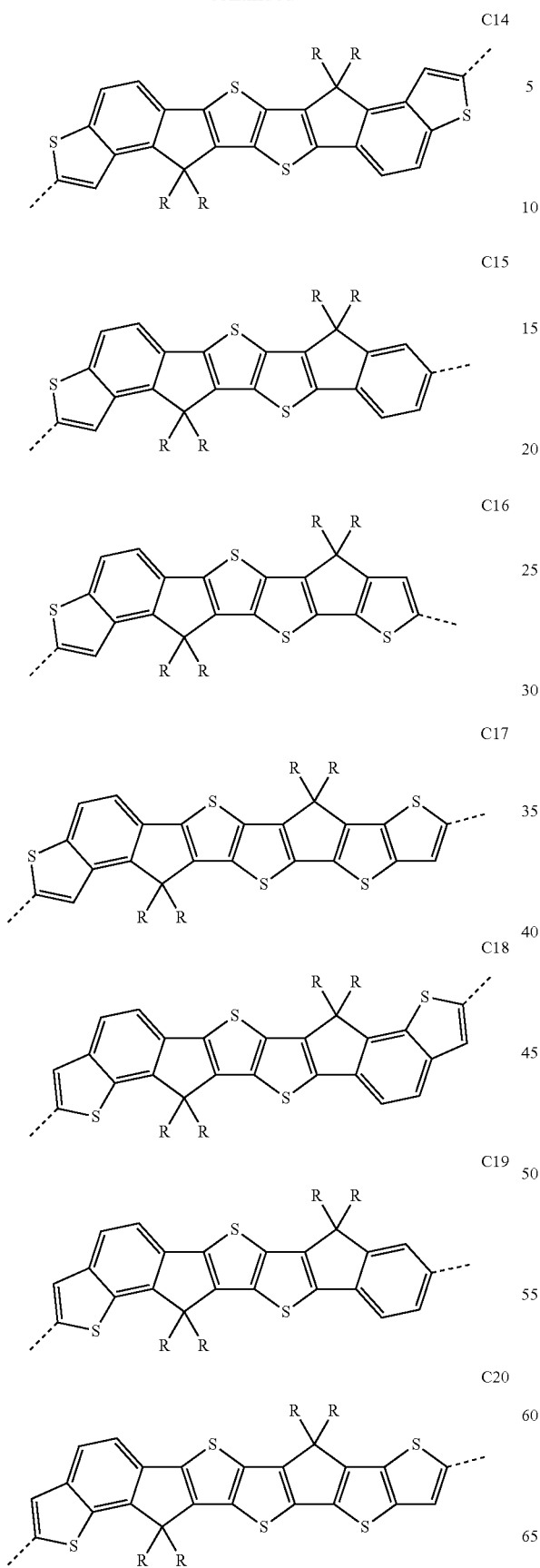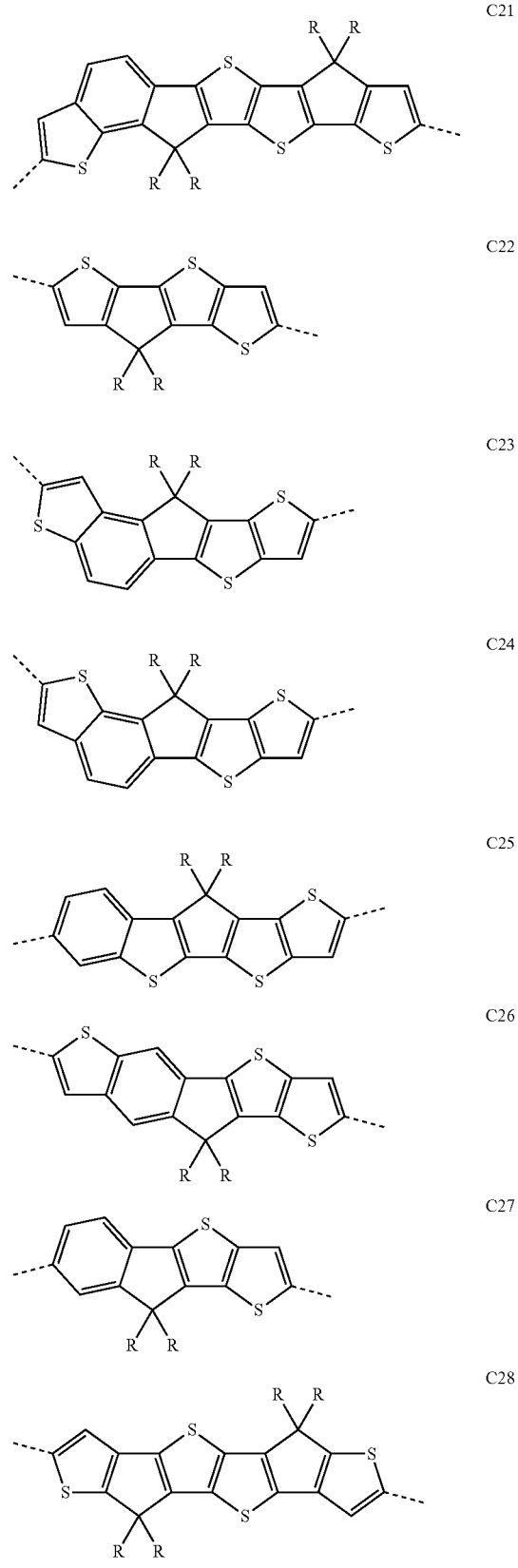
wherein R has on each occurrence identically or differently one of the meanings of $R^1$ as given in claim 1.

13. The compound according to claim 1, characterized in that it is selected from the following subformulae
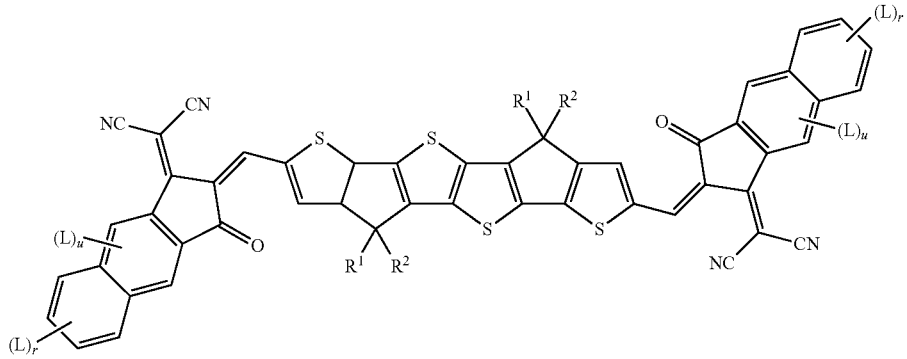
I1A1
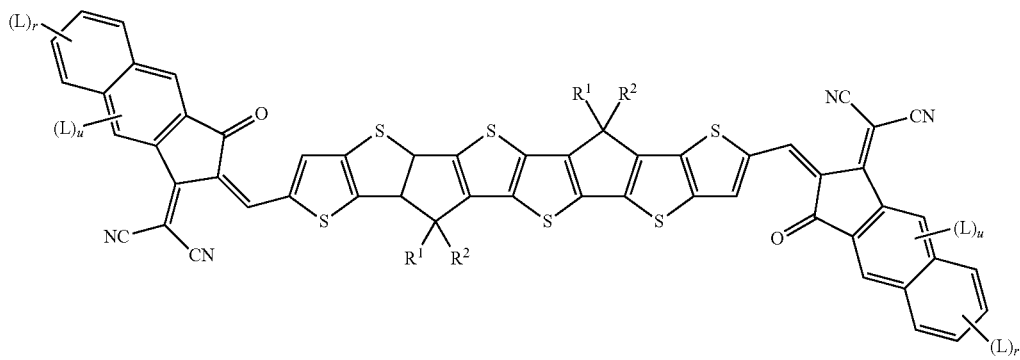
I1A2
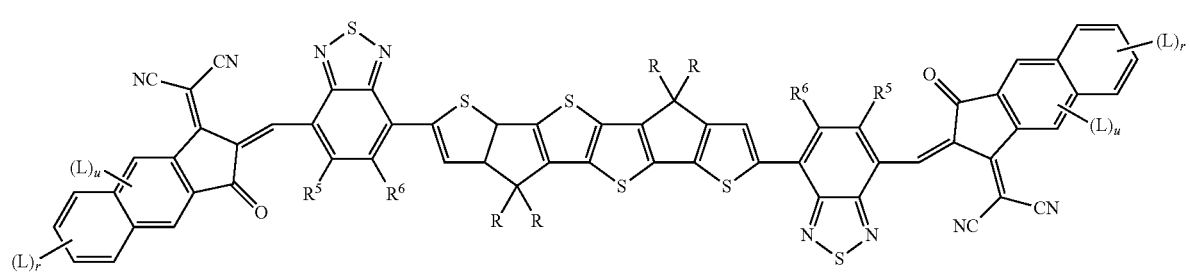
I1A3
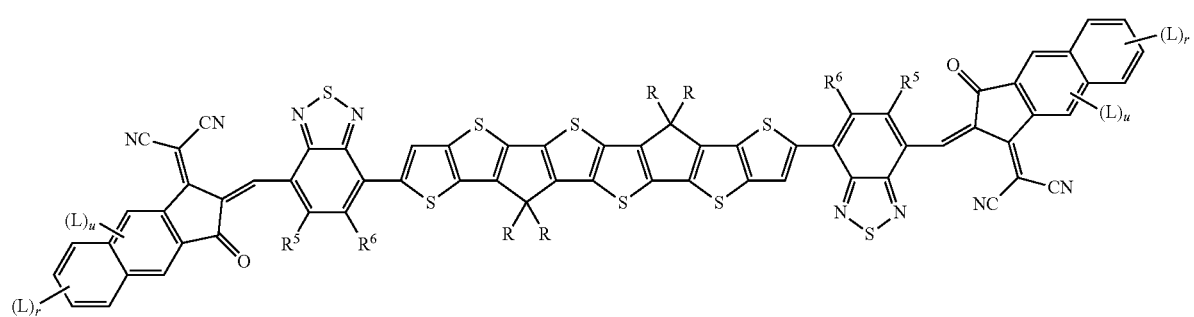
I1A4

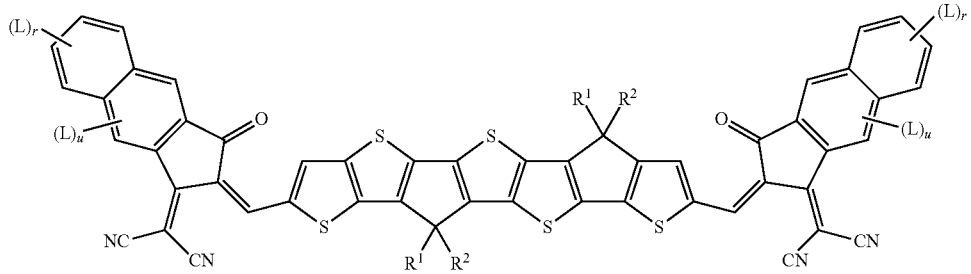

I1A5

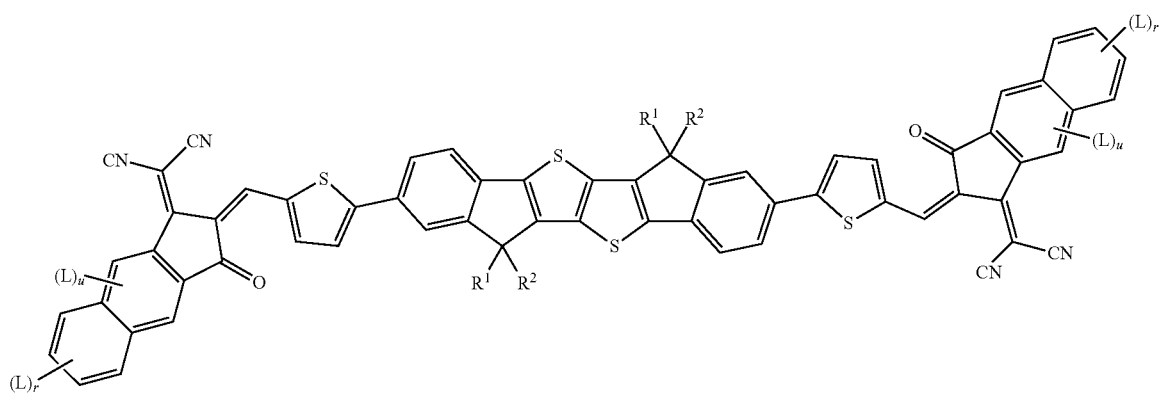

I1A6

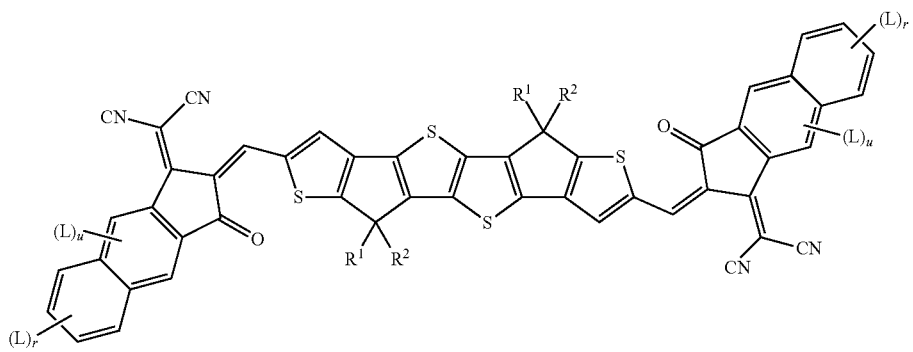

I1A7 wherein R¹, R², R⁵, R⁶, L, r and u have the meanings given in claims 1 and 8.

14. The compound according to claim 1, characterized in that R¹ and R² are selected from F, Cl, CN, straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms.

15. The compound according to claim 1, characterized in that R¹ and R² are selected from mono- or polycyclic aryl or heteroaryl, each of which is optionally substituted with one or more groups $L^S$ as defined in claim 1 and has 5 to 20 ring atoms, and wherein two or more rings may be fused to each other or connected with each other by a covalent bond.

16. The compound according to claim 1, characterized in that at least one of $R^{3-8}$ is different from H, and is selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated.

17. A composition comprising one or more compounds according to claim 1, and further comprising one or more compounds having one or more of a semiconducting, hole or electron transporting, hole or electron blocking, electrically conducting, photoconducting, photoactive or light emitting property, and/or a binder.

18. The composition of claim 17, comprising one or more n-type semiconductors, at least one of which is a compound according to claim 1, and further comprising one or more p-type semiconductors.

19. The composition according to claim 17, comprising one or more n-type semiconductors selected from fullerenes or fullerene derivatives.

20. Use of a compound according to claim 1, or of a composition according to claim 17, in an electronic or optoelectronic device, or in a component of such a device or in an assembly comprising such a device.

21. A formulation comprising one or more compounds according to claim 1, or a composition according to claim 17, and further comprising one or more solvents selected from organic solvents.

22. An electronic or optoelectronic device, or a component thereof, or an assembly comprising it, which comprises a compound according to claim 1, or a composition according to claim 17.

23. The electronic or optoelectronic device according to claim 22, which is selected from organic field effect transistors (OFET), organic thin film transistors (OTFT), organic light emitting diodes (OLED), organic light emitting transistors (OLET), organic light emitting electro-chemical cells (OLEC), organic photovoltaic devices (OPV), organic photodetectors (OPD), organic solar cells, dye-sensitized solar cells (DSSC), perovskite-based solar cells (PSC), organic photoelectrochemical cells (OPEC),laser diodes, Schottky diodes, photoconductors, photodetectors, thermoelectric devices.

24. The component according to claim 22, which is selected from charge injection layers, charge transport layers, interlayers, planarizing layers, antistatic films, polymer electrolyte membranes (PEM), conducting substrates and conducting patterns.

25. The assembly according to claim 22, which is selected from integrated circuits (IC), radio frequency identification (RFID) tags, security markings, security devices, flat panel displays, LC windows, backlights of flat panel displays, electrophotographic devices, electrophotographic recording devices, organic memory devices, sensor devices, biosensors and biochips.

* * * * *